(12) United States Patent
Tyler et al.

(10) Patent No.: US 10,589,087 B2
(45) Date of Patent: Mar. 17, 2020

(54) SYSTEMS AND METHODS FOR ALTERING BRAIN AND BODY FUNCTIONS AND FOR TREATING CONDITIONS AND DISEASES OF THE SAME

(71) Applicant: Wicab, Inc., Middleton, WI (US)

(72) Inventors: Mitchell Eugene Tyler, Madison, WI (US); Yuri Petrovich Danilov, Middleton, WI (US); Paul Bach-y-Rita, Madison, WI (US)

(73) Assignee: WICAB, INC., Middleton, WI (US)

( * ) Notice: Subject to any disclaimer, the term of this patent is extended or adjusted under 35 U.S.C. 154(b) by 0 days.

(21) Appl. No.: 14/692,419

(22) Filed: Apr. 21, 2015

(65) Prior Publication Data
US 2015/0290454 A1    Oct. 15, 2015

Related U.S. Application Data

(63) Continuation-in-part of application No. 11/925,393, filed on Oct. 26, 2007, now abandoned, which is a
(Continued)

(51) Int. Cl.
*A61B 5/00* (2006.01)
*A61N 1/05* (2006.01)
(Continued)

(52) U.S. Cl.
CPC .......... *A61N 1/0548* (2013.01); *A61B 5/1124* (2013.01); *A61B 5/4005* (2013.01);
(Continued)

(58) Field of Classification Search
CPC .............. A61N 1/0548; A61N 1/36014; A61N 1/36103; A61F 9/08; G06F 3/011;
(Continued)

(56) References Cited

U.S. PATENT DOCUMENTS

| 3,952,728 A | 4/1976 | Levinson et al. |
|---|---|---|
| 4,092,633 A | 5/1978 | Fletcher et al. |

(Continued)

FOREIGN PATENT DOCUMENTS

| EP | 1035463 | 9/2000 |
|---|---|---|
| EP | 0799597 | 11/2000 |

(Continued)

OTHER PUBLICATIONS

Allum JH, Carpenter MG, Adkin AL, Balance control analysis as a method for screening and identifying balance deficits, Ann N Y Acad Sci. Oct. 2001;942:413-27.
(Continued)

*Primary Examiner* — Max F Hindenburg
(74) *Attorney, Agent, or Firm* — Casimir Jones; Tyler Sisk

(57) ABSTRACT

The present invention relates to systems and methods for management of brain and body functions and sensory perception. For example, the present invention provides systems and methods of sensory substitution and sensory enhancement (augmentation) as well as motor control enhancement. The present invention also provides systems and methods of treating diseases and conditions, as well as providing enhanced physical and mental health and performance through sensory substitution, sensory enhancement, and related effects.

19 Claims, 22 Drawing Sheets

Related U.S. Application Data continuation-in-part of application No. 11/234,635, filed on Sep. 23, 2005, now abandoned, which is a continuation-in-part of application No. 10/998,222, filed on Nov. 26, 2004, now abandoned.

(60) Provisional application No. 60/615,305, filed on Oct. 1, 2004, provisional application No. 60/605,988, filed on Aug. 31, 2004, provisional application No. 60/525,359, filed on Nov. 26, 2003.

(51) Int. Cl.
| | |
|---|---|
| *G06F 3/01* | (2006.01) |
| *A61B 5/11* | (2006.01) |
| *A61N 1/36* | (2006.01) |
| *G06F 3/038* | (2013.01) |
| *G06F 3/0354* | (2013.01) |
| *A61B 5/1455* | (2006.01) |
| *A61B 5/0492* | (2006.01) |

(52) U.S. Cl.
CPC .............. *A61B 5/486* (2013.01); *A61B 5/682* (2013.01); *A61B 5/7455* (2013.01); *A61N 1/36103* (2013.01); *G06F 3/011* (2013.01); *G06F 3/012* (2013.01); *G06F 3/015* (2013.01); *G06F 3/016* (2013.01); *G06F 3/038* (2013.01); *G06F 3/0383* (2013.01); *G06F 3/03547* (2013.01); *A61B 5/0492* (2013.01); *A61B 5/112* (2013.01); *A61B 5/1116* (2013.01); *A61B 5/1123* (2013.01); *A61B 5/14553* (2013.01); *A61B 5/4023* (2013.01); *A61B 5/4047* (2013.01); *A61B 5/4528* (2013.01); *A61B 5/6803* (2013.01); *A61B 5/686* (2013.01); *A61B 5/726* (2013.01); *A61B 5/7225* (2013.01); *A61B 5/7475* (2013.01); *A61B 2562/046* (2013.01); *A61N 1/36025* (2013.01); *A61N 1/36082* (2013.01)

(58) Field of Classification Search
CPC . G06F 3/015; G06F 3/016; G06F 3/12; G06F 3/0383; G06F 3/03547; A61B 5/11; A61B 5/1116; A61B 5/1123; A61B 5/1124; A61B 5/682; A61B 5/486; A61B 5/4005; A61B 5/7455

See application file for complete search history.

(56) References Cited

U.S. PATENT DOCUMENTS

| | | | |
|---|---|---|---|
| 4,305,402 A | 12/1981 | Katims | |
| 4,503,863 A | 3/1985 | Katims | |
| 4,558,703 A | 12/1985 | Mark | |
| 4,667,676 A | 5/1987 | Guinta | |
| 4,813,419 A | 3/1989 | McConnell | |
| 4,817,628 A | 4/1989 | Zealear et al. | |
| 4,817,633 A | 4/1989 | McStravick et al. | |
| 4,830,024 A | 5/1989 | Nashner et al. | |
| 4,938,476 A | 7/1990 | Brunelle et al. | |
| 5,026,151 A | 6/1991 | Waltuck et al. | |
| 5,035,500 A | 7/1991 | Rorabaugh | |
| 5,052,406 A | 10/1991 | Nashner et al. | |
| 5,209,240 A | 5/1993 | Jain et al. | |
| 5,303,715 A | 4/1994 | Nashner et al. | |
| 5,304,112 A | 4/1994 | Mrklas et al. | |
| 5,335,657 A | 8/1994 | Terry et al. | |
| 5,337,757 A | 8/1994 | Jain et al. | |
| 5,368,042 A | 11/1994 | O'Neal et al. | |
| 5,591,216 A | 1/1997 | Testerman et al. | |
| 5,627,237 A | 5/1997 | Halasa et al. | |
| 5,749,372 A | 5/1998 | Allen et al. | |
| 5,833,714 A | 11/1998 | Loeb | |
| 5,878,154 A | 3/1999 | Schimmelpfennig | |
| 5,919,149 A | 7/1999 | Allum | |
| 6,063,046 A * | 5/2000 | Allum | A61B 5/1036 600/595 |
| 6,077,237 A | 6/2000 | Cambell et al. | |
| 6,219,578 B1 | 4/2001 | Collins et al. | |
| 6,267,733 B1 * | 7/2001 | Peterson | A61B 5/0053 600/552 |
| 6,314,324 B1 | 11/2001 | Lattner et al. | |
| 6,326,901 B1 | 12/2001 | Gonzales | |
| 6,366,813 B1 | 4/2002 | DiLorenzo | |
| 6,401,249 B2 | 6/2002 | Haar et al. | |
| 6,421,185 B1 | 7/2002 | Wick | |
| 6,429,196 B1 | 8/2002 | Gao | |
| 6,430,450 B1 | 8/2002 | Bach-y-Rita | |
| 6,430,459 B1 | 8/2002 | Moore | |
| 6,546,291 B2 * | 4/2003 | Merfeld | A61B 5/1112 607/62 |
| 6,748,275 B2 | 6/2004 | Lattner et al. | |
| 6,943,754 B2 | 9/2005 | Aughey | |
| 7,145,461 B2 | 12/2006 | Lehrman et al. | |
| 7,309,128 B2 | 12/2007 | Cappo et al. | |
| 7,352,356 B2 | 4/2008 | Roberts et al. | |
| 7,463,929 B2 | 12/2008 | Simmons | |
| 2002/0010497 A1 | 1/2002 | Merfeld et al. | |
| 2002/0026219 A1 | 2/2002 | Collins et al. | |
| 2002/0072781 A1 | 6/2002 | Lattner et al. | |
| 2002/0103429 A1 | 8/2002 | deCharms | |
| 2003/0117371 A1 | 6/2003 | Roberts | |
| 2003/0149450 A1 | 8/2003 | Mayberg | |
| 2003/0199944 A1 | 10/2003 | Chapin et al. | |
| 2004/0005859 A1 | 1/2004 | Ghercioiu et al. | |
| 2004/0057013 A1 | 3/2004 | Cappo et al. | |
| 2004/0068481 A1 | 4/2004 | Seshardi et al. | |
| 2004/0127954 A1 | 7/2004 | McDonald | |
| 2004/0215236 A1 | 10/2004 | Lattner et al. | |
| 2004/0249302 A1 | 12/2004 | Donoghue | |
| 2005/0240253 A1 | 10/2005 | Tyler et al. | |
| 2006/0045287 A1 | 3/2006 | Abrams et al. | |
| 2006/0058619 A1 | 3/2006 | Deyoe et al. | |
| 2006/0161218 A1 | 7/2006 | Danilov | |
| 2006/0204045 A1 | 9/2006 | Antonucci | |
| 2006/0241718 A1 | 10/2006 | Tyler et al. | |
| 2008/0009772 A1 | 1/2008 | Tyler et al. | |
| 2009/0326604 A1 | 12/2009 | Tyler et al. | |
| 2010/0069995 A1 * | 3/2010 | Danielsson | A61N 1/36114 607/50 |

FOREIGN PATENT DOCUMENTS

| | | |
|---|---|---|
| EP | 1220179 | 7/2002 |
| JP | 2001-029485 | 2/2001 |
| WO | 97/20305 | 6/1995 |
| WO | 01/60282 | 8/2001 |
| WO | 2005040989 | 5/2005 |
| WO | 2005051329 | 6/2005 |

OTHER PUBLICATIONS

Allum, JH, Honegger F., (1992) A postural model of balance-correcting movement strategies, J Vestib Res 2:323-347.

Altenmueller E, Cornelius CP, Buettner UW (1990) Somatosensory evoked potentials following tongue stimulation in normal subjects and patients with lesions of the afferent trigeminal system, Electroencephalogr Clin Neurophysiol. Nov.-Dec. 1990; 77(6):403-15.

Angelaki DE and Dickman JD. Spatiotemporal processing of linear acceleration: primary afferent and central vestibular neuron responses. J Neurophysiol 84: 2113-2132, 2000.

Ardic FN, Latt LD, and Redfern MS. Paraspinal muscle response to electrical vestibular stimulation. Acta Otolaryngol 120: 39-46, 2000.

B.S. Troy, D.E. Kenney, E.E. Sabelman, "Sit-to-Stand as an Evaluation Tool for Balance," 52nd Annual Scientific Meeting, Gerontological Society of America, (San Francisco, Nov. 19-23, 1999); The Gerontologist, 39(S-1): 375, 1999.

B.S. Troy, E.E. Sabelman. D.E. Kenney, R. Yap, B. Lee, "Distinguishing Characteristics of Parkinson's Sit-to Stand Using

(56) References Cited

OTHER PUBLICATIONS

Accelerometry," RESNA 2000 (Rehabilitation Engineering Society of North America), Orlando, Florida, Jun. 28-Jul. 2, 2000, pp. 340-342.
Bach-y-Rita P, Collins CC, Saunders FA, White B, Scadden L. (1969) Vision substitution by tactile image projection, Nature. Mar. 8, 1969;221(5184):963-4.
Bach-y-Rita, P., & Tyler, M. (2000). "Tongue man-machine interface." In: J. D. Westwood, H. M. Hoffman, G. T. Mogel, R. A. Robb, & D. Stredney (eds.), Medicine Meets Virtual Reality 2000, (pp. 17-19). Amsterdam, IOS.
Bach-y-Rita, P., Kaczmarek, K. A., &Tyler, M. E. (2003). A Tongue-based Tactile Display for Portrayal of Environmental Characteristics. In L. Hettlinger &M. Haas (Eds.), Psychological Issues in the Design and Use of Virtual and Adaptive Environments. Mahwah, NJ: Lawrence Erlbaum Associates, pp. 169-186.
Bach-y-Rita, P., Kaczmarek, K.A., &Meier, K (1998). the tongue as a man-machine interface: a wireless communication system. Proc of the 1998 Internat Symp. on Info Theory & its Applications, 79-81.
Bach-y-Rita, P., Kaczmarek, K.A., Tyler, M.E, and Garcia-Lara, J. (1998). "Form Perception With a 49-Point Electrotactile Stimulus Array on the Tongue." Journal. of Rehab. Research & Develop., Oct.-Nov. pp. 427-430.
Bach-y-Rita, P., Tyler, M.E., & Kaczmarek, K.A. (2003). "Seeing with the Brain." In: International Journal on Human-Computer Interaction: Special Edition on Mediated Reality. 15:2, pp. 285-295.
Bent LR, McFadyen BJ, and Inglis JT. Visual-vestibular interactions in postural control during the execution of a dynamic task. Exp Brain Res 146: 490-500, 2002.
Borger L., Whitney S., Redfern M., Furman, J., "The influence of dynamic visual environments on postural sway in the elderly" J of Vistibular Research 1999; 9(3) 197-205.
Brandt T, Krafczyk S, Malsbenden I. (1981) Postural imbalance with head extension: improvement by training as a model for ataxia therapy, Ann N Y Acad Sci. 1981;374:636-49.
Britton Te, Day BL, Brown P, Rothwell JC, Thompson PO, and Marsden CD. Postural electromyographic responses in the arm and leg following galvanic vestibular stimulation in man. Exp Brain Res 94: 143-151, 1993.
Clendaniel et al. Vestibular Rehabilitation Strategies in Meniere's Disease, Otolaryngol Clin North Am, Dec. 1997; 30(6), 1145-1158.
Coats A. Effects of varying stimulus parameters on the galvanic bodysway response. Ann Otol Rhinal Laryngol 82:96-102,1973.
Cohen H., Vestibular rehabilitation reduces functional disability, Otolaryngol Head Neck Surg. Nov. 1992;107(5):638-43.
Collins CC, Bach-y-Rita P. (1973) Transmission of pictorial information through the skin, Adv Bioi Med Phys. 1973;14:285-315.
Courjon JH, Precht W, and Sirkin OW. Vestibular nerve and nuclei unit responses and eye movement responses to repetitive galvanic stimulation of the labyrinth in the rat. Exp Brain Res 66: 41-48, 1987.
Danilov Y.P., Tyler M.E., Bach-y-Rita P. (2004) "Spectral analysis of head based stabilogram in young and elderly subjects." Proc. of the 34th International Meeting of the Society for Neuroscience, Oct. 23-28; San Diego, CA.
Danilov, Y., Tyler, M., & Bach-y-Rita, P. (2003). "Effects of electrotactile substitution on bilateral vestibular dysfunction subjects". Proc. of the 2003 Annual Fall Meeting of the Biomedical Engineering Society, Oct. 23-28, Nashville, TN.
Danilov, Y.P., Tyler, M.E., Bach-Y-Rita, P. (2004). "Vestibular Substitution for Postural Control" In Proceedings of the 17th Annual International Conference on Technological Innovations in Disability, Garches, Institute, B. Bussel, editor.
Day BI, Guerraz M, and Cole J. Sensory interactions for human balance control revealed by galvanic vestibular stimulation. Adv Exp Med Bioi 508: 129-137,2002.
Day BL, Severac Cauquil A, Bartolomei L, Pastor MA, and Lyon IN. Human body-segment tilts induced by galvanic stimulation: a vestibularly driven balance protection mechanism. J Physiol 500: 661-672,1997.

Ezure K, Cohen MS, and Wilson VJ. Response of cat semicircular canal afferents to sinusoidal polarizing currents: implications for input-output properties of second-order neurons. J Neurophysiol 49: 639-648, 1983.
Fernandez C and Goldberg JM. Physiology of peripheral neurons innervating semicircular canals of the squirrel monkey. II. Response to sinusoidal stimulation and dynamics of peripheral vestibular system. J Neurophysiol 34: 661-675, 1971.
Fitzpatrick Ref Marsden J, Lord SR, and Day BL. Galvanic vestibular stimulation evokes sensations of body rotation. Neuroreport 13: 2379-2383, 2002.
Girolamo et al. Virtual Reality in Vestibular Assessment and Rehabilitation, Virtual Reality (1999) 4; 169-183.
Goldberg JM, Smith CE, and Fernandez C. Relation between discharge regularity and responses to externally applied galvanic currents in vestibular nerve afferents of the squirrel monkey. J Neurophysiol 51: 1236-1256, 1984.
Griffin MJ, Brett MW (1997) Effects offore-and-aft, lateral and vertical whole-body vibration on a head-positioning task. Aviat Space Environ Med 68:1115-1122.
Guerraz M and Day B. Human body response to galvanic vestibular stimulation is not affected when the stimulus is self-triggered. J Physiol 531 P: 142,2001.
Horak FB et al. Effects of vestibular rehabilitation on dizziness and imbalance. OtoIHNS 1992: 175-180.
Tang; Beebe, D.J.; An ultra-flexible electrotactile display for the roof of the mouth, [Engineering in Medicine and Biology, 1999. 21st Annual Conf. and the 1999 Annual Fall Meeting of the Biomedical Engineering Soc.] BMES/EMBS Conference, 1999. Proceedings of the First Joint, vol. 1, Oct. 13-16, 1999, p. 626, vol. 1.
Inglis JT, Shupert CL, Hlavacka F, and Horak FB. Effect of galvanic vestibular stimulation on human postural responses during support surface translations. J Neurophysiol 73: 896-901, 1995.
Kaczmarek, K.A. & Tyler, M.E. (2000). "Effect of electrode geometry and intensity control method on comfort of electrotactile stimulation on the tongue." Proc. of the ASME Haptics in VR Conference, Orlando, FL, pp. 1239-1243.
Kaczmarek, K.A., Tyler, M.E., Bach-y-Rita, P., Electrotactile haptic display on the fingertips; preliminary results, Engineering in Medicine and Biology Society, 1994. Engineering Advances: New Opportunities for Biomedical Engineers. Proceedings of the 16th Annual International Conference of the IEEE, vol., Iss., 1994, pp. 940-941 vol. 2.
Kaczmarek, K.A., Webster. J.G., (1989) Voltage-current characteristics of the electrotactile electrode-skin 69 interface. Paper presented at the Proc. Annu. In!. Conf. IEEE Eng. Med. Biol. Soc., Seattle, WA, pp. 1526-1527.
Keeler C, Placek E, Yap R. Sabelman EE. Time sequence of pressure changes during weight relief activities on different wheelchair cushions. RESNA 25th Intl Conf Technology and Disability, Jun. 27-Jul. 1, 2002, pp. 360-362.
Kennedy PM and Inglis JT. Interaction effects of galvanic vestibular stimulation and head position on the soleus H reflex in humans. Clin Neurophysiol 113: 1709-1714, 2002.
Kercel, S.W., and Bach-y-Rita, P., "Noninvasive Coupling of Electronically Generated Data into the Human Nervous System,"Wiley Encyclopedia of Biomedical Engineering, Metin Akay, Ed.. John Wiley &Sons, Inc. (New York), 2003. This is a book and is not being supplied at this time. If the Examiner would like to examine the book, Applicants' will supply it.
Lobel E, Kleine JF, Leroy-Willig A, Van de Moortele PF, Le Bihan 0, Grusser OJ, and Berthoz A. Cortical areas activated by bilateral galvanic vestibular stimulation. Ann NY Acad Sci 871: 313-323, 1999.
Magnusson M, Johansson R, and Wiklund J. Galvanically induced body sway in the anterior-posterior plane. Acta Otolaryngol 110: 11-17, 1990.
McGibbon et al., "Stepping stability: effects of sensory perturbation,"J Neuroengineering Rehabil. May 27, 2005;2:9.
Norre ME, Beckers A .. Vestibular habituation training: exercise treatment for vertigo based upon the habituation effect, Otolaryngol Head Neck Surg. Jul. 1989;101(1):14-9.

(56) References Cited

OTHER PUBLICATIONS

Page, S.J., "Mental practice: a promising technique in stroke rehabilitation," Topics Stroke Rehabil, 8, 2001, pp. 54-63.
Pastor M, Day B, and Marsden C. Vestibular induced postural responses in Parkinson's disease. Brain 116: 1177-1190, 1993.
Pavlik AE, Inglis JT, Lauk M, Oddsson L, and Collins JJ. The effects of stochastic galvanic vestibular stimulation on human postural sway. Exp Brain Res 124:273-280, 1999.
Petersen H, Magnusson M, Fransson PA, and Johansson R. Vestibular disturbance at frequencies above 1 Hz affects human postural control. Acta Otolaryngol 114: 225-230, 1994.
Ptito M., Moesgaard S.M., Gjedde A., Kupers R., Cross-model plasticity revealed by electroctactile stimulation of the tongue in the congenitally blind, Brain (2004) 1-9.
Fitzpatrick and Day, Probing the human vestibular system with galvanic stimulation, Appl Physiol 96: 2301-2316, 2004.
Kupers, R., Ptito, M. (2004). "'Seeing' through the tongue: cross-modal plasticity in the congenitally blind." International Congress Series, pp. 79-84.
Ross MD. The evolution of concepts of vestibular peripheral information processing: toward thedynamic, adaptive, parallel processing macular model. Acta Otolaryngol123: 784-794, 2003.
Sabelman EE, Hu M, Kim D, Hentz VR. Differential migration of fibroblasts and Schwann cells in a geometrically anisotropic 3-dimensional collagen matrix. 9th Inti Neural Regeneration Symp, Pacific Grove, CA, 2001, pp. S19-S20.
Sabelman EE, Schwandt D, Jaffe DL. The WAMAS (wearable accelerometric motion analysis system: combining technology development and research in human mobility. Conf Intellectual Property in the VA: Changes, Challenges & Collaborations, Arlington, VA, 2001.
Sabelman EE, Troy SS, Kenney DE, Yap R, Lee S. Quantitative balance analysis: accelerometric lateral sway compared to age and mobility status in 60-90-year-olds. Proc RESNA 2001 Ann Conf, Reno, NV, 2001, pp. 224-226.
Sabelman, E. E, J. van Hotten, J., Analysis of head and waist motion during falls from a tilting platform, 52nd Annual Scientific Meeting, Gerontological Society of America (San Francisco, Nov. 19-23, 1999); The Gerontologist, 39(5-1):467,1999.
Sabelman, E.E., "Toward appropriate technology for the elderly", 20th Conf on Unity of the Sciences, Seoul, Korea, Aug. 20-27,1995, pp. 167-168.
Sabelman, EE, Troy, BS, Kenney, DE, Dunn-Gabrielli, S, Alternatives in Quantitative Geriatric Balance and Mobility Assessment, Proc RESNA '97 (Pittsburgh, PA, Jun. 20-Jun. 24, 1997), pp. 463-465.
Sadato N, Hallett M. (1999) fMRI occipital activation by tactile stimulation in a blind man, Neurology. Jan. 15, 1999;52(2):423.
Sampaio E, Maris S., Bach-y-Rita P (2001) Brain Plasticity: "Visual" Acuity of Blind Persons via the Tongue, Brain Research 908:204-207.
Scinicariello AP, Inglis JT, and Collins JJ. The effects of stochastic monopolar galvanic vestibular stimulation on human postural sway. J Vestib Res 12: 77-85, 2002.
Severac Cauquil A, Gervet MF, and Ouaknine M. Body response to binaural monopolar galvanic vestibular stimulation in humans. Neurosci Lett 245: 37-40, 1998.
Severac Cauquil A, Martinez P, Ouaknine M, and Tardy-Gervet MF. Orientation of the body response to galvanic stimulation as a function of the inter-vestibular imbalance. Exp Brain Res 133: 501-505, 2000.
Tetrud JW, Sabelman EE, Yap R. Accelerometric identification of freezing-of-gait in parkinson's syndrome. 7th Inti Congr Parkinson's Disease and Movement Disorders, Miami Beach, FL, Nov. 10-14, 2002, p. S343.
Troy, Betty S., Sabelman, Eric E., Kenney, Deborah E., Dunn-Gabrielli, Sandy, Accelerometric Motion Analysis of Balance-Impaired Elderly Subjects, Proc RESNA 96 Annual Conference (Salt Lake City, UT, Jun. 7-12), 1996, pp. 78-80.
Troy, BS, Sabelman, EE, Kenney, DE, Dunn-Gabrielli, S, Yap, R, Willits, M. "Analysis of Sit-to-Stand Performed by Young Normals, Using Forceplate and Accelerometric Data", Proc RESNA 1998 Conf, Minneapolis, MN, Jun. 26-30, 1998, pp. 60-62.
Troy, BS, Sabelman, EE, Kenney, DE, Yap, R, Willits, M, Dunn-Gabrielli, S., Examination of the momentum transfer stage of sit-to-stand performed by healthy elderly using accelerometric & video data. Proc RESNA 1999 Annual Conference, Long Beach, CA, Jun. 25-29, 1999, pp. 213-215.
Danilov Y.P., Tyler M.E., Bach-y-Rita P. (2004). "Asymmetry of head and body interactions during posture control in patients with bilateral vestibular dysfunction." Proc. of the 34th International Meeting of the Society for Neuroscience, Oct. 23-28, 2004, San Diego, CA.
Tyler, M.E., Danilov, Y.P., Bach-y-Rita, P., (2003). "Closing an open-loop control system: Vestibular substitution through the tongue" International Journal of Integrative Neuroscience; 2:2, pp. 159-164.
Tyler, M.E., Haase, S.J., Kaczmarek, K.A. and Bach-y-Rita, P., "Development of an electrotactile glove for display of graphics for the blind: Preliminary results," In: Proceedings of the 2nd Joint Conference of the IEEE Engineering in Medicine and Biology Society and the Biomedical Engineering society; Houston TX; Oct. 23-26, 2002, pp. 2439-2440.
Van Boven RW, Johnson KG, The limit of tactile spatial resolution in humans: grating orientation discrimination at the lip, tongue, and finger, Neurology. Dec. 1994;44(12):2361-2366.
Wardman DL, Day BL, and Fitzpatrick RC. Position and velocity responses to galvanic vestibular stimulation in human subjects during standing. J Physiol 547: 293-299, 2003.
Wardman DL, Taylor JL, and Fitzpatrick RC. Effects of galvanic vestibular stimulation on human posture and perception while standing. J Physiol 551: 1033-1042,2003.
Welgampola MS and Colebatch JG. Selective effects of ageing on vestibular-dependent 105 lower limb responses following galvanic stimulation. Clin Neurophysiol 113: 528-534, 2002.
Wilson VJ, Peterson BW, Fukushima IS, Hirai N, Uchino Y (1979) Analysis of vestibulocollic reflexes by sinusoidal polarization of vestibular afferent fibers. J Neurophysiol 42:331-346.
Ptito et al., "Cross-modal plasticity revealed by electrotactile stimulation of the tongue in the congenitally blind" Brain, 128(Pt 3):606-14 (2005).
Smith and Curthoys, "Mechanisms of recovery following unilateral labyrinthectomy: a review" Brain Res Brain Res Rev 14, 155-180, (1989).
Telian and Shepard, "Update on vestibular rehabilitation therapy" Update on Otology and Neurotology, Part I, Otolaryngol Clin North Am 29, 359-371 (1996).
Mathog and Peppard, Exercise and recovery from vestibular injury, Am J Otolaryngol. Nov.-Dec. 1982;3(6):397-407.
Wiener, Spatial and behavioral correlates of striatal neurons in rats performing a self-initiated navigation task, The Journal of Neuroscience, vol. 13 (1993), pp. 3802-3817.
Rubakhin, V. F.; Poltorak, M. I., A study of the processing of multimodal signals by man. Voprosy Psychologii, vol. 5, Sep.-Oct. 1974, 71-80. (abstract in English on last page).
Talairach & Tournoux, Co-planar stereotaxic atlas of the human brain: 3-dimensional proportional system : an approach to cerebral imaging, Thieme 1988 (book, no copy provided at this time).
Bach-y-Rita et al., Sensory Substitution and the Human-Machine Interface, Trends in Cognitive Sciences, vol. 7, No. 12, Dec. 2003, pp. 541-546.

* cited by examiner

FIG. 7
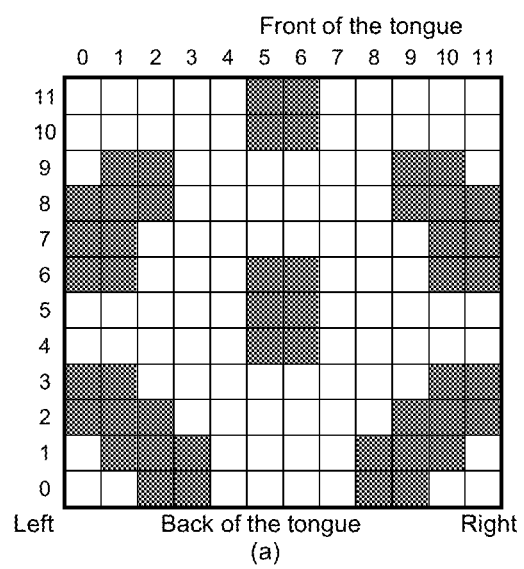
(a)
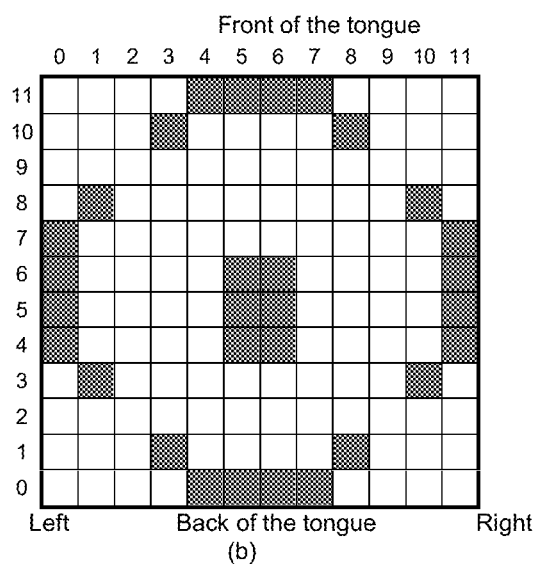
(b)

SPATIAL TONGUE STIMULATION EXAMPLE
(FOR 'SLIT' OBJECT USING THE CONE PROBE)
COLOR INTENSITY MAP

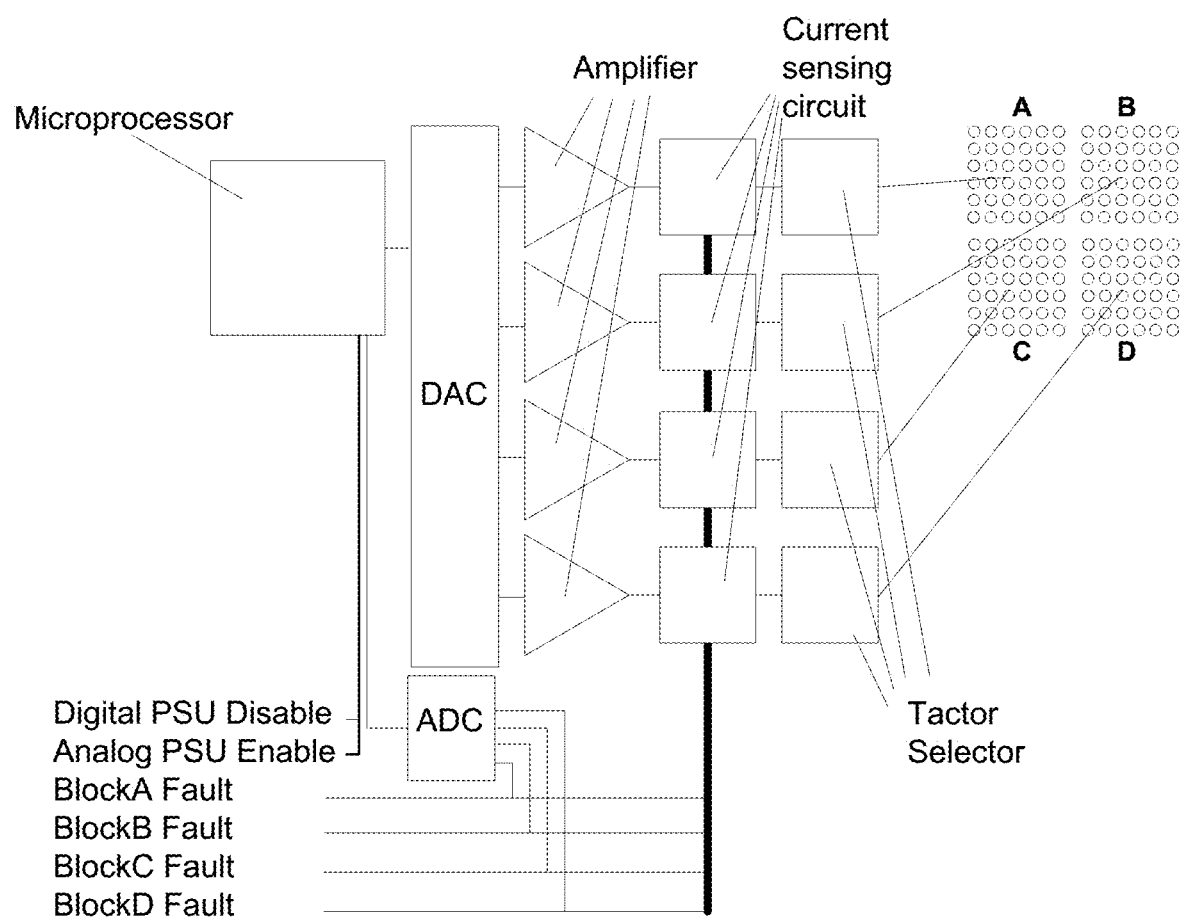

US 10,589,087 B2

SYSTEMS AND METHODS FOR ALTERING BRAIN AND BODY FUNCTIONS AND FOR TREATING CONDITIONS AND DISEASES OF THE SAME

This application is a continuation-in-part of U.S. patent application Ser. No. 11/925,393 filed Oct. 26, 2007, which is a continuation-in-part of U.S. patent application Ser. No. 11/234,635, filed Sep. 23, 2005, which is a continuation-in-part of U.S. patent application Ser. No. 10/998,222, filed Nov. 26, 2004, which claims the benefit of or priority to U.S. Provisional Patent Application Ser. Nos. 60/525,359 filed Nov. 26, 2003, 60/605,988, filed Aug. 31, 2004, and 60/615,305, filed Oct. 1, 2004. The entire contents of each of the aforementioned applications are hereby expressly incorporated by reference herein.

The present invention was made in part under funds from NSF Grant No. IIS-0083347, NIH Grant Nos. R01-EY10019, R43/44-DC04738, R43/44-EY13487, and DARPA Grant No. BD-8911. The government may have certain rights in the invention.

FIELD OF THE INVENTION

The present invention relates to systems and methods for management of brain and body functions and sensory perception. For example, the present invention provides systems and methods of sensory substitution and sensory enhancement (augmentation) as well as motor control enhancement. The present invention also provides systems and methods for treating diseases and conditions, as well as providing enhanced physical and mental health and performance through sensory substitution, sensory enhancement, and related effects.

BACKGROUND OF THE INVENTION

The mammalian brain, and the human brain in particular, is capable of processing tremendous amounts of information in complex manners. The brain continuously receives and translates sensory information from multiple sensory sources including, for example, visual, auditory, olfactory, and tactile sources. Through processing, movement, and awareness training, subjects have been able to recover and enhance sensory perception, discrimination, and memory, demonstrating a range of untapped capabilities. What are needed are systems and methods for better expanding, accessing, and controlling these capabilities.

DESCRIPTION OF DRAWINGS

FIG. 7 shows a sensor pattern in a surgical probe embodiment of the present invention.

FIG. 22 shows a stimulation circuit of some embodiments of the present invention.

DEFINITIONS

Figure 1:
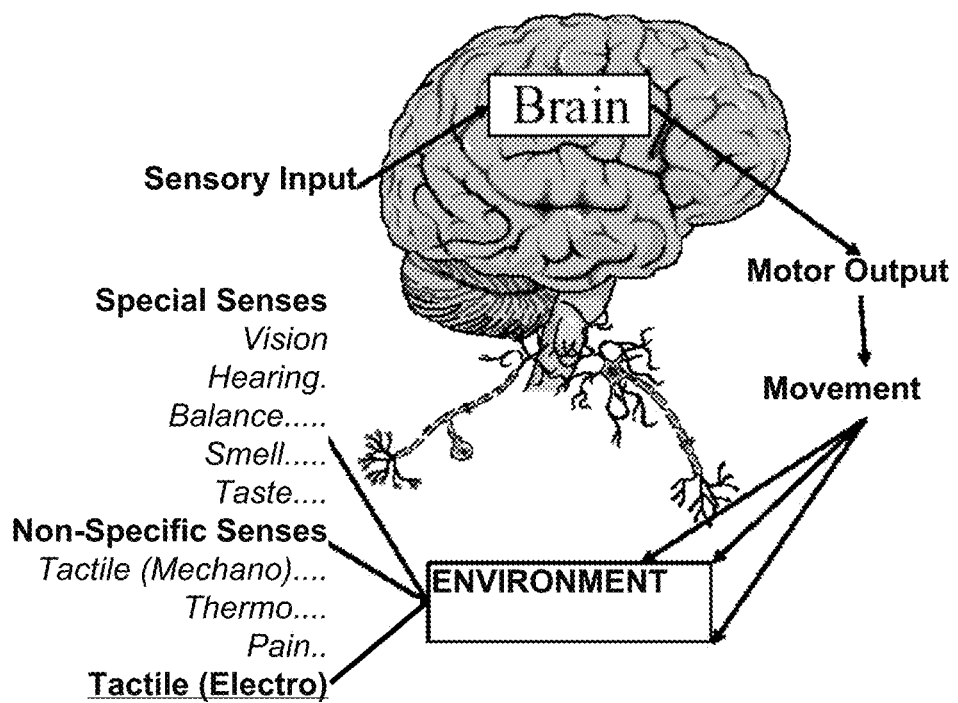
FIG. 1 shows a schematic diagram of information flow to and from the brain.

To facilitate an understanding of the present invention, a number of terms and phrases are defined below:

As used herein, the term "subject" refers to a human or other vertebrate animal. It is intended that the term encompass patients.

As used herein, the term "amplifier" refers to a device that produces an electrical output that is a function of the corresponding electrical input parameter, and increases the magnitude of the input by means of energy drawn from an external source (i.e., it introduces gain). "Amplification" refers to the reproduction of an electrical signal by an electronic device, usually at an increased intensity. "Amplification means" refers to the use of an amplifier to amplify a signal. It is intended that the amplification means also includes means to process and/or filter the signal.

As used herein, the term "receiver" refers to the part of a system that converts transmitted waves into a desired form of output. The range of frequencies over which a receiver operates with a selected performance (i.e., a known level of sensitivity) is the "bandwidth" of the receiver.

As used herein, the term "transducer" refers to any device that converts a non-electrical parameter (e.g., sound, pressure or light), into electrical signals or vice versa.

As used herein, the terms "stimulator" and "actuator" are used herein to refer to components of a device that impart a stimulus (e.g., vibrotactile, electrotactile, thermal, etc.) to tissue of a subject. When referenced herein, the term stimulator provides an example of a transducer. Unless described to the contrary, embodiments described herein that utilize stimulators or actuators may also employ other forms of transducers.

The term "circuit" as used herein, refers to the complete path of an electric current.

As used herein, the term "resistor" refers to an electronic device that possesses resistance and is selected for this use. It is intended that the term encompass all types of resistors, including but not limited to, fixed-value or adjustable, carbon, wire-wound, and film resistors. The term "resistance" (R; ohm) refers to the tendency of a material to resist the passage of an electric current, and to convert electrical energy into heat energy.

The term "magnet" refers to a body (e.g., iron, steel or alloy) having the property of attracting iron and producing a magnetic field external to itself, and when freely suspended, of pointing to the magnetic poles of the Earth.

As used herein, the term "magnetic field" refers to the area surrounding a magnet in which magnetic forces may be detected.

As used herein, the term "electrode" refers to a conductor used to establish electrical contact with a nonmetallic part of a circuit, in particular, part of a biological system (e.g., human skin on tongue).

The term "housing" refers to the structure encasing or enclosing at least one component of the devices of the present invention. In preferred embodiments, the "housing" is produced from a "biocompatible" material. In some embodiments, the housing comprises at least one hermetic feedthrough through which leads extend from the component inside the housing to a position outside the housing.

As used herein, the term "biocompatible" refers to any substance or compound that has minimal (i.e., no significant difference is seen compared to a control) to no irritant or immunological effect on the surrounding tissue. It is also intended that the term be applied in reference to the substances or compounds utilized in order to minimize or to avoid an immunologic reaction to the housing or other aspects of the invention. Particularly preferred biocompatible materials include, but are not limited to titanium, gold, platinum, sapphire, stainless steel, plastic, and ceramics.

As used herein, the term "implantable" refers to any device that may be implanted in a patient. It is intended that the term encompass various types of implants. In preferred embodiments, the device may be implanted under the skin (i.e., subcutaneous), or placed at any other location suited for the use of the device (e.g., within temporal bone, middle ear or inner ear). An implanted device is one that has been implanted within a subject, while a device that is "external" to the subject is not implanted within the subject (i.e., the device is located externally to the subject's skin).

As used herein, the term "hermetically sealed" refers to a device or object that is sealed in a manner that liquids or gases located outside the device are prevented from entering the interior of the device, to at least some degree. "Completely hermetically sealed" refers to a device or object that is sealed in a manner such that no detectable liquid or gas located outside the device enters the interior of the device. It is intended that the sealing be accomplished by a variety of means, including but not limited to mechanical, glue or sealants, etc. In particularly preferred embodiments, the hermetically sealed device is made so that it is completely leak-proof (i.e., no liquid or gas is allowed to enter the interior of the device at all).

As used herein the term "processor" refers to a device that is able to read a program from a computer memory (e.g., ROM or other computer memory) and perform a set of steps according to the program. Processor may include non-algorithmic signal processing components (e.g., for analog signal processing).

As used herein, the terms "computer memory" and "computer memory device" refer to any storage media readable by a computer processor. Examples of computer memory include, but are not limited to, RAM, ROM, computer chips, digital video disc (DVDs), compact discs (CDs), hard disk drives (HDD), and magnetic tape.

As used herein, the term "computer readable medium" refers to any device or system for storing and providing information (e.g., data and instructions) to a computer processor. Examples of computer readable media include, but are not limited to, DVDs, CDs, hard disk drives, magnetic tape, flash memory, and servers for streaming media over networks.

As used herein the terms "multimedia information" and "media information" are used interchangeably to refer to information (e.g., digitized and analog information) encoding or representing audio, video, and/or text. Multimedia information may further carry information not corresponding to audio or video. Multimedia information may be transmitted from one location or device to a second location or device by methods including, but not limited to, electrical, optical, and satellite transmission, and the like.

As used herein, the term "Internet" refers to any collection of networks using standard protocols. For example, the term includes a collection of interconnected (public and/or private) networks that are linked together by a set of standard protocols (such as TCP/IP, HTTP, and FTP) to form a global, distributed network. While this term is intended to refer to what is now commonly known as the Internet, it is also intended to encompass variations that may be made in the future, including changes and additions to existing standard protocols or integration with other media (e.g., television, radio, etc). The term is also intended to encompass non-public networks such as private (e.g., corporate) Intranets.

As used herein the term "security protocol" refers to an electronic security system (e.g., hardware and/or software) to limit access to processor, memory, etc. to specific users authorized to access the processor. For example, a security protocol may comprise a software program that locks out one or more functions of a processor until an appropriate password is entered.

As used herein the term "resource manager" refers to a system that optimizes the performance of a processor or another system. For example a resource manager may be configured to monitor the performance of a processor or software application and manage data and processor allocation, perform component failure recoveries, optimize the receipt and transmission of data, and the like. In some embodiments, the resource manager comprises a software program provided on a computer system of the present invention.

As used herein the term "in electronic communication" refers to electrical devices (e.g., computers, processors, communications equipment) that are configured to communicate with one another through direct or indirect signaling. For example, a conference bridge that is connected to a processor through a cable or wire, such that information can pass between the conference bridge and the processor, are in electronic communication with one another. Likewise, a computer configured to transmit (e.g., through cables, wires, infrared signals, telephone lines, etc) information to another computer or device, is in electronic communication with the other computer or device.

As used herein the term "transmitting" refers to the movement of information (e.g., data) from one location to another (e.g., from one device to another) using any suitable means.

As used herein, the term "electrotactile" refers to a means whereby sensory channels (e.g., nerves) responsible for sensory functions are stimulated by an electric current. In some embodiments, the term refers to a means by which sensory channels (e.g., nerves) responsible for human touch (and/or taste) perception are stimulated by an electric current (applied via surface (or implanted) electrodes). The term electrotactile may be used interchangeably with the terms "electrocutaneous" and "electrodermal."

SUMMARY OF THE INVENTION

The present invention relates to systems and methods for management of brain and body functions as they relate to sensory perception, as well as other brain and body functions. For example, the present invention provides systems and methods of sensory substitution and sensory enhancement as well as motor control enhancement. The present invention also provides systems and methods of treating diseases and conditions, as well as providing enhanced physical and mental health and performance through sensory substitution, sensory enhancement, and related effects.

Experiments conducted during the development of the present invention have demonstrated that machine/brain interfaces may be used to, among other things, permit blind and vision impaired individuals to acquire advanced vision from a video camera or other video source, permit subjects with disabling balance-related conditions to approximate normal body function, permit subjects using surgical devices to feel the environment surrounding the ends of catheters or other medical devices, provide enhanced motor skills, and provide enhanced physical and mental health and sense of well-being. In some embodiments, the present invention provides methods for simulating meditative and stress relief benefits without the need for intense meditation training, concentration, and time commitment.

The present invention provides a wide range of systems and methods that allow sensory substitution, sensory enhancement, motor enhancement, and general physical and mental enhancement for a wide variety of application, including but not limited to, treating diseases, conditions, and states that involve the loss or impairment of sensory perception; researching sensory processes; diagnosing sensory diseases, conditions, and states; providing sensory enhanced entertainment (e.g., television, music, movies, video games); providing new senses (e.g., sensation that perceives chemicals, radiation, etc.); providing new communications methods; providing remote sensory control of devices; providing navigation tools; enhancing athletic, job, or general performance; and enhancing physical and mental well-being.

The benefits described herein are obtained, in some embodiments, through the transmission of information to a subject through a sensory route that is not normally associated with such information. For example, in the case of balance improvement, a physical sensor may be used to detect the physical position of the head or body of a subject with respect to the gravity vector. This information is sent to a processor that then encodes and transmits the information, for example, to a transducer array (e.g., stimulator array). The transducer array is contacted with the body of the subject in a manner that provides sensory stimulation (and thus, information)—for example, electrical stimulation on the tongue of the subject. The transducer array is configured such that different head or body perceptions trigger different stimulation to the subject. Through the use of training exercises that permit the subject to associate these patterns with head, body part, or body position, the subject learns to perceive, without conscious thought, the orientation of that body part relative to earth referenced gravity as it is relayed to their brain through their tongue. Experiments conducted during the development of the present invention demonstrated that subjects gained the ability to walk normally and carry out other balance functions (e.g., riding a bicycle) that were impossible without the addition of the new sense. Surprisingly, it was found that the brain became effectively reprogrammed for balance, as subjects were able to maintain the benefit after removal of the device. In a long-term study, true rehabilitation was observed, as benefits (e.g., improved balance) were maintained weeks after use of the device and training were discontinued. Thus, the systems of the present invention not only provide a means for sensory enhancement and substitution, but also provide a means to train the brain to function at a higher level, even in the absence of the device.

Experiment conducted during the development of the invention also demonstrated that the brain is able to integrate and extrapolate the new sensory information in complex ways, including integration with other senses, the ability to react on instinct to the new sensory information, and the ability to extrapolate the information beyond the complexity level actually received from the electrode array. For example, experiments conducted during the development of the invention demonstrated the ability of blind subjects to catch a rolling ball, a task that involves not only seeing the ball, but also coordinating arm movement with a visual cue in a natural manner.

Surprisingly, the system and methods of the present invention provide enhanced brain function that is not directly tied to the specific information provided by the methods. For example, Example 20 describes the treatment of a subject suffering from spasmodic dysphonia who was unable to speak normally prior to treatment, having his oral communication reduced to a whisper. The subject underwent treatment whereby information related to body position and orientation in space was transmitted to the subject's tongue via electrotactile stimulation while the subject maintained body position. The subject was asked to attempt to vocalize during training. Following training, the subject regained the ability produce vocalized speech. Thus, electrotactile information corresponding to body position with respect to the gravitational plane, in conjunction with activation of brain activity associated with speech, was used to increase brain function related to muscle control of the larynx (a motor control function). This example demonstrates that the systems and methods of the present invention find use in general brain function enhancement through the use of, for example, electrotactile stimulation associated with activation of specific brain activity. While an understanding of the mechanism is not necessary to practice the present invention and while the present invention is not limited to any particular mechanism of action, it is contemplated that the use of tactile stimulation (e.g., electrotactile stimulation of the tongue) conditions the brain for improving general function (e.g., motor control, vision, hearing, balance, tactile sensation) associated with a specific task and in general. While an understanding of the mechanism is not necessary to practice the present invention and while the present invention is not limited to any particular mechanism of action, it is contemplated that the systems and methods of the present invention provide or simulate long-term potentiation (long-lasting increase in synaptic efficacy which follows high-frequency stimulation) to provide enhanced brain function. The residual and rehabilitative effect of training seen in experiments conducted during the development of the present invention upon prolonged stimulation is consistent with long-term potentiation studies. Thus, the present invention provides systems and methods for physiological learning that extends for long periods of time (e.g., hours, days, weeks, etc.).

It is further contemplated that the tactile stimulation of the present invention (e.g., electrotactile stimulation of the tongue) provides benefits similar to those achieved by deep brain stimulation methods, and finds use in application where deep brain stimulation is used and is contemplated for use. Chronic deep brain stimulation in its present U.S. FDA-approved manifestation is a patient-controlled treatment for tremor that consists of a multi-electrode lead implanted into the ventrointermediate nucleus of the thalamus. The lead is connected to a pulse generator that is surgically implanted under the skin in the upper chest. An extension wire from the electrode lead is threaded from the scalp area under the skin to the chest where it is connected to the pulse generator. The wearer passes a hand-held magnet over the pulse generator to turn it on and off. The pulse generator produces a high-frequency, pulsed electric current that is sent along the electrode to the thalamus. The electrical stimulation in the thalamus blocks the tremor. The pulse generator must be replaced to change batteries. Risks of DBS surgery include intracranial bleeding, infection, and loss of function. The non-invasive systems and methods of the present invention provide alternatives to invasive deep-brain stimulation for the range of current and future deep-brain stimulation applications (e.g., treatment of tremors in Parkinson's patients, dystonia, essential tremor, chronic nerve-related pain, improved strength after stroke or other trauma, seizure disorders, multiple sclerosis, paralysis, obsessive-compulsive disorders, and depression). While an understanding of the mechanism is not necessary to practice the present invention and while the present invention is not limited to any particular mechanism of action, it is contemplated that the systems and methods of the present invention activate portions of the brain stem and mid-brain that are activated by deep-brain stimulation (e.g., by providing electrotactile stimulation to the tongue).

The present invention further provides systems and methods for enhancing the ability of the brain to utilize damaged tissue to accomplish tasks that it had lost the ability to accomplish or to acquire such abilities that were never previously accomplished. Experiments conducted during the development of the present invention demonstrated that damaged tissues, upon training using the systems and methods of the present invention had enhanced residual ability to re-acquire higher function. Thus, in some embodiments, the systems and methods of the present invention are used to regenerate function from damaged tissue by re-training the brain.

The systems and methods of the present invention may also be used in conjunction with other devices, aids, or methods of sensory enhancement to provide further enhancement or substitution. For example, subjects using cochlear implants, hearing aids, etc. may further employ the systems and methods of the present invention to produce improved function. The systems and methods of the present invention also find use with other devices, systems and methods used for neural monitoring (e.g., the NeuroPort™ System, disclosed in U.S. Pat. App. No. 20040249302, herein incorporated by reference in its entirety for all purposes). The systems and methods of the present invention also find use in combination with other forms of therapy, including, but not limited to rehabilitative therapy (e.g., physical therapy) following, among other thing, traumatic brain injury, stroke or onset of disease (e.g., Parkinson's disease, Alzheimer's disease, neurodegenerative disease, etc.).

Thus, the present invention provides a wide array of devices, software, systems, methods, and applications for treating diseases and conditions, as well as providing enhanced physical and mental health and performance.

In some embodiments, the present invention provides devices, software, systems, methods, and applications related to vestibular function. For example, the present invention provides a method for altering a subject's physical or mental performance related to a vestibular function, comprising: exposing the subject to tactile stimulation under conditions such that said physical or mental performance related to a vestibular function is altered (e.g., enhanced or reduced).

The present invention is not limited by the nature of the vestibular function. In some embodiments, the vestibular function comprises balance. Balance includes all types of balance, such as perception of body orientation with respect to the gravitational plane, to another body part, or to an environmental object (e.g., in low to no gravity environments, under water, etc.)

The present invention is also not limited by the nature of the subject. The subject may be healthy or may suffer from a disease or condition directly or indirectly related to vestibular function. For healthy subjects, the systems and methods of the present invention find use in enhancing vestibular function (e.g., balance) over normal. Athletes, soldiers, and others can benefit from such super-stability.

In some embodiments, the subject has a disease or condition. In some embodiments, the disease or condition is associated with a dysfunction of sensory-motor coordination. In some embodiments, the disease or condition is associated with vestibular function damage, including both peripheral nervous system dysfunction and central nervous system dysfunction. Subjects having a variety of diseases and conditions benefit from the systems and methods of the present invention, including subjects having, or predisposed to, unilateral or bilateral vestibular dysfunction, epilepsy, dyslexia, Meniere's disease, migraines, Mal de Debarquement syndrome, oscillopsia, autism, traumatic brain injury, Parkinson's disease, and tinnitus. The present invention finds use with subjects in a recovery period from a disease, condition, or medical intervention, including, but not limited to, subjects that have suffered traumatic brain injury (e.g., from a stroke) or drug treatment. The systems and methods of the present invention find use with any subject that has a loss of balance or is at risk for loss of balance (e.g., due to age, disease, environmental conditions, etc.).

In some preferred embodiments, the tactile stimulation (e.g., electrotactile stimulation via the tongue) communicates information to the subject, where the information pertains to orientation of the subject's body with respect to the gravitational plane.

The present invention is not limited to treatments that provide tactile information of body position. For example, in some embodiments, treatment and training involves maintaining stabilization of the body (e.g., head) with respect to a reference point (e.g., the gravitational plane) for a period of time (e.g., 10 minutes, 20 minutes, 30 minutes, etc). In some embodiments, the stabilization is facilitated by sensory information (e.g., a video screen) that conveys body position information. In some embodiments, the stabilization is coupled with electrotactile stimulation. In some embodiments, the electrotactile stimulation provides information about body position to the subject. In some embodiments, the position of the head is monitored and provided back to the head of the subject (e.g., via video, audio, tactile information (e.g., on the tongue)).

It is contemplated that, in some embodiments, the systems and methods of the present invention imitate functions of the vestibular system. The vestibular system is located within the head (in the vestibulum in the inner ear) and comprises monitoring components (e.g., semicircular canals that sense/monitor rotational movements and otoliths that sense/monitor linear translations) and information signaling components (e.g., nerves that send signals to the neural structures that control eye movement and to muscles involved in posture). Although an understanding of the mechanism is not necessary to practice the present invention and the present invention is not limited to any particular mechanism of action, in some embodiments, the systems and methods of the present invention provide vestibular-like monitoring components (e.g., balance sensing device) and information signaling components (e.g., arrayed electrotactile stimulation through the tongue) that provide a superior form of treatment because the systems and methods of the present invention use the head (e.g., for monitoring and providing information regarding orientation) to mimic the normal function of the vestibular system. Thus, in some embodiments, systems and methods of the present invention supplement, enhance and/or correct defects in the vestibular system of a subject (e.g., a subject using or being treated with the systems and methods of the present invention).

Experiments conducted during the development of the present invention demonstrated that improvements in vestibular function persisted for a period of time after exposure to tactile stimulation. Improvements were noted over an hour, six hours, twenty-four hours, a week, a month, and six months after exposure to tactile stimulation.

The present invention also provides systems for altering a subject's physical or mental performance related to a vestibular function. The systems find use in the methods described herein. In some preferred embodiments, the system comprises: a) a sensor that collects information related to body position or orientation with respect an environmental reference point; b) a stimulator configured to transmit information (e.g., tactile information) to a subject; and c) a processor configured to: i) receive information from the sensor; ii) convert the information into information to be sent to the subject; and iii) transmit the information to the stimulator in a form that communicates the body position or orientation to the subject. In some preferred embodiments, the sensor is a sensor of angular or linear motion (e.g., an accelerometer or a gyroscope).

The present invention is not limited by the nature of the stimulator used. In some preferred embodiments, the stimulator is provided on a mount configured to fit into a subject's mouth to permit tactile stimulation to the tongue. In some preferred embodiments, the communication between the processor and the stimulator is via wireless methods. In particular preferred embodiments, the processor is provided in a portable housing to permit a subject to easily transport the processor on or in their body.

The present invention further provides systems for training subjects to correlate tactile information with environmental or other information to be perceived to improve vestibular function. In some preferred embodiments, the system comprises: a) a stimulator configured to transmit tactile information to a subject, and b) a processor configured to i) run a training program that produces an perceivable event that correlates to the subject's body position or orientation, and ii) transmit tactile information to the stimulator in a form that correlates the body position or orientation to the perceivable event (e.g., visualized as a video image on a display screen).

The present invention further provides methods for diagnosing vestibular dysfunction. In some preferred embodiments, the method comprises measuring a skill of a subject associated with vestibular function in response to tactile stimulation. In some embodiments, the measured skill is compared to a predetermined normal skill value to determine increase or decrease in function. The predetermined normal skill value may be obtained from any source, including, but not limited to, population averages and prior measures from the subject. In some preferred embodiments, the skill comprises balance or sway stability. The method finds particular use in detecting vestibular damage during a treatment or procedure, such that, when detected, the treatment regimen may be altered to reduce or eliminate long-term damage. For example, bilateral vestibular dysfunction may be avoided in subjects undergoing treatment with medications (e.g., antibiotics such as gentamycin) that can cause bilateral vestibular dysfunction.

Experiments conducted during the development of the present invention demonstrated that the use of the systems and methods of the present invention provide subjects with the physical or emotional benefits associated with meditation and/or stress relief. Thus, the present invention provides methods comprising the step of contacting a subject with tactile stimulation (e.g., electrotactile stimulation via the tongue) under conditions that provide such benefits. In some embodiments, the subject is provided with 10 or more minutes (e.g., 15 minutes, 20 minutes, 30 minutes, 40 minutes, . . . ) of tactile stimulation. In some embodiments, the subject maintains a controlled body position while receiving tactile stimulation (e.g., upright, straight back; standing position). Exemplary physical and emotional benefits that can be achieved are described herein and include, but are not limited to, improved motor coordination, improved sleep, improved vision, improved cognitive skills, and improved emotional health (e.g., increased sense of well-being).

In some embodiments, the present invention provides a method of providing long-term (e.g., one hour, six hours, one day, one week, one month, six months, etc.) improvement in a brain function, comprising: providing electrotactile stimulation to a tongue of a subject for a period of 10 or more minutes (e.g., 15, 20, 30, 40, . . . ). The present invention is not limited by the nature of the brain function improved. Numerous examples are described herein (e.g., vestibular functions such as balance). In some embodiments, the improvement is achieved wherein the electrotactile stimulation conveys information (e.g., information about a subject's body position in one embodiment of balance improvement applications). In preferred embodiments, the long-term improvement comprises improved brain function after the electrotactile stimulation is discontinued.

In some embodiments, subjects having a disease or condition associated with loss of motor control are treated with the systems and methods of the present invention. For example, experiments conducted during the development of the present invention demonstrated improved ability to speak in a subject having spasmodic dysphonia.

Additional embodiments of the present invention are described below.

DETAILED DESCRIPTION OF THE INVENTION

The present invention provides systems and methods for managing sensory information by providing new forms of sensory input to replace, supplement, or enhance sensory perception, motor control, performance of mental and physical tasks, and health and well being. The systems and methods of the present invention accomplish these results by providing sensory input from a device to a subject. The sensory input is provided in a manner such that, through the nature of the input, or through subject training, or a combination thereof, a subject receiving the input receives information and the intended benefit. Thus, the present invention provides a machine-brain interface for the transmission of sensory information (e.g., through the skin). Unlike methods that simply provide physical stimulation of a skin surface, preferred embodiments of the systems and methods of the present invention provide structure to the signal such that information is conveyed to the brain, affecting brain function.

Brain Computer Interface (BCI) technology is one of the most intensely developing areas of modern science and has created numerous significant crossroads between neuroscience and computer science. The goal of BCI technology is to provide a direct link between the human brain and a computerized environment. However, the vast majority of recent BCI approaches and applications have been designed to provide the information flow from the brain to the computerized periphery. The opposite or alternative direction of flow of information (computer to brain interface—CBI) remains almost undeveloped.

The systems of the present invention provide a Computer Brain Interface and other systems and methods for providing information to the brain that offers an alternative symmetrical technology designed to support a direct link from a computerized or machine environment (or from any other system that can provide information about the environment) to the brain and to do it, if desired, non-invasively.

In the majority of modern industrial and technological control processes, the human is still needed "in the loop"—perhaps even more urgently than ever before. This is because the complexity and scale of technologies requiring computer control is increasing in parallel to the exponential development of available computational power. Thus, rather than simplifying the human operator's environment, these advancing technologies make increasingly more complex demands on the operators (e.g., requiring increased interaction with stored memory capacity, increased speed of reaction while maintaining precision of decision making processes and attention to diverse tasks, rapid learning of new knowledge-based skills, etc.). These unavoidable and escalating demands can and do lead to critical psychological pressures on the human mind that can lead to weakening of the human link in the technological chain. The increasing information flow leads to the overloading of the human brain, increasing the risk of human malfunction, ranging, e.g., from decision-making errors to complete psychological break-down of the human operator.

Why does this happen? FIG. 1 shows a simplified sketch of a human operator. In essence, this is an analog of the physical "black box" diagram, where the brain (as a central processing unit) receives inputs from the various sensory systems and generates outputs to various muscular systems (motor output), producing muscular movement. The product of the motor output is then sensed and compared with the original motor plan. Subsequent motor outputs may be generated depending upon how well the resultant movement fit the initial sensory-motor action plan. For the majority of mammals, environmental information input to the brain is typically organized by five special senses and a few non-specific ones. The five special senses are: vision, hearing, balance, smell and taste. They are "special" because the actual sensors (receptors) are localized and specialized (physically, chemically and anatomically) to acquire specific environmental data, but within a limited range of changes. For example, the sensitivity of photoreceptors is limited in terms of wavelength: humans cannot see in the infrared part of the spectrum (as do snakes) or the ultraviolet range (as do some insects). Similarly, humans cannot hear in the infra- or ultra-sonic ranges of sound frequency as do, respectively, elephants or bats.

Non-specific senses for mechanical signal, thermal changes, or pain, do not have a specific location or specialized apparatus for reception. Nevertheless, all non-specific senses are also limited in terms of the ranges of environmental information that can be sensed (frequency of vibration, temperature range, etc.).

During technological processes, humans encounter additional sensory limitations. In the execution of their duties, human operators mainly use vision, the most developed human sense, although other senses are occasionally used as principal inputs, typically as warning signals (e.g., auditory stimuli such as alarms, smell for detecting chemicals such as natural gas, and smell and taste as "quality control" during cooking or brewing processes), the vast majority of human/machine interfaces are designed to communicate information visually. In complex technical environments, competing visual inputs can tax the ability of the operator to handle the incoming information. For example, if one looks at the thousands of visual indicators and monitors that saturate the cockpit of a modern aircraft or a nuclear power station control room, it makes one wonder how it is possible to continuously look attentively at the entire console of instrumentation, much less to read, analyze, and understand all of the quantitative and qualitative information presented during the hours of a working shift or during an intercontinental flight. For this reason, modern computers are becoming indispensable for monitoring and controlling most complex routine processes and they are highly satisfactory when everything is operating smoothly. However, situations of unpredictable change can rapidly exceed the capabilities of computerized controllers. Unexpected fluctuations, equipment malfunctions, and environmental disturbances—any of these events necessitates immediate operator intervention employing the human brain's innate and massively parallel or simultaneous analytical capabilities for decision-making and creative problem solving—something that modern computational technology is still missing.

The output of the human operator is motor output, i.e., movement. In fact, the only output of the brain is a signal for control of movement. For example, just keeping the human body in an upright posture seems mundane, yet it is an astonishingly complicated pattern of continuous action involving nearly every skeletal muscle in the human body. Emotional reactions too, immediately change the tension in many muscles of the human face and/or internal body musculature. While voice commands might be perceived as a non-movement output, speech itself is the result of very sophisticated combination of movement patterns in different muscles in the tongue, laryngeal area, lungs and diaphragm.

Figure 2:
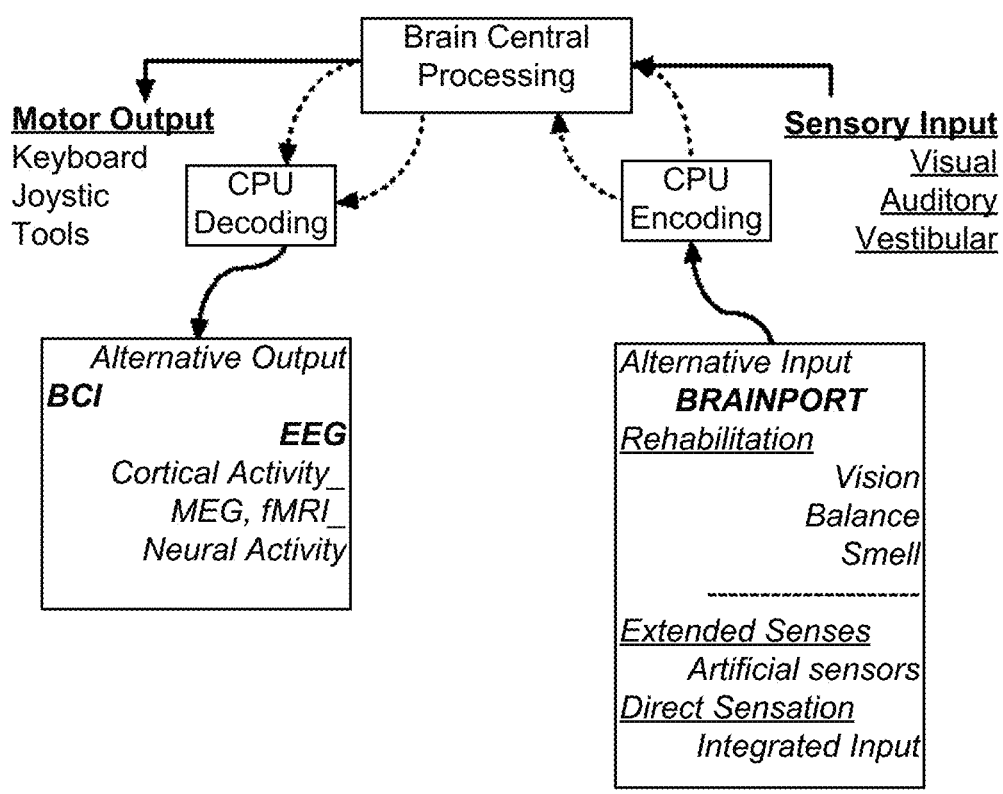
FIG. 2 shows a schematic diagram of information flow to and from the brain from traditional means, and from employing systems and methods of the present invention.

The most complex and sophisticated output apparatus available to the human operator, including both natural parts of the body and external devices, is the human hand—specifically the fingers. Pressing a button, turning a switch, keyboard typing, using a joystick control—all are complicated movement patterns, involving synchronous action of thousands of muscular fibers. The result can be as coarse as turning a valve handle, or as subtle as sensing the friction of a computer mouse. Yet humans typically have only two hands—consequently the human operator can perform only a limited number of tasks at one time. These various motor outputs are shown in the upper left-hand portion of FIG. 2. Clearly, the natural biological limitations of the human are key factors in creating input/output information saturation and operator overload. The results can be likened to a traffic jam in the technological information loop.

It is doubtful that following the present path of increasing technological development will lead to a reduction in information flow to the operator in the near future. Thus, there are two basic ways to address the present situation: 1) Improve the information processing capacity through education and training, to improve the operator's capacity and efficiency in solving process problems and thereby improve their analytical brain power; and 2) Improve the operator's input and output information processing capacity by optimizing the ways in which the data is presented to the operator. One aspect of the present invention is to alleviate or correct information bottlenecks, e.g., at overused input channels such as the visual input channel, distributing a portion of the information flow to the operator's brain over one or more alternative sensory channels.

A contemporary technological solution to the latter challenge is to implement a Brain Computer Interface (BCI)—that is, to utilize an interface technology designed to transfer information from the brain to the computer or vice versa, by employing alternate but underutilized natural biological pathways. The present invention provides systems and methods that address this approach. This novel approach is diagrammed in the FIG. 2. As described in the Examples, below, these systems and methods have achieved tremendous results in a wide range of human enhancements for healthy and disabled subjects.

The majority of modern BCI technologies are designed to provide alternative outputs from the brain to a computer. An early application of BCIs was to aid completely paralyzed patients, who have lost ability to move, speak, or otherwise communicate. Various levels of neuronal activity can be considered as potential sources for output, from single fibers and neurons up to the sum total of signals from large cortical and subcortical areas, such as EEG or fMRI signals, the integrated output of which can range as high as thousands and even millions of neurons.

In the vast majority of these BCI scenarios, the main goal is to use "internal" brain signals derived from the outputs of various areas of the brain to control computer-based peripherals, e.g., to control cursor movement on a computer monitor, to select icons or letters, to operate neuroprostheses. There are many successful examples of such an approach. Microchips implanted in a human hand or animal brain can be used to transfer electronic copies of neural spike flows from goal-directed movements to an artificial limb to produce an exact replica of the original movement. Another example involves using certain components of acquired EEG signals that can be extracted, digitized, and applied as supplemental flight controls for drones or other unmanned aircraft.

However, few BCI's address alternate information inputs to the brain, or to be more precise—CBI's (Computer Brain Interface). This technology is realized in the systems and methods of the present invention. The present invention provides unique ways of presenting meaningful information to the brain by, for example, electrotactile stimulation of the tongue. The present invention is not limited to electrotactile stimulation of the tongue, however. A wide variety of sensory input methods may be used in the various methods of the present invention. In some embodiments, the sensory input provided by the present invention is tactile input. In some embodiments, the tactile input is vibrotactile input. In particularly preferred embodiments, the tactile input is electrotactile input. In some embodiments, the sensory input is audio input, visual input, heat, or other sensory input. The present invention is not limited by the location of the sensory input. For audio inputs, the input may be from an external audio source to a subject's ears. In alternative embodiments, the input may be from an implanted audio source. In yet other audio inputs, the audio source may provide input by non-implanted contact with a bony portion of the head, such as the teeth. For tactile inputs, any external or internal surface of a body may be used, including, but not limited to, fingers, hands, arms, feet, legs, back, abdomen, genitals, chest, neck, and face (e.g., forehead). In particularly preferred embodiments, the surface is located in the mouth (e.g., tongue, gums, palette, lips, etc.). In some embodiments, the input source is implanted, e.g., in the skin or bone. In other embodiments, the input source is not implanted.

The present invention is not limited by the nature of the device used to provide the sensory input. A device that finds use for electrotactile input to the tongue is described in U.S. Pat. No. 6,430,450, herein incorporated by reference in its entirely. Many of the embodiments of the present invention are illustrated below via a discussion of electrotactile input to the tongue. While this mode of input is a preferred embodiment for many applications, it should be understood that the present invention is not limited to input to the tongue, electrotactile input, or tactile input.

Figure 3:
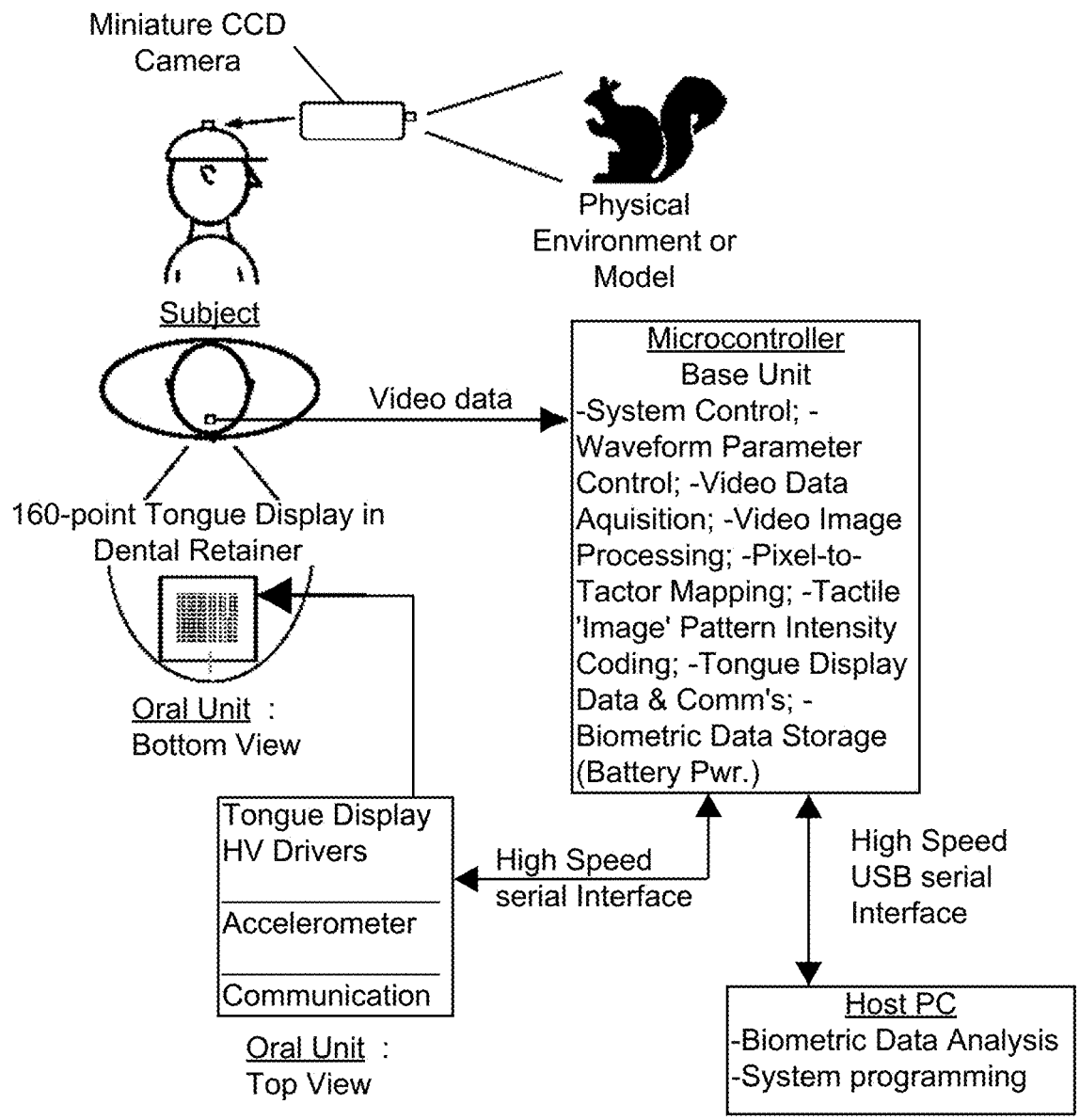
FIG. 3 shows a schematic diagram of information flow from a video source to the brain using a tongue-based electrotactile system of the present invention.

A specific preferred embodiment of the present invention is shown in FIG. 3 and discussed herein to highlight various features of the present invention. FIG. 3 shows a tongue-based electrotactile input of the present invention configured to provide video information. Such a system finds use in transferring video information to blind or vision-impaired subjects or to enhance or supplement the perception of sighted subjects. The configuration of the device shown comprises two main components: an intra-oral tongue display unit, and a microcontroller base-unit. These two elements are connected by a thin 12-strand tether that carries power, communication, and stimulation control data between the base and oral units, as shown in the schematic diagram (FIG. 3).

In the embodiment shown, the oral unit contains circuitry to convert the controller signals from the base unit into individualized zero to +60 volt monophasic pulsed stimuli on a 160-point distributed ground tongue display. The gold plated electrodes are on the inferior surface of a PTFE circuit board using standard photolithographic techniques and electroplating processes. This board serves as both a false palate for the tongue and the foundation to the surface-mounted devices on the superior side that drives the electrotactile (ET) stimulation. This unit also has a MEMS-based 1, 2, 3, 6-axis accelerometer for tracking head motion during visual image scanning and for vestibular feedback applications. This configuration utilizes the vaulted space above the false palate to place all necessary circuitry to create a highly compact and wearable sub-system that can be fit into individually molded oral retainers for each subject. With this configuration, only a slender 5 mm diameter cable protrudes from the corner of the subject's mouth and connects to the belt-mounted base unit. Alternatively, wireless communication systems may be used. The present invention is not limited by the method of signal transfer from a base unit to a mouth component.

The base unit in the embodiment shown in FIG. 3 is built around a Motorola 5249 controller running compiled code to manage all control, communications, and data processing for pixel-to-tactor image conversion. It is user configurable for personalized stimulation iso-intensity mapping, camera zooming and panning, and other features. The unit has a removable 512 MB compact flash memory cards on board that can be used to store biometric data or other desired information. Programming and experimental control is achieved by a high-speed USB between the controller and a host PC. An internal battery pack supplies the 12 volt power necessary to drive the 150 mW system (base+oral units) for up to 8 hours in continuous use.

In preferred embodiments, the system is designed with electrical safety protection measures for both the power supply and electrical stimulation components of the system. Other modes of electrical protection required by consensus standards may also be included (e.g., physical and environmental protection) and are well known by those of skill in the art.

Figure 21:
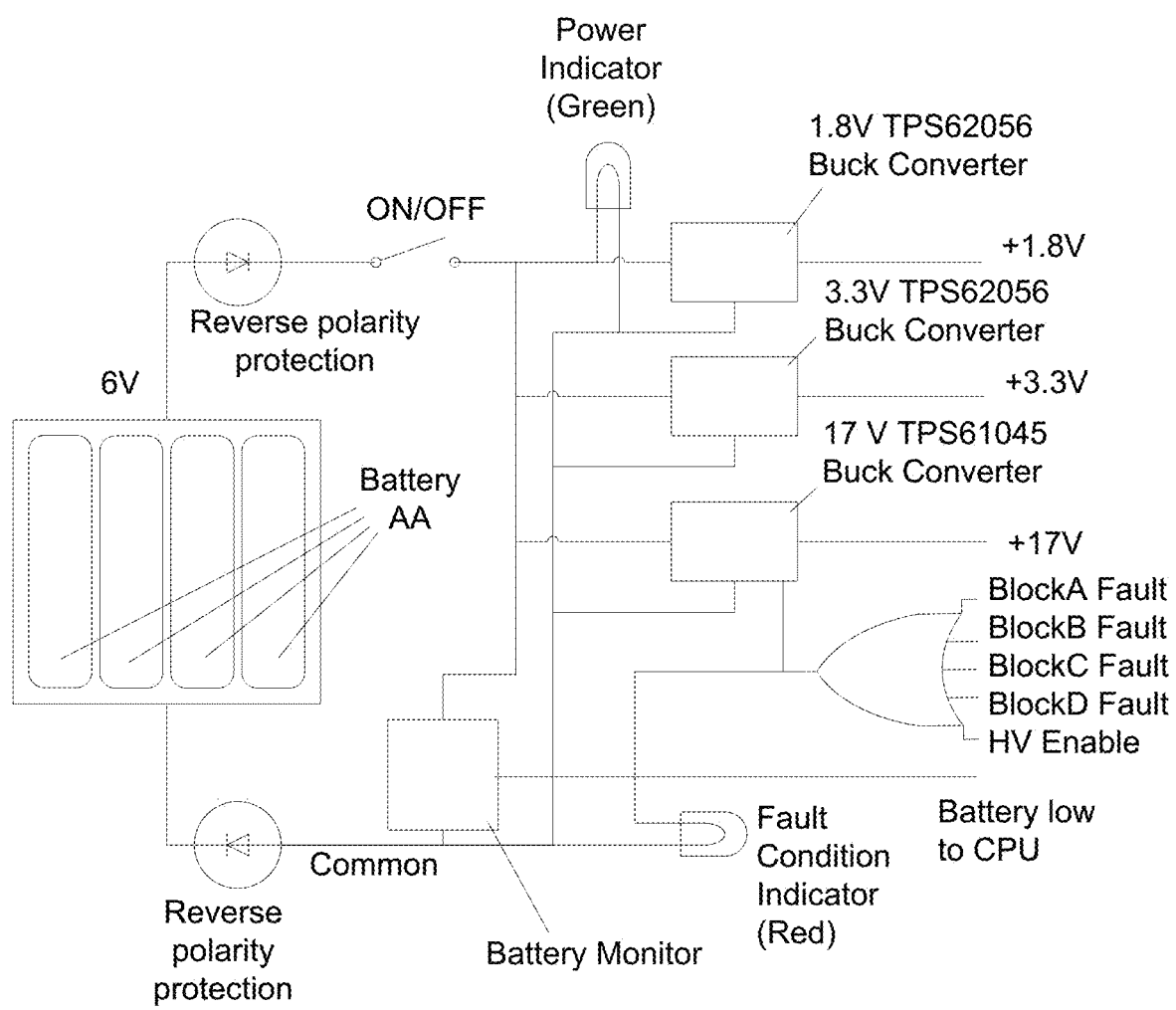
FIG. 21 shows a power supply unit of some embodiments of the present invention.

An exemplary power supply unit is depicted in FIG. 21. The power supply unit can be configured to accept multiple safety triggers thereby ensuring a proper controlled power-down sequence (e.g., in the event of a failure or occurrence of a risk event) including the ability to individually power down the analog and digital portions of the circuit.

A stimulation circuit of some embodiments of the present invention is depicted in FIG. 22. In some preferred embodiments, the stimulation circuit comprises a microprocessor, a digital to analog converter, an amplifier, a current sensing circuit, addressing logic and electrodes. In some embodiments, the stimulation circuit comprises 144 electrodes with 4 amplifiers that drive tongue stimulation (e.g., wherein only four electrodes can be active at any one time). The present invention is not limited to this particular configuration. Indeed, in other embodiments, the stimulation circuit may comprise more (e.g., 150-200 or more) or less (e.g., 1-140) electrodes, or more (e.g., 5-20 or more) or less (e.g., 1-3) amplifiers.

The stimulation circuit may be configured such that an independent current sensing circuit exists for each of the amplifiers (e.g., for each of the 4 amplifiers). The current sensing circuit may consist of an instrumentation amplifier, voltage reference, resistor, and comparator. The comparator can be calibrated to shut down the analog portion of the power supply if a predetermined threshold is reached (e.g., 8.5 mA). Under these circumstances, the digital portion of the circuit could still be powered (e.g., allowing the processor time to log the conditions under which the over current condition occurred and to shut down in a controlled manner).

The current sensed can also be captured by an analog to digital converter (e.g., to allow the processor to monitor current in real time). In some embodiments, an additional layer of protection can be provided by a fault detection subroutine (e.g., that monitors the values sent to the analog to digital converter).

Multiple configurations of the intra-oral tongue display assembly are contemplated to be useful in the systems of the present invention. In some embodiments, a potting technique may be used for encapsulation of the intra-oral display assembly. For example, a medical grade silicone (e.g., SILASTIC) can be used to fill the volume between the back side of the electrode array and a rigid plastic cap. Configuring in this manner protects electronic components from saliva. It may be desirable, in some embodiments, after this assembly is complete to apply a second coating (e.g., with a medical grade silicone or similar material) thereby encapsulating the rigid cap. In some preferred embodiments, this layer of coating is thin (e.g., ~0.05 inches) and dried to a smooth (e.g., glossy) surface thereby improving the aesthetics of the device. In other embodiments, a plastic injection molding technique can be used to encapsulate the intra-oral display assembly (e.g., to generate an overmolded intra-oral display).

In some embodiments, a removable cap or cover is generated for components of the intra-oral display assembly (e.g., for the electrode array, rigid plastic cap, or both). Caps/covers can be configured in multiple ways that do not interfere with the systems and methods of the present invention. For example, caps/covers can be generated that are disposable, or may comprise a coating that permits sterilization (e.g., by submersion in alcohol or autoclaving). Furthermore, caps/covers may be optimized for individual patients (e.g., for a child) or for unique characteristics of a specific patient's tongue (e.g., a cap/cover my comprise means—e.g., a ridge, bump, or other tactile marker—that permits a user to place the intra-oral tongue display on his or her tongue in the same location each time the display is used).

In some embodiments, the device is configured to permit any portion that comes in contact with the subject (e.g., an intra-oral component) to be detachable from the rest of the system. This may have several advantages. For example, it permits each subject using a device (e.g., at a physician's office) to have a personal (e.g., sterile, optimized, etc.) device. Each user need only attach their personal component to the system when using the system and detach when completed. The same process may be accomplished with detachable caps or covers (e.g., disposable, sterilizable, etc.) that shield the user from the intra-oral component. In some embodiments, the cap or cover entirely encompasses the portion of the system that contacts the subject. In some such embodiments, the cap or cover is made of conductive plastics to permit electrotactile stimulation through the material. In some embodiments, the system is configured such that multiple different detachable (or wireless) components may be used simultaneously with the same base unit. For example, multiple users may "plug in" to a single base unit to receive training, therapy, etc. With wireless systems in particular, a single base system may serve many users in parallel without, for example, being in the same room or area.

Electrodes of the intra-oral tongue display can be plated with any medically compatible metal (e.g., gold or platinum) to protect a patient from material (e.g., copper) used to make the circuit. Finite element analysis has revealed hotspots (e.g., spots of increased electrical current density) at the edges of electrodes (e.g., active and ground path return electrodes). These points of increased current density may be responsible for pain or discomfort perceived by a user when high amounts of energy are used. Thus, reduction of current density (e.g., at the edges of the electrodes while supplying the same voltage stimulus) may be used to increase the dynamic range.

One way this can be achieved is by changing the resistivity of the electrode as a function of the radius of the electrode. For example, to reduce the hot spots, the resistivity of the electrode can be increased as a function of radius such that the outer edge of the electrode are more resistive than the center of the electrode. This reduces current density by spreading current across the full area of the electrode so that it can enter or exit the tongue over a larger surface area. Several coating techniques or other fabrication processes can be used to accomplish a desired change in electrical resistivity as a function of radius including, but not limited to, generating a gradient electrical resistant electrode (GERE) (e.g., that is similar to a gradient index of refraction optical lenses (GRIN)).

Another way to avoid or decrease the occurrence of hotspots is through tactor shape. Certain shapes (e.g., circles) are known to distribute current density better than other shapes (e.g., squares). Thus, in some embodiments, tactor shape is used to decrease hot spots on the electrode terminal, wherein the tactor shape is circular. Furthermore, tactor shape can be combined with wave-form schemes (see below) to optimize the delivery of information to a user. Thus, decreasing the occurrence of hot spots expands the dynamic range, thereby permitting an increase in energy delivered (e.g., range of usable current), that in turn permits an increase in information conveyable to a patient. In some preferred embodiments, electrodes are 1.7 mm diameter, flat, spaced 2.3 mm apart, and arranged in a square grid. However, the present invention is not limited to this configuration. Other configurations are also useful, including, but not limited to, smaller electrodes (e.g., between 1.7 mm and 0.3 mm in diameter) arranged in a hexagonal grid (e.g., allowing an increase in number of tactors). Thus, in some embodiments, there are 300-500 tactors per square centimeter. Additionally, different tactor material may be used in order to decrease hotspost (e.g., conductive plastics and/or conductive epoxy mixed in with insulating plastic and/or epoxy). Furthermore, instead of tactors having a flat terminus, tactors may be curved at the end (e.g., generating a small bump).

Multiple wave-form schemes can be delivered to a user and find use with the systems of the present invention. In some embodiments, square-pulse is used for tactile stimulation. However, the present invention is not limited to square-pulse schemes. Specifically, any signal monotonically rising from zero that has some portion of stable duration before monotonically falling to zero again is useful with the present invention. For example, in some embodiments, a damped-sinusoid pulse can be used. Use of a sinusoid pulse is contemplated to permit an improved dynamic range as the sinusoid pulse more resembles a natural signal (e.g., a pulse shape similar to natural nerve signaling). Furthermore, a wavelet may be provided to a patient (e.g., that resembles natural nerve firing of biological system thereby permitting a broader dynamic range). In some embodiments, use of wavelets avoid sharply defined edges of time and amplitude (See, e.g., Chui, An Introduction to Wavelets (Wavelet Analysis and Its Applications, Volume 1), Academic Press (1992); Debnath, Wavelet Transforms and Time-Frequency Signal Analysis, Birkhäuser Boston Inc. (2001); Fernandes et al., IEEE Trans Image Process. January; 14(1):110-24 (2005)).

The damped sine is $$\text{Amplitude} = c \times e^{-at} \times \sin(2\pi \cdot f \cdot t).$$

In some preferred embodiments, sine f=20 kHz and damping parameter a=2.218*f=4.436×10$^4$, providing an amplitude of 12 volts peak with 0.05 volts after 2.5 cycles (or 125 microseconds). Thus, in some embodiments the present invention provides duplication or simulation of natural nerve firing. For example, the systems and methods of the present invention can duplicate natural nerve pulse form that has a smooth starting, rapid rise to peak and then slower fall. In some embodiments, the time course is about 1 millisecond start to finish, with pulse amplitude of 0.1 volts measured on the surface of the nerve. Although an understanding of the mechanism is not necessary to practice the present invention and the present invention is not limited to any particular mechanism of action, duplicating natural nerve firing improves the dynamic range of the systems and methods of the present invention because a patient's pain threshold is higher with replicated natural firings.

In some embodiments, systems and methods of the present invention present the same wave form on every tactor with variable amplitude (e.g., eliminating the need to raster scan the image). For example, one module will create the wave form, and other modules will act as multipliers.

Also useful in the present invention is the damped lorentzian:

$$\text{Amplitude} = c \frac{\frac{\Gamma}{2} \times \sin(2\pi \cdot f \cdot t)}{t^2 + \left(\frac{\Gamma}{2}\right)^2}$$

In these cases, it is the rising portion of the sine function that determines how the wave rises, and its peak amplitude is modified by the damping portion. The parameters c, a, f and Γ determine peak amplitude and time before zero crossing.

A simple wave form that finds use with the present invention is a square pulse with a fixed width. In some embodiments, square pulse with a fixed width can be used wherein the time and amplitude are varied, or a fixed amplitude with variable width (e.g., pulse width modulation).

In some embodiments, the amount of wave-form energy provided to any particular patient is variable. Thus, a range of wave-form energy (e.g., sub-detectable up to painful) is useful in the systems of the present invention. For example, because each patient is unique, different amounts of energy may be provided to each user (e.g., taking into account electrode shape, position, energy form, and sensitivity of the patient). In some preferred embodiments, the systems and methods of the present invention provide between 100 microwatts (0.1 milliwatts) in 1 microsecond (i.e., 100 picojoules) and 1 Joule. Furthermore, the present invention provides the ability to map the dynamic range of each user. Once determined, such a map allows an optimized amount of wave-form energy to be delivered to each patient (e.g., maximizing the amount of information conveyable to each patient), should this be desired.

Thus, this system is a computer-based environment designed to represent qualitative and quantitative information on the superior surface of the tongue, by electrical stimulation through an array of surface electrodes. The electrodes form what can be considered an "electrotactile screen," upon which necessary information is represented in real time as a pattern or image with various levels of complexity. The surface of the tongue (usually the anterior third, since it has been shown experimentally to be the most sensitive area), is a universally distributed and topographically organized sensory surface, where a natural array of mechanoreceptors and free nerve endings (e.g. taste buds, thermo sensitive receptors, etc.) can detect and transmit the spatially/temporally encoded information on the tongue display or 'screen', encode this information and then transfer it to the brain as a "tactile image." With only minimal training the brain is capable of decoding this information (in terms of spatial, temporal, intensive, and qualitative characteristics) and utilizing it to solve an immediate need. This requires solving numerous problems of signal detection and recognition.

To detect the signal (as with the ability to detect any changes in an environment), it is useful to have systems of the highest absolute or differential sensitivity, e.g. luminance change, indicator arrow displacement, or the smell of burning food. Additionally, the detection of the sensory signals, especially from survival cues (about food, water, prey or predator), usually must be fast if reaction times are to be small in life threatening situations. It is important to note that the sensitivity of biological and artificial sensors is usually directly proportional to the size of the sensor and inversely proportional to the resolution of the sensorial grid.

Information utilized during this type of detection task is usually qualitative information, the kind necessary to make quick alternative decisions (Yes/No), or simple categorical choices (Small/Medium/Large; Green/Yellow/Red).

The recognition process is typically based on the comparison of given stimuli (usually a complex one such as a pattern or an image, e.g. a human face) with another one (e.g. a stand alone image or a set of original alphabet images). To solve the recognition problem it is useful to have sensors with maximal precision (or maximal resolution of the sensorial grid) to gather as much information as possible about small details.

Often this is related to the measurement of signal parameters, gathering quantitative information (relative differences in light intensity, color wavelength, surface curvature, speed and direction of motion, etc.), where and when precision is more important than speed.

Figure 4:
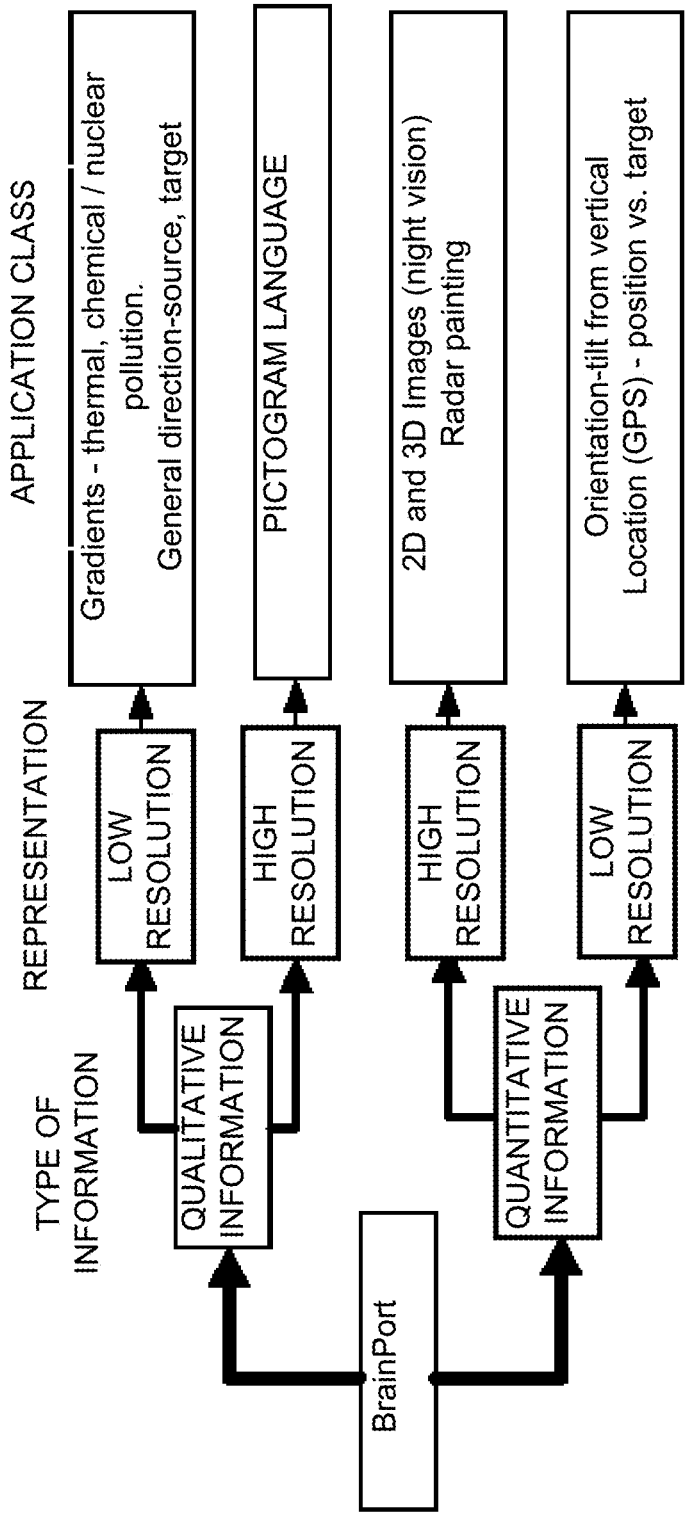
FIG. 4 shows examples of different types of information that may be conveyed by the systems and methods of the present invention.

The systems of the present invention are capable of transferring both qualitative and quantitative information to the brain with different levels of a "resolution grid," providing basic information for detection and recognition tasks. The simple combination of two kinds of information (qualitative and quantitative) and two kinds of a stimulation grid (low and high resolution) results in four different application classes. Each class can be considered as a root (platform) for multiple applications in research, clinical science and industry, and are shown in FIG. 4.

The first class (qualitative information, low resolution) can be illustrated by the combination of external artificial sensors (e.g., radiation, chemical) with the systems of the present invention for detection of environmental changes (chemical or nuclear pollution) or explosives detection. The presence of selected chemical compounds (or sets of compounds) in the air or water can be detected using the systems of the present invention simply as "Yes/No" paradigms. By using a distributed array of stimulators and a corresponding presentation of signal gradients on the system array it is also possible to use the system for source orientation relative to the operator. With minimal training, the existence of the otherwise undetectable analyte in the environment is perceived by the subject as though it were detectable by the normal senses.

The second class (qualitative information, high resolution) can be illustrated by an application for underwater navigation and communication. A simple alphabet of images or tactile icons (sets of moving bars in four directions, a flashing bar in the center and flashing triangles on left and right sides of system array) constitute a system of seven navigation cues that are used to correct deviation and direction of movement along a designated path. In experiments conducted during the development of the present invention, after less than five to ten minutes of preliminary training, blindfolded subjects were capable of navigating through a computer generated 3-D maze using a joystick as a controlling device and a tongue-based electrotactile device for navigation signal feedback.

The third class (quantitative information, low resolution) can be illustrated by another existing application for the improvement of balance and the facilitation of posture control in persons with bilateral damage of their vestibular sensory systems (BVD—causing postural instability or "wobbling", and characterized by an inability to walk or even stand without visual or tactile cues). A quantitative signal acquired from a MEMS accelerometer (positioned on the head of subject) is transferred through the oral electrotactile array as a small, focal stimulus on the tongue array. Tilt and sway of the head (or the body) are perceived by the subject as deviations of the stimulus from the center of the array, providing artificial dynamic feedback in place of the missing natural signals critical for posture control.

The fourth class (quantitative information, high resolution) can be illustrated by another existing system that implements a great scientific challenge—that of 'vision' through the tongue. Signals from a miniature CCD video camera (worn on the forehead) are processed and encoded on a PC and transferred through the array as a real-time electrotactile image. Using this electrotactile display, subjects are capable of solving many visual detection and recognition tasks, including navigation and catching a ball. The system may also be used for night (infrared) or ultraviolet vision, among other applications.

On the basis of the four strategic classes of applications it is possible to develop multiple practical industrial applications that can include a human operator in the loop. The present invention provides for the development of alternative information interfaces so that the brain capacity of the human operator in the loop can be more fully and efficiently utilized in the technological process.

As described above, the modern tendency is toward designing instrumentation with increased density and complexity of visual representations. For example, the numerous light and arrow indicators of past displays are being replaced by computer monitors that condense the information into lumped static and dynamic 2D and 3D images or video streams. There are various rationales behind the development of these kinds of cumulative information presentations. One is to decrease the physical area of the visual information field, thereby limiting the space the operator must scan to monitor the instrument. Some size reduction is accomplished by condensing multiple parameters into a single image. However, to control modern technological processes, an operator must be able to efficiently observe and make decisions about hundreds of changing parameters. If each parameter is represented by a simple indicator, like a light, arrow, or dial, the control panel will consist of hundreds of the same kinds of indicators. By miniaturizing and grouping all of these indicators, the resultant ergonomically designed displays become extremely intensive information panels, like the ones presently found in modern aircraft (Electronic Flight Instrument Systems, EFIS) or nuclear power stations.

The main problem with these approaches is the distribution of attention required by observer. In the presence of multiple visual stimuli, the operator is forced to limit his/her attention capacity to one or a few of the elements being displayed. The operator must shift attention from one element to another in order to perceive all of the information contained in the complex display. Such complex information display requires that the operator be systematic in monitoring the panel, to minimize the chances of overlooking any particular element. Anything that distracts the operator can cause a failure in the system. In addition, the ability of an operator to monitor a complex display tends to diminish during extended periods of observation (e.g., over the course of a work shift). One possible solution is to decrease the number of indicators and replace them with more condensed, more complicated visual images that combine multiple parameters into a single image. For example, a single 3D scatter plot can represent up to 12 simultaneously changing parameters, using multiple features of single elements as coding variables (e.g. size, dimension, shape, color, orientation, opacity, pattern of single elements, etc.) Although useful, this approach still relies on distributing the information using exclusively visually representable features.

An alternative approach is to use the systems and methods of the present invention as a supplemental input for processing information.

As previously mentioned, the systems are capable of working in various modes of complexity: As a simple indicator, such for (first application class) signal detection; as a target location device (third application class) for position control of signals on a 2D array, much like a "long range" target location radar plot; in almost all computer action games; as a simple GPS monitor. The systems can also work in more complex modes such as for more complete vision substitution device, an infrared or ultraviolet imaging system creating complex electrotactile images using in addition to two dimensions of its electrode array, the amplitude and frequency of the main signal, the spatial and temporal frequency of the signal modulation, and a few internal parameters of the signal waveform. In other words the systems and methods of the present invention are capable of creating a complex multidimensional electrotactile image—similar to that of visual imagery.

Thus, the present invention provides systems that afford processing of artificial sensory signals (from any source) by natural brain circuitry and organizational behavioral, thereby providing direct sensation or direct perception by the operator.

People usually do not think about such natural behavioral acts like breathing or digestion as fully "automatic", internally "built-in" processes. Even if we think about them, we cannot stop or permanently change them. Walking, swimming, riding a bike or driving a car are other examples of very complex biomechanical processes that also use multiple sensory and motor coordination, but we learn them early in our lives; performing them also almost naturally (without thinking about each component), quickly and with great precision and efficiency. The present invention provides means for efficiently training the brain to carry out new tasks and perceive and utilize new information "automatically." Experiments conducted using the technology of the present invention demonstrated after training with the systems, fMRI screening of the brain activity in blind subjects during the electrotactile presentation of visual images revealed strong activation in areas of the primary visual cortex. This means that after training with systems, the blind person's brain begins to use the most sophisticated analytical part of the cortex for analysis of electrotactile information displayed on the tongue during visual tasks. Before training, it is contemplated that these areas were not active. The activation of normal analytical resources (e.g. the 'visual' part of the brain) in response to artificial sensory stimulation was "automatic" in that it did not rely on the use of the eyes for directing the information to the primary visual cortex.

With the systems of the present invention, a blind person can navigate, a BVD patient can walk, a video game player or fighter pilot can perceive objects outside of their field of view, a doctor can conduct remote surgery, a diver can sense direction underwater, a bomb squad member can sense the presence of explosive chemicals, all as naturally as an experienced person would ride a bike, play an instrument reading sheet music, or drive a car.

In some embodiments, the systems and methods of the present invention find use in numerous applications for sensory substitution. In such embodiments, sensory perception is provided to a subject to compensate for a missing or deficient sense or to provide a novel sense.

In some such embodiments, the sensory substitution provides the subject with improved balance or treats a balance-associated condition. In such embodiments, subjects are trained to associate tactile or other sensory inputs with body position or orientation. The brain learns to use this added sensory input to compensate for a deficiency. For example, the systems and methods may be used to treat bilateral vestibular dysfunction (BVD) (e.g., caused by ototoxicity, trauma, cancer, etc.). Example 1, below, describes successful treatment of a number of BVD patients using the systems and methods of the present invention. Examples 2-8 describe additional benefits imparted on one or more of the subjects during or following their clinical rehabilitation. Based on these results, the present invention finds use in the treatment of other diseases and conditions related to the vestibular system, including but not limited to, Meniere's disease (see Example 25), migraine (see Example 26), motion sickness, MDD syndrome, dyslexia, and oscillopsia. The systems and methods also provide the tangential benefits of improved sleep recovery, fine movement recovery, psychological recovery, quality of life improvement, and improved emotional well-being.

The balance-related sensory substitution methods may be applied to a wide range of subjects and uses. For example, the methods find use in ameliorating or eliminating aging related balance problems for both fall prevention and general enhancement. The methods also find use in balance recovery after injury.

The present invention also provides systems and methods for the treatment of a variety diseases and conditions including, but not limited to, sicknesses or conditions in which a subject suffers from a defect in vestibular function (e.g., balance), proprioception, motor control, vision, posture, cognitive functions, tinnitus, emotional conditions and/or sleep. Subjects known to experience these defects include those diagnosed with, experiencing symptoms of and/or displaying symptoms of multiple diseases, sicknesses or conditions, including, but not limited to, vestibular disease, autism, traumatic brain injury, stroke, attention deficit disorder, hyperactivity, addiction, narcolepsy, coma, schizophrenia, shaken baby syndrome, Alzheimer's, Parkinson's, Gerstmann's Syndrome, dementia, delusion, Fetal alcohol syndrome, Cushing's disease, Creutzfeldt-Jakob Disease, Huntington's Disease, Kearns-Sayre Syndrome, Metachromatic Leukodystrophy, Mucopolysaccharidosis, Niemann-Pick disease, Pelizaeus-Merzbacher Disease, phobias, Persistent Vegetative State, Postpartum depression, depression of any kind, Reye's Syndrome, Rett's syndrome, Sandhoff Disease, developmental disorders, Meniere's disease, balance disorders, Septo-Optic Dysplasia, Soto's Syndrome, Spastic disorders, migraine, Sturge-Weber Syndrome, Subacute Sclerosing Panencephalitis, Toxic Shock Syndrome, Transient Ischemic Attack, Williams Syndrome, Wilson's Disease, Down Syndrome, Limbic encephalitis, Vascular dementia, Heavy metal exposure, Lewy body disease, Normal pressure hydrocephalus, Post-traumatic dementia, Pick's disease, Multiple sclerosis, Jakob-Idiopathic basal ganglia calcification, Neurosyphilis and Acquired immune deficiency syndrome (AIDS).

For example, in some embodiments, the present invention provides systems and methods for improving or correcting vestibular function (e.g., balance), proprioception, motor control, vision, posture, cognitive functions, tinnitus, emotional conditions and/or sleep in a subject with traumatic brain injury (See, e.g., Example 21).

In some embodiments, the present invention provides systems and methods for correcting or improving verbal and non-verbal communication, social interactions, sensory integration (e.g., tactile, vestibular, proprioceptive, visual and auditory), and leisure or play activities in a subject with a Pervasive Developmental Disorder (PDD), including, but not limited to an Autistic Disorder, Asperger's Disorder, Childhood Disintegrative Disorder (CDD), Rett's Disorder, and PDD-Not Otherwise Specified (PDD-NOS) (See, e.g., Example 22).

In some embodiments, the present invention provides systems and methods for correcting or improving symptoms associated with Parkinson's disease (e.g., defects in motor control, including, but not limited to, walking, talking, or completing simple tasks that depend on coordinated muscle movements) (See, e.g., Example 23).

In some embodiments, the present invention provides systems and treatments for correcting or improving weakness of the face, arm or leg, (e.g., on one side of the body), correcting or improving numbness of the face, arm, or leg, especially on one side of the body; correcting or improving confusion, trouble speaking or understanding speech; correcting or improving vision disturbances, trouble seeing in one or both eyes; correcting or improving trouble walking, dizziness, loss of balance or coordination; correcting or improving severe headache; correcting or improving slurred speech, inability to speak or the ability to understand speech; correcting or improving difficulty reading or writing; correcting or improving swallowing difficulties or drooling; correcting or improving loss of memory; correcting or improving vertigo (spinning sensation); correcting or improving personality changes; correcting or improving mood changes (depression, apathy); correcting or improving drowsiness, lethargy, or loss of consciousness; and correcting or improving uncontrollable eye movements or eyelid drooping in a stroke subject or subject displaying stroke-like symptoms (See, e.g., Example 24).

While an understanding of the mechanism is not necessary to practice the present invention and while the present invention is not limited to any particular mechanism of action, in some embodiments, it is contemplated that the use of tactile stimulation (e.g., electrotactile stimulation of the tongue) conditions the brain for correcting or improving a general function (e.g., motor control, vision, hearing, balance, tactile sensation). The preferred route is electrotactile stimulation of the tongue.

For example, in some embodiments, it is contemplated that systems and methods of the present invention correct, improve and/or activate residual tissue (e.g., neurological cells and tissue) not otherwise active or, to the contrary, overloaded with information. In some embodiments, the present invention provides a clarifying effect, reducing the signal to noise ratio and thereby providing beneficial effects to a subject. In some embodiments, the systems and methods of the present invention act to repair or reprogram the machinery (e.g., through patterned electrical currents embedded with information) required for motor control, vision, hearing, balance, tactile sensation, etc. In some embodiments, the present invention provides the brain access to signals (e.g., weak signals), that, over time and with treatment (e.g., training on the systems herein) permits the brain to respond to the signals (e.g., sensory signals, balance, motor coordination information, etc.). In some embodiments, access to these signals and/or treatment (e.g., training on the systems herein) provides a subject a new or improved function (e.g., motor control, balance, etc.).

While an understanding of the mechanism is not necessary to practice the present invention and while the present invention is not limited to any particular mechanism of action, it is contemplated that, in some embodiments, the systems and methods of the present invention provide or simulate long-term potentiation (long-lasting increase in synaptic efficacy which follows high-frequency stimulation) to provide enhanced brain function. The residual and rehabilitative effect of training seen in experiments conducted during the development of the present invention upon prolonged tactile stimulation is consistent with long-term potentiation studies. For example, in some embodiments, the systems and methods of the present invention utilize electrical currents similar to those used in long-term potentiation studies (e.g., 50-200 Hz).

In some embodiments, the tongue is relevant for improving or correcting residual balance. In some embodiments, one or more nerves present in the tongue function to conduct information from the systems and methods of the invention to the brain. In some embodiments, the signals (e.g., electrical) sent through the tongue provide the brain access to signals it otherwise has difficulty (e.g., does not or cannot) perceive. Although an understanding of the mechanism is not necessary to practice the present invention and the present invention is not limited to any particular mechanism of action, in some embodiments, signals presented to the tongue (e.g., via an electrotactile screen) are "seen" by the brain via channeling of the signals through nerves present within and/or sending signals to or from the tongue (e.g., the facial nerve, the hypoglossal nerve, the glossopharyngeal nerve, etc). The present invention is not limited by the form of stimulation of the nerves within the tongue. Indeed, a variety of stimulation (e.g., signals capable of communicating with the tongue) are contemplated to be useful in the systems and methods of the present invention including, but not limited to, signals distal to the nerves of the tongue and signals in direct contact with the nerves of the tongue. In some embodiments, the benefit a subject receives through the systems and methods of the present invention are correlated with the length of exposure the subject receives treatment (e.g., electrical stimulation through the tongue using the system). In some embodiments, benefits occur immediately. In some embodiments, the benefit is additive as training continues. In some embodiments, systems and methods of the present invention are used in combination with other treatments or procedures. In some embodiments, a synergistic beneficial effect is seen when a combinatorial approach is taken (e.g., when the systems and methods of the present invention are used in combination with other known therapies or treatments).

In some embodiments, systems and methods of the present invention benefit a subject through molecular events (e.g., activation or repression of genes present in brain tissue or cells). In some embodiments, cfos is activated. It is contemplated that gene expression patterns are altered through repetitive training using the systems and methods of the present invention. The expression of such genes may also be used diagnostically to monitor treatment or identify subjects suitable for treatment.

Thus, the present invention provides systems and methods for physiological learning that extends for long periods of time (e.g., hours, days, weeks, etc.). In some embodiments, the systems and methods of the present invention function via sensitizing/energizing the component machinery required for motor control, vision, hearing, balance, tactile sensation, etc. In other embodiments, the systems and methods of the present invention sensitize/energize the brain in general, thereby producing brain physiology that is able to function properly or in an enhanced fashion. In some embodiments, the systems and methods of the present invention work via pure physical stimulation (e.g., chemically or electrically). In other embodiments, the invention works through means similar to the benefits received through meditation or other forms of focus or stress relief (e.g., yoga). In still other embodiments, the systems and methods of the present invention provide improved cerebellum function (e.g., activation of brain regions) (See, e.g., Ptito et al., Brain, 128(Pt 3):606-14 (2005), herein incorporated by reference in its entirety).

In some embodiments, the systems and methods of the present invention are used to treat various symptoms or improve normal body function. The present invention is not limited by the type of symptom treated. Indeed a variety of symptoms can be treated using the systems and methods of the present invention including, but not limited to, dizziness, headache, inability to walk on uneven surfaces, loss of memory, inability to walk in a crowd, inability to walk up or down stairs, inability to look up or down, impaired vision, impaired speech, rigid or otherwise disturbed gait, shaking, nervousness, twitching, anxiety, depression, sleeplessness, tremor, motion sickness, confusion, insomnia, numbness, pain, achiness, paralysis, blurry vision, difficulty breathing (e.g., dyspnea), dementia, difficulty concentrating, swallowing problems (e.g., dysphagia), discomfort, lack of confidence, drowsiness, forgetfulness, hallucination, hypersensitivity, hyposensitivity, impaired balance, impaired memory, inattentiveness, neurosis, jerkiness, lack of feeling or sensation, manic, moodiness, tingling, difficulty with speech, paranoid, peripheral vision problems, respiration problems, tingling, unsteadiness, lack of ability to multitask, vision problems, delusion, detachment, disorientation, problems with posture, lack of strength, lack of tone, seizure, tunnel vision, weakness, lack of alertness, inability to concentrate, difficulty comprehending or understanding speech and/or spoken words, vertigo, apathy, lethargy, unconsciousness, and uncontrolled eye movements.

In some embodiments, it is contemplated that the systems and methods of the present invention provide direct effects beneficial to a subject. These include, but are not limited to, immediate correction or improvement of vestibular function (e.g., balance), proprioception, motor control, vision, posture, cognitive functions, tinnitus, emotional conditions, and correction or improvement (e.g., lowering the level or elimination) of the symptoms listed above. In some embodiments, the correction or improvement occurs over time after training with the systems and methods mentioned herein. In addition to direct effects, it is also contemplated that the systems and method of the present invention provide indirect effects that benefit a subject. These indirect effects include, but are not limited to, regaining or acquiring a physical, cognitive, emotional, and/or neurologic function, and/or overall sense of well-being. Thus, in some embodiments, a direct effect targeted at a specific function is provided (e.g., improved balance in response to body position information provided to a subject by the systems of the present invention), an indirect effect that relates to the specific function is provided (e.g., improved motor control that is at least partially independent of the nature of the information provided), and indirect effects not directly related to the specific function is provided (e.g., improved sense of well-being, sleep, etc.). In some embodiments, the direct effect and associated benefits sensitize the subject to allow receipt of the indirect effects. In other embodiments, the indirect effects sensitize the subject to obtain direct effect. Thus, in some embodiments, all effects, over time, enhance the benefits achieved by the others. For example, in some embodiments, improvement to vestibular function are provided by the systems of the present as described in Example 1. While not being limited to any particular mechanism of action, it is contemplated that this improvement permits additional physical and mental improvements, as many other brain functions are associated directly or indirectly with the vestibular system. Likewise, the indirect effects provide a more general enhancement of brain function, permitting, for example, better reception for training and improvement of the direct effect.

The systems and methods may also be used in research application to study balance and balance-associated conditions, including, but not limited to, the study of the central mechanisms associated with balance and balance-associated conditions, sensory integration, and sensory motor integration. Example 15 provides methods of studying brain function by MRI in response to the systems of the present invention.

Healthy individuals may also use such systems and methods to enhance or alter balance. Such applications include use by athletes, soldiers, pilots, video game players, and the like.

The vestibular uses of the present invention may be used alone or in conjunction with other sensory substitution and enhancement applications. For example, blind subjects may use systems and methods that improve vestibular function as well as vision. Likewise, video game players may desire a wide variety of sensory information including, for example, balance, vision, audio, and tactile information.

In some embodiments, the sensory substitution provides the subject with improved vision or treats a vision-associated condition. In such embodiments, subjects are trained to associate tactile or other sensory inputs with video or other visual information, for example, provided by a camera or other source of video information. In some embodiments, blind subjects are trained to visualize objects, shapes, motion, light, and the like. Such applications have particular benefit for subjects with partial vision loss and provides methods for both enhancement of vision and rehabilitation. Training of blind subjects can occur at any time. However, in preferred embodiments, training is conducted with babies or young children to maximize the ability of the brain to process complex video information and to coordinate and integrate the information higher cognitive functions that develop with aging. Example 12 describes the use of the methods of the invention to allow a blind subject to catch a baseball, perceive doors, and the like. The present invention also finds use in vision enhancement for subjects that are losing vision (e.g., subjects with macular degeneration).

In some embodiments, the sensory substitution provides the subject with improved audio perception or clarity or treats an audio-associated condition. In such embodiments, subjects are trained to associate tactile or other sensory inputs, directly or indirectly, with audio information, to reduce unwanted sounds or noises, or to improve sound discrimination. Example 11 describes the use of the methods of the present invention to enhance the ability of deaf subjects to lip read. More advanced hearing substitution systems may also be applied. Example 8 describes the successful use of the invention to reduce tinnitus in a subject. In some embodiments, arm bands (electrotactile or vibrotactile) or tongue-based devices are used to communicate various qualities of music or other audio (e.g., rhythm, pitch, tone quality, volume, etc.) to subjects either through location of or intensity of signal.

In some embodiments, the sensory substitution provides the subject with improved tactile perception or treats a condition associated with loss or reduction of tactile sensation. In such embodiments, subjects are trained to associate tactile or other sensory inputs at one location, directly or indirectly, with tactile sensation at another location. Example 9, below, describes the use of tactile substitution for use in generating sexual sensation, for, for example, persons with paralysis. Other applications include providing enhanced sensation for subjects suffering from diabetic neuropathy (to compensate for insensitive legs and feet), spinal stenosis, or other conditions that cause disabling or undesired tactile insensitivity (e.g., insensitive hands). The systems and methods of the present invention also find use in sex application for healthy individuals. Example 9 further describes sex applications, including Internet-based sex applications that permit remote subjects to have a wide variety of remote "contact" with one another or with programmed or virtual partners.

In some embodiments, the sensory substitution provides the subject with improved ability to perceive taste or smell. Sensors that collect taste or olfactory information (e.g., chemical sensors) are used to provide information that is transmitted to a subject to enhance the ability to perceive or identify tastes or smells. In some such embodiments, the system is used to mask or otherwise alter undesirable tastes or smells to assist subjects in eating or in working in unpleasant environments.

In addition to applications that provide sensory substitution, the present invention provides systems and methods for sensory enhancement. In sensory enhancement applications, the systems and methods supply improvement to existing senses or add new sensory information that permits a subject to perform tasks in an enhanced manner or in a manner that would not be possible without the sensory enhancement.

In some embodiments, the sensory enhancement is used for entertainment or multimedia applications. Example 10, below, describes the enhancement of videogame and television or movie applications by transmitting novel non-traditional sensory information to the user in addition to the normal audio and video information. For example, video game players can be given 360 degree "vision," visual images received from tactile stimulation can be provided with music or can be provided along with normal video. Users can be made to feel unbalanced or otherwise altered in response to events occurring in a movie or theme park ride. Deaf subject can be provided with information corresponding to music playing in a dance venue to permit them to perceive simple or advanced aspects of the music being played or performed. For example, in some embodiments, a tactile patch is provided on the arm (or other desired body location) that transmits music information. In some embodiments, the patch further provides aesthetic appeal.

In some embodiments, the sensory enhancement provides a new sense by training the user to associate a tactile or other sensory input with a signal from an external device (e.g. a piece of equipment or machine) that perceives an object or event. For example, subjects can be provided with the ability to "see" infrared light (night vision) by associating tactile input with signals received from an infrared camera. Ultraviolet light, ultrasonic noise (e.g., as detected by sonar), radiation or other particles or waves acquired by artificial sensors (e.g., radar or instruments capable of monitoring sound wave time of flight, for example, ultrasonic sensors) can likewise be detected and sensed. Any material or event that can be identified by a sensory device can be combined with the systems of the present invention to provide new senses. For example, chemical sensors (e.g., for volatile organic compounds, explosives, carbon monoxide, oxygen, etc.) are adapted to provide, for example, an electrotactile signal to a subject (e.g., via the tongue). Similarly, sensors for detection of biological agents (e.g., environmental pathogens or pathogens used in biological weapons) are adapted to provide such a signal to a subject (e.g., from molecular detection or other types of biological equipment). In addition to the presence of a detected compound or agent, the amount, nature of, and/or location may also be perceived by the subject. Such sensors may also be used to monitor biological systems. For example, diabetic subjects can use the system associated with a glucose sensor (e.g., implanted blood or saliva-based glucose sensor) to "see" or "feel" their blood glucose levels. Athletes can monitor ketone body formation. Organ transplant patients can monitor and feel the presence of cytokines associated with chronic rejection in time to seek the appropriate medical care or intervention. Likewise, an individual can monitor and feel the presence of a pathogen (e.g., a virus such as HIV or a bacterium such as *N. gonorrhoeae* and/or *C. trachomatis*) in their own self or in others (e.g., through intimate contact). The present invention can similarly be adapted to blood alcohol level (e.g., providing a user with accurate indication of when blood alcohol level exceeds legal limits for driving or machine operation). Numerous other physical and physiochemical measurements (e.g., standard panels conducted during routine medical testing that are indicative of health-related conditions are equally as adaptable for "sensing" using the present invention).

In preferred embodiments, a new sense is provided to a user through training the user to use the systems and methods of the present invention to associate a tactile or other sensory input with a signal from an external device. In some preferred embodiments, the sensory or tactile input is provided to the user through the tongue. It is contemplated that systems of the present invention are capable of monitoring and/or receiving information from an external, artificial sensor, and translating the information into tactile or other sensory input to the user via the tongue. For example, in some embodiments, the external, artificial sensor is an ultrasonic sensor (e.g., sonar) capable of sending and receiving signals (e.g., sound wave signals). In some embodiments, the ultrasonic sensor further comprises means (e.g., software and a computer processor) for calculating sound wave time of flight. In some embodiments, the sensor may emit a burst (e.g., a short or long burst) of ultrasonic sound (e.g., 40 kHz) from a transducer (e.g., a piezoelectric transducer). In preferred embodiments, the sensor further comprises a detector (e.g., another piezoelectric transducer). In some embodiments, the sound (e.g., generated by the transducer) is reflected by objects in front of the device, returned to the sensor unit and detected (e.g., by a detector). In some embodiments, the sound burst emitted by the transducer is detected by a detector present on a second separate sensor (e.g., on a second user such as a hiking companion or fellow soldier in an active zone). In some embodiments, the ultrasonic sensor further comprises a receiver amplifier that sends the signals (e.g., either a reflected signal/echo, or, a direct signal from a separate sensor) to a micro-controller (e.g., a microprocessor) that calculates (e.g., times the sound waves) how far away an object is (e.g., using the speed of sound in air). In preferred embodiments, the calculated range is converted into a constant current signal (e.g. that can be further translated into a discrete bundle of information) that is then provided to a user as a sensory or tactile input through the tongue.

In some embodiments, the sound waves sent from a transducer are at a constant interval such that if two or more persons are all using systems of the present invention that are capable of sending and receiving signals, the users are able to determine (e.g., through ultrasonic sensors and the sensory or tactile input translated therefrom provided to the users) the real-time location of each person using only the "sense" provided to the user from the systems and methods of the present invention.

In some embodiments, the sensory enhancement provides a new means of communication by training the user to associate a tactile or other sensory input with some form of wireless, visual, audio, or tactile communication. Such systems find particular use with soldiers, emergency response personnel, hikers, mountain climbers and the like. In some embodiments, coded information is provided via wireless communication to a user through, for example, an electrotactile tongue system. With prior training, the user perceives the signal as language and understands the message. In some embodiments, two-way communication is provided. Examples 14 and 17, below, describe such embodiments in more detail. In some such embodiments, the user encodes a return message through the device located in the mouth through, for example, movement of the tongue or the touching of teeth. In addition to standard languages and coded languages, the system may be used to send alarm messages in a wide array of complexities. Additional information may also be provided, including, for example, the relative physical location of co-workers (e.g., firemen, soldiers, stranded persons, enemies). In some embodiments, the language transmitted by the system is a pictographic language. In some embodiments, information sent to the device (e.g., for covert communication) can come from any source (e.g., wireless Internet or telecommunications). It is contemplated that the device have two-way communication means (e.g., that allows the user to activate buttons or their equivalent with the tongue). Thus, in some embodiments, a subject can monitor and communicate with the Internet (e.g., perceive sports scores, stock prices, weather, etc.) or another user through the use of an in-mouth or under skin device.

In some embodiments, the sensory enhancement provides remote tactile sensations to a user. For example, surgeons may use the device to gain increased "touch" sensitivity during surgery or for remote surgery. An example of the former embodiments is described in Example 13. An example of the latter embodiments is also described in Example 13. In some such embodiments, the tactile interface with the user is a glove that provides tactile information to the fingers and/or hand. The glove receives signals from a remove location and permits the user to "feel" the remote environment. In other embodiments, the tactile interface is an alternative input, e.g., an electrotactile tongue array, that provides the user with sensitivity to a non-touch related aspect of the remote environment (e.g., electroconductivity of local tissue, or the presence or absence of chemical or biological indicators of tissue condition or type). In addition to medical uses, such application find use in distant robot control, remote sensing, space applications (grip control, surface texture/structure monitoring), and work in aggressive or hostile environments (e.g., work with pathogens, chemical spills, low-oxygen environment, battle zones, etc.). Thus, in some embodiments, the present invention provides brain-controlled robots. The robots can have a wide variety of sensors (e.g., providing position, balance, limb position, etc. information) including specific chemical, temperature, and/or tactile sensors. With the interface and with sufficient training, the human user will sense the robots environment on multiple levels as though the users brain occupied the robot's body.

In some embodiments, the sensory enhancement provides navigation information to a user. By associated the systems of the present invention with global positioning technology or other devices that provide geographic position or orientation information, users gain enhanced navigation abilities (See e.g., Example 14). Information about geographic features of the surrounding environment may also be provided to enhance navigation. For example, pilots or divers can sense hills, valleys, current (water or air), and the like. Firefighters can sense temperature and oxygen levels in addition to information about position and information about the structure or structural integrity of the surrounding environment.

In some embodiments the sensory enhancement provides improved control of industrial processes. For example, an operator in an industrial setting (e.g., manufacturing plant, nuclear power plant, warehouse, hospital, construction site, etc.) is provided with information pertaining to the status, location, position, function, emergency state, etc. of components in the industrial setting such that the operator has an ability to perceive the environment beyond sensory input provided by their vision, hearing, smell, etc. This finds particular use in settings where a controller is expected to manage complex instrumentation or systems to ensure safe or efficient operation. By sensing status or problems (e.g., unsafe temperatures or pressure, the presence of gas, radiation, chemical leakage, hardware or software failures, etc.) through, for example, information flow from monitoring device to the an electrotactile array on the operators body, the operator can respond to problems in real time with additional sensory bandwidth.

In addition to sensory substitution and sensory enhancement applications, the present invention also provides motor enhancement applications.

Experiments conducted during the development of the present invention identified improved motor skills subjects undergoing training with the systems and methods of the present invention (see e.g., Example 2). Subjects reported more fluid body movement, more fluid, confident, light, relaxed and quick reflexes, improved fine motor skills, stamina and energy, as well as improved emotional health. In particularly preferred embodiments, subjects undergo training (see e.g., Example 1) in a seated or standing position. Training includes maintaining body position while concentrating on a body position training procedure. An understanding of the mechanism is not necessary to practice the present invention and the present invention is not limited to any particular mechanism of action. However, it is contemplated that such training provides the benefits achieved by meditation and stress management exercises. Unlike meditation however, which takes substantial training and time commitment to achieve the benefits, the methods of the present invention achieve the same benefits with minimal training and time commitment. With little training and short exposure, subject obtain a wide range of improvements to physical and mental well-being. Thus, such methods find use by athletes, pilots, martial artists, sharp shooters, surgeons, and the general public to improve motor skills and posture control. The methods find particular use in embodiments where subjects seek to regain normal physical capabilities, such as after flight rehabilitation or in flight enhancement for astronauts. Such uses may be coupled with sensory enhancement and/or substitution. For example, a sharp shooter may use the system to gain enhanced motor control and focus, but also to use the system to transmit aiming information and/or to allow the shooter to sense their heart rate (to pull the trigger between heart beats) or environmental conditions to enhance accuracy.

In some embodiments, the present invention provides systems and methods for treating (e.g., independently or in combination with other programs or therapeutic treatments) individuals recovering from addiction to a substance (e.g., drugs, alcohol, and the like.). For example, in some embodiments, systems and methods of the present invention are used in rehabilitation settings (e.g., drug and alcohol rehabilitation programs). In some embodiments, systems and methods of the present invention reduce and/or correct symptoms (e.g., headache, nausea, dizziness, disorientation, and the like) associated with recovery (e.g., withdrawal) from an addictive substance (e.g., drug or alcohol).

The methods also find use in general enhancement of physical and emotional well-being. Examples 2-8 describe a wide range of benefits achieved by subjects. These benefits include, but are not limited to, relaxation, pain relief, improved sleep and the like. Thus, the methods find use in any area where meditation has shown benefit (e.g., post menopause recovery).

In some embodiments, the systems and methods of the present invention are used in combination with other therapies to provide an enhanced benefit. Such uses may, for example, allow for the lowering of drug dose of the complementary therapy to reduce side effects and toxicity.

In some embodiments, the systems are used diagnostically, to predict or monitor the onset or regression of systems or to otherwise monitor performance (e.g., by athletes). For example, the systems may be used to test proficiency in training exercise and to compare results to a database of "normal" and "non-normal" results to predict onset of an undesired physical state. For example, subjects taking gentamycin are monitored for loss of vestibular function to permit physicians to discontinue or alter treatment so as to prevent or reduce unwanted side effects of the drug. In such embodiments, head displacement as a function of body position may be monitored and compared to a normal baseline or to look for variation in a particular subject over time. Because posture and balance deteriorate with age, the system may also be used to as a biomarker of biological age of a subject. Diagnostic methods may be used as an initial screening method for subject or may be used to monitor status during or after some treatment course of action.

The systems and methods of the present invention also find use in providing a feeling of alternative reality through, for example, a combination of sensory substitution and sensory enhancement. Through balance training exercises, subjects can be made to experience a loss of balance or orientation. Images can also be projected to the subject to enhance the state of alternate reality. When combined with other sensory stimulation, the effect can provide entertainment or provide a healthy alternative for illegal drugs.

Sensory Input Devices

A wide range of sensory input devices find use with the present invention. In some preferred embodiments, the device provides one or more tactile stimulators that communicate (e.g., physically, electronically) with the surface of a subject (e.g., skin surface, tongue, internal surface). The number, size, density, and position (e.g., location and geometry) of stimulators are selected so as to be able to transmit the desired information to the subject for any particular application. For example, where the device is used as a simple alarm, a single stimulator may be sufficient. In embodiments where visual information is provided, more stimulators may be desired. In embodiments where only direction needs to be perceived, a limited ring of stimulators indicating 180-degree, 360-degree direction may be used (or 4 stimulators for N, W, E, S direction, used in combination to indicate intersections). In some embodiments, stimulators are positioned and signals are timed to produce a tactile phi phenomenon (i.e., an optical illusion in which the rapid appearance and disappearance of two stationary objects is perceived as the movement back and forth of a single object). With correct placement and timing, a "phantom" or apparent movement can be achieved in one or more directions. Using such a method increases the amount of information that can be conveyed with a limited number of stimulators. Increase in complexity of information with a limited set of stimulators may also be achieved by varying gradients of signal (intensity, pitch, spatial attribute, depth) to create a palette of tactile "colors" or sensations (e.g., paraplegics perceive one level of gradient as a "bladder full" alarm and another level of gradient with the same stimulator or stimulators as a "object in contact with skin" perception).

The nature of the sensors and devices may be dictated by the application. Examples include use of a microgravity sensor to provide vestibular information to an astronaut or a high performance pilot, and robotic and minimally invasive surgery devices that include MEMS technology sensors to provide touch, pressure, shear force, and temperature information to the surgeon, so that a cannula being manipulated into the heart could be "felt" as if it were the surgeon's own finger.

Particularly preferred embodiments of the present invention employ electrotactile input devices configured to transmit information to the tongue (See, e.g., U.S. Pat. No. 6,430,450, incorporated herein by reference in its entirety, which provides devices for electrotactile stimulation of the tongue). The present invention makes use of, but is not limited to, such devices. In some embodiments, a mouthpiece providing a simulator or an array of stimulators in used. In other embodiments, stimulators are implanted in the skin or in the mouth (see, e.g., WO 05/040989, incorporated by reference herein in its entirety). Additional devices are described in the Examples section, below.

Preferred devices of the present invention receive information via wireless communication to maximize ease of use.

The following embodiments are provided by way of example and are not intended to limit the invention to these particular configurations. Numerous other applications and configurations will be appreciated by those skilled in the art.

In preferred embodiments, the tongue display unit (TDU) has output coupling capacitors in series with each electrode to guarantee zero dc current to minimize potential skin irritation. The output resistance is approximately 1 kΩ. The design also employs switching circuitry to allow all electrodes that are not active or "on image" to serve as the electrical ground for the array, affording a return path for the stimulation current.

In preferred embodiments, electrotactile stimuli are delivered to the dorsum of the tongue via flexible electrode arrays placed in the mouth, with connection to the stimulator apparatus via a flat cable passing out of the mouth or through wireless communication technology. The electrotactile stimulus involves 40-μs pulses delivered sequentially to each of the active electrodes in the pattern. Bursts of three pulses each are delivered at a rate of 50 Hz with a 200 Hz pulse rate within a burst. This structure yields strong, comfortable electrotactile percepts. Positive pulses are used because they yield lower thresholds and a superior stimulus quality on the fingertips and on the tongue.

In some embodiments, electrodes comprise flat disc surfaces that contact the skin. Other embodiments employ different geometries such as concave or convex surfaces or pointed surfaces.

Experiments conducted during the development of the present invention have determined that the threshold of sensation and useful range of sensitivity, as a function of location on the tongue, is significantly inhomogeneous. Specifically, the front and medial portions of the tongue have a relatively low threshold of sensation, whereas the rear and lateral regions of the stimulation area are as much as 32% higher. Example 16 describes methods to optimize signaling for any particular application. The differences are likely due to the differences in tactile stimulator density and distribution. Concomitantly, the useful range of sensitivity to electrotactile stimulation varies as a function of location, and in a pattern similar to that for threshold.

To compensate for sensory inhomogeneity, the system utilizes a dynamic algorithm that allows the user to individually adjust both the mean stimulus level and the range of available intensity (as a function of tactor location) on the tongue. The algorithms are based on a linear regression model of the experimental data obtained. The results from the tests show that this significantly improved pattern perception performance.

The sensory input component of the system is either part of or in communication with a processor that is configured to: 1) receive information from a program or detector (e.g., accelerometer, video camera, audio source, tactile sensor, video game console, GPS device, robot, computer, etc.); 2) translate received information into a pattern to be transmitted to the sensory input component; 3) transmit information to the sensory input component; and/or 4) store and run training exercise programs; and/or 5) receive information from the sensory input component or other monitor of the subject; and/or 6) store and record information sent and received; and/or 7) send information to an external device (e.g., robotic arm).

Electrode arrays of the present invention may be provided on any type of device and in any shape or form desired. In some embodiments, the electrode arrays are included as part of objects a subject may otherwise possess (e.g., clothing, wristwatch, dental retainer, arm band, phone, PDA, etc.). For babies (e.g., to train blind infants), electrode arrays may be included in the nipples of food bottles or on pacifiers. In some embodiments, electrode arrays are implanted under the skin (an array tattoo) (See e.g., Example 18). In preferred embodiments, the device containing the array is in wireless communication with the processor that provides external information. In some preferred embodiments, the array is provided on a small patch or membrane that may be positioned on any external (including mucosal surfaces) or internal portion of the subject.

The devices may also be used to output signals, for example, by using the tongue as a controller of external systems or devices or to transmit communications. Example 17 provides a description of some such applications. In some embodiments, the tongue, via position, pressure, touching of buttons or sensor (e.g., located on the inside of the teeth) provides output signal to, for example, operate a wheelchair, prosthetic limb, robot device, medical device, vehicle, external sensor, or any other desired object or system. The output signal may be sent through cables to a processor or may be wireless.

Training Systems and Methods

Many of the applications described herein utilize a training program to permit the user to learn to associate particular patterns of sensory input information with external events or objects. The Examples section describes numerous different training routines that find use in different applications of the invention. The present invention provides software and hardware that facilitate such training. In some embodiments, the software not only initiates a training sequence (e.g., on a computer monitor), but also monitors and controls the amount of and location of signal sent to the tactile sensory device component. In some embodiments, the software also manages signals received from the tactile sensory device. In some embodiments, the training programs are tailored for children by providing a game environment to increase the interest of the children in completing the training exercises.

EXAMPLES

The following Examples are provided in order to demonstrate and further illustrate certain preferred embodiments and aspects of the present invention and are not to be construed as limiting the scope thereof.

Example 1

Vestibular Substitution for Posture Control

The vestibular system detects head movement by sensing head acceleration with specialized peripheral receptors in the inner ear that comprise semicircular canals and otolith organs. The vestibular system is important in virtually every aspect of daily life, because head acceleration information is essential for adequate behavior in three-dimensional space not only through vestibular reflexes that act constantly on somatic muscles and autonomic organs (see Wilson and Jones, Mammalian Vestibular Physiology, 2002, New York, Plenum), but also through various cognitive functions such as perception of self-movement (Buttner and Henn, Circularvection: psychophysics and single-unit recordings in the monkey, 374:274 (1981); Guedry et al., Aviat. Space Environ. Med., 50:205 (1979); Guedry et al., Aviat. Space Environ. Med., 52:304 (1981); Guedry et al., Brian Res. Bull., 47:475 (1998); Jell et al., Aviat. Space Environ. Med., 53:541 (1982); and Mergner et al., Patterns of vestibular and neck responses and their interaction: a comparison between cat cortical neurons and human psychophysics, 374:361 (1981)), spatial perception and memory (Berthoz et al., Spatial memory of body linear displacement: what is being stored? 269:95 (1995); Berthoz, The role of inhibition in the hierarchical gating of executed and imagined movements, 3:101 (1996); Bloomberg et al., Vestibular-contingent voluntary saccades based on cognitive estimates of remembered vestibular information, 41:71 (1988); and Nakamura and Bronstein, The perception of head and neck angular displacement in normal and labyrinthine-defective subjects. A quantitative study using a 'remembered saccade' technique, 188:1157 (1995)), visual spatial constancy (Anderson, Exp. Psychol. Hum. Percept. Perform., 15:363 (1989) and Bishop, Stereopsis and fusion, 26:17 (1974)), visual object motion perception (Mergner, Role of vestibular and neck inputs for the perception of object motion in space, 89:655 (1992) and Mesland, Object motion perception during ego-motion: patients with a complete loss of vestibular function vs. normals, 40:459 (1996)), and even locomotor navigation (Wiener, Spatial and behavioral correlates of striatal neurons in rats performing a self-initiated navigation task, 13:3802 (1993)). Vestibular input functions also include: egocentric sense of orientation, coordinate system, internal reference center, muscular tonus control, and body segment alignment (Honrubia and Greenfield, A novel psychophysical illusion resulting from interaction between horizontal vestibular and vertical pursuit stimulation, 19:513 (1998)).

Persons with bilateral vestibular damage, such as from an adverse reaction to antibiotic medications, experience functional difficulties that include postural "wobbling" (both sitting and standing), unstable gait, and oscillopsia that make it difficult or impossible, for example, to walk in the dark without risk of falling. Bilateral vestibular loss can be caused by drug toxicity, meningitis, physical damage or a number of other specific causes, but is most commonly due to unknown causes. It produces multiple problems with posture control, movement in space, including unsteady gait and various balance-related difficulties, like oscillopsia (Baloh, Changes in the human vestibulo-ocular reflex after loss of peripheral sensitivity, 16:222 (1991)). Unsteady gait is especially evident at night (or in persons with low visual acuity). The loss is particularly incapacitating for elderly persons.

Oscillopsia, due to the loss of vestibulo-ocular reflexes is a distressing illusory oscillation of the visual scene (Brant, Man in motion. Historical and clinical aspects of vestibular function. A review. 114:2159 (1991)). Oscillopsia is a permanent symptom. When walking, patients are unable to fixate on objects because the surroundings are bounding up and down. In order to see the faces of passerbies, they learn to stop and hold their heads still. When reading, such patients learn to place their hand on their chin to prevent slight movements associated with pulsation of blood flow.

In the absence of a functional vestibular system, the roles of the remaining inputs to the multisensory integration process of normal upright posture are amplified. Under these circumstances, subjects extensively use the fingertips to provide additional spatial orientation cues.

The systems and methods of the present invention provide alternative, and substantially better cues. The use of vestibular sensory substitution produces a strong stabilization effect on head and body coordination in subjects with BVD. Under experimental conditions, three characteristic and unique motion features (mean-position drift, sway, and periodic large-amplitude perturbations) were identified that consistently appear in the head-postural behavior of BVD subject. With vestibular substitution, however, the magnitude of these features are greatly reduced or eliminated. During the experiments, the BVD subjects reported feeling normal, stable, or having reduced perceptual "noise" while using the system and for periods after removing the stimulation.

For experiments conducted during the development of the present invention, subjects with bilateral vestibular loss, the most severe damage possible to the balance sensory system, were selected. All of the subjects were identified as disabled or handicapped.

Device:

A miniature 2-axis accelerometer (Analog Devices ADXL202) was mounted on a low-mass plastic hard hat. Anterior-posterior and medial-lateral angular displacement data (derived by double integration of the acceleration data) were fed to a tongue display unit (TDU) that generates a patterned stimulus on a 144-point electrotactile array (12×12 matrix of 1.5 mm diameter gold-plated electrodes on 2.3 mm centers) held against the superior, anterior surface of the tongue (Tyler et al., J. Integr. Neurosci., 2:159 (2003)).

Head-Motion Sensing

The accelerometer is nominally oriented in the horizontal plane. In this position, it normally senses both rotation and translation. However, given the nature of the task—quiet upright sitting, at least to a first approximation, all non-zero acceleration data recorded in both the x- and y-axis (the M/L and A/P direction, respectively), can be ascribed to angular displacement or tilt of the head and not translation. After instructing the subject to assume the test position, the initial value of the sensor is recorded at the start of each trail and subsequently used as the zero-reference. Using a small angle approximation, and given that the sensor output is proportional to the angular displacement from the zero position, the instantaneous angle is calculated as:

$$\Theta_x = \sin^{-1} a_x/g \qquad (\text{Eq. 1})$$

$$\Theta_y = \sin^{-1} a_y/g \qquad (\text{Eq. 2})$$

where g is the gravity vector and both $a_x$ and $a_y$ are the vector components in the respective axis.

"Target" Motion Control

The tilt data from the accelerometer is used to drive the position of both the visual and tactile stimulus pattern or 'target' presented on the respective displays. The data is sampled at 30 Hz and the instantaneous x and y vales for the target position is calculated as the difference between the values of the position vector at $t_n$ and $t_o$, by:

$$x_n = c \sin(\Theta_{x|n} - \Theta_{x|0}) \qquad (\text{Eq. 3})$$

$$y_n = c \sin(\Theta_{y|n} - \Theta_{y|0}) \qquad (\text{Eq. 4})$$

where the values for $\Theta_{x|n}$, $\Theta_{x|0}$, $\Theta_{y|n}$, and $\Theta_{y|0}$ are the instantaneous and initial tile angles in x and y, respectively. A linear scaling factor, 'c', is used to adjust the range of target movement to match that of the subject's anticipated or observed head-tilt. To prevent disorientation due to stimulus transits off the display in the event the subject momentarily exceeds the maximum range initially calculated, the maximum displacement of the target is band limited to the physical area of the display. This gain can be easily adjusted to the match maximum expected range of motion. The actual stimulation pattern on the tongue display is a 4 tactor (2×2) square array whose area centroid is located at $x_n$, $y_n$ at any instant in time. After calibration at the initial upright condition, the subject then moves the head to keep the target centered in the middle of the display to maintain proper posture. For initial training a visual analog of the outside edge of the square tactile array is presented on an LCD monitor. The resultant position vector used to drive the visual target motion is low pass filtered at 10 Hz, and smoothed using a 20-sample moving-window average to make the image more stable.

Subjects readily perceived both position and motion of a small 'target' stimulus on the tongue display, and interpreted this information to make corrective postural adjustments, causing the target stimulus to become centered.

Signals from the accelerometer, located in the hat on top of the head, deliver position information to the brain via an array of gold plated electrodes in contact with the tongue. Continuous recording from the accelerometer produced the head base stabilogram (HBS). The HBS is the major component of the data recording and analysis system.

Subjects:

Ten individuals with bilateral vestibular dysfunction (BVD) tested and trained using the Electro-tactile Vestibular Substitution System (EVSS). Five participants were female and five were male. The average age of the female group was 51.4 years with the average age of the male group being 64.4 years.

Of both groups, the dysfunction of seven of the participants was a result of ototoxicity from the use of the aminogylcoside antibiotic gentamycin. One subject had a Mal de Debarquement syndrome, one patient had vestibular dysfunction as a result of bilateral surgery to correct perilymphatic fistulas, and one subject's loss of vestibular functions bilaterally was a result of an unknown phenomenon.

Testing and Training Procedure:

To determine abilities prior to testing, each subject completed a health questionnaire as well as a task ability questionnaire, along with the required informed consents forms. Prior to testing, each individual was put through a series of baseline tests to observe their abilities in regards to balance and visual control (oscillopsia). These baseline tests were videotaped.

Prior to undergoing any 20-minute trials, each individual underwent a series of data captures with the EVSS designed to obtain preliminary balance ability baselines as well as to train them in the feel and use of the system. These data captures included 100, 200 and 300-second trials both sitting and standing, eyes open and eyes closed.

Upon completion of the balance ability baselines and confirmation from the subjects that they fully understood the EVSS and how it operates, each individual proceeded into the 20 minute trials and/or were trained to stand on soft materials or in tandem Romberg posture. For all patients, both conditions were "unimaginable" to perform. Indeed, none of the subjects could complete more than 5-10 seconds stance in any conditions.

Typical testing/training included 9 sessions 1.5-2 hours long (depending on patient stamina and test difficulty). The shortest series a patient completed was five sessions, while the longest for 65 sessions.

Results:

As a result of training procedures with the EVSS, all ten patients demonstrated significant improvement in balance control. However, speed and depth of balance recovery varied from subject to subject. Moreover, it was found that training with the EVSS demonstrated not one, but rather several different effects or levels of balance recovery.

Balance recovery effects of EVSS training can be separated into at least two groups: direct balance effects and residual balance effect. In addition to balance recovery effects, it was found that multiple effects directly or indirectly related to the vesitibular system were observed (see Examples 2-8).

Immediate Effect:

The immediate effect was observed in the sitting and standing BVD subjects almost immediately (after 5-10 minutes of familiarization with EVSS) and included the ability to control stable vertical posture and body alignment (sitting or standing with closed eyes) during extended periods (up to 40 minutes after 1-2 experimental sessions).

Training Effect:

Some of the BVD patients, especially after long periods of compensation and extensive physical training during many years, had developed the ability to stand straight, even with closed eyes, on hard surface. However, even for well-compensated BVD subjects standing on soft or uneven surfaces or stance with limited bases such as during a tandem Romberg stance, standing was challenging, and unthinkable with closed eyes.

Using the EVSS, BVD patients not only acquired the ability to control balance and body alignment standing on hard surfaces, but also the ability to extend the limits of their physical conditioning and balance control. As an example, standing in the tandem Romberg stance with closed eyes became possible. After one training session of 18 training trials each 100 seconds long (total EVSS exposure time 30 minutes), a BVD patient was capable of standing in the tandem Romberg stand with closed eyes for 100 seconds.

Residual Balance Effects:

Residual balance effects also were observed in all tested BVD patients; however strength and extent of effects significantly varied from subject to subject depending on the severity of vestibular damage, the time of subject recovery, and the length and intensity of EVSS training.

At least three groups of residual balance effects were noted: short term residual effects (sustained for a few minutes), long term residual effects (sustained for 1 to 12 hours) and a rehabilitation effect that was observed during several months of training in a subject. All residual effects were observed after complete removal of EVSS from the subject's mouth.

Short Term after Effects:

This effect usually was observed during the initial stages of EVSS training Subjects were able to keep balance for some period of time, without immediately developing an abnormal sway; as it usually occurred after any other kind of external tactile stabilization, like touching a wall or table. Moreover, the length of short term aftereffects was almost linearly dependent on the time of EVSS exposure. After 100 seconds of EVSS exposure, stabilization continued during 30-35 seconds, after 200 seconds EVSS exposure 65-70 seconds and after 300 seconds EVSS trial the subject was able to maintain balance for more than 100 seconds. Short term after-effect continued during approximately 30-70% of the EVSS exposure time.

Long Term after Effects:

This group of effects developed after longer (e.g., up to 20-40 minutes) sessions of EVSS training in sitting or standing subjects and continued for a few hours. The duration of the balance improvement after-effect was much longer than after the observed short-term after effect: instead of the expected seven minutes of stability (if one were to extrapolate the 30% rule on 20 minute trials), from one to six hours of improved stability was observed. During these hours BVD subjects were able to not only stand still and straight on a hard or soft surface, but were also able to accomplish completely different kinds of balance-challenging activities, like walking on a beam, standing on one leg, riding a bicycle, and dancing. However, after a few hours all symptoms returned.

The strength of long term after effects was also dependent on the time of EVSS exposure: 10 minute trials were much less efficient than 20 minute trials, but 40 minutes trails had about the same efficiency as 20 minutes. Usually, 20-25 minutes was the longest comfortable and sufficient interval for standing trials with closed eyes. Sitting trials were less effective than standing trials.

The shortest effects were observed during initial training sessions, usually 1-2 hours. The longest effect after a single EVSS exposure was 11-12 hours. The average duration of long term after effects after single 20 minute EVSS exposure was 4-6 hours.

Rehabilitation Effect:

It was possible to repeat two or three 20-minute EVSS exposures to a single subject during one day. After the second exposure, the effect was continued in average about 6 hours. In total, after two 20-minute EVSS stabilization trials, BVD subjects were capable of feeling and behaving what they described as "normal" for up to 10-14 hours a day.

One BVD subject was trained continuously during 20 weeks, using one or two 20-minute EVSS trials a day. The data collected on this subject demonstrated a systematic improvement and gradual increase of the long-term aftereffect during consistent training. Moreover, it was found that repetitive EVSS training produced both accumulated improvement in balance control, and global recovery of the central mechanisms of the vestibular system.

For the same BVD subject, after two months of intensive training, EVSS exposure was completely stopped. Regular checking of the subject's balance and posture control were continued. During the 14 weeks after the last EVSS training, the subject was able to stay perfectly still with closed eyes, while standing for 20 minutes on hard or soft surfaces. This demonstrated rehabilitation capability of the method. Effects have been seen for over six months.

Summary of Effects:

Subjects experienced the return of their sense of balance, increased body control, steadiness, and a sense of being centered. The constant sense of moving disappeared. The subjects were able to walk unassisted, reported increased ability to walk in dark environments, to walk briskly, to walk in crowds, and to walk on patterned surfaces. Subjects gained the ability to stand with their eyes closed with or without a soft base, to walk a straight line, to walk while looking side-to-side and up and down. Subjects gained the ability to carry items, walk on uneven surfaces, walk up and down embankments, and to ride a bike. Subjects became willing to attempt new challenges and, in general, became much more physically active.

Although discussed above in the context of persons with bilateral vestibular loss, the invention finds use with many types of vestibular dysfunction and persons with Meniere's disease, Parkinson's disease, persons with diabetic peripheral neuropathy, and general disability due to aging. The invention also has applicability to the field of aviation to avoid spatial disorientation in aircraft pilots or astronauts.

Additional data. A subject with BVL due to gentamicin ototoxicity was treated for one week with the systems and methods of the present invention. The subject's response to treatment is documented in Table 1 below.

TABLE 1

| Test | Pre-treatments Score | Post-treatment Score |
| --- | --- | --- |
| Neurocom SOT composite | 31 | 47 |
| Total # of falls on SOT | 7 | 6 |
| # of falls on SOT 5 and 6 | 6 | 6 |
| Dynamic Gait Index | 21/24 | 24/24 (24 best) |
| Activities-Specific Balance Confidence Scale | 64/100 | 85/100 (100 best) |
| Dizziness Handicap Inventory | 74/100 | 0/100 (0 best) |

As described in Table 1 above, the subject demonstrated improvements with the quality of life indicators (ABC, DHI), and on the SOT. Walking in crowds became significantly easier for the subject.

Example 2

Improved Posture, Proprioception and Motor Control

Experiments conducted during the development of the present invention identified unexpected benefits in improved posture, proprioception, and motor control of subjects. Training was conducted with an EVSS as described in Example 1. Observation of and questioning of subjects demonstrated that body movements became more fluid, confident, light, relaxed and quick. Stiffness disappeared, with limbs, head and body feeling lighter and less constricted. Fine motor skills returned, and gait returned to normal. Posture and body segment alignment returned to normal. Stamina and energy increased. There was an increased ability to drive both for daytime and night driving.

Example 3

Improved Vision

Experiments conducted during the development of the present invention identified unexpected benefits in vision of subjects. Training was conducted with an EVSS as described in Example 1. Observation of and questioning of subjects demonstrated that vision became more stable, clearer, and brighter. Colors were also brighter and sharper, and peripheral vision widened. Reading became smoother and easier, and it was possible to read in a moving vehicle. There were strong improvements in adaptation during transition from light to dark conditions. There was a reduction of oscillopsia and an improved depth perception.

Example 4

Improved Cognitive Functions

Experiments conducted during the development of the present invention identified unexpected benefits in cognitive function of subjects. Training was conducted with an EVSS as described in Example 1. Observation of and questioning of subjects demonstrated increases in mental awareness, creativity, clarity of thinking, confidence, multitasking skills, memory retention, concentration ability, and ability to track conversations and stay on task. Subjects felt more alert and energized, and ceased the constant awareness of balance. There was less "noise" in the head, much improvement in intensity of thinking, problem solving and decision-making.

Example 5

Improved Emotional Well being

Experiments conducted during the development of the present invention identified unexpected benefits in emotional conditions of subjects. Training was conducted with an EVSS as described in Example 1. Observation of and questioning of subjects demonstrated that subjects felt calmer, aware, confident, happy, quiet, refreshed, relaxed, a strong sense of well being, and elimination of fear.

Example 6

Improved Sleep

Experiments conducted during the development of the present invention identified unexpected benefits in sleep of subjects. Training was conducted with an EVSS as described in Example 1. Observation of and questioning of subjects demonstrated that a majority of patients noticed sleep improvement. Sleep became fuller, longer, and more restful, often with no awakenings during the night.

Example 7

Improved Sense of Physical Well being

Experiments conducted during the development of the present invention identified unexpected benefits in sense of physical well being of subjects. Training was conducted with an EVSS as described in Example 1. Observation of and questioning of subjects demonstrated a feeling of youth and vibrancy, with brighter eyes and a reduction of stress, lifting and relaxation of face muscles resulting in a "younger look." Some subject reported fewer visits to a chiropractor and increased activity.

Example 8

Treatment Tinnitus

Experiments conducted during the development of the present invention identified unexpected benefits in relieving tinnitus. Training was conducted with an EVSS as described in Example 1. A subject with tinnitus reported a reduction in symptoms.

Example 9

Sex Sensation Substitution

In some embodiments, the present invention provides systems and methods for sex sensation tactile substitution for, for example, persons with spinal chord injury that have lost sensation below the level of the injury. With training, such subjects recover, at least to some extent, sexual sensation.

Experiments conducted during the development of the present invention have demonstrated that tactile human-machine interfaces (HMI) allow artificial sensors to deliver information to the brain to mobilize the capacity of the brain to permit functional sensory and motor reorganization in persons who are bind, deaf, have loss of vestibular system, or skin sensation loss from Leprosy. Experiments also demonstrated that a substitute system can re-establish natural function is a small amount of surviving tissue is present after a lesion. Thus, in addition to providing sensory substitution, the systems of the present invention achieve a therapeutic effect. While this example describes application to sex sensation substitution, it is understood that the same techniques may be used for other sensory losses and for recovery of motor functions in spinal chord injury (SCI).

Decrease in sexual function after spinal cord injury is a major cause of decreased quality of life for both men and women. Treatment of sexual dysfunction in the SCI population has focused on the restoration of erectile function. However, sensation is impaired in the vast majority of the SCI population, which is much more difficult to treat. Loss of orgasm appears to be the major SCI sexual problem, the loss mainly being due to loss of sensation. Women with complete loss of vaginal sensation can reach orgasm by caressing of other parts of the body that have intact sensibility for touch (e.g., ear-lobes, nipples) and some men can be taught to achieve orgasm (not to be confused with ejaculation) from comparable caressing. However, there is no known technique available to re-establish or substitute penile sensibility in these patients. Such sensibility is, for most men, a prerequisite to reaching orgasm.

With sensory substitution systems of the present invention, information reaches the perceptual levels for analysis and interpretation via somatosensory pathways and structures. In some embodiments, a genital sensor with pressure and/or temperature transducers is utilized to relay the pressure and/or temperature patterns experienced by the genitals via tactile stimulation to an area of the body that has sensation (e.g., tongue, forehead, etc.). With training, subjects are able to distinguish rough versus smooth surfaces, soft and hard objects, and structure and pressure. The subject perceives the information as coming from the genitals. Thus, even though that actual man-machine interface is not on the genitals, the subject perceives the sensation on the genitals, as his/her perception over the placement of the substitute tactile array directs the localization in space to the surface where the stimulation.

In some embodiments, the present invention provides a penile sheath with embedded sensors and radiofrequency (e.g., BlueTooth) transmission to an electrotactile array built into a dental orthodontic retainer that is contacted by the tongue of the user. This system, with minimum training, provides sexual sensation for spinal cord injured men and women (for whom the penile sheath will be worn by her partner).

In one embodiment, the electrotactile array has 16 stimulators. The sheath likewise has 16 sensors. The sheath is made of an elastic and cloth matrix, such as that used in stump socks for amputees. The sheath is molded over an artificial penis, with the sensors arranged in four rings of four, each sensor at in $\pi/2$ increments (radially) about the principal axis of the cylinder. Each sensor is approximately 5 mm in diameter and the ring is placed at 10 mm intervals, beginning at the distal end of the cylindrical portion of the sheath. The sensors are attached with a silicon adhesive with the lead wires traveling to the base of the sheath from where a BlueTooth device transmits the sensory information to the tongue interface. Over this entire sheath structure is applied an off-the-shelf condom. The system is thus designed to prevent the subjects from coming into direct contact with the sensing array electronics, to provide as natural as possible sensation, and to avoid contaminating the sheath in the event that the subject ejaculates.

In some embodiments, a more advance system is used with shear sensitive semiconductor-based tactile sensors and miniaturized integrated electronics. The advanced system has a greater number of sensors and refinement of an application of the Phi effect (perception moving in between stimulating electrodes) and the ability to control the type of input signal. Because shear is a vector, it is contemplated that the components of the sensory output create a more sophisticated stimulation signal, allowing for the addition of a greater variety of possible sensations or 'color' qualities to the electrotactile stimulus. In some embodiments, the system includes multiplexed input from several sensory substitution systems simultaneously, such as for foot and lower limb position information to aid in ambulation, and for bladder, bowel and skin input.

The tongue electrode array is built into an esthetically designed clamshell that is held in the mouth and contains 16 stimulus electrodes. The pulses are created by a 16-channel electrotactile waveform generator and accompanying scripting software that specifies and controls stimulus waveforms and trial events. A custom voltage-to-current converter circuit provides the driving capability (5-15 V) for the tongue electrode, having an output resistance of this circuit of approximately 500 k$\Omega$. Active or 'on' electrodes (according to the particular pattern of stimulation) deliver bursts of positive, functionally-monophasic (zero net dc) current pulses to the exploring area on the tongue, each electrode having the same waveform. The nominal stimulation current (0.4-4.0 mA) is identical for all active or 'on pattern' electrodes on the array, while inactive or 'off pattern' electrodes are effectively open circuits. Preliminary experiments identified this waveform as having the best sensation quality for the particular electrode size, array configuration, and timing requirements for stimulating all electrodes. The quality and intensity of the sensation on the tongue display is controlled by manipulating the parameters of the waveform and may be done by input from external devices (both analog and digital) as well as computers or related devices (e.g., signals sent over an Internet).

In some embodiments, subjects are trained to use the equipment. As a first exercise, subjects are instructed how to place the tongue array in the mouth and to set/optimize the comfort level of the stimulus. With an artificial penis as a model, the subjects then are shown how to place the sensory sheath over an erect penis. Sexual encounters are then used with the system to optimize settings for manual stimulation, vaginal stimulation, and the like, intensity, etc.

Example 10

Tactile Multimedia

The present invention provides system and methods for enhanced multimedia experiences. In some embodiments, existing multimedia information is transmitted via the systems of the present invention to provide enhanced, replacement, or extra-sensory perception of the multimedia event. In other embodiments, multimedia applications are provided with a layer of additional information intended to create enhanced, replacement, or extra-sensory perception.

Experiments conducted during the development of the present invention have demonstrated that visual information not perceived by the eyes can be imparted by the systems of the present invention. In particular, subjects lacking vision or with closed eyes were able to navigate a graphic maze through the transmission of the maze information from a computer program to the subject through a tongue-based electrotactile system.

One application of the systems of the present invention is to provide enhanced perception for video game play. For example, a game player can gain "eyes in the back of their head" through the transmission of information pertaining to the location of a video object not in the field of view to a stimulator array configured to relay the information to the tongue of the user. With minimal training, the user will "see" and respond to both the presence and location of video objects outside of their normal field of vision. The sensory information may be imparted through tactile stimulation to the hands via a traditional joystick or game controller, or may be through the tongue or other desired location. The ability to operate extra-sensorialy may be integrated into game play. For example, games or portion of games may be conducted "blind" (e.g., closing of eyes, blackout of audio and/or video, etc.). Such games find use for entertainment, but also for training (e.g., flight simulation training, military training to operate in night vision mode, under water, etc.). Balance, emotional comfort level, physical comfort level, etc. may all be altered to enhance game play.

Thus, in some embodiments, the present invention provides game modules (e.g., PlayStation, XBox, Nintendo, PC, etc.) that comprise, or are configured to receive, a hardware component that contains a stimulator array for transmitting information to a subject through, for example, electrotactile stimulation (e.g., via a tongue array, a glove, etc.). In some embodiments, software is provided that is compatible with such game modules or configured to translate signal provided by such game modules, wherein the software encodes information suitable for use with the systems and methods of the present invention. In some embodiments, the software encodes a training program that provides a training exercise that permits the user to learn to associate the transmitted information with the intended sensory perception. The subject proceeds to actual gameplay after completing the training the exercise or exercises. In some embodiments, a video camera is simply pointed at existing video game displays and relays the video information to a user though the systems of the present invention. The use can play the game solely using this information (e.g., without looking at the video screen) or can use this information to enhance sensory perception while viewing the video screen.

In some embodiments, media content is layered with sensate information. Certain non-limiting embodiments include:

Sensate movies that carry any kind of sensory messages: the sensation of a kiss; the heat of a fire; or the scratch of a cat.

Sensate Internet that allows the user at home to feel the texture of a dress or suit; allows a surgeon to perform a telerobotic operation; and provides sexual feedback to one or more body parts from a long distance partner.

Sensate telephones, video games, etc.

In some embodiments, the present invention provides a body suit (e.g., full-body suit) that contains stimulators on multiple body parts (e.g., all over the body). Subsets of the stimulators are triggered in response to information obtained from a program, movie, interactive Internet site, etc. For example, in Internet sex applications a subject receives information from a program or from an individual located elsewhere that activates stimulator groups to simulate touching, body to body contact, other types of contact, kissing, and intercourse. Visual information may also be conveyed either through sensory substitution or directly through a visor (providing video, snapshot images, virtual reality images, etc.). Sound (e.g., voice) may be provided by sensory substitution or traditional channels (e.g., telephone line, realtime via streaming media, etc.). In some embodiments, the body suit has higher stimulator density in regions typical engaged in sexual contact. The suit may cover the entire body or particular desired portions. In some embodiments, the user sets a series of parameters in the control software to designate levels of stimulation desired or undesired, activities desired or undesired, and the like. In some embodiments, the system provides privacy features and security features, to, for example, only permit certain partners to participate. In some embodiments, a registry service is provided to ensure that participates are honest and legal with respect to age, gender, or other criteria.

Example 11

Lipreading Applications

Many people with hearing impairment recognize the spoken word by the process of lipreading, i.e., recognizing the words being spoken by the movement of the lips and face of the speaker. Lipreaders, however, cannot resolve all spoken words and have difficulty with meaning that is carried in intonation. In addition, lipreaders do not have access to the full syllabic structure of speech.

Word spotting, as it is called in the speech-processing field, is a difficult computational task. For example, some different sounds do not to look very different on the lips. Lipreading is plagued by homophenes, i.e., speech sounds, words, phrases, etc., that are identical or nearly identical on the lips. For example, the bilabial consonants "p", "b", and "m" sound different, but they are identical on the lips. For the words "park", "bark", and "mark", the difference between /b/ and /p/ is that in the former the vocal folds start vibrating upon lip opening, whereas they remain open for around 30 ms longer with /p/. This cannot be seen, so these words appear identical. The nasal /m/ is produced by lowering the velum and allowing the air stream to escape via the nasal cavity. Again, this action cannot be seen, so /p, b, m/ form one homophenous group.

There are 24 consonants in English. Each one is a distinct unit to the normal hearing listener, but the information available via lipreading is much less. For example, when the consonants are presented to a lipreader, e.g., sound grouping such as [apa], [aba], [ama], etc., even the best lipreaders have difficulties. Lipreaders will confuse those consonants that share the same place of articulation where the sound is produced, for example, the lips, the alveolar, etc. This means that the set of 24 is reduced to a much smaller number. Sets of sounds that appear the same to a lipreader include the following:

| 1. | Bilabials | p, b, m |
| 2. | Labio-dentals | f, v |
| 3. | Interdentals | th, th |
| 4. | Rounded labials | w, r |
| 5. | Alveolars | t, d, n, l, s, z |
| 6. | Post-alveolars | sh, zh, ch, j |
| 7 | Palatals and velars | y, k, g, ng |
| 8 | Glottal | h |

Vowels are also a great problem because many appear to be almost identical on the lips. The lipreader has very little access to suprasegmental information intonation, pitch changes, rate, etc. and this again makes the task of understanding potentially ambiguous sentences so much harder. The lack of access to many cues obviously results in a reduced amount of sensory information. As a result, lipreaders have to work harder to derive understanding from speech.

Part of the problem though is that syllable boundaries are blurred by the presence of voicing continuant consonants. Information that would enable the lipreader to reliably identify whether a consonant is voiced or voiceless is found in the low frequencies of speech (100 500 Hz). Information on high frequency speech energy (the region above 5 kHz) can allow the lipreader to reliably identify the sibilant consonants /s, z, sh, zh/ and their affricate cousins.

There have been numerous tactual devices developed to aid lip-readers, two examples being the Tactaid (Audiological Engineering, Somerville, Mass.) and the Minivib (KTH, Stockholm, Sweden). Both of these are vibrotactile (i.e., vibrating) devices for use on the hand or wrist. These devices present one or two channels of limited information, they do not remove a sufficient amount of ambiguity in lipreading mentioned earlier and they are not convenient to use.

Other approaches to lipreading technology include systems to permit lipreading while using a telephone by presenting the remote caller as a speaking avatar whose lips can be read on the computer screen (The SpeechView (Tikva, Israel), and speech-to-text processors. The KTH at the Royal Swedish Academy in Stockholm speech processing group is working on a quasi speech-to-text project, Syn-Face, under license with Microsoft. Microsoft purchased the Entropics Software company that developed products called wave surfer and waves+ for word spotting using pitch and formant algorithms. Commercially available speech-to-text word processing software IBM Via Voice and Dragon Naturally Speaking are useful products but they require specific-speaker training for use, and thus are not applicable to the problem of reading the lips of speakers in general. The lipreading system of the present invention provides more useful information in a higher quality and more flexible display format than is currently available.

Cues from tactile aids for lipreading can provide access to the syllabic structure of speech and, when used together with lip-reading cues, can improve the speed and accuracy of lip reading. For example, a tactile aid cue may be triggered when the intensity or another measurable feature of a speech unit falls within predetermined range or level, e.g., every time a particular vowel or a vowel-like consonant such (e.g., w, r, l, y) is produced. A cue of this kind to the listener from the tactile aid provides additional information on the syllabic structure, and thus the meaning, of the speech.

In preferred embodiments, the present invention makes use of electrotactile input devices using the tongue as a stimulation site. In some embodiments, a mouthpiece providing a simulator or an array of stimulators in used. In other embodiments, stimulators are implanted in the skin or in the mouth.

The detected speech signal is processed for transmission to the sensory input device. Processing may be done, e.g., with the software-based virtual instrument environment Labview, National Instruments (Austin, Tex.). Labview transfers the processed information to the tongue display stimulator e.g., via a dll-driven USB interface (DLP Design, San Diego, Calif.). The stimulator processes the information into four channels of spatial and amplitude display for the tongue.

Supplemental Information Supplied Via the Tongue

In some embodiments, the following information is provided via the tongue, with the intention of reducing the inherent ambiguity in lipreading.

1) Partial access to the word structure of speech.
   High-pass filtering of raw speech above 500 Hz to give cues about word spotting. Together with item #4 below this gives access the syllabic structure of speech
2) Determine whether a consonant is voiced or voiceless
   Band pass filtering 100 Hz to 500 Hz—this cues whether a consonant was oral or nasal. Activity in this range indicates a nasal consonant.
3) High frequency information to identify the sibilant consonants /s, z, sh, zh/ and the related sounds of /ch, j/. High pass filter above 5 kHz.
4) Recognition of vowels and vowel-like consonants /w, r, l, y/—gives good cues to the syllabic structure of speech.
   Amplitude threshold sensor such that a signal is given each time the threshold is crossed.

The information is presented to the tongue in two major forms:
1. A signal similar to an oscilloscope tracing. A moving time tracing 6 electrodes wide (approximately 12 mm) with 3 electrodes above and 2 electrodes below the baseline for amplitude deviations.
2. An indicator of activity, such a blinking dot, to indicate the presence of sound energy in a particular frequency band like above 5 kHz to distinguish fricatives or that an amplitude threshold has be crossed to indicate the presence of a vowel.

In the case of amplitude thresholds relative amplitude threshold compared to a moving average can be used to compensate for mean changes in speech volume and ambient noise.

In addition to the all the visual information available to lip readers, the subjects perceive speech with their tongues and integrate the additional information into their linguistic interpretation. The supplemental information feels like unobtrusive buzzing on the tongue with varying spatial and intensity information. Experience with the tongue display has shown that subjects learn to ignore the tongue sensations while attending to the information presented.

In some embodiments, a fifth channel of higher complexity level sound and word identification via more information-rich codes memorized by the subjects may be used to further reduce ambiguity in lip reading.

Training

In some embodiments, the present invention comprises specific training. In some embodiments, the training comprises:

1:1 training: A training program comprising practice in the use of the tactile device as a supplement to lipreading. In each session the subject receives training in the following areas:

Consonants—practice recognition of consonants in the /aCa/ environment only—1 list (5 random presentations of each consonant) via lipreading alone, and lipreading plus the tactile device.

Words—practice recognition of the 500 most common words in English via lipreading alone and lipreading plus the tactile device. The words are presented in blocks of 10 words with the subject having to attain a criterion level of 90% correct for 10 random presentations of each word before proceeding to the next block. At the completion of five blocks, each of the words is presented for identification twice in a random order.

Phrases and Sentences—provide practice in the recognition of phrases and sentences consisting of the 500 most frequently used words of English. The sentences are presented in blocks of 10, and the subject is expected to score 95% correct before proceeding to the next block.

Speech Tracking—the subject is administered multiple tracking sessions, e.g., 4×5 minutes, via lipreading alone and lipreading plus the tactile device using the KTH modification of the Speech Tracking procedure. This is a computer-assisted procedure that allows live-voice presentation, but computer scoring of all errors and responses. Speech Tracking (De Filippo and Scott, 1978) requires the talker to present a story phrase by phrase for identification. The receiver's task is to repeat the phrase/sentence verbatim, no errors are allowed. If the receiver is unable to identify a word correctly it will be repeated twice. If s/he is still unable to identify the word, it will be shown to her/him via a computer monitor. At the completion of each five-minute block, the following measures are made automatically:
1. Tracking Rate in words-per-minute
2. Ceiling Rate in words-per-minute
3. The Proportion of Words in the passage that have to be repeated
4. The number of words displayed via the monitor
5. The identity of ALL words repeated once, twice, and three times.

Example 12

Vision Sensory Substitution

Mediated by the receptors, energy transduced from any of a variety of artificial sensors (e.g., camera, pressure sensor, displacement, etc.) is encoded as neural pulse trains. In this manner, the brain is able to recreate "visual" images that originate in, for example, a TV camera. Indeed, after sufficient training subjects, who were blind, reported experiencing images in space, instead of on the skin. They learned to make perceptual judgments using visual means of analysis, such as perspective, parallax, looming and zooming, and depth judgments. Although the systems used with these subjects have only had between 100 and 1032-point arrays, the low resolution has been sufficient to perform complex perception and "eye"-hand coordination tasks. These have included facial recognition, accurate judgment of speed and direction of a rolling ball with over 95% accuracy in batting the ball as it rolls.

We see with the brain, not the eyes; images that pass through our pupils go no further than the retina. From there image information travels to the rest of the brain by means of coded pulse trains, and the brain, being highly plastic, can learn to interpret them in visual terms. Perceptual levels of the brain interpret the spatially encoded neural activity, modified and augmented by nonsynaptic and other brain plasticity mechanisms. However, the cognitive value of that information is not merely a process of image analysis. Perception of the image relies on memory, learning, contextual interpretation (e.g. we perceive intent of the driver in the slight lateral movements of a car in front of us on the highway), cultural, and other social factors that are probably exclusively human characteristics that provide "qualia."

The systems of the present invention may be characterized as a humanistic intelligence system. They represent a symbiosis between instrumentation, e.g., an artificial sensor array (TV camera) and computational equipment, and the human user. This is made possible by "instrumental sensory plasticity", the capacity of the brain to reorganize when there is: (a) functional demand, (b) the sensor technology to fill that demand, and (c) the training and psychosocial factors that support the functional demand. To constitute such a systems then, it is only necessary to present environmental information from an artificial sensor in a form of energy that can be mediated by the receptors at the human-machine interface, and for the brain, through a motor system (e.g., a head-mounted camera under the motor control of the neck muscles), to determine the origin of the information.

A simple example of sensory substitution system is a blind person navigating with a long cane, who perceives a step, a curb, a foot and a puddle of water, but during those perceptual tasks is unaware of any sensation in the hand (in which the biological sensors are located), or of moving the arm and hand holding the cane. Rather, he perceives elements in his environment as mental images derived from tactile information originating from the tip of the cane. This can now be extended into other domains with systems of the present invention associated with artificial sensory receptors such as a miniature TV camera for blind persons, a MEMS technology accelerometer for providing substitute vestibular information for persons with bilateral vestibular loss, touch and shear-force sensors to provide information for spinal cord injured persons, from an instrumented condom for replacing lost sex sensation, or for a sensate robotic hand.

Although the systems used in experiments conducted during the development of the present invention have only had between 100 and 1032 point arrays, the low resolution has been sufficient to perform complex perception and "eye"-hand coordination tasks. These have included facial recognition, accurate judgment of speed and direction of a rolling ball with over 95% accuracy in batting a ball as it rolls over a table edge, and complex inspection-assembly tasks.

In the studies cited above, the stimulus arrays presented only black-white information, without gray scale. However, the tongue electrotactile system does present gray-scaled pattern information, and multimodal and multidimensional stimulation is may be used. Variations of different parameters provide "colors," for example, by varying the current level, the pulse width, the interval between pulses, the number of pulses in a burst, the burst interval, and the frame rate. All six parameters in the waveforms can be varied independently within certain ranges, and may elicit distinct responses.

A tongue interface presents a preferred method of providing visual information. Experiments with skin systems have shown practical problems. The tongue interface overcomes many of these. The tongue is very sensitive and highly mobile. Since it is in the protected environment of the mouth, the sensory receptors are close to the surface. The presence of an electrolytic solution, saliva, assures good electrical contact. The results obtained with a small electrotactile array developed for a study of form perception with a finger tip demonstrated that perception with electrical stimulation of the tongue is somewhat better than with finger-tip electrotactile stimulation, and the tongue requires only about 3% of the voltage (5-15 V), and much less current (0.4-2.0 mA), than the finger-tip.

For blind persons, a miniature TV camera, the microelectronic package for signal treatment, the optical and zoom systems, the battery power system, and an FM-type radio signal system to transmit the modified image wirelessly are included, for example, in a glasses frame. For the mouth, an electrotactile display, a microelectronics package, a battery compartment and the FM receiver is built into a dental retainer. The stimulator array is a sheet of electrotactile stimulators of approximately 27×27 mm. All of the components including the array are a standard package that attaches to the molded retainer with the components fitting into the molded spaces of standard dimensions. Although the present system uses 144 tactile stimulus electrodes, other systems have four times that many without substantial changes in the system's conceptual design For blind persons the system would preferably employ a camera sensitive to the visible spectrum. For pilots and race car drivers whose primary goal is to avoid the retinal delay (much greater than the signal transduction delay through the tactile system) in the reception of information requiring very fast responses, the source is built into devices attached to the automobile or airplane; and robotics and underwater exploration systems use other instrumentation configurations, each with wireless transmission to the tongue display.

For mediated reality systems using visible or infrared light sensing, the image acquisition and processing can now be performed with advanced CMOS based photoreceptor arrays that mimic some of the functions of the human eye. They offer the attractive ability to convert light into electrical charge and to collect and further process the charge on the same chip. These "Vision Chips" permit the building of very compact and low power image acquisition hardware that is particularly well suited to portable vision mediation systems. A prototype camera chip with a matrix of 64 by 64 pixels within a 2×2 mm square has been developed (Loose, Meier, & Schemmel, Proc. SPIE 2950:121 (1996)) using the conventional 1.2 µm double-metal double-poly CMOS process. The chip features adaptive photoreceptors with logarithmic compression of the incident light intensity. The logarithmic compression is achieved with a FET operating in the sub-threshold region and the adaptation by a double feedback loop with different gains and time constants. The double feedback system generates two different logarithmic response curves for static and dynamic illumination respectively following the model of the human retina.

The user can use the system in a number of ways. At one level, the system can provide actual "pattern vision" enabling the user to recognize objects displayed. In such a case the quality of the vision depends on the resolution (acuity) of such system and on the dynamic range of the system (number of discriminable gray levels). If the field of view of the camera is more than 30 degrees in diameter and there are about 30 elements square in the system, the resolution is low but comparable to peripheral visual resolution.

The native resolution of such system is extended by the user by using zoom (magnification) to explore in more details objects of interest (effectively reducing the field of view and increasing field resolution temporarily). The "static" resolution and dynamic range of the system is further increased by scanning the system and integrating the results over time.

Scanning is possible in two ways: either by scanning the display with the tongue or by scanning the camera using head movements. It is expected that head movement scanning will provide more benefit than tongue scanning but will require more training Last the system may be used as a radar system exploring the environment with a fairly narrow aperture and enabling the user to detect and avoid obstacles.

High Performance Blind Subjects

Experiments were conducted with a blind subject that is an extreme athlete who lost vision in his teenage years and presently has 2 artificial eyes. He is a mountain climber, a hang glider and skier. In his initial session with the tongue system he very quickly learned to perform recognition and hand "eye" coordination tasks. He was able to discern a ball rolling across a table to him and to reach out and grasp the ball, he was able to reach for a soft drink on a table, and he was able to play the old game of rock, paper, scissors. He walked down a hallway, saw the door openings, examined a door and its frame, noting that there was a sign on the door. He identified door frames that were painted the same color as the walls, merely due to the very slight shadow cast by the overhead light. The subject equated the learning process to that which he encountered with Braille. At first, the dots under his fingertips were just that, dots. Eventually the dots, through a laborious thinking process, became actual letters and words. And eventually, the physical aspect of the dots was bypassed and the dots were transmitted effortlessly to the brain as words and sentences. The brain had re-circuited itself. It is contemplated that the sensory substitution provided by the present invention has the same result.

Camera System Design and Development

In some embodiments, image data comes one of two sources; either an standard CCD miniature video camera (e.g. modified Philips "ToUCam-2", 240×180 pixel resolution, 30 Hz full-frame rate, 14-bit), or a long-infrared sensing microbolometer set to image in the 7.5-13.5 µm wavelength (Indigo Systems "Omega", 160×128 pixels resolution, 30 Hz, 14-bit). Either input to the base unit is via high-speed USB for continuous streaming. Using interleaving and odd-line scanning techniques allows frame rates of up to 60 Hz. (or greater) without significant image data degradation due to the high pixel-to-tactor mapping ratio (300⇒150:1). Both are capable of low power operation, a pixel by pixel address mode, and accommodate lenses with a 40 to 50 angle of view. The focus preferably is adjustable either mechanically or electronically. Depth of field is important, but not as significant as the other criteria.

The camera is mounted to a stable frame of reference, such as an eyeglass frame that is individually fitted to the wearer. The mounting system for the camera uses a mount that is adjustable, maintains a stable position when worn, and is comfortable for the wearer. An adjustable camera alignment system is useful so that the field of view of the camera can be adjusted.

External Camera Control and TDU Interface

The oral unit contains sub-circuitry to convert the controller signals from the base unit into individualized zero to +60 volt monophasic pulsed stimuli on the 160-point distributed ground tongue display. Gold-plated electrodes are created and formed on the inferior surface of the PTFE circuit board using standard photolithographic techniques and electroplating processes. This board serves as both a false palate for the tongue array and the foundation to the surface-mounted devices on the superior side that drives the ET stimulation. The advantage of this configuration is that one can utilize the vaulted space above the false palate to place all necessary circuitry and using standard PC board layout and fabrication techniques, to create a highly compact and wearable sub-system that can be fit into individually-molded oral retainers for each subject. With this configuration, only a slender 5 mm diameter cable protrudes from the corner of the subject's mouth and connect to the chest- or belt-mounted base unit.

The unit has a single removable 512 MB compact flash memory cards on board that can be used to store biometric data. Subsequent downloading and analysis of this data is achieved by removing the card and placing it in a compact flash card reader. Programming and experimental control is achieved by a high-speed USB between the Rabbit and host PC. An internal battery pack already used on the present TDU supplies the 12-volt power necessary to drive the 150 mW system (base+oral units) for up to 8 hours in continuous use.

Waveform Control System

The electrotactile stimulus comprises 40-µs pulses delivered sequentially to each of the active electrodes in the pattern. Bursts of three pulses each are delivered at a rate of 50 Hz with a 200 Hz pulse rate within a burst. This structure was shown previously to yield strong, comfortable electrotactile percepts. Positive pulses are used because they yield lower thresholds and a superior stimulus quality on the fingertips and on the tongue.

Orthodontic Appliance

The present electrode array is positioned in the mouth by holding it lightly between the lips. This is fatiguing and makes it difficult for the subject to speak during use. Thus, a preferred configuration is a orthodontic retainer, individually molded for each subject that stabilizes the downward-facing electrode array on the hard palate. Integrated circuits to drive the electrode elements are incorporated into the mouthpiece so as to minimize the number of wires used to connect the interface to the TDU. One embodiment employs the Supertex HV547 (can drive 80 electrodes). Four such devices can be implanted in the orthodontic mouthpiece. This also provides more repeatable placement of the electrode array in the mouth. Devices with 160 electrodes and 320 electrodes are used in some embodiments.

In particularly preferred embodiments, the orthodontic dental retainer has a large standard cut-out into which a standard instrumentation and stimulator package is inserted. To make the device wireless and cosmetically acceptable, an electronics microchip, battery and a RF receiver are built into a dental orthodontic retainer.

Training

During adjustment tests, participants are first given an opportunity to adjust an intensity control knob from zero intensity up to the point where they could detect a weak electrotactile stimulation. Once this level is attained, they are instructed to increase and decrease the intensity slightly, to observe how the percept changes with changes in stimulation intensity.

Minimum Intensity Adjustment Test (MIAT).

Purpose: a fast estimate of perceptual threshold for electrotactile stimulation. Once participants are familiar with how the stimulation felt and changed with increases in intensity, they practice obtaining their sensation threshold, defined as the weakest level of intensity that can barely be perceived. They are instructed to tweak the knob up and down to obtain the most precise measurement possible in a reasonable period of time (up to 60 sec. in the practice trials, reduced to 30 sec. for the experimental trials). For all measurements of sensation threshold using knob adjustment, a random offset (30%) is applied to the knob so that participant are not able to use knob position as a cue. The average reading of 5 repetitions is considered as a minimum intensity level for future considerations.

Maximum Intensity Test (MXAT).

Purpose: A fast estimate of maximum comfortable level for electrotactile stimulation. After several practice trials, participants are instructed to set a higher level of intensity, but one not so high as to be uncomfortable. The average reading of 5 maximum intensity levels without discomfort is considered as a maximum intensity range for future considerations. Difference between maximum and minimum intensities is considered as dynamic range data.

Two Alternative Force Choice (2AFC) Task Training.

Purpose: to train participants for more precise procedures of threshold measurements, important for waveform optimization. For the 2AFC task, each trial consists of two temporal intervals, separated by tones. Each interval lasts approximately 3 sec. In a randomly determined one of the intervals, an electrotactile stimulus is presented. At the end of the two interval sequence, the participant is instructed to respond with which interval they believed contained the stimulus and is informed that every trial contains a stimulus in a random one of the two intervals. For practice, the higher level is used as a starting value to make the task relatively easy and straightforward for the participant. In the actual experimental trials, a method of threshold adjustment is used as the starting value as a reasonable approximation of threshold. The computer employs an algorithm to maintain an overall 75% correct level of performance across a run of 2AFC trials. The algorithm is such that the intensity increases by 3% following an incorrect response and decreased by 3% following 3 correct responses (not necessarily consecutive). This procedure is referred to as forced-choice tracking.

Array Mapping Test.

Purpose: To measure non-linearity of tongue sensation thresholds across the TDU array. After training with full array stimulation MIAT and MXAT tests are repeated for each fragment of TDU array. Therefore, the initial TDU array (144 electrodes) is fragmented at 16 parts (group 3×3 electrodes). Dynamic range measurements are repeated for each fragment. For the tip of the tongue, the test is repeated with smaller fragment size. Results of the tests are used in developing perceived pattern intensity compensation procedures. The individual (experiment to experiment) and population (across participants) variability are considered.

Training.

A program is used to provide a number of aspects of visual perception with the stimulator. The program includes basic testing aimed at determining the level of pattern vision provided by the system in ways similar to testing of basic visual function in sighted observers starting with static stimuli generated by the computer, as well as full function assessments enabling the user to combined all of the flexibility and active exploration provided by head mounted camera in a simulated environment.

Basic functions to be assessed include:
1) Two line separation (1-D function)
2) Two point separation in a 2-D plane (unknown orientation)
3) CSF-grating detection
4) Orientation discrimination
5) Suprathreshold contrast magnitude estimation for the determination of the dynamic range
6) Direction of motion in 1-D Complex pattern vision and acuity will be tested
1) Letter acuity
2) Tumbling E
3) Pediatric shapes acuity All these functions are tested in a few modes:
1) Direct feed from the computer into the tongue display providing fixed stimuli that can only be explored with tongue motion over the display.
2) Direct feed from the computer including jitter or oscillatory motion of the stimuli providing a scanning of the stimuli on the display as would be with head motion but the movement is passive not active
3) Feed of the stimuli through camera movements. Head mounted camera aimed at a visual display of the stimuli.

Virtual environment testing includes two types of tests:
1) Perception of visual direction by pointing
2) Obstacle avoidance while walking in a virtual environment (virtual Shopping Mall while walking on a treadmill)

For complex pattern vision testing, one may use a clinical vision testing device: the BVAT (Waltuck et al 1991). This system, providing a standard NTSC output, provides a complete set of targets for acuity testing. These include a random letter presentation testing at various sizes. A tumbling E test and pediatric test patterns with shapes such as Cake, Jeep, Telephone. The ability of the subject to recognize these various shapes can be easily assessed with this system and the level of "visual" acuity for such performance can also be determined over a wide range.

A recently developed system for testing visual direction is available and may be tailored for the tongue study. A large screen rear projection system provide stimuli and a mouse on very large graphic tablet placed under a wooden cover that locks the view of the hand from the eyes (or here the camera) is used to measure pointing in the direction of perceived objects. A virtual walking system developed includes a treadmill and a virtual shopping mall projected on a large screen. The user may walk through the full range of the mall, change direction with a hand held mouse and respond to obstacles (static or dynamic) that appear in his/her path. Head tracking is available as well to correct for the mall perspective in accordance with user's head position.

For the purpose of navigation the user needs to perceive correctly direction in space as displayed on the tongue and corrected for the subject's own head movements. To train this ability the subject sits in front of a large rear projected screen on which visual targets are superimposed on a video picture. The picture and the target are acquired by the TVS video camera and are provided to the subject via the tongue display. The subject arm is placed on a mouse on the surface of a large graphic tablet under a wooden cover that blocks view of the arm from the camera avoiding visual feedback. Following camera adjustment and calibration that are verified with visual feedback the subject is asked to point to the direction target which appeared following audio tone and click the mouse button. After clicking the subject takes his arm all the way to the right to reduce the possibility of mechanical propriecptive feedback. This movement triggers the initiation of the next target presentation. In separate trials the subject is directed to aim his head in three different directions straight ahead and to the right and left. Feedback is provided on the accuracy of the pointing.

Learning and Adaptation for Reaching in 3-D Space

Subjects are asked to reach for a 1" cube in their immediate reaching space. The cube is placed in one of 5 locations for each of 100 trials. Cube placement is randomized. Subjects wear sound attenuating devices and the TVSS camera is occluded between trials. Then the direction of the camera is shifted 15° laterally and subjects and the procedures repeated to determine rate and means of adaptation.

Learning to Catch Moving Stimuli

Subjects are asked to capture a 2" ball moving across their immediate work space. The ball is controlled by a variable torque motor capable of generating 5 different speeds. A ready cue is given prior to the ball coming into view. Subjects wear sound attenuating devices and the TVSS camera is occluded between trials. The speed and delay of ball presentation is randomly varied.

Orientation and Mobility

The TVSS is used continuously during testing sessions. It may worn with the camera covered for testing skills without TVSS information. Testing is done with and without the benefit of each subject's other assistive devices (guide dog, white cane . . . ).

Task 1. The Ability to Locate a Metal Pole and Walk to it without Veering

In a laboratory setting utilizing only the TDU, the subject is tested on recognition, localization, and approach of a variety of metal poles of varying diameter. Distance traveled is held at 40-50 feet to simulate the distance of crossing a street. Outdoor training and testing is conducted and tested as possible.

Task 2. The Ability to Shoreline a Vertical Wall

In an indoor environment the subject is asked to follow a wall in a corridor of approximately 60 feet in length, without contacting it with their cane, while wearing the TDU, and locate an open doorway. Testing involves being able to locate open versus closed doorways in an unfamiliar part of the building.

Task 3. The Ability to Follow a Curved Grass Line

In an outdoor environment utilizing a cane, the subject learns to differentiate between the concrete and the grass using the TDU and locate intersecting sidewalks over an area of 120 feet.

Results with Blind Children

Experiments were conducted with congenitally blind children between the ages of 8 and 18 on a tongue based system. Past studies and training programs have indicated that 15-20 hours of training is generally useful to develop perceptual competency.

Subject characteristics and progress are indicated in Table 2. The number of hours trained and lesson number accomplished are also shown. The subjects have been listed in order of the number of hours of training they received. The number of lessons accomplished relate closely to the number of hours available for training with the exception of Subject 5.

passing all tests of spatial ability, dynamic perception and use of information given to her. She generated uses for the system, asking to use the system to observe cars moving on her street in the winter and to follow the movements of her choir director conducting with flashlights in his hands. She plans to major in music and wants to use the system for conducting classes.

Subject 1 met and exceeded all expectations and goals of the project. There were a number of contributing factors to her success. First, she was frequently able to train 2-3 times a week, was consistently available for training and could work for over and hour at the task. Thus, she had 30 hours of training Second, she is very bright and verbal. She would consistently tell the trainer what she was feeling on her tongue and how she was approaching the tasks. Finally, she is the only subject with light perception and who knew the alphabet. She has a small area on her left retina located in on the nasal aspect with which she can detect edges if they are of high enough contrast. She had learned the alphabet by having letters (about 18") projected onto a screen. She would then capture an edge and follow it to derive the full form through her movement along the edge. She talked to the trainer as she viewed displays by biting down on the strip to hold it in her mouth as she talked with a kind of gritted teeth sound. This was very helpful. For example, in pre-testing, when asked to trace a line that went down diagonally to the right she produced a line generally going down and to the left. As she drew she described the line "jumping" to the left each time she tracked to the right. She would go back to "capture" it and direct her pencil in the direction it seemed to move.

Thus, one could tell that she initially did not know moving one direction would result in the image moving across the visual field in the opposite direction.

Subjects 2 Through 6:

The remaining five subjects could not be trained sufficiently long for most of the formal testing. Learning rates suggest a linear trend with the exception of Subject 5. This

TABLE 2

| Subject No. | Age | Gender | Vision status training | Time | Most advanced learning |
|---|---|---|---|---|---|
| 1 | 16 | F | Distinguishes direction of bright light. Small L Nasal area of retina capable of edge detection with adequate contrast. Onset 19 months | 30 Hrs. | Exceeded Curriculum |
| 2 | 18 | F | Blind from Birth No light detection | 17 hrs | Pursuit Tracking Shape Recognition Overlapping Shapes |
| 3 | 11 | F | Blind from 6.5 months secondary to tumor Juvenile Pilocytic Astrocytoma No light Detection | 16 hrs | Shape Recognition Beginning Letters Linear Perspective Interposition |
| 4 | 18 | F | Blind From Birth secondary to Prematurity No light Detection | 12.8 hrs | Intersecting Lines |
| 5 | 11 | M | Blind from Birth No light detection | 10 hrs | Pursuit tracking Moving object recognition Shape recognition. |
| 6 | 9 | M | Blind from Birth No light detection | 7 hrs | Size discrimination of curved lines |

Subject 1:

Subject 1 demonstrated that the tongue interface system meets and exceeds the capabilities of earlier vibrotactile versions of the TVSS. She finished and surpassed the curriculum. She developed signature skills and was beginning to develop tracing skills at 25 hours of training She progressed from being unable to do any of the pre-tests to bright 11 year-old boy who was an accomplished drummer and pianist (self-taught) enjoyed using the system but had difficulty attending to tasks either becoming tired or anxious after a short time. The curriculum was circumvented a bit and moved right into the 3-D reaching, moving and pursuit tracking to keep his interest. Investigators could then backtrack using shapes to develop differentiation skills in these tasks. His rate of accomplishment was much higher using the perceptually richer 3-D context. The progress of Subject 3 was consistent with this approach also, as she developed spatial understanding prior to adequate shape recognition for formal testing. All of the children needed instructions to move their heads either up and down or side to side for initial scanning. Subjects 2 and 3 had the most difficulty with this and experienced the greatest difficulty interpreting the sensations on their tongue. Subject 2 had the additional problem of making ballistic head movements and overshooting target positions most of the time. In spite of her age and keen intelligence she still could not move through her own home with ease either. Her highest skill was pursuit tracking which she found quite easy, perhaps due to the fact that it give feedback for controlling head movements. Subjects 4 and 6 had good head control and both made nice progress relative to the amount of time they were available for training Subject 4 attended a residential school two hours away and came in on the weekends. Subject 6 was the youngest child with a low attention span, distracting training environment and frequent congestion. He was a mouth breather even when free of congestion and this made use of the system more difficult for longer periods of time.

Task:

reduce or eliminate developmental delays in spatial cognition

Subject 1 Accomplishments: Pre-Test 0%, Post-Test 100%:

She was 100% accurate in a Piagetian perspective taking tests at 0 degrees, 180 degrees, 90 degrees and 270 degrees when tested with 22 hours of training She was not testable on the task prior to training Understanding of linear perspective was demonstrated as she by consistently using size and height cues for placement of objects on the table in front of her. For example, when three candles were placed diagonally in front of her she asked "why did you place them diagonally?" When asked how she knew she replied, "the bottoms of the one on the center and left candles are higher up and besides the one on the left is smaller looking." She used the same type of cue to judge items interposed like a square placed in front and overlapping a triangle.

Subject 3:

This 11 year-old girl was informally tested on interposition and perspective taking.

She demonstrated understanding of 3-D space that exceeded her learning in 2-D. She was consistently able to use cues of relative height and size in performing the interposition test to place shapes in their relative overlapping positions. Her ability to differentiate individual forms, however, was deficient so that she would place the wrong shape but in the right orientation. For example, when given a display of a square in front of a circle she would select a triangle but place it in the correct position that would have replicated the target display. Thus, she developed an understanding of 3-D concepts without having the differentiation and conceptual understanding of forms that may or not hold relevant information for guiding action. She could tell if shapes were "curved" or "pointed" but as she reported she could not distinguish within these two broad categories.

Task:

use dynamic spatial information from the TVSS for trajectory prediction and intercept for capture.

Subject 1 Accomplishments: Pre-Test 0%, Post-Test 90%.

She was tested in a task with a ball rolling down a ramp aimed to roll off of the table in front of her in one of five different positions. The ball always began at midline with each path being about 15 degrees from the neighboring paths. The time from ball release to falling off the table was 2 seconds. Trials were randomized. She wore headphones with white noise and her camera was covered between trails to control for auditory cues or observation of the tester. Pre-testing score was 0% on five trials. Posttesting (@26 hours of training) score was 90% correct on 20 trials. She became skilled at rolling a ball back and forth with the trainer. She demonstrated preparatory placement and hand opening for capture of the ball. She was tested informally by moving the angle of the camera she was wearing and observing that she made initial errors consistent with the previous camera position for 8-10 captures and then self-corrected or recalibrated.

Subjects 2-6:

all accomplished at pursuit tracking of stimuli across the frontal plane.

Subjects 3 and 5:

were both learning ball capture with the rolling task and showed some calibration of space but did not reach the level of making aimed anticipatory reaches to moving stimuli.

Task:

accuracy and processing time for recognition of 2-dimensional figures.

Subject 1 Accomplishments: Pre-Test Unable. Post-Test Mean Time to Recognition 3.4 Seconds, 100% Correct.

She became very good and fast at letter recognition. On ten randomized trials she identified letters with an average time of 3.4 seconds in a range from 1.2-6.7 seconds. Her strategy was to center the image and then with one quick up and down movement determine the letter. Through observation and her excellent reporting one could determine that she frequently recognized the letter immediately but adopted the strategy of movement to disambiguate the image. Because of the relatively poor resolution of 144 pixels diagonal lines would look curved to her as a stair-step pattern appeared and reappeared. Moving helped her to tell if the stair patterns were part of the image or an artifact of the system.

Subject 3:

was the only other child, beside Subject 1, to have any exposure to alphanumeric characters prior to training on the TVSS. Subject 3 had decided she wanted to learn letters and was using her hands to explore signs and other displays with raised letters. Using the TVSS system helped but she had difficulty differentiating letters in part, because she tended to tilt her head making rectilinear forms fall on the diagonal. Diagonal lines tend to flicker or appear more rounded because of the low resolution of the TDU.

Subjects 2, 3 & 5:

all became proficient at recognizing and differentiating the shapes of circle, oval, square, rectangle, and triangle as both solid shapes and outlined shapes. Recognition times were not formally tested.

General Summary

While group data analyses were not possible, the data from Subject 1 and the rates of progress of the other five subjects demonstrate that the tongue based TVSS is an effective technology for delivering pictorial and video images for functional interpretation and use. Perceptual acuity of the tongue was sufficient for all of the subjects to use the 144-pixel array for differentiation and perception of forms. Indeed, the low resolution of the system was frequently a problem with subjects describing a "sparkle" effect with diagonal and curved forms that would make particular pixels turn off and on with a stair-step pattern. The subjects compensated by moving or jiggling the image to determine what was artifact from the system. All of the subjects enjoyed the training and were excited about being able to perceive things that they had not been able to without the TVSS.

Gray Scale Perception

At around 20 hours of training Subject 1 began to ask questions that suggested she perceived gray scale with the system. The TVSS generates small electrical currents relative to the luminance of each pixel. Optimal conditions are of high contrast and have always been used in training with white forms against black backgrounds. When she was viewing a set of nesting dolls for size discrimination and placement she asked "what is that in the middle?" The dolls were high contrast on the top, black on the bottom, and had a wide band of detail in the middle that was projected as gray when broken in 144 pixels. She reported feeling something but not as much as the faces of the dolls. Her working level of stimulation was around 30% of the maximum 40 V of the system so bright white would provide about 13 V. The Gray would be then about 6 or 7 V. This capability was not anticipated so the system was not set up to have exact quantification of the differences she could detect. Subject 3 also started to describe perception of gray scale. Training was conducted in her home facing a corner painted white. All black materials and a board were placed in front of her and training used white stimuli against this black background. She liked to look up at the white ceiling between activities "to get a good tingle" on her tongue. One evening she asked, "What am I looking at now?" She pointed the camera to the intersection of the walls and ceiling. She perceived the slightly darker shade of the wall with less direct light.

When it was realized that subjects could perceive gray scale it was decided to pilot orientation and mobility tasks, as possible, with the relatively non-portable system. The first attempt was with subject 1 trying shorelining down a white hallway with dark doors on either side. The brightness was adjusted and contrast levels to include gray scale and put the system on a cart that could be pushed behind her. She was able to go down the hall, turn a corner and stop before touching a door with a black sign mounted at eye height.

Later in her training orientation skills were tested for walking a street crossing distance without veering. Outdoors in natural light we had a figure in white stand against evergreen trees. Subject 1 had to scan the environment until she found the figure and the walk to the figure. Using an ABAB design she first made three attempts to walk to the figure without the TDU in her mouth. On the first trial she stopped short, second and third she veered approximately 10-15°. With the TDU in she walked directly to the figure. Veering was seen again when the TDU was not used showing that the effect of being able to walk directly to the figure was not due to learning on the first 3 trials. Indeed on one trial she veered right and when she tried to orient again went even further right seeking the figure.

Example 13

Surgical Assistance

Guidance and Control of Surgical Devices

In some embodiments, the systems of the present invention are used to assist in the guidance of surgical probes for surgeries. Current techniques for guiding catheters contain inherent limitations on the level of attainable information about the catheter's environment. The physician at best has only a 2-dimensional view of the catheter's position (a fluoroscopic image that is co-planer with the axis of the catheter). There does exist some force feedback along the axis of the catheter, however this unidirectional information provides only low-level indications regarding impediments to forward catheter motion. These factors greatly limit the surgeon's haptic perception of objects in the immediate vicinity of the catheter tip. For example, when humans touch and manipulate objects, we receive and combine two types of perceptual information. Kinesthetic information describes the relative positions and movements of body parts as well as muscular effort. Tactile information describes spatial pressure patterns on the skin given a fixed body position. Everyday touch perception combines tactile and kinesthetic information and is known as haptic perception. From the surgeon's perspective, little or no tactile or kinesthetic feedback from the catheter can exist because control is generally in the form of thumb and forefinger levers that alter guide-wire tension and therefore control distal probe movements.

The embodiment of the present invention described herein utilizes the tongue as an alternate haptic channel by which both catheter orientation and object contact information can be relayed to the user. In this approach, pressure transducers located on the distal end of the catheter relay sensor-driven information to the tongue via electrotactile stimulation. Thus, based on the perceived stimulator orientation and corresponding tongue stimulation pattern, the physician remotely feels the environment in immediate contact with the catheter tip. In other words, this alternate haptic channel provides sensation that could be perceived as if the surgeon was actually probing with his/her fingertip. If one could "feel" the environment, in conjunction with camera and fluoroscopic images, tissues and organs could be probed for differences in surface qualities and spatial orientation. This Example describes the methods and results of developing and testing two prototype probes in conjunction with a tongue display unit The overall goal was to demonstrate the feasibility of a novel sensate surgical catheter that could close the control loop in a surgery by providing tactile feedback of catheter orientation and contact information to the user's tongue. To that end, a prototype system was developed that affords a tactile interface between two prototype probes and a human subject.

The first consideration was the need to satisfy a reasonably small size requirement while providing a sensor resolution capable of yielding useful results. Conductive polymer sensors from Interlink Electronics, Inc. (Force Sensing Resistor (FSR), Model #400) and Tekscan, Inc. (Flexiforce, Model A101) were chosen for use because of their small size (diameter and thickness) and variable resistance output to applied forces. Having a resistance output also allowed the design of relatively simple amplification circuitry. A spring-loaded calibrator was designed and built to facilitate repeatable force application over a range of 0 to 500 gm. Testing each sensor for favorable output characteristics aided the decision to proceed with the FSR sensor. The output response, although slightly less linear than the Flexiforce sensor, was determined acceptable given the FSR's smaller physical dimensions. Each sensor was 7.75 mm in diameter, had an interdigitated active sensing area of 5.08 mm, a thickness of 0.38 mm, and 30 mm dual trace leads. This allowed probe size optimization for various sensor patterns and although the final prototypes are much larger than required for surgical application, the idea underlying this project was to prove the utility of the concept. Thus, in surgical devices, these components are used in smaller configurations.

Initial probe design criteria included the probe's ability to detect normally and laterally applied forces. This suggested, at the very least, a cube mounted on a shaft with sensors located on the remaining five sides. This design however, was quickly observed to contain considerable 'dead space' for forces not applied within specific angles to each sensor. For example, the probe would not sense a force applied to any of the corners. Many permutations of this preliminary design were considered before reaching two possible solutions: a ball design and a cone design. Each utilizes a piece of High Density Polyethylene (HDPE) machined to form the substrate upon which the FSR sensors were mounted.

The ball probe design uses four FSR sensors located 90° apart, with each attached at 27° taper. Because the active sensing area and trace leads are of similar thickness, a 'force distributor' was added to the active area by applying a 3 mm×3 mm×2 mm (W×L×H) square of semi-compliant self-adhesive foam (3M, St. Paul, Minn.). To activate the sensors, a 14.7 mm diameter glass sphere was placed inside the machined taper therefore contacting the foam sensor pads. The lead wires were gathered and inserted into a 12.8 mm×10.6 mm×38 cm aluminum shaft (OD×ID×L), which was then attached to the HDPE tip using an epoxy adhesive. To maintain contact between the sphere and sensors, as well as to protect the probe during testing, a 0.18 mm thick latex sleeve (Cypress, Inc.) was stretched over the distal portion and affixed using conventional adhesive tape (3M, St. Paul, Minn.).

The design of the Ball probe offered a robust and simple solution to the sensing needs of the system. Having the sensors and trace leads mounted internally provides a level of protection from the outside environment. A glass sphere helps forces from a wide range of angles to be detected by one or more sensors. The design, using only the four perimeter sensors, reduces the amount of necessary hardware and utilizes software to calculate the presence of a virtual fifth sensor for detecting and displaying axially normal forces. This software essentially monitors the other sensors to see when similar activation levels exist, then creates an average normal force intensity. The probe does however contain limitations. Even though the ball helps distribute off-axis forces, it cannot distinguish more than one discrete force. For example, if the probe passes through a slit that applies force on two opposing sides, the probe will only detect the varying normal component of the two forces.

The cone probe configuration employs six of the FSR sensors. The substrate is a 17 mm diameter cylinder of HDPE externally machined to a 30° taper. Five sensors are located on the taper in a pentagonal pattern, and the sixth is mounted on the flat tip. The 'force distributor' foam pads were also added to each sensor and a 8.5 mm wide ring of polyolefin (FP-301VW, 3M, St. Paul, Minn.) was heat-molded to fit the taper. The purpose of the polyolefin is to help distribute forces that are not normal to one of the five perimeter sensors thereby decreasing the amount of 'dead space' between sensors. A common ground wire was used to decrease the amount of necessary wire leads and once bundled, they were ran along the outside of a 6.35 mm×46 cm (OD×L) steel shaft threaded into the HDPE tip. The probe was also protected by a 0.18 mm thick latex sleeve (Cypress, Inc.) attached using 3M electrical tape.

One of the main design features of the Cone probe is the increased sensor resolution. The five perimeter sensors afford detection of forces on more axes than with the Ball probe, and the discrete normal force sensor allows for simple software implementation. The design was pursued because it eliminates the opposing force detection problem found with the Ball probe design. Forces in more than one location can be detected as discrete stimulations regardless of the plane in which they occur. Because each design has merits and limitations, both required testing to determine how subjects react to the stimulations they provide.

Figure 5:
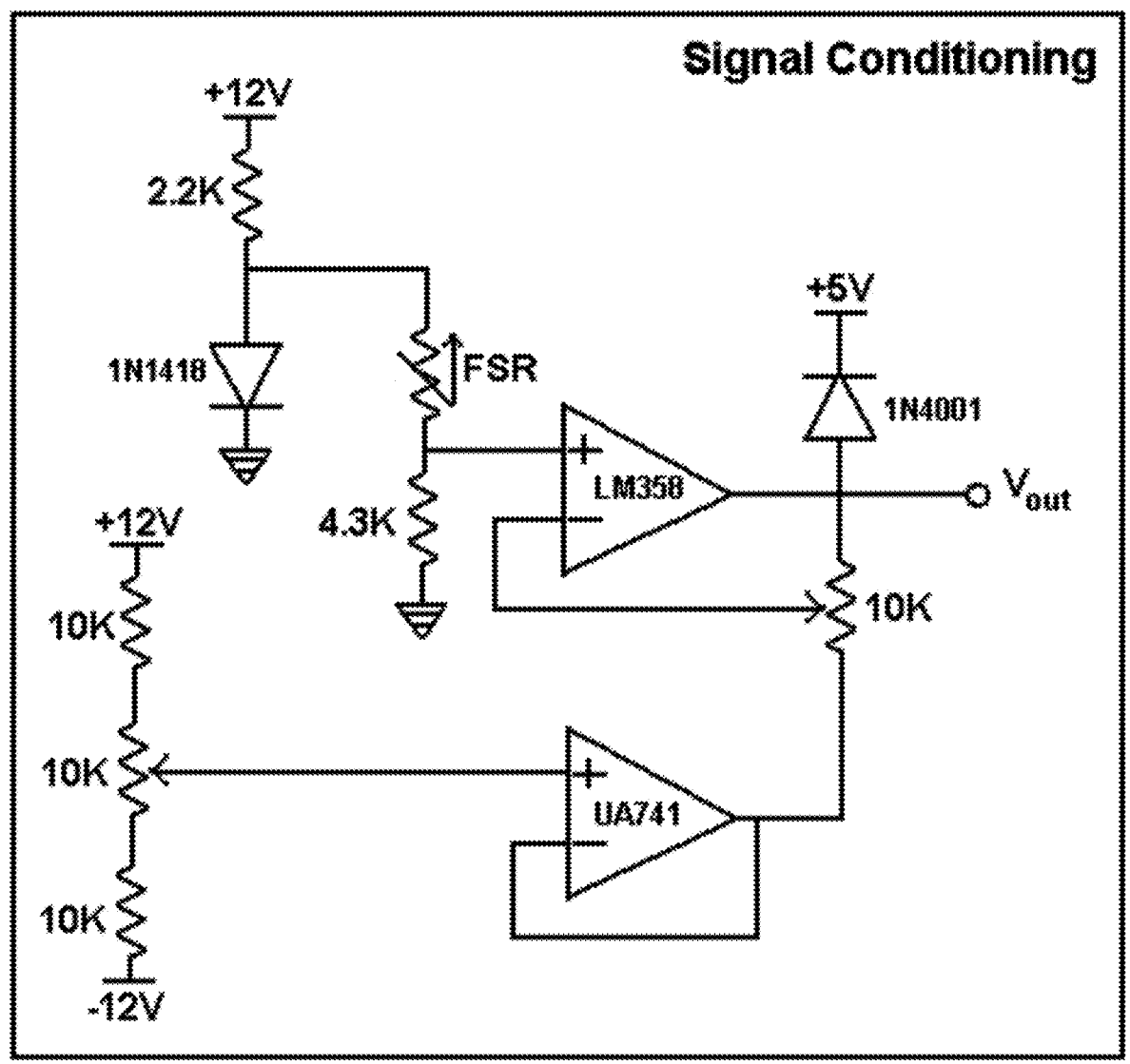
FIG. 5 shows a circuit configuration for an enhanced catheter system of the present invention.

Contact stimulus information is relayed from the sensors and modified by conditioning circuitry to produce 0-5 volt potential changes. These voltages are then connected to the analog input channels of a Tongue Display Unit (TDU 1.1, Wicab, Inc., Madison, Wis.) that converts them into variable intensity electrotactile stimulations on the user's tongue. The TDU is a programmable tactile pattern generator with tunable stimulation parameters accessed via a standard RS-232C serial link to a PC. The circuit in FIG. 5 was replicated for each sensor and serves as an adjustable buffer amplifier with an output voltage limiter. The amplifier and voltage limiter are important for adjusting the sensitivity of each sensor and limiting the output voltage to below the 5-volt maximum input rating on the TDU. To compensate for preloading effects of the force distribution foam on the sensors, the adjustable buffer facilitates 'no-load' voltage zeroing. Each sensor is modeled as a variable resistor and labeled as "FSR" in the schematic below.

Figure 6:
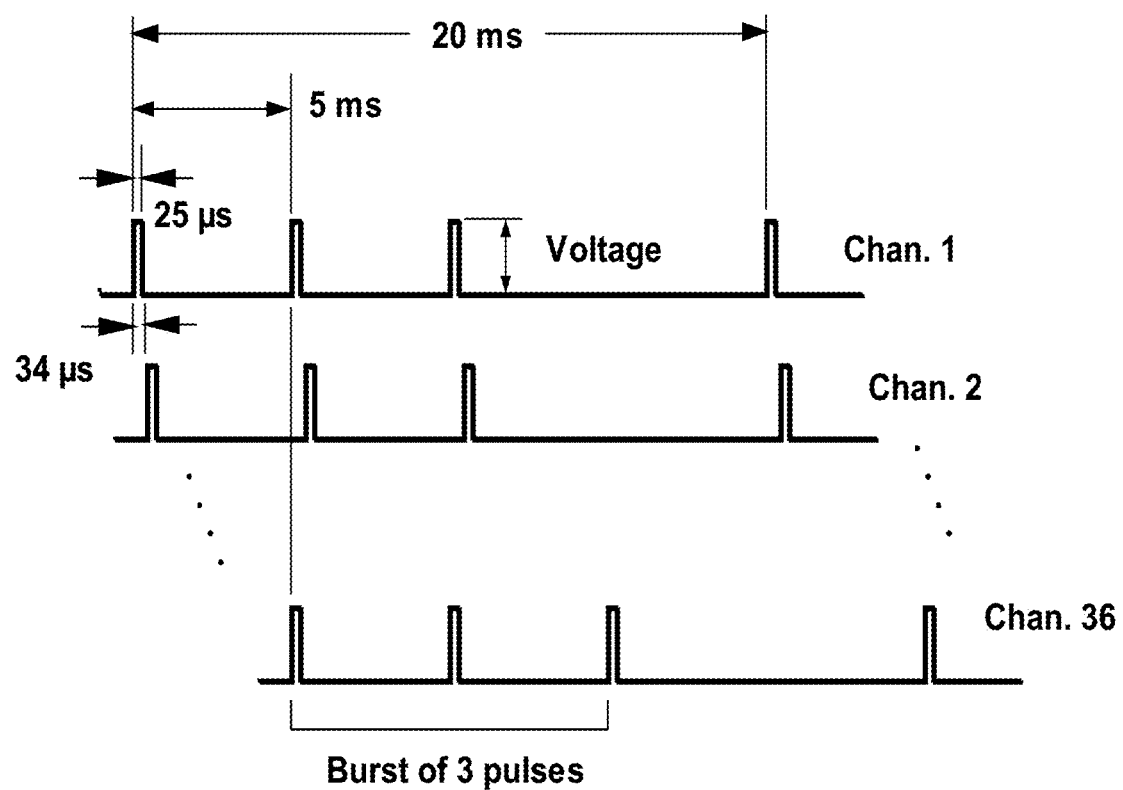
FIG. 6 shows a waveform pattern used in some embodiments of the present invention.

Software was developed for each prototype probe so that sensor information could be monitored and processed. An output voltage (Vout) for each sensor corresponds to the force magnitude applied to each FSR. This voltage is then interfaced to the TDU through an analog input and subsequently converted into a corresponding electrotactile waveform shown in FIG. 6. Using an existing GUI, an image of the probes with discrete areas resembling the actual sensor patterns was created. Data from the analog channels are digitally processed and shown as a varying color dependent upon the voltage magnitude. Therefore, as contact is made with the probe, the graphical regions corresponding to those sensors in contact with the test shape change from black (0 volts) to bright yellow (5 volts), depending on a linear transform of contact force magnitude ($v_s$), to voltage amplitude of the stimulation waveform ($v_t$).

This is a graphical representation of what the user should be feeling on their tongue, thus providing a means of self-training and error checking in the sensor-tactile display mapping function. In both cases, the general orientation of the image (i.e. Top, Bottom, Left, Right) corresponds to the probe when viewed from the tail looking forward. Typically the central front portion of the tongue is most sensitive with less sensitivity toward the side and rear. The average intensities for each sensor were adjusted with amplification gains to compensate for this variation.

A final software modification provided an electrode stimulation pattern that spatially matched the sensors for each probe. Groups of electrodes were assigned to each sensor and are represented as gray areas in FIG. 7. The stimulation pattern on the user's tongue therefore reflects the spatial information received by the TDU from the sensors and is output to a lithographically-fabricated flexible electrotactile tongue array consisting of 144 electrodes (12×12 matrix). The number of electrodes assigned to each sensor was based on an area weighed average of the local sensitivity of the tongue. Thus, for equal sensor output levels, the intensity of the tactile percept was the same, regardless of location on the tongue. The user can set the overall stimulation intensity with manual dial adjustments, thus allowing individual preference to determine a comfortable suprathreshold operating level.

Figure 8:
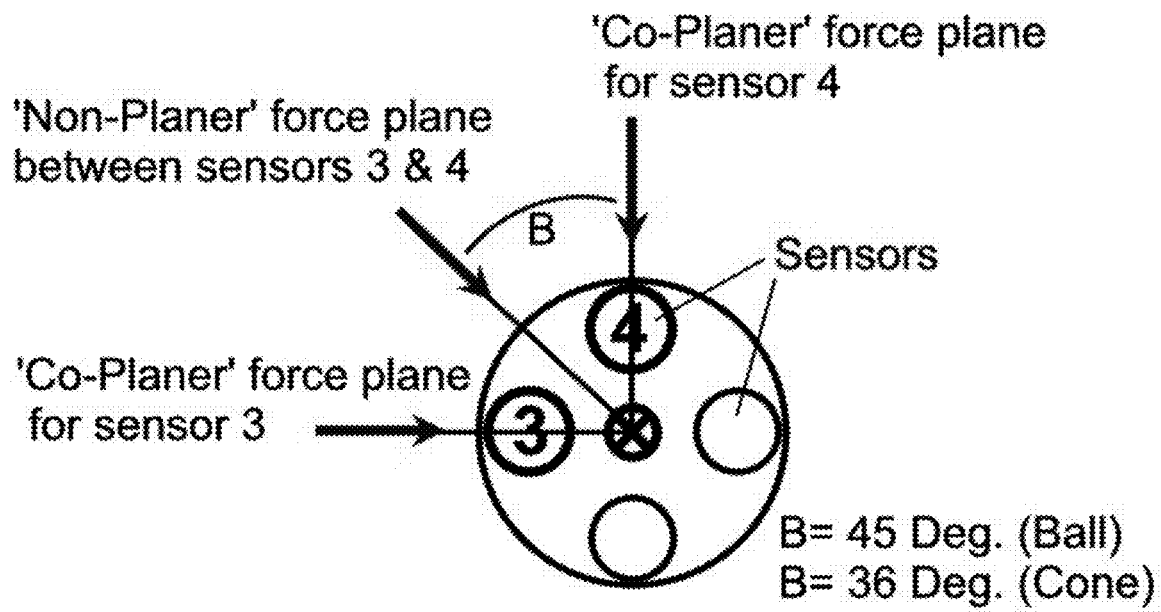
FIG. 8 shows a testing system for testing a surgical probe system of the present invention.

To aid in the understanding of how subjects might perceive object contact information provided by the prototype sensate probes, it was important to first investigate how the probes themselves react to controlled discrete forces. A calibration and characterization experiment was performed on each prototype using a 200 gm force applied at 0° (normal), 30°, 60°, and 90° angles. The test was first employed for angles co-planer to each sensor, and then repeated for non-planer angles between two adjacent sensors (45° for Ball probe, 36° for Cone probe) (see FIG. 8). Tables 3 and 4 show typical sensor output voltages, as a function of applied force angle, for the Ball and Cone probe respectively. The force response data in Tables 3 and 4, presents a quantitative analysis of each probe's technical merits and limitations. The first observation is that, for co-planer forces applied to each sensor, both probes produce output intensities that vary according to each sensor's location.

TABLE 3

Ball probe response for: (a) co-planer forces (performed on all sensors), (b) forces applied 45° to sensors 3 & 4

| SENSOR | Vout (Volts) Co-axial (normal) | 30° | 60° | 90° |
|---|---|---|---|---|
| (a) | | | | |
| 1 (Top) | 1.03 | 1.7 | 1.9 | 1.3 |
| 2 (R) | 1.4 | 2.7 | 2.9 | 2.4 |
| 3 (Back) | 1.75 | 3.3 | 3.8 | 3.1 |
| 4 (L) | 1.81 | 3 | 3.4 | 2.5 |
| 5* | 1.50 | 0 | 0 | 0 |
| (b) | | | | |
| 1 (Top) | 1.03 | 0 | 0 | 0 |
| 2 (R) | 1.4 | 0 | 0 | 0 |
| 3 (Back) | 1.75 | 2.6 | 2.5 | 1.6 |
| 4 (L) | 1.81 | 2.7 | 2.5 | 1.7 |
| 5* | 1.50 | 0 | 0 | 0 |

*Phantom center sensor

TABLE 4

Cone probe response for: (a) co-planer forces (performed on all sensors), (b) forces applied 36° to sensors 3 & 4

| SENSOR | Vout (Volts) Co-axial (normal) | 30° | 60° | 90° |
|---|---|---|---|---|
| (a) | | | | |
| 1 (Top) | 0 | 1 | 1.5 | 1.7 |
| 2 (Upper R) | 0 | 1.6 | 2.1 | 2.5 |
| 3 (Lower R) | 0 | 1.75 | 2.8 | 3.1 |
| 4 (Lower L) | 0 | 1.8 | 3 | 3.1 |
| 5 (Upper L) | 0 | 1.5 | 2.2 | 2.6 |
| 6 (Center) | 0.8 | 0.4 | 0.1 | 0 |
| (b) | | | | |
| 1 (Top) | 0 | 0 | 0 | 0 |
| 2 (Upper R) | 0 | 0 | 0 | 0 |
| 3 (Lower R) | 0 | 0.4 | 0.9 | 0.5 |
| 4 (Lower L) | 0 | 0.5 | 1.0 | 0.5 |
| 5 (Upper L) | 0 | 0 | 0 | 0 |
| 6 (Center) | 0.8 | 0 | 0 | 0 |

For the Ball probe in Table 3, the results show that peak output occurs when co-planer forces were applied at approximately 63° from the shaft axis. Because of the four sensor Cartesian pattern, forces applied at 45° to the sensor plane activate at most two sensors. Maximum output voltage, at this angle, occurs for forces applied approximately 30° from the shaft axis. By comparison, the Cone probe characterization in Table 4 shows co-planer maximum output for forces at 90° to the shaft axis. This response was somewhat surprising since it was thought that sensitivity would be maximal at about 60°. However, the molded polyolefin ring in contact with the sensors likely distributed the off-axis forces and contributed to this result. Non-planer forces applied at a 36° angle yielded output in two sensors (3 & 4), similar to that of the Ball probe, but with significantly lower magnitudes.

The net result of the tests indicates that the Ball probe provides higher output response to non-planer forces than does the Cone probe. The Cone probe did, however, respond more favorably to transitions from normal to 90° co-planer forces, however, neither probe provided exceptional output for transitions from normal to 90° non-planer forces. Having a limited number of discrete sensors may account for the discontinuous force detection regardless of applied angle. Thus, in other versions of probe design, increased sensor resolution is used to improve the angular transitional response.

Figure 9:
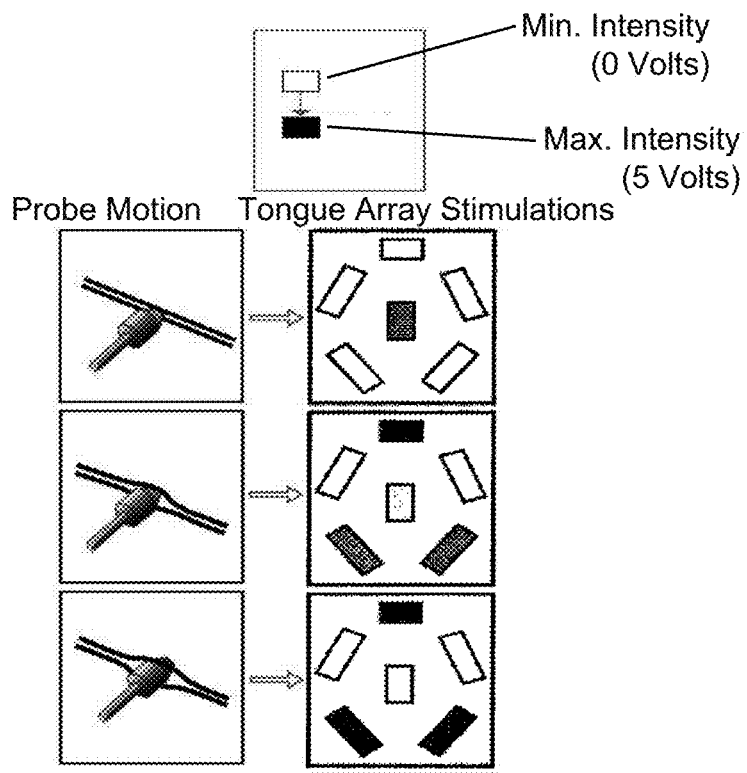
FIG. 9 shows a sensor pattern in a surgical probe embodiment of the present invention.

The system was tested on subject. Subjects observed tongue electrotactile stimuli from both probes (i.e. no visual feedback) while contacting one of 4 different test objects. Six adult subjects familiar with electrotactile stimulation participated in this experiment. Each subject was first shown the prototype probe, the 4 possible test shapes, the TDU, and the sensor-to-tongue display interface program. The 4 object stimuli were as follows: A 'Rigid' stimulus was created using hard plastic. A 'Soft' stimulus was designed from a 3 cm thick piece of compliant foam. A 'Slit' force stimulus was achieved using two pieces of foam sandwiched together. A 'Shear' force stimulus was realized from a tapering rigid plastic tube. The 'Rigid' and 'Soft' surfaces were used to test the ability of users to discern normal force intensities as unique characteristics of the test shapes. The 'Slit' force stimulus is intended to mimic a catheter passing between two materials (see FIG. 9) and the 'Shear' stimulus provided by the tapered tube were used to test if subjects can perceive the orientation of probe contact force.

Subjects were then trained to use the graphical display of sensor activation pattern to aid perception of the electrotactile stimulation on their tongue. The experimenter maintained control over probe movements, and once participants were able to correctly identify each of the four test stimuli without visual feedback, they were blindfolded and the formal experiment began.

During the experiment, subjects were instructed not to adjust the main intensity level. The four test configurations were randomly (without replacement) presented in two blocks of 12 trials (equal representation) with one block given for each probe. Two data values were collected for each trial: (1) first the subjects were asked to identify the stimulus as representing one of the four possible test shapes. If the choice was incorrect, the subject's incorrect choice was recorded and used to check for correlations between test stimuli and/or probes. (2) The participants were then asked to describe what they "visualize" and/or "feel" as the environment in contact with the probe. For example, a subject may comment that the sensations on the left side of their tongue leads them to perceive the probe contacting the left side of the vessel wall and that a lateral shift to the right is necessary. This qualitative information aided in identifying the merits and limitations of the prototype system.

TABLE 5

Confusion matrix for overall subject correct perception using, (a) the Cone probe and (b) the Ball probe

| ACTUAL STIMULUS | PERCEIVED STIMULUS | | | |
|---|---|---|---|---|
| | RIGID | SOFT | SLIT | SHEAR |
| (a) | | | | |
| RIGID | 77.8 | 5.6 | 0.0 | 16.7 |
| SOFT | 5.6 | 83.3 | 11.1 | 0.0 |
| SLIT | 0.0 | 16.7 | 83.3 | 0.0 |
| SHEAR | 0.0 | 5.6 | 0.0 | 94.4 |
| (b) | | | | |
| RIGID | 77.8 | 5.6 | 5.6 | 11.1 |
| SOFT | 5.6 | 61.1 | 27.8 | 5.6 |
| SLIT | 5.6 | 22.2 | 66.7 | 5.6 |
| SHEAR | 5.6 | 0.0 | 11.1 | 83.3 |

The results of the study reveal that, overall, subjects were generally able to correctly identify the four test shapes using only electrotactile stimulation on the tongue. Table 5 presents the results of this study as a confusion matrix for the Cone and Ball probe respectively. The results show that subjects attained higher perceptual recognition using the Cone probe (avg. 85% correct) than with the Ball probe (avg. 72% correct). 'Shear' force stimuli yielded the highest percentage correct for both probes with one subject scoring perfectly on all trials using the Cone probe. While significantly lower for the Ball probe, the 'Soft Normal' and 'Slit' force recognition rates are also promising. The results also show evidence of perceptual difficulties in some trials and should be noted. In particular, for the Cone probe trials, confusion between 'Soft Normal' and 'Slit' stimulus accounted for most errors. It is conceivable that this is because sensor activations can be similar for these two objects. If the central stimulus was not felt during the 'Soft Normal' force stimulus (possibly due to lateral masking effects), the percept may be that of the 'Slit' condition, which produces a "pinching" stimulus that is felt on the perimeter of the tongue.

During Ball probe trials, misperceptions frequently occurred between the 'Slit' and 'Soft Normal' force stimuli. The probe lacked the ability to discretely sense two opposing forces, as is the case of the 'Slit' shape, and contact information for the 'Slit' was therefore presented as a varying normal force. In other trials, it was reported that while scanning the tongue array for stimulation, spatial orientation on the array was sometimes lost, making perception of tip to rear stimulation transitions difficult to distinguish. This problem could be eliminated by incorporating a small nib or bump at the center of the tongue array that would allow users to "feel" their way back to a reference position similar to the home position on a numeric keypad. Another note is that two subjects expressed that having an alternate tongue mapping function may have helped them visualize the probe in contact with the test shapes more accurately. Their main concern was that the top of the probe was mapped to the tip of the tongue whereas mapping it to the back of the tongue may be more spatially intuitive. Thus, with additional training or alternative configurations, accuracy is greatly increased.

With practice, users learn to process substitute sensory information to the point where catheterization tasks are perceived as unconscious extensions of the hands and fingers. Implementation of MEMS-based sensors, partially due to their small size, low power consumption, and mode of sensing flexibility, operational catheters will facilitate spatial perceptions far beyond the results of the results reported above. It was demonstrated that the external sensor design (Cone probe) resulted in better perceptual performance than did the internal sensor design (Ball probe). However, a modified Ball design that provided greater internal sensor resolution through active perimeter sensors located on the ball surface could create an optimal synthesis of the two current designs and their respective performance features.

With the aid of sensor equipped catheters, relaying critical information regarding probe position and tissue/organ surface qualities as patterned electrotactile stimulation is contemplated. The surgeon's new ability to "feel" how the catheter is progressing through the vessel may increase the speed with which probes can be navigated into position. This additional diagnostic tool may therefore decrease the amount of time patients are anesthetized and/or under radiation.

Retinal Surgery Enhancement

In some operations on the retina, the retinal surgeon must separate the pathological tissue in the retina using a pick by vision only, since the forces on the pick are so minimal that they cannot be felt. To enhance such surgeries a surgical pick can be configured with sensors so as to supply information about the surface of the tissue through a tactile device to the operating surgeon. For example, on the pick, several mm behind the tip, a MEMs (tiny) accelerometer or other sensor is placed. The sensor is configured to pick up the tiny vibrations as the pick is used to separate the tissue. The signal from the sensor is sent to an amplifier and to a piezoelectric vibrator or other means of delivering the amplified signal through intensity of signal provided on the pick. A small battery is included in the package. Thus, when the surgeon uses the pick on the retina he/she perceives an amplified version of the forces on the tip of the pick that would be delivered to the brain via the fingers holding the pick. The device may be configured a single-use throw-away instrument, since it is quite inexpensive to make and it might be impractical to sterilize and maintain. However, it could also have other formulations, such as a removable instrumentation package clipped on the sterile retinal pick Robotic Control In some embodiments, the present invention provides a fingertip tactile stimulator array mounted on the surgical robot controller. The electrode arrays developed for tongue stimulation (12×12 matrix, approx. 3 cm square) are modified to allow mounting (e.g., via pressure-sensitive adhesive) on the hand controller. This is accomplished largely by changing the lithographic artwork used by the commercial flexible-circuits vendor (All-Flex, Inc., St. Paul, Minn.). Software is configured to receive data from the tactile sensors and format it appropriately for controlling the stimulation patterns on the fingertips. The resulting system provides a tactile-feedback-enabled robotic surgery system.

An electrode array is made of a thin (100 μm) strip of flexible polyester material onto which a rectangular matrix of gold-plated circular electrodes have been deposited by a photolithographic process similar to that used to make printed circuit boards. The electrodes are approximately 1.5 mm diameter on 2.3 mm centers. A 2×3 array of 6 electrodes is mounted on the concave surface of the finger-trays. Each array is connected via a 6 mm wide ribbon cable to the Fingertip Display Driver, which generates the highly controlled electrical pulses that are used to produce patterns of tactile sensations.

The electrical stimulus is controlled by a device that generates the spatial patterns of pulses. The sensor displacement data is processed and output by the host PC as serial data via the RS-232 port, to the Fingertip Display Driver (FDD). The FDD electrotactile stimulation pulses are controlled by a 144-channel, microcontroller-based, waveform generator. The waveform signal for each channel is fed to a separate 144-channel current-controlled high voltage amplifier. The driver set-up, according to the particular pattern of stimulation, delivers bursts of positive, functionally-monophasic (zero net dc) current pulses to the electrode array, each electrode having the same waveform. Intensity and pulse timing parameters are controlled individually for each of the electrodes via a simple command scripting language. Operation codes and data are transferred to the TDU via a standard RS-232 serial link at up to 115 kb/s, allowing updating the entire stimulation array every 20 ms (50 Hz).

Sweat-related effects on the fingertip array are addressed by providing means to wick sweat away from the electrode surface via capillary tubes, etc., designed into the electrode array substrate.

Electrotactile stimulation is used to produce controlled texture sensations on the fingertips to allow tactile feedback with much greater realism than existing technology.

In one embodiments a one-to-one, spatially-corresponding mapping of sensor elements to stimulator elements (electrodes) is used. However, given that the robotic end-effector may be very small and irregularly shaped, depending on the particular surgical procedure, other spatial mapping schemes may be employed. For example, the system may employ a level of "zoom" (i.e., ratio of tactile display size to sensor array size), as well as the effects of convergence (multiple sensors feeding each tactile display element) and divergence (use of multiple tactile display elements to represent each sensor).

Example 14

Underwater Orientation Experiments

Navy divers, researchers, and recreational divers operating in the littoral and deep-water often must perform activities in murky or black water conditions limiting the effectiveness of visual cues. When performing salvage or rescue/recovery or egress from sunken structures, available visual references may cause individuals to misperceive their orientation and lead to navigational errors. For military personnel, requirements for clandestine operations and the need to maintain dark adaptation for nighttime ops preclude the use of dive lights and make illuminated displays undesirable.

Tasks such as search and rescue, egress, mine countermeasures and salvage are interrupted when using visual aids for navigation and communications. Meanwhile the remaining human sensory systems remain under-utilized, leading to inefficient use of diver cognitive capabilities. The present invention provides a system for military and other divers that enhances navigation and, as desired, provides other desired sensory function (e.g., alarms, chemical sensors, object sensors). This device has been termed BRAINPORT Underwater Sensory Substitution System (BUDS$^3$) and provides additional interface modality for warfighters in the underwater operational environment that increase effectiveness by improving data understanding for navigation, orientation and other underwater sensing needs.

In preferred embodiments, the system is worn in the mouth like a dental bridge or mouth guard and interfaces electrically to the tongue and lips.

DARPA and other research agencies have developed methods of enhancing human and human-system performance by detecting bioelectric signals, both invasively (neural implants) and non-invasively (skin surface or non-contact electrodes) to allow direct control of external systems. Dynamic feedback is a key element for the use of these brain machine interfaces (BMIs). The BUDS$^3$ sensory interface is used to augment both the visual and sensory motor training with current BMIs concepts as well as the accuracy of detection of intent in concert with other bioelectric BMIs. The BUDS$^3$ system exploits the relatively high representation in the cerebral cortex of the tongue and lips.

In some preferred embodiments, in addition to providing navigation information, the BUDS$^3$ is configured to display other underwater data such as sonar or communications (from the surface or from other divers) and has integration of EMG capabilities which would provide a subvocal communication capability and detect operator input commands that could be used to control unmanned underwater (or surface) vehicles. Preferably, the system is fully wireless and self-powered. Non-diving military applications include control of manned and unmanned vehicles, control of multispectral electronic sensing and detection platforms, control and monitoring of automated systems, management of battlespace C4ISR, among others.

Divers using the BUDS$^3$ system operationally will have improved orientation and navigational capabilities and extended sensory capabilities based on sonar and other technologies.

It is widely observed that the mind constructs a virtual space, experiencing the body and the tools attached to it as a single unit filling the space. The nervous system readily extends to experience an external object as if it were a part of the body. Anyone who has ever slowly backed a car into a lamppost, and perceived the collision as direct physical pain has experienced this process. Similarly, a blind person using a long cane perceives objects (a foot, a curb, etc.) in their real spatial location, rather than in the hand, which is the site of the human-device interface. This capacity represents a powerful but untapped resource for process monitoring, with many significant practical applications. Rensink (2004) notes that power is seen in the ability to sense that a situation has changed before being able to identify the change, using "mindsight." He exposed 40 subjects to a series of images each shown for 0.25 second. Sometimes the image would be repeated throughout the trial; sometimes it would be alternated with a slightly different image. When the image was alternated, about a third of subjects reported feeling that the image had changed before they could identify the change. In control trials, the same subjects were confident that no change had occurred. The systems of the present invention provide a way to exploit this rapid understanding of information.

In some embodiments, the BUDS$^3$ data interface provides an electrotactile tongue interface that is incorporated into a rebreather mouthpiece of the diver. A similar device may be incorporated into emergency air bottles. Molds of current rebreather and scuba system mouthpieces are made and replacement castings are formed with electrotactile arrays embedded into the lingual and buccal surfaces. Additionally, switches are integrated into the bite blocks to allow diver control of the interface. The mouthpiece is connected to drive electronics and power mounted to the dive gear. Two hardware stages are used to control the array. The driver, located close to the mouthpiece, provides the actual waveforms to the individual tactors. An embedded computer/power supply module mounted to the buoyancy control device or dive belt controls the driver via serial link. The control computer connects to sensors such as accelerometers, inertial navigation systems, digital compasses, depth gauges, etc. and runs the software that determines what signal is presented to the diver.

The Institute for Human and Machine Cognition (IHMC) has developed a modular, software agent based integration architecture under the DARPA IPTO Improving Warfighter Information Intake Under Stress Program that may be used to implement the BUDS³ device. This architecture uses Java (or any other programming language that can communicate via Java or TCP/IP). The architecture is cross platform (currently supported on Windows and Linux OSs) and provides a standardized interface protocol for disparate heterogeneous elements. Drivers are provided for each sensor device (digital compass, inertial navigation unit, etc) and for the BUDS³ prototype. This allows for rapid integration and side-by side testing, training, and usage of different sensors. Waterproofing is accomplished through use of waterproof housings, using off the shelf waterproof connectors/cabling and potting of circuits.

Persons with no eyes have learned complex three dimensional perceptual tasks using the systems of the present invention, including hand-"eye" coordination, such as catching a ball rolling across a table, in a single training session. In addition, individuals who have lost vestibular (balance) organ function due to drug toxicity (e.g., gentamycin) have demonstrated rapid improvement in postural sway and gait when using the system to represent tilt sensed by a head worn accelerometer. The key to its operation is the user's nervous system's ability to use the data provided by the system to abstract semantic cues (the meaning of the data stream, or in psychological parlance, analog information, rather than the data values themselves, or digital information) that describe the process being sensed. Sensation can be experienced and unconsciously integrated into the operator's awareness.

Experimental studies of implicit learning show that individuals engaged in a learning task are consciously focused on functional features of the task, rather than the underlying structural characteristics of the material. This is seen in the infant's acquisition of knowledge of the semantic and syntactic structure of its natural language. The infant's attention is directed toward the functional aspects of verbal communication (getting what it needs, understanding the caretakers), not on the structural features of the language. Yet, over time, the child comes to speak in a manner that reflects the complex array of linguistic and paralinguistic rules necessary for successful interaction in social settings—without having acquired conscious knowledge of either the rules that govern its behavior or the ongoing processes of rule acquisition. Remarkably, the process goes beyond learning the rules of a coherent situation; it extends to the ability to identify and engage in interpersonal deception.

Prior research demonstrated that dissimilar but related sensory inputs facilitate the interpretation of data. Rubakhin & Poltorak, (1974), for example, studied visual, auditory and tactile information presented simultaneously under two conditions: identical or duplicated information in all three perceptual systems, or different information in each perceptual system. They found that multi-modally presented information must be processed simultaneously, because sequential processing limits the overall channel capacity of the brain. Deiderich (1995) performed a simple reaction time (RT) experiment in which subjects were asked to react to stimuli from three different modalities (i.e. visual, auditory, and tactile). The stimuli were presented alone, as a pair from two different modalities, or as a triple from all three modalities. Double stimuli conditions showed shorter RTs when compared to single stimulus conditions. Triple modality stimuli showed a further reduction in RT, demonstrating inter-sensory facilitation of RT. Given that the human orientation system is multisensory, it follows that multisensory (e.g., vision augmented with BUDS3) data leads to more rapid and accurate situation awareness and thereby lead to more efficient and effective mission execution.

In preferred embodiments, the system is provided as a wireless communication system. By removing the wired link between the array and the control computer, the system is less obtrusive, dive compatible, and provides intra-oral substrates. For example, orthodontic retainers from a cross-section of orthodontic patients were examined to determine the dimensions of compartments that could be created during the molding process to accommodate the FM receiver, the electrotactile display, the microelectronics package, and the battery. The dimensions and location of compartments that could be built into an orthodontic retainer have been determined. For all the retainers of adolescent and adult persons examined, except for those with the most narrow palates, the following dimensions are applicable: in the anterior part of the retainer, a space of 23×15 mm, by 2 mm deep is available. Two posterior compartments could each be 12×9 mm, and up to 4 mm deep. Knowledge of these dimensions allows the development of a standard components package that could be snapped into individually molded retainers, and the wire dental clips would double as the FM antenna.

These reduced size arrays may be used in conjunction with dive gear, but also open up applications in non-diving environments. For example, divers could use the system underwater and on ground during amphibious operations, switching between display of sonar or orientation to display of night vision, communications and overland navigation data. Similarly, a wireless connection allows incorporation of the system into aviation environments and for civilian use by firefighters rescue workers and the disabled. The transmission of information from the sensor/control computer to the high-density array should be done at high speed using minimal battery power. In some embodiments, near visible infrared (IR) light, which can pass through human is used as a direct IR optical wireless communication method.

In some embodiments, electromyogram/electropalatogram capabilities are added to mouthpiece for efferent control of external systems. The facial muscles, tongue and oropharynx may be exploited as machine interface to external systems. By using a system with an integrated electromyogram (EMG) and electropalatogram (EPG) capability in the orthodontic device, the user gains a precision interface device that finds use to control unmanned aerial/ground/undersea vehicles. In addition, recent research has shown that speech patterns can be detected from EMG/EPG when subjects pretend to speak but make no actual sound. These patterns can be recognized in software and used to generate synthetic speech. This capability, coupled with audio transduction via the system permits clandestine communications between divers on a team or with the surface. With a wireless system, troops on the ground could also communicate without any acoustic emissions.

Example 15

MRI Research Applications

Previously developed substitution systems have not been appropriate for MRI studies. However, electrotactile tongue human-machine interface finds use for imaging studies. The tongue is very sensitive and the presence of an electrolytic solution, saliva, assures good electrical contact. The tongue also has a very large cortical representation, similar to that of the fingers, and is capable of mediating complex spatial patterns.

The tongue is an ideal organ for sensory perception. The results obtained with a small electrotactile array developed for a study of form perception with a finger tip demonstrated that perception with electrical stimulation of the tongue is significantly better than with finger-tip electrotactile stimulation, and the tongue requires much less voltage (3-8 V) than the finger-tip (150-500 V), at threshold levels which depend on the individual subject. Electrical stimulation of the fingertips requires currents of approx. 1-3 mA (also subject dependent) to achieve sensation threshold; the tongue requires about half this much current. The electrode-tongue resistance is also more electrically stable than the electrode-fingertip resistance, enabling the use of voltage control circuitry in preference to the more complex current-control circuitry used for the fingertip, abdomen, etc.

To establish initial feasibility of using the tongue tactile display unit in conjunction with MRI, two tests were performed with a 1.5 T G.E. Signa Horizon Magnet equipped with high-speed magnetic field gradients that afford the use of single-shot echo-planar imaging (EPI) pulse sequences. These experiments were designed to determine whether (1) the time-varying magnetic fields in the MRI machine would induce perceptible sensations on the tongue electrode array, and (2) whether the presence of the tongue array and related electrical activity would yield artifacts on the MRI image.

(a)—Calculation of Maximal Induced Emf in Tongue Electrode Array.

The maximal emf induced in the tongue electrode array occurs when the RF magnetic field $B_1$ is perpendicular to the plane of the tongue array. The tongue array is approximately 22 in long, and the largest receiving loop would be created by shorting together the two electrodes at the furthest corners of the array. These two electrodes are approximately 1 inch apart.

Induced emf, E, in a coil placed in a time varying magnetic field, B, is calculated by:

$$E = -N \cdot A \cdot \frac{dB}{dt}$$

where: N is the number of turns in the coil (1),
A is the area of the coil (0.0142 m$^2$), and $$\frac{dB}{dt}$$

is the maximal rate of change of the $B_1$ magnetic field;

(0.012 T)/(150 µs)=80 T/s=80 Wb/s·m$^2$

So, the maximal expected emf, E=1.14 Wb/s=1.14 V.

This prediction was confirmed by direct measurement. The tongue electrode strip was affixed to a calibration phantom, and shorted together the two electrodes on the array corresponding to the flat cable traces encompassing the largest-area loop comprising the electrode-cable assembly. Digital storage oscilloscope measurements on the free ends of the cable during a spin-echo MRI scan (acquisition parameters: 500/8 ms TR/TE, 256×256 matrix, slice thickness=5 mm, 24 cm×24 cm field of view, 1 NEX) showed that the maximal induced emf (for all three perpendicular orientations of the electrode array in the scanner), was no more than 4 V. Both predicted and measured emf for both conditions are near or below the sensation threshold for electrotactile stimulation on the tongue (3-8 V), and hence pose no risk to the subject.

(b) Stimulation Waveforms and Control Method.

The electrotactile stimulus consists of 25-µs pulses delivered sequentially to each of the active electrodes in the pattern. Bursts of three pulses each are delivered at a rate of 50 Hz with a 200 Hz pulse rate within a burst to the 36 channels. This structure was shown previously to yield strong, comfortable electrotactile percepts. Positive pulses are used because they yield lower thresholds and a superior stimulus quality on the fingertips and on the tongue. Both current control and voltage control have been tested. It was found that for the tongue, the latter has preferable stimulation qualities and results in simpler circuitry. Output coupling capacitors in series with each electrode guarantee zero dc current to minimize potential skin irritation. The output resistance is approximately 1 kΩ.

(c) Scan with Tactile Stimulation.

The electrode array was placed against the dorsum of the tongue in a healthy volunteer, and the flexible cable passed out of the mouth, stabilized by the lips. A 4-m cable connected the electrode array to the stimulator, located as far as possible from the axis of the main magnet. All 144 electrodes delivered a moderately-strong perceived level of stimulation throughout the experiment. A whole-brain, spin-echo MRI scan (acquisition parameters as in (b) above) was performed and displayed as nine sagittal slices.

None of the images revealed any artifact due to the presence of the electrode array or related stimulation. The subject, who was familiar with the types of sensations normally elicited by the stimulation device, did not feel any unusual sensations during the scan. These results establish proof of concept for using the tongue tactile stimulator in an MRI environment.

However, the equipment (which was not constructed to withstand the MRI environment) was apparently damaged by the induced activity produced by the imaging sequence. Thus, the methods are preferably conducted with electrical isolation via, for example, long lead wires to be able to distance the electronic instruments from the MRI machine.

All of the imaging performed on the GE Signa MR scanner is controlled by software referred to as pulse sequences. Pulse sequences can be provided by General Electric or created by the researcher. Pulse sequences generate digitized gradients, RF waveforms, and data acquisition commands on a common board, the Integrated Pulse Generator (IPG). RF waveforms are then converted to an analog format through an RF modulator on a separate board and then sent to the RF power amplifier housed in another chassis. The pulse sequence is also responsible for generating the necessary control signals to activate the modulator and RF power amplifier during RF excitation. The control signal to activate the RF power amplifier is used to activate the electronic disconnect circuit and thus electrically disconnect the tongue driver from the tongue array, The pulse sequence software can also generate a control signal at specific points in the imaging sequence. This control signal is used to synchronize and trigger the tongue driver from the imaging sequence. Since the tongue driver sequence has a period of 20 ms, the control signal is generated immediately after the RF excitation and 20 ms later during the imaging sequence. Thus two cycles of the tongue driver sequence are executed for every one repetition period of the imaging sequence. The time during the RF excitation is the only time in the pulse sequence when the MRI procedure can damage the ET device. Allowing for 1 ms of RF excitation where no tongue stimulation is allowed, stimulation can still occur with a duty cycle over 97% if the imaging repetition time is set at 46 ms.

This provides two levels of redundancy. The RF signal to activate the RF amplifier disconnects the tongue driver from the tongue array. The tongue array is also synchronized with the pulse sequence to avoid periods when there is both RF excitation and a connected array. The pulse sequence control signals are flexible and can be coded to synchronize or randomize more elaborate stimulation periods with the imaging sequence.

(a) Scanning Protocol.

Scanning is performed on a clinical 1.5T GE Signa Horizon magnet equipped with gradients for whole-body EPI. The subject's head is positioned within a radio-frequency quadrature birdcage coil with foam padding to provide comfort and to minimize head movements. Aircraft-type earphones with additional foam padding are placed in the external auditory canals to reduce the subject's exposure to ambient scanner noise and to provide auditory communication. Preliminary anatomical scans include a sagittal localizer, followed by a 3D spoiled-GRASS (SPGR) whole-brain volume (21/7 ms TR/TE; 40 degree flip angle; 24 cm FOV; 256×256 matrix; 124 contiguous axial slices including vertex through cerebellum; and 1.2 mm slice thickness). A series of 22 coronal T1-weighted spin-echo images (500/8 ms TR/TE; 24 cm FOV; 256×192 matrix; 6 mm slice thickness with 1 mm skip) from occipital pole to anterior frontal lobe is acquired. EPI fMRI scanning is acquired at the same slice locations, thickness and gap as the spin-echo coronal anatomical series. EPI parameters: single-shot acquisition, 2000/40 ms TR/TE; 85 degree flip angle; 24 cm FOV; 64×64 matrix (in-plane resolution of 3.75×3.75 mm); +/−62.5 kHz receiver bandwidth. Transmit gain and resonant frequency are also manually tuned prior to the functional scan.

Figure 10:
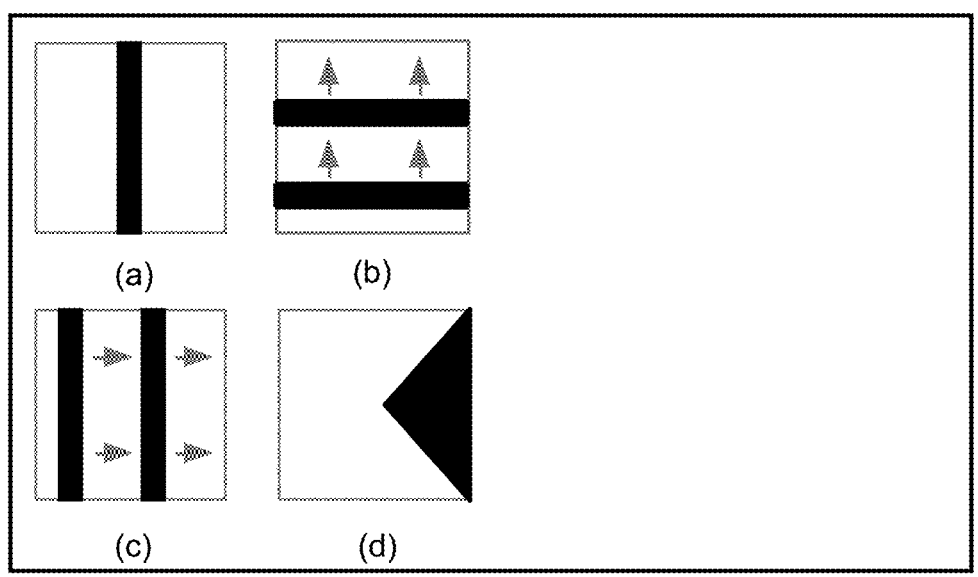
FIG. 10 shows four trajectory error cues as displayed on the tongue display for use in a navigation embodiments of the present invention: (a) "On course; proceed." (b) "Translate, step 'Up'." (c) "Translate 'Right'." (d) Rotate 'Right'." Forward motion along trajectory is indicated by flashing of displayed pattern. Black areas on diagrams represent active regions on 12×12 array. Gray arrows indicate direction of image on display.

Data has been obtained outside the MRI environment demonstrating how to best present spatial and directional information on the tongue tactile display. However, during this entire process, little information about the cognitive processes are taking place in response to the tactile stimulation is known. This information is useful to improve upon the functionality of the device. Learning how the brain responds to the tactile perception aids in the training process. Knowledge of brain activity allows modifications of the device to speed up the training process and to improve learning. To visualize brain function during navigation using fMRI, a program to create 2- and 3-D virtual environments was developed and a quasi-3-D navigation task was devised through a virtual building. The subjects move through the virtual maze using a joystick. Using the navigation task as a test platform, with the appropriate tactile display interface, users perform a virtual 'walk-through' in real time. The users are given tactile directional cues as well as error correction cues. The error correction cues provide navigation information based on the calculated error signal derived from the users' current position and direction vector and the prescribed trajectory between any two nodes along the desire path in the maze. For example, a single line sweeping to the right is very readily perceived, and indicates that the user should "step" to the right. By contrast, an arrow on the right hand side of the tactile display instructs the user to rotate their viewpoint until it is again parallel with the desired trajectory. The error tolerances for the virtual trajectory, and the sensitivity of the controls are programmable, allowing the novice user to get a 'feel' for the task and learn the navigation cues, whereas the experienced user would want to train with a tighter set of spatial constraints. A sample of the cues is shown in FIG. 10. If the subject is "on course" and should proceed in their current direction, they sense a single, slowly pulsating line on the ET tongue array as shown in FIG. 10A. If they need to rotate up, they sense 2 distinct lines moving along the array as indicated in FIG. 10B. If a rotation to the right is required, they sense 2 lines moving toward the right (FIG. 10C). A right translation is indicated by a pulsating arrow pointing to the right (FIG. 10D).

During the development of the navigation/orientation icon sets, it was also considered how to integrate "Alert" information to the user to get their attention if they stray from the path in the maze. In the normal Navigation/Orientation Mode, the display intensity level is set at the users preferred or "Comfortable" range. In "Alert" Mode the stimulus intensity is automatically set to the maximum tolerable level (which is above the maximum level of the "Comfortable" range), and pulses at 5-15 Hz. to immediately attract the user's attention and action. Once the subject returns to the correct path, the ET stimulation switchs back to the pattern shown in FIG. 5a. The mode and event sequence as indicated in Table 6 was developed.

TABLE 6

ET mode and corresponding tactile icons. Comments give information about icon meaning.

| Mode | Tactile Icon | Comments |
| --- | --- | --- |
| Navigation [N] | Moving & Flashing Arrows or Bars [See FIG. 10] | Tactile display gives specific directional cues for maintaining course on desired trajectory. |
| Orientation [O] | Moving & Flashing Arrows or Bars [See FIG. 10] | Tactile display gives specific orientation feedback on present body orientation in space. |
| Alert [A!] | Flashing "X" or "Box" Flashing diagonal line, (or other patterns to be defined). | Imminent environmental or physiological hazard. |

Both sighted (blindfolded) and blind subjects (early and late blind) are trained to navigate the maze while outside the MRI environment. Once they are able to navigate the maze successfully within a 10-minute period of time, they are moved on to fMRI analysis.

The fMRI paradigm is patterned after an fMRI study of virtual navigation by Jokeit et al (Jokeit et al. 2001). The paradigm comprises 10, 30 s activation blocks and 10, 30 s control blocks. Each block is introduced by spoken commands. During the activation block, the subjects is asked to navigate through the maze by moving the joystick in the appropriate direction using the tactile cues learned in the training session. After 30 s, their route is interrupted by the control task which consists of covertly counting odd numbers starting from 21. After the rest period, the subjects continue their progress through the maze. EPI scanning is continuous throughout the task with acquisition parameters described above.

fMRI Data Analysis.

Image analysis includes a priori hypothesis testing as well as statistical parametric mapping, on a voxel-by-voxel basis, using a general linear model approach (e.g. Friston, Holmes & Worsley 1995). fMRI analysis using SPM99 and related methods involve: (1) spatial normalization of all data to Talairach atlas space (Talairach & Tournoux 1988), (2) spatial realignment to remove any motion-related artifacts with correction for spin excitation history, (3) temporal smoothing using convolution with a Gaussian kernel to reduce noise, (4) spatial smoothing to a full width half maximum of approximately 5 mm and (5) optimal removal of signals correlated with background respiration and heart rate. Analysis of activation on an individual or group basis is obtained using a variety of linear models including cross-correlation to a reference function and factorial and parametric designs. This method is used to generate statistical images of hypothesis tests. Additionally, a ramp function is partialed out during the cross-correlation to remove any linear drifts during a study. Additional signal processing with high and low pass filters to remove any residual systematic artifacts that can be modeled may be used. The reference function for hypothesis testing in the studies will match the timing pattern of the event stimulation sequences. The output of the fitted functions provides statistical parametric maps (SPM's) for Student's-t, relative amplitude, and signal-to-noise ratio. Pixels with a t-statistic exceeding a threshold value of $p<0.001$ are mapped onto the anatomic images.

The brain imaging studies allow one to make two very fundamental contributions: (1) gain valuable information about brain plasticity and function in blind vs. sighted individuals or other application of the system of the present invention; and (2) use of fMRI to guide future development of the device to optimize training and learning.

Example 16

Tongue Mapping

The present invention provides methods for mapping the tongue to assist in optimizing information transfer through the tongue. For any particular application, the location and amount of signal provided by electrodes is optimized. Understanding variations allows normalization of signal to transmit the intended patterns with the intended intensity. In some embodiments, weaker areas of the tongue are utilized for simpler "detection" type applications, while stronger areas are used in application that require "resolution." Thus, when a multisensory signal is provided, optimal position of the different signals may be selected.

Tongue Mapping Experiment Procedure
Materials:
1 Mouth guard
1 Plastic sheet
1 Hole punch
1 Sharpie marker
2 Pull-tabs
Scissors
Warm water Procedure
1. a. Fit Mouth Guard
   Heat water in microwave (about 4-5 minutes)
   Submerge mouth guard and hold until sticky and soft
   Insert softened guard into the top of the participant's mouth and have them bite down until a comfortable fit is established
   Remove air between guard and teeth by sucking the air out
   Close mouth around guard
   Mold top teeth and roof of mouth into mouthpiece
   Bite down to get an impression of teeth
  b. Make Plastic Piece
   Place bottom of guard on plastic sheet
   Trace around guard with a Sharpie (hold marker perpendicular to the sheet to avoid getting marker on the guard)
   Cut this shape out of the plastic sheet
   Invert the guard so that the bottom is facing upwards and place the plastic piece on the bottom of the guard
   Trim the plastic piece and round the edges as necessary to achieve a smooth shape that will fit the guard and not jut into the participant's mouth
  c. Prepare Guard to Attach Plastic Piece
   Punch a hole in the front outermost ridge of the last molar on both sides of the guard
   Punch a hole in the side adjacent (90°) to each of the existing holes
   Align the plastic with the guard and mark the locations of the holes on the sheet with a Sharpie
   Punch out the holes in the plastic
  d. Attach Plastic Piece to Guard
   Insert a pull-tab into the left side hole with the notched (rough) side facing the bottom of the guard
   Pull the tab through the left molar hole of the guard and then through the plastic
   Close the tab by inserting its end into the box portion of the tab
   Secure and tighten
   Repeat this procedure on the right side so that the plastic is secure and flat on the bottom of the guard
   Clip excess parts of the tabs as necessary
   Sand the ends to ensure a comfortable fit with no sharp protrusions
   Test the device in the participant's mouth and make any further adjustments, if needed
2. Preparing Guard for Trials
   Superimpose the right strip on the left strip so that the left strip is the upper most part of the array. The upper portion of the array will represent A and B on the display while the lower portion represents areas C and D.
   Align array end even with the anterior portion of the last molar imprint
   Use double sided tape to attach the array to the plastic
   Place guard and array in participant's mouth
3. Trials (Minimum Threshold)
   Open "TDU Tongue Mapping Experiment" program
   Set for remote code
   Set for 115 kband communication rate with PC
   Always set min. threshold channel to "3"
   Always choose "COM 3" in Poll Ports
   Begin with 1×1 granularity, sampling a first block of electrodes
   Check voltage to verify connection by rotating knob and observing change in voltage value
   Set knob so voltage reads 0
   Save file
   Set file name to include initials, granularity (i.e. 1×1), and block number e.g. ab1×1-1
   Hide the display from the participant so they cannot see where the array is activated
   Run 1×1 block 1 at minimum threshold only
   When block 1 is completed, proceed to block 2—keep all parameters constant and check voltage to verify connection
   Save block 2 file as done with block 1, but input new block number in file name Repeat for 1×1 blocks 2 and 3, doing minimum thresholds only Collect data for all 3 blocks of 2×2 and 3×3 at minimum thresholds only There should be a total of 9 files at the end of this testing Make sure all files are saved in "tests" folder and backup on diskette 4. Trials (Maximum Threshold)

Repeat set up procedure as laid out above in "minimum threshold"

Begin with 1×1 block 1

Set file name with initials, granularity, block number, followed by "max" e.g. ab1×1-1max Hide the display from the participant Run the 1×1 blocks at maximum threshold only Save block 2 as done for block 1, but rename the file to indicate block 2

Repeat for 1×1 blocks 2 and 3, doing maximum thresholds only

Collect data for all 3 blocks of 2×2 and 3×3 at maximum thresholds only

There should be a total of 9 "max" files at the end of this testing

There should be a total of 18 total files for the participant, including minimums and maximums FIGS. 11-14 show data collected using such methods.

Figure 13:
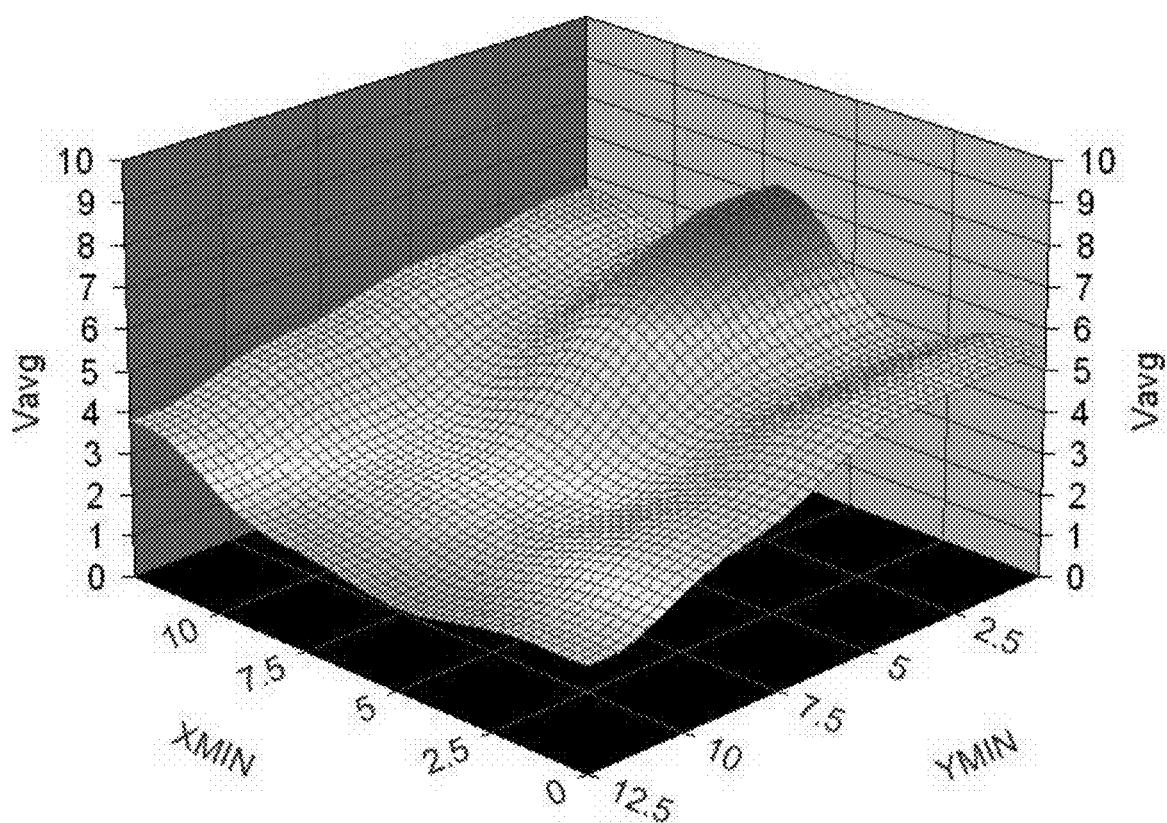
FIG. 13 shows data from a tongue mapping experiment of the present invention.

1×1 Min (FIG. 13)

The figure shows the minimum threshold voltage to detect electrotactile stimulation on randomized parts of the tongue. The stimulus was a 1×1 electrode contiguous pattern on a 12×12 array of electrodes. The function is slightly asymmetric, with a slightly lower average voltage required to stimulate the left side of the tongue towards the front. Thus, this left anterior area of the tongue is most sensitive to electrotactile stimulation. The anterior medial portion of the tongue is generally more sensitive to stimulation than the rest of the tongue. In contrast, the posterior medial section of the tongue had the highest threshold. Therefore, the posterior medial section of the tongue is least sensitive to stimulation.

Figure 14:
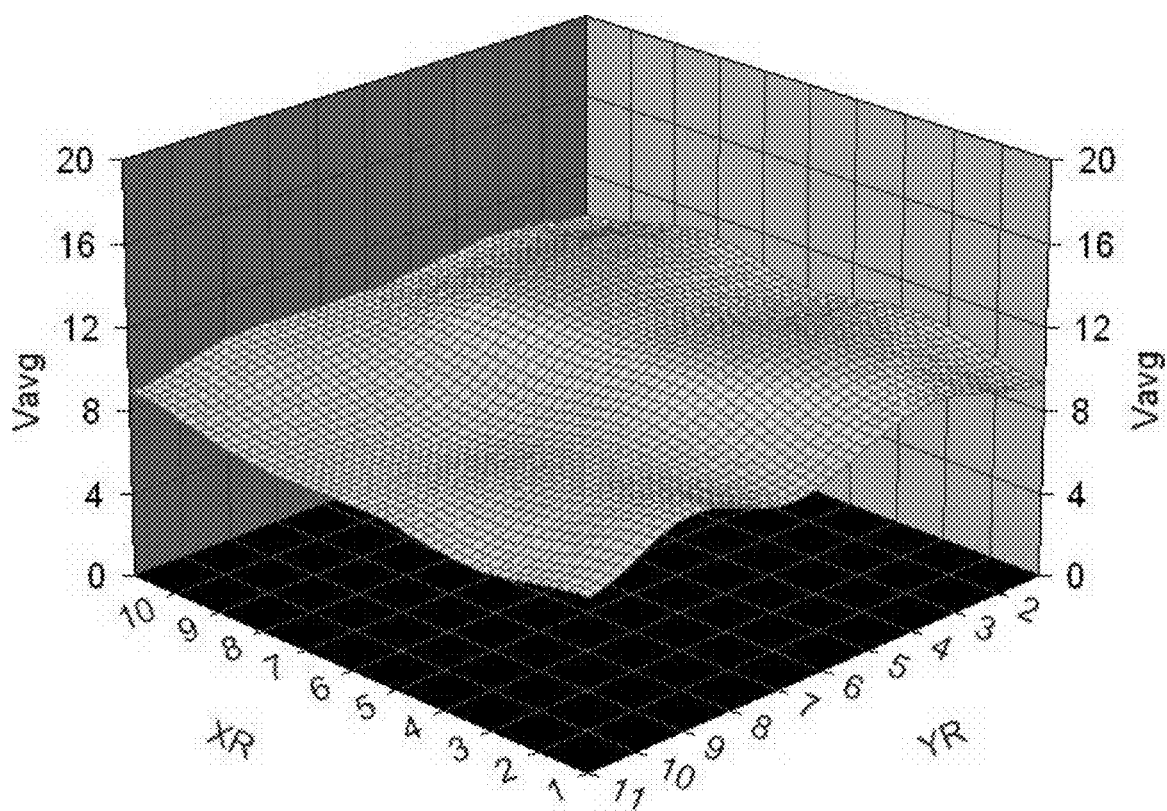
FIG. 14 shows data from a tongue mapping experiment of the present invention.

2×2 Min (FIG. 14)

The figure shows the minimum threshold voltage necessary to detect electrotactile stimulation on various portions of the tongue. The stimulus was a random pattern of 2×2 square of electrodes on a total array of 12×12 electrodes. Again, the function is slightly skewed to the anterior left side of the tongue. This finding is consistent with the 1×1 minimum figure. The general shape of the curve is also similar to the 1×1 minimum function. The same phenomena are seen in the 2×2 mapping as were observed in the 1×1 map. The anterior medial section of the tongue is most sensitive, requiring the least voltage to sense electrode activation. The medial posterior area of the tongue showed the least sensitivity.

Comparison of Mins

It is worthwhile to note that the 2×2 minimum curve had a lower overall threshold when compared with the 1×1 minimum curve. The 2×2 minimum function also appears to be flatter and more uniform than the 1×1 minimum. The lower threshold in the 2×2 function could be a result of the larger area activated on the tongue. By increasing the area activated, the stimulus can be felt sooner due to more tongue surface covered and more nerves firing. This is analogous to a pinprick versus the eraser of a pencil on your finger. Covering a larger stimulus area will activate more nerves sooner, causing the voltage to be lower for the 2×2 map.

The uniformity of the 2×2 curve may also be explained by this phenomenon, as the increased stimulus surface area led to less specificity. The 1×1 curve has more contouring because it was more specific to activating certain areas of the tongue and causing certain nerves to fire. On the other hand, the 2×2 square stimulus may have involved multiple nerves that may have been excitatory or inhibitory.

Additionally, there seems to be a diagonal that runs along the tongue from the anterior right side to the posterior left side. It is along this diagonal that the transition from high sensitivity to low sensitivity occurs. Possibly this is caused by the anatomical arrangement of the nerves in the tongue, as the hypoglossal nerve runs in the same direction.

Both the 1×1 and 2×2 curves show decreased sensitivity (represented by higher voltages in the figures) at the sides of the tongue. This can be explained by the spread of nerves in the center of the tongue. Because the nerves are more spread out, there is a higher nerve density at the middle of the tongue when compared with the sides.

Figure 11:
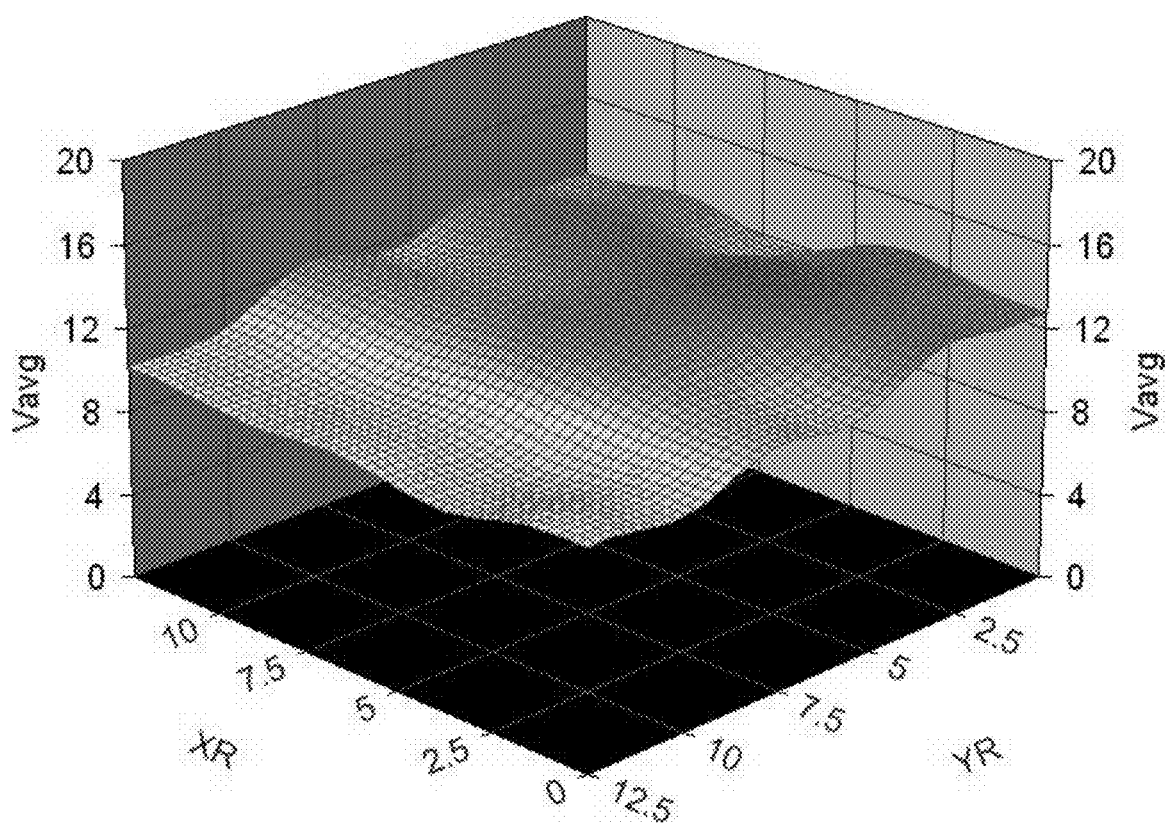
FIG. 11 shows data from a tongue mapping experiment of the present invention.

1×1 Range (FIG. 11)

The 1×1 range was determined by finding the difference between the minimum and maximum voltages for the 1×1 array mapping. The range was slightly higher on the left side of the tongue and also in the posterior region. This may indicate that the anterior and/or right side of the tongue is less variable than the left side and/or the posterior region.

Figure 12:
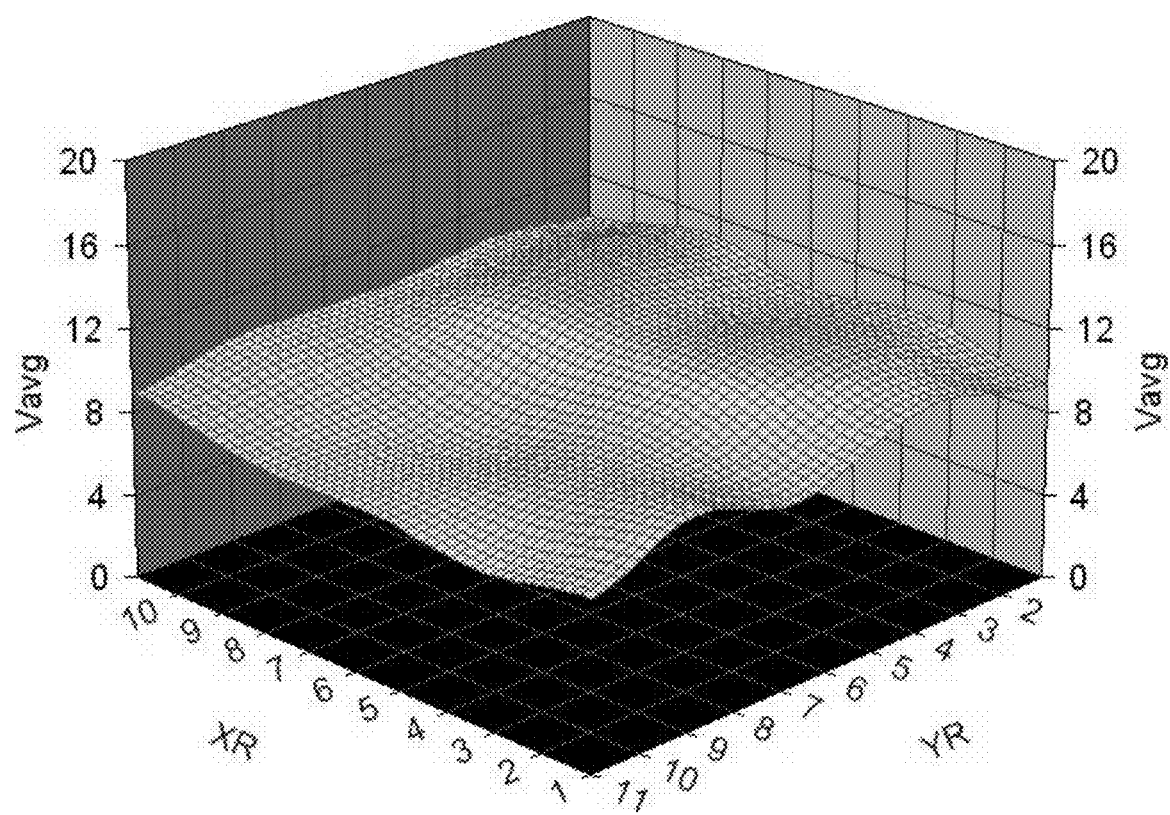
FIG. 12 shows data from a tongue mapping experiment of the present invention.

2×2 Range (FIG. 12)

The 2×2 range was found as explained above. The 2×2 range figure appears to be flatter than the 1×1 range figure. This can be explained by the loss of specificity when using a larger stimulus area. When the stimulus covers a larger area, less detail can be detected, causing the map to be less particular and more uniform.

Range Comparison

The ranges were based on the difference between the maximum and the minimum threshold voltages for each array (1×1, 2×2). The ranges were fairly constant among the subjects and both curves (1×1 and 2×2) appear to be similar. The range was slightly higher for the 1×1 stimulus when compared to the 2×2 stimulus for reasons previously explained. More variability is expected for a more specific stimulus that affects a smaller surface area of the tongue.

The shapes of the curves are also similar in their characteristics. Both functions have noticeable "bumps" in the posterior section of the tongue. These bumps indicate that a broader range in threshold levels at the posterior section of the tongue.

The range figures show that there is a small variation in tongue maps across the subjects tested.

Experiments conducted during the development of the present invention identified that the anterior portion of the tongue is an optimal location for providing video information for vision substitution or enhancement.

Example 17

Tongue-Based 2-Way Communication for Command & Control

The present invention provides a self-contained intra-oral device that permits eyes, ears, and hands-free 2-way communications. Preferably, the device is small, silent, and unobtrusive, yet provides simple command, control and navigation information to the user thereby augmenting their situational awareness while not obstructing or impeding input from the other senses. The device preferably contains a small electrotactile array to present patterned stimulation on the tongue that is automatically or voluntarily switched into a 'command' for sending information, a power supply and driver circuitry for these subsystems, and an RF transceiver for wireless transmission.

Human/computer interfaces are most often associated with keyboard/mouse inputs and visual feedback by means of a display. However, in many scenarios this mode may not be optimal. Many scenarios exist where an individual's visual and auditory fields and finger/hand are occupied with other demands. For such scenarios the development of unconventional interfaces is needed.

Tactile displays have been designed for the fingertip and other body locations of relatively larger area. However, few researchers have targeted the oral cavity for housing a tactile interface despite its high sensitivity, principally because the oral cavity is not easily accessible and has an irregular inner surface. Nevertheless, an oral tactile interface provides an innovative approach for information transmission or human-machine interaction by taking advantage of the high sensitivity of the oral structures, with hidden, silent, and hand-free operation. Potential applications may be found in assistance for quadriplegics, navigation guidance for the blind and scuba divers, or personal communication in mobile environments.

In many military relevant situations, it would be advantageous to utilize the tactile sensory channel for communication. While the tactile sensory channel has a limited bandwidth compared to the visual and auditory channels, the tactile channel does offer some potential advantages. The tactile channel is "directly wired" into a spatio-temporal representation on the neocortex of the brain, and as such is less susceptible to disorientation. In addition, the use of the tactile channel reduces the incidence of information overload on the visual and auditory channels and frees those channels to concentrate on more demanding and life-threatening inputs. Finally, the use of the tactile channel allows communication even in conditions where visual and audio silence is required. When combined with intelligent information filters and appropriate personnel training, even a low-bandwidth channel (the tactile channel) is effective in decision making and command & control.

Figure 19:
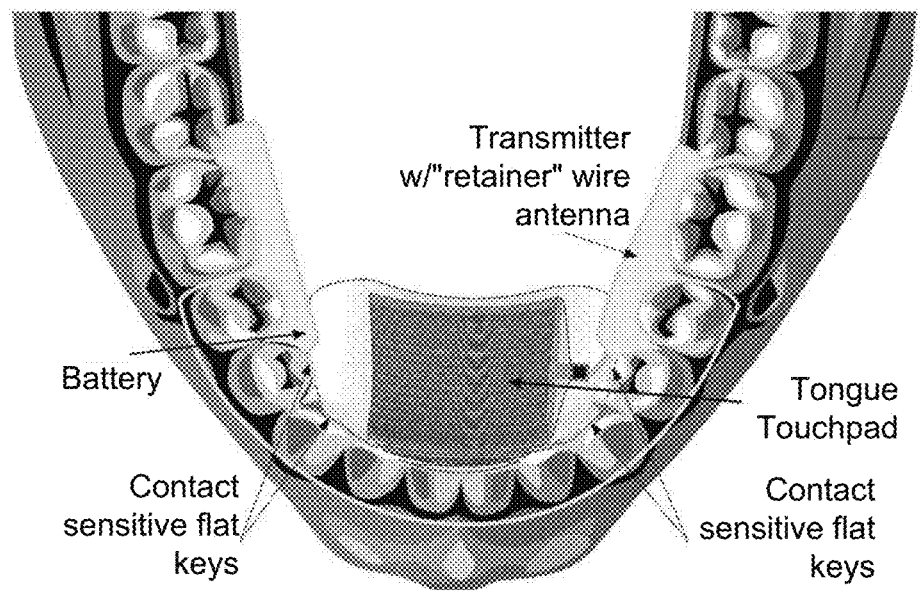
FIG. 19 shows an exemplary in-mouth signal output device of the present invention.

The tongue is capable of very precise, complicated, and elaborate movements. Devices having a switching device can interact with the tongue and provide an alternative method for communication (see e.g., FIG. 19). Tongue operated devices can provide an alternate computer input method for those who are unable to use their hands or need additional input methods besides hands during a specific operation, such as scuba divers and other military personnel. Several companies have recognized the potential merits of tongue-based devices, such as NewAbilities Systems' tongue touch keypad (TTK) (Mountain View, Calif.), and IBM's TonguePoint prototype. Though, innovative, none of these devices are easy to use, and consequently have not achieved commercial success.

Exemplary applications of the system are described briefly below.

Dismounted Soldier Scenario

At the platoon/squad echelon, the dismounted soldier is the primary personnel type. It is imperative for the dismounted soldier to continually scan the immediate surrounding using both visual and auditory sensory channels. Traditional communication visually (hand gestures) or audibly (speaking/shouting) may degrade the soldier's ability to see and hear the enemy. In addition, it is often necessary to maintain auditory silence during maneuvers. Because of the limited bandwidth of the tactile sensory channel the "vocabulary" used via the tactile channel must be limited. Because the dismounted soldier has a fairly narrow relevant area of concern, a few key phrases/commands may be sufficient. The soldier needs to convey to his platoon leader information regarding his physical condition (I'm wounded), location (rally point), target information (enemy sighted), equipment status (need ammunition), etc. Conversely, the platoon/squad leader needs to communicate commands to the soldier (retreat, speed up, rally point, hold position, etc.). Such a limited vocabulary (as well as more complex vocabularies) can be effectively transmitted using the tactile sensory channel.

Command and Control Personnel Scenario

The cocktail party analogy is often used to describe the situation in a command center. It is a crowded, noisy place filled with a range of personnel with different information needs. Often visual and auditory alerts are ineffective and inconvenient. For example, if one person wants to get a subset of the command center personnel to converge their attention to one display area they are currently forced to verbally attempt to redirect each individuals attention to the display of interest or physically go to each person and tap them on the shoulder to get their attention. The confined space in most command posts do not allow for easy movement and the visual means of communication is already overloaded for many personnel. In this environment a silent (auditory and visual) tactile low bandwidth communication system has great use for attention getting, cueing and simple messages. The use of tactile stimulators as "virtual taps" greatly facilitates the coordination within a command center without adding to the auditory and visual noise of a command center. With a single input, a commander can simultaneously "tap" a selected subgroup within the command center. Similar scenarios in video conferencing and virtual sandboxes can be provided where the use of a "virtual tap" is used to redirect an individuals attention or to transmit simple messages.

Navigation Scenario

To facilitate navigation for dismounted soldiers and during underwater scuba operations, geospatial cues are required. With the advent of low cost Global Positioning Systems (GPS), precise absolute position information is available. However, existing methods for communicating navigational information to persons are limited to visual cues (hand signals) and auditory directions. It is important for the auditory and visual channels to remain clear as they provide important situational cues in battlefield scenarios. The tactile channel is ideal for providing geospatial cues. The brain easily adapts to associate semantic content in tactile cues. In some embodiments, the invention provides a tactile interface in the mouth which provides geospatial relevant cues to a subject while underwater. Stimulators in contact with the roof of the mouth provide simple directional cues. An impulse to the back of the mouth might signal stop or slow down depending on its perceived intensity or frequency. Likewise, stimulus to the sides would mean turn and stimulus to the front speed up. Similar cues would be advantageous for extraction operations where silent communication is critical. The incorporation of sensors would also provide an output channel and allow soldiers to relay information silently to one another within a squad for example.

Other Scenarios

Other tasks require continual tactile manipulation (inspection, mixing chemicals, operating equipment). In these situations, it would be advantageous for the subject to be able to adjust weapons parameters, for example, without interrupting the manipulative task. Often relatively high noise levels make speech recognition communication schemes difficult. Similar scenarios, for example, are found in airplane cockpits, where the pilot is overloaded with visual cues/information on a variety of displays and must manipulate a large number of controls. A wide variety of other scenarios exist in which the human operator's interaction with the machine is limited by the other demands on visual and hand/finger manipulations. The use of a mouth-based tactile interface allows the flow of critical communication to continue without interrupting manual manipulation skills thereby increasing task performance.

In addition, an oral interface has many applications in the civilian world (including manufacturing, persons with disabilities, etc.).

An interface with both input and output capability through the oral tactile channel has been developed and tested. A demonstration of two-way tactile communication has been performed to show the application of the tactile interface for navigational guidance. The oral tactile interface is built into a mouthpiece that can be worn in the roof of the mouth. A microfabricated flexible tactor array is mounted on top of the mouthpiece so that it is in contact with the palate, while the tongue operated switch array (TOSA) is located on the bottom side of the mouthpiece. An interfacing system has been developed to control both the tactor array and the tongue touch keypad. The system is programmed to simulate the scenario of navigation guidance with simple geospatial cues. Initial device characterization and system psychophysical studies demonstrated feasibility of an all oral, all-tactile communication device. Subsequent modification and psychophysical analysis of the TOSA configuration yielded superior task performance, improved device reliability, and reduced operator fatigue and errors. Such a signal output system can be combined with a tongue-base tactile information input system to provide two-way communication.

In preferred embodiments, the system operates in one of two modes: command or display. Specifically, when the tongue is making complete (or nearly complete) contact with the electrotactile array, the circuitry detects that there is continuity across the entire array and locks into display mode. When the user removes the tongue from the array, or the sensed average contact area drops below a predetermined threshold (e.g. 25%), the system automatically switches to 'command' mode and remains in this state until either all contact is lost or the sensed average contact area is greater than 50%. When in the 'command' mode, the sensing circuitry detects all electrodes that are making contact with the tongue by performing a simple, momentary, sub-sensation threshold continuity check. Firmware in the system then calculates the net area that is in contact, and then the centroid of that area. The locus of this point on the display then serves as the command input to be communicated to central command or to other personnel in the area. The commanded signal can then be used by the recipient as either explicit position and orientation information or can be encoded in an iconic form that gives the equivalent and other information.

In between pulses and bursts, the system presently switches all inactive electrodes to ground so that the entire array acts as a distributed ground plane. For the command and control system, there is an addition of a $3^{rd}$ state, one that allows the injection of a sub-threshold stimulus for the 'continuity check' function. These continuity pulses are periodic and synchronous (e.g. every $4^{th}$ burst) since their only purpose is to poll the array to determine how much of the tongue is making contact with it at any given time. This stimulus, however, should be phase-shifted so that there is no chance that it will occur when the electrodes proximal to an active one need to be switched to the ground state to localize the current and the resultant sensation. Thus the continuity polling takes place continuously in the background so that the system calculates the location of the tongue and instantaneously switches modes when the appropriate state conditions are met. This alleviates the need for manual mode switching unless requested by the user by completely removing the tongue from the array.

In command mode, the device may be configured to send out physiological information for monitoring in-field personnel (or patients, children, etc.). Such information could include salivary glucose levels, hydration, APR's, $PCO_2$, etc.

Example 18

Stimulator Implant

The present invention provides tactile input systems that reduce or eliminate many of the problems encountered in prior systems by providing stimulators that are implanted beneath the epidermis or otherwise positioned under the skin or other tissues. One advantage of such a system is the ability to substantially reduce size of the stimulators because their output is closer to the nerves of the skin (or other tissue) and is no longer "muffled." Such size reduction allows higher stimulator densities to be achieved. Additionally, interconnectivity problems, and issues inherent in providing input signals from an external camera, microphone, or other input device to an internal/subdermal stimulator (i.e., the need to provide leads extending below the skin), may be avoided by providing one or more transmitters outside the body, and preferably adjacent the area of the skin where the stimulator(s) are embedded, which wirelessly provide the input signals to the embedded stimulator(s).

A description of several exemplary versions of the implanted system follows. In preferred embodiments, the implantable stimulator(s) are implanted in the dermis, the skin layer below the epidermis (the outer layer of skin which is constantly replaced) and above the subcutaneous layer (the layer of cells, primarily fat cells, above the muscles and bones, also sometimes referred to as the hypodermis). Most tactile nerve cells are situated in the dermis, though some are also located in the subcutaneous layer. Therefore, by situating a stimulator in the dermis, the stimulator is not subject to the insulating effect of the epidermis, and more direct input to the tactile nerve cells is possible. Perceptible tactile mechanical (motion) inputs may result from stimulator motion on the order of as little as 1 micrometer, whereas above-the-skin tactile input systems require significantly greater inputs to be perceivable (with sensitivity also depending where on the body the system is located). If the stimulators use electrical stimulation in addition to or instead of mechanical (e.g., motion) stimulation, a problem encountered with prior electrotactile systems—that of maintaining adequate conductivity—is also reduced, since the tissue path between the stimulators and the tactile nerve cells is short and generally conductive. Additionally, so long as a stimulators is appropriately encased in a biocompatible material, expulsion of the stimulator from the skin is unlikely. In this respect, it is noted that when tattoos are applied to skin, ink particles (sized on the micrometer scale) are driven about ⅛ inch into the skin (more specifically the dermis), where they remain for many years (and are visible through the translucent, and oven nearly transparent, epidermis). In contrast, implantation in the epidermis would cause eventual expulsion, since the epidermis is constantly replaced. However, expulsion may be desired for certain application.

Figure 15:
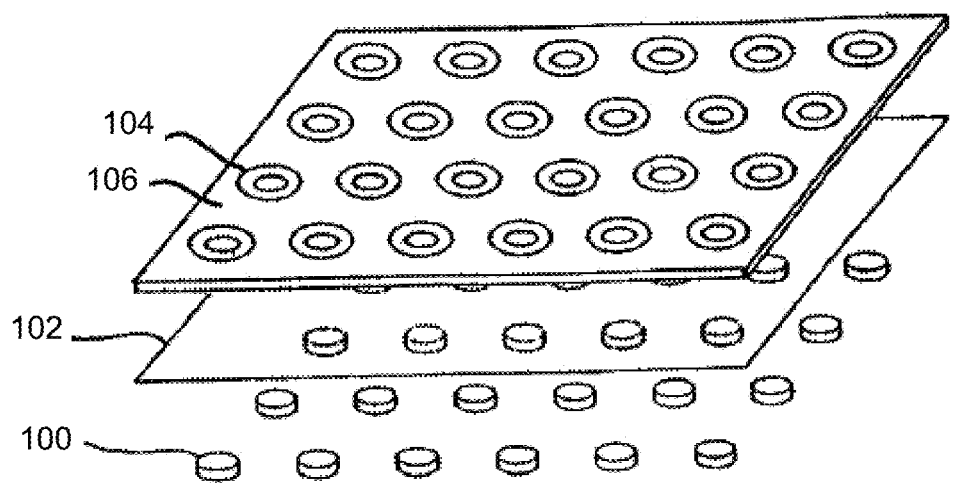
FIG. 15 is a simplified perspective view of an exemplary input system wherein an array of transmitters 104 magnetically actuates motion of a corresponding array of stimulators 100 implanted below the skin 102.

A first exemplary version of the device, as depicted in FIG. 15, involves the implantation of one or more stimulators 100 formed of magnetic material in an array below the skin (with the external surface of the epidermis being depicted by the surface 102), and with the array extending across the area which is to receive the tactile stimulation (e.g., on the abdomen, back, thigh, or other area). Several transmitters 104 are then fixed in an array by connecting web 106 made of fabric or some other flexible material capable of closely fitting above the skin 102 in contour-fitting fashion (with the web 106 being shown above the surface of the skin 102 in FIG. 15 for sake of clarity). The transmitters 104 are each capable of emitting a signal (e.g., a magnetic field) which, when emitted, causes its adjacent embedded stimulator 100 to move. The transmitters 104 may simply take the form of small coils, or may take more complex forms, e.g., forms resembling read/write heads on standard magnetic media data recorders, which are capable of emitting highly focused magnetic beams sufficiently far below the surface 102 to cause the stimulators 100 to move. Thus, when an input signal is applied to a transmitter 104, it is transformed into a signal causing the motion of a corresponding stimulator 100, which is then felt by surrounding nerves and transmitted to the user's brain.

The input signals provided to the transmitters 104 may be generated from camera or microphone data which is subjected to processing (by a computer, ASIC, or other suitable processor) to convert it into desired signals for transmission by the transmitters 104. (Neither the processor, nor the leads to the transmitters 104, are shown in FIG. 15 for sake of clarity). While the signals transmitted by the transmitters 104 could be simply binary on-off signals or gradually varying signals (in which case the user might feel the signals as a step or slow variation in pressure), it is expected that oscillating signals that cause each of the stimulators 100 to oscillate at a desired frequency and amplitude allows a user to learn to interpret more complex information inputs—for example, inputs reflecting the content of visual data, which has shape, distance, color, and other characteristics.

The stimulators 100 may take a variety of forms and sizes. As examples, in one form, they are magnetic spheres or discs, preferably on the order of 2 mm in diameter or less; in another form, they take the form of magnetic particles having a major dimension preferably sized 0.2 mm or less, and which can be implanted in much the same manner as ink particles in tattooing procedures (including injection by air pressure). The stimulators 100 may themselves be magnetized, and may be implanted so their magnetic poles interact with the fields emitted by the transmitters 104 to provide greater variation in motion amplitudes.

It should be understood that each transmitter 104 might communicate signals to more than one stimulator 100, for example, a very dense array of stimulators 100 might be used with a coarse array of transmitters 104, and with each transmitter 104 in effect communicating with a subarray of several stimulators 100. Arrays of stimulators 100 which are denser than transmitter arrays 104 are also useful for avoiding the need for very precise alignment between stimulators 100 and transmitters 104 (with such alignment being beneficial in arrays where there is one transmitter 104 per stimulator 100), since the web 106 may simply be laid generally over the implanted area and each transmitter 104 may simply send its signal to the closest stimulator(s) 100.

If precise alignment is needed, one or more measures may be used to achieve such alignment. For example, a particular tactile signal pattern may be fed to the transmitters 104 as the user fits the web 106 over the stimulators 100, with the user then adjusting the web 106 until it provides a sensation indicating proper alignment; and/or certain stimulators 100 may be colored in certain ways, or the user's skin might be tattooed, to indicate where the boundaries of the web 106 should rest. (Recall that if the stimulators 100 are implanted in the dermis, they will be visible through the translucent epidermis in much the same manner as a tattoo unless they are colored in an appropriate fleshtone).

Figure 16:
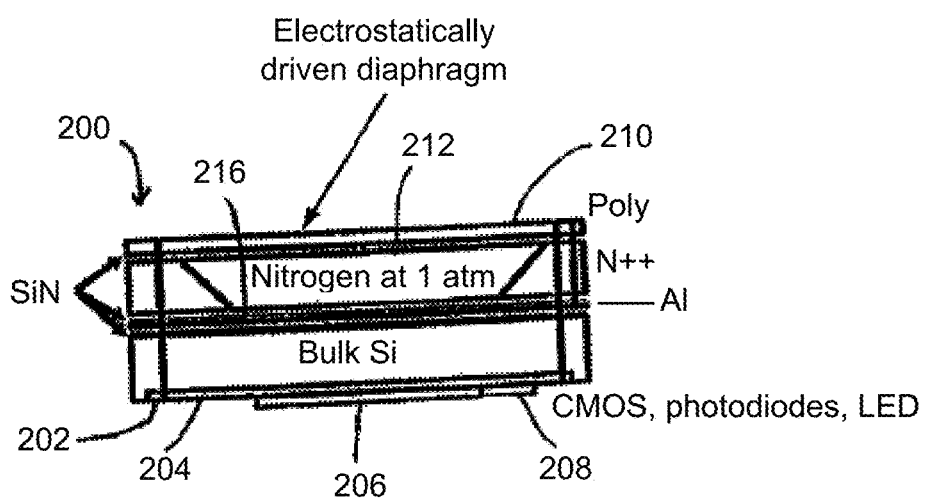
FIG. 16 is a simplified cross-sectional side view of a stimulator 200 of a second exemplary input system, wherein the stimulator 200 delivers motion output to a user via a deformable diaphragm 212.
Figure 17:
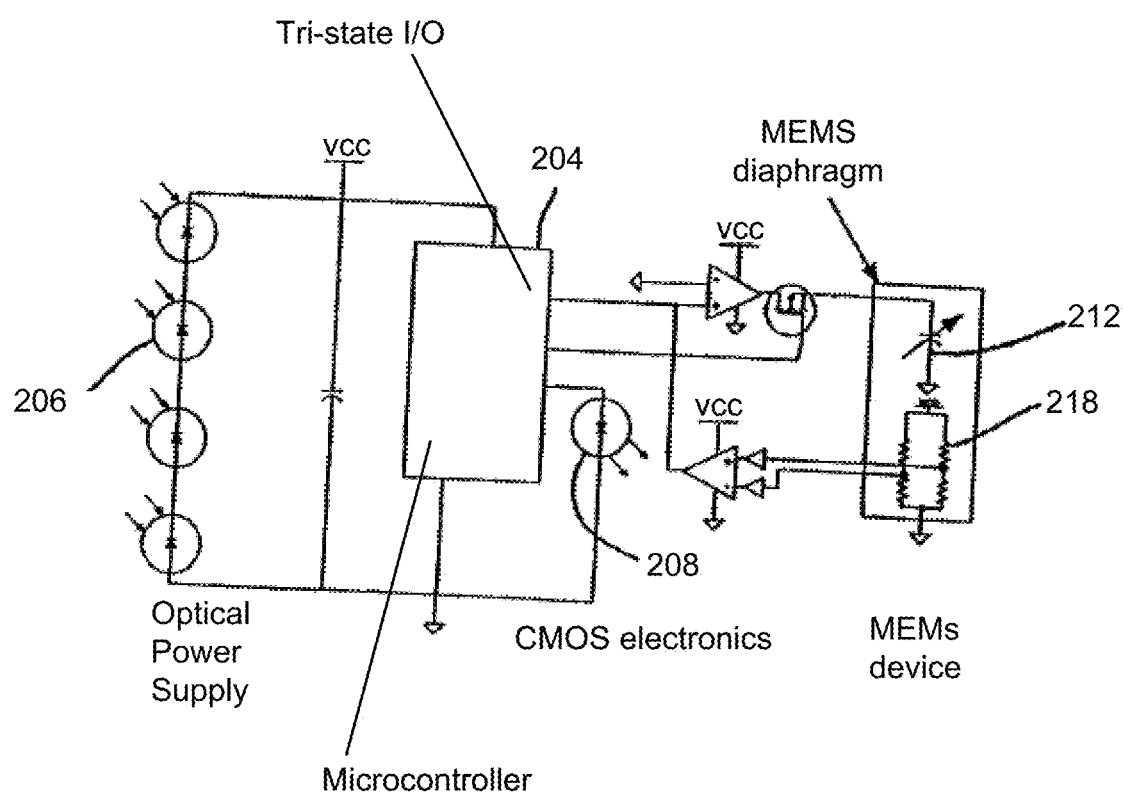
FIG. 17 is a simplified circuit diagram showing exemplary components suitable for use in the stimulator 200 of FIG. 16.
Figure 18:
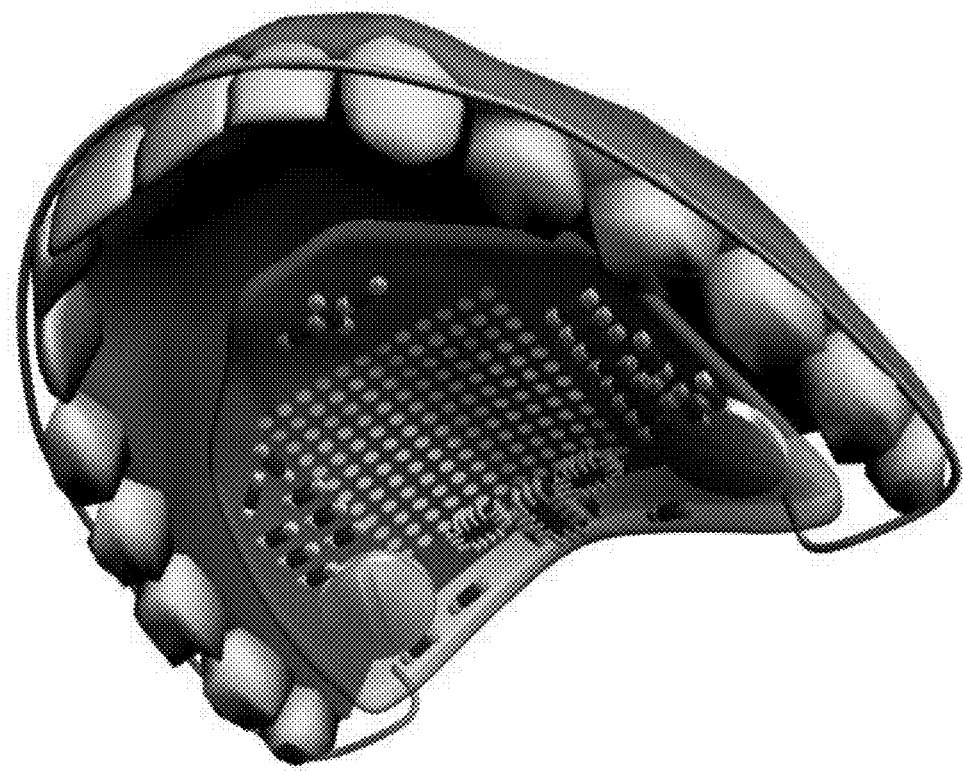
FIG. 18 shows an exemplary in-mouth electrotactile stimulation device of the present invention.

The foregoing version of the invention is "passive" in that the stimulators 100, that are effectively inert structures, are actuated to move by the transmitters 102. However, other versions of the invention wherein the stimulators include more "active" features are may be used, e.g., the stimulators may include features such as mechanical transducers that provide a motion output upon receipt of the appropriate input signal; feedback to the transmitters; onboard processors; and power sources. As in the tactile input system discussed above, these tactile input systems preferably also use wireless communications between implanted stimulators and externally-mounted transmitters. To illustrate, FIGS. 16 and 17 present a second exemplary version of the invention. Here, a stimulator 200 has an external face 202 which includes a processor 204 (e.g., a CMOS for providing logic and control functions), a photocell 206 (e.g., one or more photodiodes) for receiving a wireless (light) signal from a transmitter, and an optional LED 208 or other output device capable of providing an output signal to the transmitter(s) (not shown) in case such feedback is desired. Light send by the transmitter(s) to the photocell 206 both powers the processor 204 and conveys a light-encoded control signal for actuation of the stimulator 200. On the internal face 210 of the stimulator 200, a diaphragm 212 is situated between the dermis or subcutaneous layer and an enclosed gas chamber 214, and an actuating electrode 216 is situated across the gas chamber 214 from the diaphragm 212. Light signals transmitted by the transmitter(s), discussed in greater detail below, are received by the photocell 206, which charges a capacitor included with the processor 204, with this charge then being used to electrostatically deflect the diaphragm 212 toward or away from the actuating electrode 216 when activated by the processor 204. Since the diaphragm 212 only needs to attain peak-to-peak motion amplitude of as little as one micrometer, very little power is consumed in its motion. Piezoelectric resistors (218) (FIG. 17) situated in a Wheatstone bridge configuration on the diaphragm 212 measure the deformation of the diaphragm 212, thereby allowing feedback on its degree of displacement, and such feedback can be transmitted back to the transmitter via output device 208 if desired.

The stimulator 200 is preferably scaled such that it has a major dimension of less than 0.5 mm. With appropriate size and configuration, stimulators 200 may be implanted in the manner of a convention tattoo, with a needle (or array of spaced needles) delivering and depositing each stimulator 200 within the dermis or subcutaneous layer at the desired depth and location. Using state of the MEMS processing procedures, it is contemplated that the stimulator 200 might be constructed with a size as small as a 200 square micrometer face area (e.g., the area across the external face 202 and its internal face 210), with a depth of approximately 70 micrometers. An exemplary MEMS manufacturing process flow for the stimulator 200 is as follows:

| Step | Side of wafer | Comment |
|---|---|---|
| 2 um CMOS process | Top | More tolerant to defects |
| Attach handling wafer | Top | |
| Planarize (CMP) | Bottom | Thin to approximately 50 um |
| Deposit SiN | Bottom | Insulate lower electrode |
| Sputter Al | Bottom | Lower electrode |
| Lithography | Bottom | Electrode and pads for vias |
| Deposit SiN | Bottom | Insulate lower electrode |
| Deposit poly | Bottom | Approximately 150 um |
| Deposit SiN | Bottom | Mask for cavity |
| Lithography | Bottom | Pattern hole for cavity |
| Etch | — | KOH to form cavity (timed) |
| Deposit poly | Bottom | Seal cavity and strengthen diaphragm |
| Etch (RIE) | Bottom | Vias; 2 through-hole, 1 stops a lower electrode metal |
| Fill vias | Bottom | Tungsten |
| Planarize (CMP) | Bottom | Planarize |
| Deposit Ti | Bottom | Titanium (bio-compatible) |
| Lithography | Bottom | Cover only tungsten, or do not do litho at all if diaphragm is unaffected |
| Planarize (CMP) | Top | Remove handling wafer |
| Lithography | Top | Pattern for via to pad interconnect |
| Deposit Al | Top | Deposit via a pad interconnect |
| Lithography | Bottom | Pattern for via to pad and via to via interconnect |
| Deposit Al | Bottom | Deposit via to pad and via to via interconnet |

The transmitter (not shown) may take the form of a flexible electro fluorescent display (in which case it may effectively provide only a single transmitter for all stimulators 200), or it could be formed of an array of LEDs, electro fluorescent displays, or other light sources arrayed across a (preferably flexible) web, as in the transmitter array of FIG. 15. The transmitter(s) supply light to power the photocells 206 of the stimulators 200, with the light bearing encoded information (e.g., frequency and/or amplitude modulated information) which deflects the diaphragms 212 of the stimulators 200 in the desired manner. The light source(s) of the transmitter, as well as the photocells 206 of the stimulator 200, preferably operate in the visible range since photons in the visible range pass through the epidermis for efficient communication with the powering of the stimulators 200 with lower external energy demands.

With appropriate signal tailoring, it is possible to have one transmitter provide distinct communications directed to each of several separate stimulators 200. For example, if the transmitter delivers a frequency modulated signal that is received by all stimulators 200, but each stimulator only responds to a particular frequency or frequency range, each stimulator 200 may provides its own individual response to signals delivered by a single transmitter. An additional benefit of this scheme is that the aforementioned issue of precise alignment between individual transmitters and corresponding stimulators is reduced, since a single transmitter overlaying all stimulators 200 may effectively communicate with all stimulators 200 without being specifically aligned with any one of them.

The description set out above is merely of exemplary versions of the invention. It is contemplated that numerous additions and modifications can be made. As a first example, in active versions of the invention wherein an actuator is used to deliver motion output to the user, actuators other than (or in addition to) a diaphragm 212 may be used, e.g., a piezoelectric bimorph bending motor, an element formed of an electroactive polymer that changes shape when charged, or some other actuator providing the desired degree of output displacement.

As a second example, while the foregoing tactile input systems are particularly suitable for use with their stimulators imbedded below the epidermis, the stimulators could be implemented externally as well, provided the output motion of the stimulators has sufficient amplitude that it can be felt by a user. To illustrate, the stimulators might be provided on a skullcap, and might communicate with one or more transmitters provided on the interior of a helmet.

As an additional example, the foregoing versions of the invention find use with other forms of stimulation, e.g., electrical, thermal, etc., instead of (or in additional to) mechanical stimulation. Greater information is provided in some embodiments by combining multiple types of stimulation. For example, if pressure and temperature sensors are provided in a prosthetic and their output is delivered to a user via mechanical and thermal stimulators, the prosthetic may more accurately mimic the full range of feeling in the missing appendage. As another example, in a vision substitution system, mechanical inputs might deliver information related to the proximity of object (in essence delivering the "contour" of the surrounding environment), and electrical stimulation delivers information regarding color or other characteristics.

These systems may be applied to any of the range of applications described herein.

In some embodiments, the embedded components further serve aesthetic and/or entertainment purposes. Because the embedded components are, or can be designed to be, visible, they may be used to serve tattooing or cosmetic implant functions—i.e., to provide color, texture, and/or shapes under the skin with desired aesthetic features. Additional embedded components without sensory function may be added to enhance or fill out the image provided by the embedded stimulators. LED or other components can provide light to enhance the appearance of the device. For example, stimulators that are in use may be lit. Alternatively lighting patterns are provided randomly or upon cue (e.g., as a timekeeping device, upon receipt of a signal from an external device (e.g., phone)).

In some embodiments, the embedded devices are used as communication methods, much like text messaging of cell phones. Message sent via any desired method (e.g., cell phone) are perceived in the embedded devices. This allows covert communication. In some embodiments, the system is configured to receive a person-specific code in the transmitted message so that only a person with a particular stimulator array receives the code even though the message is transmitted more generally (e.g., via the airwaves). Like Internet community communication systems, groups of users can also be designated to receive the signal.

In some embodiments, the embedded stimulator is used as a covert matchmaking service. A subject has a processor that specifies: 1) criteria of others that they would seek in a relationship (e.g., friendship, romantic relationship, etc.); 2) personal criteria to transmit to others; and/or 3) a set of rules for activating or deactivating the system (e.g., for privacy). When the subject is in the physical vicinity of a match and when the match's system is transmitting a willingness to meet people, the embedded stimulator triggers an alarm and indicates the direction and location of the match. The subject receiving the signal, upon seeing the match can choose to send a reciprocal "are you interested" signal (or perhaps, as a default has been sending such a signal). The match can then choose to initiate actual contact. Because the subject does not know whether the match's system is "on" and therefore whether the match received signal, the subject's ego need not be hurt if the match does not respond.

In some embodiments, a large number of stimulators are provided all over the body. The stimulators may be used much like the tactile body suit described in Example 10.

Example 19

Processor Command Set

This Example describes aspects and operation of a Tactile Display Unit, or TDU, device in some embodiments of the present invention. The TDU is a wave generator in its simplest construct. Control of the TDU occurs via a ASCII based communication language. The commands that allow a computer program to communicate with the TDU are described below. Also discussed is the underlying theory behind using the TDU.

Terminology

Tactor: a single electrode on the array.

Block: a square-shaped group of tactors referenced by the upper left and lower right tactor numbers. Block sizes range from a single tactor to all 144 tactors.

Channel: a single output from the TDU to a tactor.

TDU Principles

Operating on 144 channels separated into 4 sectors, the TDU uses a scheme of transmitting pulses along an array to the user. An array consists of a 72-pin insulated cable that terminates in a rectangular matrix (12×6) of tactors. Merging two separate arrays provides the square matrix (12×12) formation that is used by the TDU. The 12×12 square matrix is subdivided into four sectors (6×6) denoted as A, B, C, and D. This formation is due to the specific implementation of the hardware and is of little concern to the user or even the developer. Specifically, because of workload and speed requirements, four processors work in parallel to handle the output to the arrays. As one might imagine, each processor corresponds to a sector on the arrays.

Tactor addresses are numbered from left to right, top to bottom. So, the top row of tactors has addresses 1-12 while the bottom row of tactors has addresses 133-144. Due to the numbering construct, it is important to note that the sectors do not contain a single contiguous list of addresses. Although from the standpoint of the user, this is abstracted away and only the addresses are available.

Any imaginable animated display can be presented to the user via the TDU. The TDU runs at a very high frame rate and has the ability to respond very quickly to user feedback. Beyond these properties, the system is mobile which provides an added level of flexibility.

Analysis of a Waveform

A waveform consists of numerous parts. The most fundamental layer is the outer burst. The waveform is simply a continuous or discrete grouping of outer bursts. Each outer burst consists of a certain number of inner bursts. Within the inner bursts, there are an arbitrary number of pulses.

Figure 20:
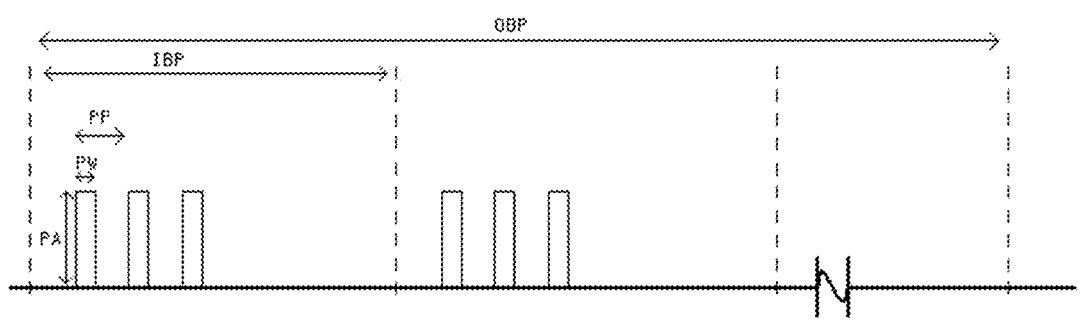
FIG. 20 shows a sample wave-form useful in some embodiments of the present invention.

Each pulse has a certain width and height along with a specifiable distance between consecutive pulses. A sample waveform for a single channel is provided in FIG. 20. Properties of this waveform that have been previously alluded to are now discussed. The first property is the outer burst number (OBN), which specifies the number of inner bursts that reside in each outer burst. The outer burst also has a period (OBP), which is its duration. Within the inner burst are the pulses. The inner burst number (IBN) is a parameter, which specifies the number of these pulses. In FIG. 20 the IBN is three. Associated with an inner burst, there is a specifiable period known as the inner burst period (IBP).

Beyond the aforementioned parameters, it is possible to specify the pulse width (PW), pulse period (PP) and pulse amplitude (PA).

For each channel the pulse width, pulse amplitude, inner block number and outer block number are specifiable. Hence, each channel is independent and can have its own specific waveform, although the period of each component of the waveform (inner burst, outer burst and inter channel periods) is constant across the entire array. The inner channel period (ICP) is a parameter that ties the channels together. This parameter specifies the time delay between channels corresponding to the beginning of each new outer burst. So, if FIG. 20 specifies channel 1 and it begins at time t=0, and the inner channel period is 100 microseconds, then channel 2 will begin stimulating at time t=100 us. Note that the inner channel period affects each block independently. Hence, for example channels 1 and 7 begin at the same time, since they occupy different blocks (A and B).

Note that valid ranges for each of these parameters are specified in Table 7.

TABLE 7

Valid Ranges for Different Parameters

| Parameter | Range |
| --- | --- |
| OBN | 0-255 bursts |
| IBN | 0-255 pulses |
| OBP | 5-1275 ms |
| IBP | 100-25500 μs |
| ICP | 2-510 μs |
| PP | 2-510 μs |
| PW | 0-510 μs |
| PA | 0-40 Volts |

Since there is an infinite number of possible waveforms that can be generated, some concern should be taken into choosing one that is 'comfortable' for the user. Comfort is an important element since electrical current is being passed through a highly conductive and sensitive region.

Communicating with the TDU

One of the most important functions of the TDU is the ability to create dynamic output to the arrays. Hence, there is concern of when and how often a waveform can be updated. Updating a waveform occurs whenever a new command is issued. The change in the TDU's output occurs on the next inner burst or outer burst, whichever comes first (See FIG. 20). When implementing code to run with the TDU, there are specific considerations to be taken into account. The first, and most important is Nyquist's Law or sometimes known as the Sampling Theorem. This law states that in order to accurately reconstruct a time-varying system, samples of the system must be taken at twice the frequency of variation or faster. In the situation presented, the TDU is performing the sampling. It is expected that the most code written to communicate with the TDU will send commands to it at a regular interval. Because the TDU is sampling the incoming signals, it should be running twice as fast as the incoming signals in order to correctly model what the computer code is sending. For example, if one is sending image updates at 25 frames per second to the TDU, then the inner burst period of the TDU should be 20 ms, which corresponds to an update rate of 50 frames per second.

Another consideration when implementing code is the type of communication scheme to use. There are two basic forms of communication in a PC environment. The first can be called "serial communications" while the other form is "parallel communications." Serial communications occurs in a format where commands are issued one at a time and a command cannot be issued until the previous one is implemented. Parallel communications allows for a multitude of commands to be issued at any given moment. They can align themselves in a queue while waiting to be processed. The TDU works in a communications mode where every command received generates a response. Write commands are followed by a single byte status response while read commands have responses of varying length. While the TDU is processing a command, it cannot receive another command. Thus, the method of communication that is the current version of the TDU utilizes is denoted as serial. In terms of Windows 98/NT/2000 programming, it is called non-overlapped I/O.

The Command Set

The command set is ASCII in nature and each command is case sensitive. The upper case is a write command, while the lower case is a read. The length of each code varies depending on the type of addressing scheme. Some commands address individual tactors, others address a subset of the array, while other commands operate on the entire array.

After any write command is issued, the TDU issues a single byte response. One must be careful to not send another command until the response has been received. It is possible to eliminate reading the TDU responses, but one must still wait a certain amount of time before sending another command.

Below is an abbreviated list of the commands.

COMMAND: A/a Pulse Amplitude (PA) for a single tactor.
B/b Pulse Width (PW) for a single tactor.
C/c Number of Inner Bursts (Outer Burst Number) for a single tactor.
D/d Number of Pulses per Inner Burst (Inner Burst Number) for a single tactor.
E/d Pulse Amplitude for each tactor in a block
F/f Pulse Width for each tactor in a block.
G/g Number of Inner Bursts (Outer Burst Number) for each tactor in a block.
H/h Number of Pulses per Inner Burst (Inner Burst Number) for each tactor in a block.
I/i Pulse Period (PP) for the entire array.
J/j Outer Burst Period (OBP) for the entire array.
K/k Inner Burst Period (IBP) for the entire array.
L/l Inter-channel Period (ICP) for the entire array.
M/m Amplitude Scaling for the entire array.
N/n Update a pre-programmed pattern.
O Start Stimulation of currently loaded pattern.
P Stop Stimulation of currently loaded pattern.
Q Display a pre-programmed pattern.
R Deliver a sequence of outer bursts.
s Current analog value for a channel
T Total comma: Pulse Amplitude, Pulse Width, Outer Burst Number and Inner Burst Number for each tactor in a block.

The command set allows for manipulation of the parameters of a single tactor, a block of tactors or the entire array.

Using the TDU

The TDU is basically a waveform generator. There is a display panel that provides useful information, a keypad to provide input, a serial communications port, connections for the arrays, and a knob that provides amplitude scaling of the entire array.

Connection of the Arrays

The arrays connect via the two 72-pin slots on the side of the TDU. The right pin slot is for the lower array, while the left slot is for the upper array. The upper array is defined as the one that stimulates the back of the tongue, while the lower array stimulates the front of the tongue.

Modes of Operation

The TDU can operate in three distinct modes. These modes are denoted as "standalone," "remote," and "programmable." Standalone mode allows for the TDU to display pre-programmed patterns without the intervention of a computer. Programmable mode allows the TDU to have patterns programmed into its memory. It is possible to program in 64 distinct patterns in the embodiment described in this example. The third mode, remote, allows for the TDU to be controlled from an external source (e.g., a laptop computer). Communication occurs via the serial communications ports on the TDU and the laptop.

TDU at Startup

On startup, the TDU presents options on its LCD screen to choose the mode of operation. In most cases, remote mode should be chosen. After choosing this mode via the keypad, another set of options is displayed. These options are the for the communications speed of the serial port on the TDU. Unless there is reason in doing so, only choose the third option: the 115,200 baud rate. Note that computer code that implements any communications with the TDU sets the baud rate to the appropriate rate. Hence, no intervention on the configuration of the laptop's communications port is required.

At this point, the TDU is ready to operate remotely and should display the message 'Status: Remote'. Programs that interact with the TDU generally need to be notified of the status of the TDU. Usually, there is a menu option in a computer program to allow for initialization of the TDU. At the point when the TDU displays the 'Status: Remote' message, it is allowable to proceed with remote initialization. After the computer code initializes the TDU, the message on the LCD panel should change to read 'Stimulation Pattern Active.' At this point output to the arrays is occurring, although the computer code may have initialized the output to be of zero potential, which causes no apparent stimulation from the arrays.

Resetting the TDU

It is possible to access the startup menu again by pressing the menu key on the keypad. This is effectively a soft reset of the TDU. A hard reset occurs by turning the TDU off and then on again.

Selecting Pre-Programmed Patterns

As mentioned previously, the TDU has the ability to display pre-programmed patterns via its standalone mode. Once this mode is selected, all that is required to initiate stimulation is to choose a pattern number via the keypad and press the 'Enter' key. If no pattern was programmed into the selected pattern number address, then there will be no stimulation. Also, the TDU will issue a message stating 'No Pre-programmed Pattern.' If the selected pattern does exist in memory, the TDU issues the message 'Pre-programmed pattern #x', where x is the pattern number chosen.

In preferred embodiments, the TDU is battery powered for portability and can operate for several hours before the internal NiCd batteries need recharging. The TDU can display one of 53 pre-programmed, non-moving patterns in a stand-alone mode; these patterns can be updated using a simple point-and-click pattern editor (Win95/98) which is supplied with the TDU. Alternatively, the TDU can be controlled by an external computer via RS-232 serial link. All of the stimulation waveforms can be controlled in this way; the entire array can be updated up to 55 times per second.

Stand Alone Mode Operation
1. Turn on power and press '1' key to select Stand Alone mode, or wait 10 seconds and this mode will be entered automatically.
2. Turn intensity knob on side panel fully counterclockwise. Operation cannot continue until this is done.
3. Select a pattern (1-53) using the 0-9 numbers or the up/down arrow keys. A brief pattern description will appear on the display. If no pattern is stored for a particular number, 'NOT INITIALIZED' will appear on the display and the stimulation cannot be turned on.
4. Press 'Start' key to turn on stimulation.
5. Use the intensity knob to control stimulation intensity (voltage). Note that individuals have varying requirements for comfortable stimulation.
6. While stimulation is on, the pattern may be changed by using the number or arrow keys. If an uninitialized pattern is selected, the previous pattern will continue to be displayed.
7. Use the 'Stop' key to turn off the stimulation.
8. Use the 'Menu' key to exit Stand Alone mode.

Remote Mode Operation
1. Make sure TDU serial port 1 (next to power switch) is connected to the external computer using a "straight-through" serial cable.
2. Turn on power and press '2' key within 10 seconds to select Remote mode.
3. Turn intensity knob on side panel fully counterclockwise. Operation cannot continue until this is done.
4. Press '1', '2', or '3' key to select serial port data rate of 9.6, 19.2, or 115.2 kbps to match the external computer data rate (determined by software used to control the TDU).
5. The TDU can now be controlled by command from the external computer. Note that the pattern number, 'Start', and 'Stop' keys will not work in Remote Mode. The intensity knob may or may not function according to the commands from the external computer.
6. See the "TDU Command Language/Protocol" document for programming information.
7. Press the 'Menu' key to exit Remote Mode.

Update Pattern Mode Operation
1. Make sure TDU serial port 1 (next to power switch) is connected to the external computer using a "straight-through" serial cable.
2. Turn on power and press '3' key within 10 seconds to select Update Pattern mode.
3. Press '1', '2', or '3' key to select serial port data rate of 9.6, 19.2, or 115.2 kbps to match the external computer data rate (determined by software used to control the TDU).
4. Use the TDU Editor program to create and edit TDU patterns.
5. Press the 'Menu' key to exit Update Pattern mode.

The waveform parameters in some embodiments of the present invention are as follows:

| Abbr. | Name | Range (resolution) | Definition |
|---|---|---|---|
| Parameters controllable tactor-by-tactor | | | |
| PA | Pulse amplitude | 0-40 (0.157) V | Pulse amplitude |
| PW | Pulse Width | 0-510 (2) µs | Width of individual pulse |
| IBN | Inner Burst Number | 0-255 (1) pulses | Number of pulses per inner burst |
| OBN | Outer Burst Number | 0-255 (1) bursts | Number of inner bursts per outer burst |
| Array-wide parameters | | | |
| PP | Pulse Period | 2-510 (2) µs | Time between onset of pulses in one channel |
| IBP | Inner Burst Period | 100-25,500 (100) µs | Time between onset of inner bursts |
| OBP | Outer Burst Period | 5-1,275 (5) ms | Time between onset of outer bursts |
| ICP | Inter-Channel Period | 2-510 (2) µs | Time btw onset of adjacent chan inner bursts |
| SQN | Sequence Number | 0-255 (1) bursts | Number of outer bursts in sequence |
| PAS | Pulse amplitude scale | 0-100 (0.392) % | Pulse amplitude scale (Actual pulse output amplitude is PA × PAS.) |

The pulse parameter ranges shown above are intentionally wide so that the TDU may be used for research purposes. Not all parameter combinations are valid or useful for stimulation. The TDU will not attempt to deliver invalid waveforms.

Note also that some parameter values become meaningless under certain conditions. For example, IBP has no meaning when OBN=1, and PP has no meaning when IBN=1. Also, some zero parameter values will result in no stimulation; this is the case for PW, IBN, OBN, PA.

PA, PW, IBN and OBN are individually controllable tactor by tactor and are updated at the beginning of each outer burst sequence. PAS, ICP, PP, IBP, and OBP control the entire array. PAS is optionally assignable to the side panel intensity control.

All burst sequences are completed before changing any parameter values. Outer bursts are normally delivered continuously, but provision is made for delivering a fixed number of outer bursts, after which the stimulation is turned off automatically. The TDU will respond to a stimulation off command during delivery of a fixed number of bursts.

A typical, or baseline, set of stimulation parameters for comfortable stimulation is:
PW 25 µs
PP N/A
IBP 5 ms
OBP 20 ms
ICP 138.9 or 138 µs
IBN 1 pulse
OBN 3 pulses
PA 10 V
PAS 100%

Controls
1. Power switch
2. Number keys 0-9 to select mode and pattern
3. Pattern up (arrow) key
4. Pattern down (arrow) key
5. Start stimulation key
6. Stop stimulation key
7. Intensity knob
8. Reset button (yellow, side panel; same function as power off/on)

Display
The front-panel LCD display indicates:
1. Operational mode (programmed or stand-alone)
2. Stimulation status (Active/Idle)

3. In Stand Alone mode, indicates pattern number and description
4. Low battery status
5. Value of intensity control (rotation 0-100%)

Safety features
1. Hardware power switch: it must turn off.
2. Internal diagnostic self-check, and watchdog hardware timer power-down.
3. Absence of spurious pulses during mode switching or programming.
4. Electrical isolation: Power and serial connections must be electrically isolated from the rest of the circuity up to 1000 V.

Output: Controlled voltage pulses, 0-40 V.
 Output resistance is normally 1 kΩ, but is adjustable by changing internal resistors.
 Output is capacitively-coupled by 0.1-µcapacitors.
 Output connection is via four 40-pin (20×2) IDC-style male connectors. A separate document "Electrode pin-out"provides details.

Analog in: The TDU has seven 0-5 V analog inputs numbered 0-6; input 0 is reserved for the side panel intensity knob. The others are externally available. All can be read via a command in Remote mode.

Example 20

Treatment of Dysphonia

Experiments conducted during the development of the present invention demonstrated that tactile simulation may be used to treat subjects suffering from dysphonia.

Foacal dystonias (Spasmodic dysphona)

Spasmodic dysphonia is one type of a family of disorders called focal dystonias. When a single muscle or small group of muscles contract spontaneously and irregularly without good voluntary control, those muscles are dystonic. While there are dystonias where a large number of muscles or a complete region of the body is involved, focal dystonias are limited to a small area or single muscle. Examples would include torticollis where a spasm of a neck muscle causes the head to rotate. Blepharospasm is when the muscle around the eye spontaneouldy twitches. Writers cramp is when the muscles of the hand spasm. Spasms of the muscles in the voice box are a laryngeal dystonia.

Laryngeal Dystonias

There are several types of laryngeal dystonia. The most common type is when the muscles that bring the vocal folds together for speaking intermittently spasm. Since the voice box serves several functions, including speaking, breathing and preventing food from getting into the lungs when swallowing; laryngeal dystonias can affect more than the voice. When the voice is the primary site affected, then the laryngeal dystonia is called spasmodic dysphonia. It has also been referred to as spastic dysphonia.

Adductor Spasmodic Dysphonia

Adductor spasmodic dysphonia is the most common type of laryngeal dystonia and involves spasms of the muscles that close the vocal folds. It could be appropriately called the strain-strangled voice. The spasms cause a choking off of the voice or interruptions of the voice. Adductor spasmodic dysphonia may also sound just like a tightness or effortfulness without any obvious cutting out type symptoms.

Abductor Spasmodic Dysphonia

Abductor spasmodic dysphonia involves the muscles that open the voice box for breathing. If they spasm while speaking the person develops an involuntary whisper while trying to speak.

Respiratory Dysphonia

Respiratory spasmodic dysphonia is from a spasms of the vocal fold muscles belonging to the adductor group but instead of spasming during speaking, they spasm during breathing. Theses spasms create noisy and difficult breathing even when a subject is not intending to make a noise.

A subject having an inability to speak was treated with the systems and methods of the present invention. Electrotactile tongue training as described in Example 1 was used to cause the subject to concentrate while receiving electrotactile stimulation. The subject was encouraged to try to talk during the training process. After training, the subject regained the ability to speak. The ability to speak was retained after electrotactile stimulation was discontinued.

Example 21

Recovery from Traumatic Brain Injury

Traumatic Brain Injury

Traumatic Brain Injury (TBI) has been defined as " . . . an acquired injury to the brain caused by an external physical force, resulting in total or partial functional disability or psychosocial impairment, or both." Therefore, in general, TBI refers to open or closed head injuries, but, generally, does not apply to "injuries that are congenital or degenerative, or to brain injuries induced by birth trauma, although the present invention find use in both categories. (See, e.g., The Individuals with Disabilities Education Act. 34 *Code of Federal Regulations* § 300.7(c)(12)).

TBI can result from, among other things, vehicular accidents, falls, assaults, and sport injuries, in which an external force causes the brain to move, inflicting trauma to the brain. Insufficient oxygen supply to the brain, infection or poisoning may also cause TBI-related dysfunctions.

TBI is generally characterized as a heterogeneous disorder, affecting an individual's physical, cognitive and psychosocial functioning. Due to the extent of trauma inflicted to the brain, the location of injury, and the availability of emergency procedures, TBI can result in serious, and in many cases life-long, impairments.

Epidemiology of Traumatic Brain Injury in the United States

The report to the United States Congress drafted by the Centers for Disease Control and Prevention indicates the following annual estimates for the years 1995 through 2001:

Annually, at least 1.4 million people sustain a Traumatic Brain Injury. Of these, about 50,000 die, 235,000 are hospitalized, and 1.1 million are treated and released from an emergency department. (Traumatic Brain Injury in the United States: Emergency Department Visits, Hospitalizations, and Deaths." National Center for Injury Prevention and Control., available at http://www.cdc.gov).

Recently, prevalence of TBI is estimated at 2.5 million to 6.5 million individuals suffering from any kind of impairment resulting from Traumatic Brain Injury in the United States. In 1995, the incidence of hospitalization for TBI was calculated at 100 per 100,000 based on population estimates. When compared with the early 80's estimates of 200 per 100,000 hospitalized cases of head injury, the incidence seems to have decreased. Nevertheless, this assumption has proved misleading due to the fact that many cases of mild Traumatic Brain Injury are not being hospitalized and/or are being undiagnosed and thus underestimated. (See, e.g., Novack "TBI Facts and Stats". Recovery after TBI Conference. September [1999] http://www.neuroskills.com).

The mortality rate for TBI is 30 per 100,000, resulting in an annual mortality rate of 52,000 individuals. 50% of deaths related to TBI occur within the first 2 hours of injury, which indicates an increased need of immediate medical attention upon an incidence of TBI. As Novack suggests, "the treatment given by paramedics and in the emergency room can make a big difference in terms of an individual's survival."

Demographic statistics indicate that males are at a greater risk, namely they are twice as likely as females to suffer from TBI. There are also specific age groups that are at a higher risk of inducing TBI than others. The highest incidence is among individuals within the age category of 15-24 years. An increased risk is also associated with people over 75 years of age and children 5 and younger.

Alcohol and drug abuse is closely connected with higher incidence rates. Alcohol abuse is reported in about half of the cases of TBI, in which either the victim or the individual causing the head trauma was under the influence of alcohol or other substances.

The greatest percentage of TBIs are the result of a vehicular accident, involving, among other instruments, vehicles, bicycles, motorbikes, and pedestrians. The second most frequent cause of TBI is falls, mostly affecting the elderly or the very young. About 20 percent of TBIs are a direct cause of violence, both firearm and non-firearm assaults. An alarming statistic regarding TBI victims who are 5 and younger indicates that a leading cause of TBI in children under five is assault. Even though only 25 percent of TBIs in young children are a result of child abuse, the "Shaken baby syndrome" is a significant contributor to high incidence of TBI in infants. Sports-related injuries are only a fraction, namely 3 percent, of all TBI. Nevertheless, approximately 90 percent of these injuries are mild TBIs that are generally unreported, underestimated and thus are not treated properly.

Degrees of Severity of Traumatic Brain Injury

Standard clinical assessment distinguishes at least three degrees of Traumatic Brain Injury based on the Glasgow Coma Scale (GCS): severe (GCS range 3-8), moderate (GCS range 9-12) and mild (GCS range 13-15). GCS is a common method of measuring the severity of TBI, generally used in emergency departments, based on the depth of coma (See, e.g., Rappaport et al., Archives of Physical Medicine and Rehabilitation, 63: 118-123 [1982]). Glasgow Coma Scale score of less than 15 during the first 24 hours after the injury is only one of three primary factors that are assessed as they may be crucial indicators of the occurrence of TBI. Besides the Glasgow Coma Scale, a documented loss of consciousness, and/or the occurrence of amnesia for the event of TBI may demonstrate a case of TBI.

A more accurate assessment of a brain injury provides the occurrence of Post-Traumatic Amnesia. The duration of post-traumatic amnesia can determine the severity of brain dysfunction as a result of TBI. Generally, amnesia that lingers up to a week indicates severe injury; if the duration of amnesia is up to a day, TBI can be assessed as moderate; and if amnesia lasts for up to an hour, it may be concluded that the brain suffered mild trauma.

Mild Traumatic Brain Injury, which usually goes undiagnosed, can be characterized by any of the following symptoms or their combinations: "a brief loss of consciousness, loss of memory immediately before or after the injury, any alteration in mental state at the time of the accident, or focal neurological deficits." Even though the victim of Mild Traumatic Brain Injury may seem "normal" and thus does not seem to need medical attention, in many cases Mild Traumatic Brain Injury results in chronic functional deficit known as Postconcussion Syndrome.

The most severe cases of TBI may result in enduring coma followed by a persistent vegetative state. Persistent Vegetative State is a condition of a complete loss of cognitive neurological functioning and awareness of the environment, but retention of sleep-wake cycle and noncognitive functions. In other words, higher cerebral functions of the brain are diminished, but the functions of the brainstem, such as respiration and circulation, remain intact.

Focal Cerebral Lesions/Cerebral Contusions

The brain, an extremely delicate tissue composed of about 15 to 20 billion neurons and additional support cells, is extremely sensitive to traumatic injuries. Due to acceleration and deceleration, which generally occur during a traumatic brain injury, the brain strikes the inside of the skull causing bruising. The most vulnerable parts of the brain, located near bony protrusions of the skull, are the brain stem, frontal lobe, and temporal lobes in particular. Consequently, these specific locations are the most frequently damaged parts during an incident of TBI.

Localized damage of the brain stem, located at the base of the brain, may cause disorientation, frustration, and anger. This area of the brain regulates basic arousal and consciousness, but it also plays an important role in normal functioning of short-term memory and attention. Consequently, localized trauma to the brain stem can result in impairment of any of these functions.

The temporal lobes, closely connected to the limbic system regulating human emotions, partake in a variety of cognitive skills, such as memory and language. Left temporal lesions generally cause dysfunction in the area of recognition of words, whereas right temporal damage may cause a loss or inhibition of talking. Similarly, left temporal lesions result in impaired memory for verbal material, while right temporal damage usually causes loss of recollection of non-verbal material. As Blumer and Benson suggest, temporal lobe lesions can result in a number of serious behavioral disorders, such as perseverative speech, paranoia and even aggressive rages. (Blumer and Benson, Frontal Lobe Function, New York: Grune & Stratton, (1975)).

Due to its large dimensions and its location near the front of the skull, the frontal lobe is the most frequently damaged area of the brain in an incidence of TBI. Consequently, the frontal lobe is the most common region of injury, particularly in mild to moderate TBI. Frontal lobe lesions can cause such a wide variety of symptoms that cannot be equaled by injury to any other part of the brain (Kolb and Milner, *Neuropsychologia*, 19:505-514 (1981)). Damage to the frontal lobe, regulating cognitive functions and controlling an individual's emotions and personality, can result in, among other things, decreased judgment, increased impulsivity, dysfunctional social and sexual behavior, impairment of motor function, problem solving, memory, language, etc. Impairment of motor function can be generally demonstrated by loss of fine movements, loss of strength of the arms, hands and fingers, and an overall dysfunction of complex body movements. Additionally, spatial orientation may be affected.

On the level of social behavior, victims of frontal lobe damage due to TBI may exhibit abnormal "behavioral spontaneity", such as fewer spontaneous facial movements and excessive or limited speech (Kolb and Milner, *Neuropsychologia*, 19:505-514 (1981)). Impacts of frontal lesions on an individual's social behavior are massive, causing significant alterations of personality and emotional status. These behavioral changes may vary, according to the area of the frontal lobe that is affected. Damage to the left side generally causes pseudodepression, while right side lesions result primarily in pseudopsychopathic behavior. (Blumer and Benson, Frontal Lobe Function, New York: Grune & Stratton, (1975)).

Even though focal contusions are typically located in the superficial brain structures, they are frequently accompanied by the formation of deep hematomas, affecting deeper layers of the brain tissue.

Hematoma is classified as a localized brain damage caused by a formation of a blood clot in a particular part of the brain. The violent movement of the brain accompanying TBI causes vessels on the brain surface to be pulled, stretched, or torn, often resulting in hematoma. Hematomas are particularly dangerous since they compress the soft brain tissue and if not treated promptly and properly may cause death. There exist several classification of hematomas based primarily on the origin of blood clotting within the brain tissue. A subdural hematoma is a blood clot that forms below one of brain's protective layers. An epidural hematoma occurs when a blot clot forms between the dura and the cranium. An intracerebral hematoma or hemorrhage is caused by bleeding within the brain tissue.

Diffuse Cerebral Lesions

Diffuse axonal injury occurs when the nerve cells are torn from one another, or rather, when axons pull and tear, disabling the communication between neurons. If axon is damaged, the cell dies, causing neural defects and deficiencies. Consequently, brain damage is no longer localized, but rather diffuse. Diffuse cerebral lesions often coexist with focal lesions, resulting in a wide spectrum of neurological, cognitive, and psychosocial impairment.

Both localized and diffuse injuries are considered primary injuries; they are a direct consequence of traumatic brain injury and, at present, medical treatments are not available to reverse the injury. The so called secondary brain injury are thought to be preventable if immediate medical attention is available.

Secondary Brain Injuries

Even though the terms anoxia and hypoxia are often used interchangeably, there is a specific difference between these medical conditions. Anoxia refers to a condition in which there is an absence of oxygen supply to an organ's tissue despite adequate blood flow to the tissue. Hypoxia is a condition in which there is a decrease of oxygen to an organ's tissue in spite of adequate blood flow to the particular tissue. The primary cause of an insufficient supply of oxygen to the brain is loss of breathing or rapid decrease of blood pressure. Besides being a potential secondary injury in an incidence of Traumatic Brain Injury, anoxia and hypoxia may also occur due to inhalation of carbon monoxide, exposure to high altitude, anesthetic accidents or poisoning. Anoxia and hypoxia result in additional brain injuries in TBI patients, in severe cases inducing coma ranging from hours to months. In the comatose state, seizures, muscle spasms, and neck stiffness typically occur.

Increased intracranial pressure can cause a severe swelling of the brain, also referred to as edema. Edema may prevent blood flow into the brain, causing a fatal condition. The occurrence of edema simultaneously with hematoma may signify a further deprivation of oxygen supply and thus a higher risk of death.

Secondary injuries to the brain following a case of TBI are reported as more rare due to the advances of current medicine and emergency procedures.

Effects of Traumatic Brain Injury

Given the heterogeneous character of TBI, there is much difficulty in characterizing it by one specific symptom or impairment. On the contrary, TBI results in sets of dysfunctions, different for each individual. Furthermore, consequences of TBI, even a mild case, often linger all life long, frequently alter their original form and even worsen as an individual meets new challenges, matures and/or ages. Accordingly, in some embodiments, if a subject presents with any of the symptoms discussed herein, the subject may have TBI.

Neurological impairment caused by TBI can affect any region of the neural axis, compromising any motor, sensory and autonomic function. Neurological consequences of TBI can be demonstrated as various movement dysfunctions, paralysis on either one side or both sides of the body, seizures, spasticity (sudden contraction of muscles), vision deficits, headaches and sleep disorders. In many cases, the Post-Trauma Vision Syndrome can be experienced as double vision, movement of stationary objects, visual fatigue, headaches, cognitive impairment, and compromised sense of balance, coordination and spatial orientation. These dysfunctions are not related to any pathology of the eye per se and therefore have often been excluded from the rehabilitation process.

Neurooptometric rehabilitation, in particular, proved to be of significant importance in treatment and management of Post-Trauma Vision Syndrome. Symptoms connected with Post-Trauma Vision Syndrome can be misinterpreted as a learning disability or even as attention deficit disorder. Post Trauma Vision Syndrome is caused by a dysfunction of the ambient visual process, which, if functioning properly, provides information needed for balance, coordination, posture and movement. The ambient visual process coordinates information from the peripheral retina to a specific level of midbrain that provides a sensory-motor feedback. As such, this process can be classified as motoric in function and as correlating the kinesthetic, proprioceptive, vestibular, and tactile systems. In Traumatic Brain Injury, the ambient visual process is unable to organize spatial information with other sensory-motor systems.

Cognitive consequences include, but are not limited to, memory impairment and concentration and attention dysfunctions. Many cognitive problems are closely associated with language use and visual perception. As mentioned previously, frontal lobe functions are frequently compromised, resulting in some cases in difficulties with problem-solving, information processing, organization, abstract reasoning, insight, and judgment.

Consequently, it is problematic for a TBI victim to learn new things and the inability to concentrate and organize one's thoughts often causes frustration, confusion and forgetfulness. Due to dysfunctional abstract thinking, understanding of irony, sarcasm, multiple meanings in jokes and figurative language is difficult to impossible. Regarding language and speech, TBI seldom inflicts a complete impairment of language, but rather causes difficulties with word-finding and sentence formation. The inability to find a term or a word results in lengthy, rather illogical, explanations and frustration when not understood. Since people with TBI are not aware of their language impairment and frequent errors, they tend to blame others for communication difficulties. Dysarthria is a common problem among TBI sufferers, caused by damage of muscles of the speech mechanism. It can be detected as slow, slurred, and indiscernible speech. Dysphagia is also common in individuals with TBI. It generally refers to any problems with swallowing. Apraxia of speech, in which speech muscles are not damaged, results in dysfunctional processing of words and inability to say words correctly and in a consistent way. Additionally, reading and writing are usually more deficient than speech, causing further difficulties in school or at work.

Behavioral deficits following TBI are numerous and difficult to treat. They include verbal and physical aggression, impulsivity, mood disorders, personality changes, depression, anxiety, poor self-awareness, and dysfunctional sexual behavior. These deficits, combined with neurological and cognitive dysfunctions, have broad social consequences. They often result in increased suicidal behavior, divorce, chronic unemployment, economic frustration, and substance abuse. TBI thus impacts heavily not only its immediate victims, but also their family members. Many dysfunctions become obvious when individuals try to return to their normal lives after an extensive medical treatment and rehabilitation. Children with TBI are most susceptible to the complex interrelation of neurological, cognitive, and behavioral impairment, since its full impact can become apparent later on in their lives, as they attempt to learn new things and as they become exposed to new environments and situations.

Brain Recovery, Rehabilitation and Treatments

Evidence suggests that the human brain, even in adult individuals, has the capacity to recover. Brain plasticity is a natural response to loss of neurons through aging. Neurogenesis, it might seem, thus provides a promising alternative for the treatment of many neurological problems, including, among other things, TBI. Nevertheless, "under normal conditions, neurogenesis in the adult brain appears to be restricted to the discrete germinal centers: the subventricular zone and the hippocampal dentate gyms" Hallbergson et al., The Journal of Clinical Investigation. 112(8): 1128-1133 [2003]).

It has been documented that, due to damage to a particular area of the brain, surrounding tissues are able to assume the functions originally coordinated by the damaged tissue. The so-called sprouting of dendrites can occur following a brain injury; in which case neurons sprout, establishing new connections. The injured brain thus has a capacity to increase the level of chemicals that promote growth of neural connections. Sprouting of dendrites may occur proportionally to the extent that a person remains active. Consequently, brain plasticity can contribute to and positively affect recovery if suitable rehabilitation procedures provide enough stimulation and brain activity.

The process of recuperation from TBI is typically a life-long effort of accommodation to multiple dysfunctions. Effects of a particular therapy depend on numerous factors, such as the extent of brain damage, the choice of a specific rehabilitation, or rather the choice of a set of particular rehabilitation procedures, the frequency and intensity of these treatments, and the level of cooperation from the patient as well as the patient's family members.

The most effective rehabilitation procedure, as reported by NIH Consensus Statement, is a comprehensive interdisciplinary rehabilitation that ensures an individual approach to every TBI patient with a unique set of deficits. This rehabilitation is complex in nature, addressing the heterogeneity of post-Traumatic Brain Injury damage.

Traumatic Brain Injury and the Systems of the Present Invention

Experiments conducted during the development of the present invention have demonstrated that healthy as well as sick or diseased subjects (e.g., bipolar vestibular dysfunction patients) demonstrate improvement or correction of, among other things, their vestibular function (e.g., balance), proprioception, motor control, vision, posture, cognitive functions, tinnitus, emotional conditions and sleep as a direct consequence of training procedures with the systems of the present invention. Thus, in some embodiments, the present invention provides methods of training with the systems of the present invention in order to treat symptoms (e.g., symptoms mentioned herein) of persons with TBI. Treatment, in some embodiments, permits these persons to incorporate themselves into normal life, to be independent, and to enjoy an increased quality of their lives. In some embodiments of the present invention, dysfunctions are treated and consequently eliminated in patients with TBI. Exemplary benefits are described below.

General Balance Improvement

In some embodiments, subjects with TBI experience the return of their sense of balance, steadiness, and a sense of being centered after rehabilitation procedures with systems and methods of the present invention (e.g., treatment with the systems of the present invention). In some embodiments, the sense of constant movement is eliminated in the TBI subjects. In some embodiments, subjects who without treatment have difficulty walking unassisted or in crowds or dark environments are capable of doing so after treatments provided by the present invention (e.g., procedures with the systems of the present invention).

TBI patients suffering from Post-Trauma Vision Syndrome have similar deficits of general balance, due to damage to their ambient visual process. The loss of the sense of the midline in TBI patients results in loss of the sense of balance and the sense of being centered. Thus, in some embodiments, the present invention provides systems and methods of using the systems of the present invention to treat (e.g., retrain) the damaged centers of the ambient visual system, thereby resulting in a general improvement of the sense of balance, steadiness, a normal sense of the midline and thus a renewed sense of being centered. It is contemplated that improvement of a TBI patient's general balance would thus have significant consequences on the overall rehabilitation process.

Posture, Proprioception and Motor Control

In some embodiments, the present invention provides a therapy with the systems of the present invention, whereby a TBI patient's body movements become more fluid, confident, relaxed and quick. In some embodiments, stiffness of movement disappears and fine motor skills return to normal. In some embodiments, posture, gait and body segments alignment return to normal.

Numerous movement dysfunctions, seizures, spasticity, and loss of fine motor movements in Traumatic Brain Injury patients are highly similar in nature with motor deficits resulting from lateral vestibular disorder. Thus, in some embodiments, the present invention provides systems and methods for treating patients with TBI (e.g., subjects displaying symptoms of bipolar vestibular disorder). In preferred embodiments, TBI patients display improvement in functioning of their motor, cognitive, and neurological functions after treatment with the systems and methods of the present invention.

Vision

In some embodiments, TBI patients display improved vision after receiving treatments according to the present invention. Improved vision includes, but is not limited to, vision becoming clearer, more stable, clearer, and brighter, reduction of oscillopsia, widening of peripheral vision, improvement of depth perception, reduction of or elimination of double vision, and reduction of or elimination of movement of stationary objects and visual fatigue.

Cognitive Functions

In some embodiments, treatments (e.g., treatments with the systems of the present invention) provided by the present invention to a subject (e.g., a TBI patient) increases, among other things, mental awareness, creativity, clarity of thinking, multitasking skills, memory retention, concentration, the ability to track conversations, and the ability to focus. In some embodiments, subjects experience less "noise" in the head, much improvement in intensity of thinking, problem solving, and decision making. Furthermore, there is improvement of major executive skills thereby resulting in increased confidence and improved self-assessment.

Sleep

Sleep disorders have been reported in most cases of TBI, resulting in complications of rehabilitation. Accordingly, in some embodiments, treatments (e.g., treatments with the systems of the present invention) provided by the present invention to a subject (e.g., a TBI patient) improve sleep. Sleep improvement occurs and is perceived as being fuller, longer, and more restful, often with no awakenings during the night. As an additional impact, in some embodiments, treatment with the systems of the present invention results in improved sleep patterns.

Exemplary Treatment

Systems and methods of the present invention were utilized for balance training in two subjects with traumatic brain injury (TBI) presenting cerebellar type ataxia.

Ataxia is frequently observed following severe TBI. It very often accompanies other motor deficiencies and thought to clinically resemble other cerebellar symptoms. CT and MRI investigations rarely show direct lesions in this part of the brain. It forms part of a mixed clinical picture; general diffused axonal lesions and extra dural haematoma being the main identifiable cerebral lesions.

Unlike other neurological symptoms, ataxia remains typically unresponsive to traditional treatment techniques.

Patients presenting with early signs of tremor, severe dysmetria and other motor based coordination problems at the onset of treatment often find they are forced to live the rest of their lives trying to come to terms with it as therapists, neurologists and neurosurgeons have yet to find a solution. Voice control and excessive salivation are also frequent. Fine manual motor skills are severely impaired and simple activities of daily life and basic social skills are permanently perturbed. Therapists can only offer over-training and compensatory strategies for this debilitating condition.

Severe psychological suffering, despair and depression often accompany the physical aspects as the frustration of possessing full limb and trunk movement but not being able to control it is a permanent and omnipresent challenge.

Two fully informed adults willingly gave their consent to participate in a study to evaluate the use of the systems and methods of the present invention and physical exercise to try and improve balance and thus regain function and mobility in traumatic ataxia following TBI.

Both subjects received emergency acute care then received regular, intensive physical therapy throughout their rehabilitation, largely provided by the same therapists.

Subject 1 was a male, 26 years old who left the treatment facility 7 years previous to experiments conducted during the development of the present invention and after two and a half years in treatment. His clinical picture remained the same since leaving the treatment facility. Initial CT scan showed with a Glasgow coma scale of 3.

He suffered from severe coordination disturbance, dysmetria, a very poor force/task correlation (inappropriately high muscle recruitment, resulting in disastrous motor responses, fatigue and a general musculature largely exceeding his actual activity level).

Motor asymmetry was also present following initial right-sided paralysis, which had recovered well (e.g., full range movements against resistance in all muscle groups). The shoulder and pelvic girdles and other segmental levels rarely moved independently. Falling was frequent with inappropriate parachute reactions and frequent minor injury.

Subject 2 is a female, 25 years old who left the treatment facility 2 years prior to treatment with the methods of the present invention, after 12 months in treatment. Her clinical picture had remained the same since leaving. She displayed an initial Glasgow coma scale of 5. Medium frequency permanent tremor accompanied movement and was present throughout the muscular system. Voice, articulation and the muscles of facial expression were also affected.

At day 1 of the trial.

Subject 1 (male). Severe in coordination forces him to use a wheel chair for all outdoor mobility and much indoor use. Some use of a 4-wheeled walker or walking between 2 people is used indoors. Independent transfers are possible though falls occur. All limb and vertebral movements are achieved in the presence of low frequency tremor and dysmetria (over or undershooting) by fixing levers with excessive muscular control and rigidity. Standing with one handhold is possible. Independent standing is possible but precarious (10 to 20 sec. before intervention of a helper is necessary).

Subject 2 (female). Outdoor walking with a stick is possible. Short distance indoor walking is independent but gait is interrupted for balance at each pace. Standing with eyes closed and feet spaced at shoulder width was impossible.

Training Patients were trained for 7 days (5 consecutive, weekend pause then 2 consecutive).

The subjects used the systems and methods of the present invention during two sessions a day for a maximum of 40 minutes per session including one 20 minute uninterrupted stabilization exercise in standing or on an 80 cm diameter Klein (Swiss) type ball with eyes closed. Each session included exercises for shoulder and pelvic girdle and other segmental level disassociation; for general and segmental relaxation and for gait analysis and retraining.

Results of training were documented by the physical therapist's observations, patients own remarks, and external observers' spontaneous remarks (e.g., family, other health professionals etc.).

Physical therapist's (PT) observations. PT found that patients tolerated the systems and methods of the present invention well with no adverse effects. Patients reported no discomfort or problems using the device. PT was pleasantly surprised that patients with this pathology were able to follow the usual general training program. PT noted that fatigue and cognitive problems did not force modification of the training regime and the patients remained motivated throughout the trial.

PT noted that the two subjects have no language problems. PT noted that memory and organizational handicaps did not affect learning as the subjects acquired personal strategies (increased question asking and checking, note pads, etc.) and were provided repeat instructions (e.g., "key word" reminders).

At the end of training, PT noticed a significant improvement in static posture, both in terms of stability, endurance and in the quality of vertical segmental alignment in both subjects. Muscular tension in postural groups was more appropriate—accessory movements and inappropriate muscle group recruitment diminished in both subjects resulting in a more energy effective work rate and lower general and muscular fatigue.

PT noted that Subject 1 was able to stand for several minutes with closed eyes or sit on the ball for 20 minutes un-assisted with eyes closed and feet at 40 cm (e.g., compared to day 1, when Subject 1 sat for 5 minutes feet were wide spread eyes open and the ball partially deflated with severe muscular tremor from fatigued over-active quadriceps femoris.)

PT noted that Subject 2 was able to stand for 20 min un-assisted with feet together and eyes closed after training (e.g., versus feet apart, eyes open and rapid onset of severe tremor before treatment with systems and method of the present invention).

PT noted that the two subjects saw transfers from sit/stand and from stand/sit improve both in quality of movement an in security. Gait improved in both subjects. PT noted that Subject 1 was able to take up to 8 steps un-assisted under close surveillance; whereas he had not been able to take any independent steps since his accident. Use of a 4 wheeled walker un-assisted was improved on flat ground with a smoother movement flow and the integration of several gait components previously absent such as weight transfer, knee flexion in stepping, foot positioning, more equal and appropriate step length, shoulder girdle coordination and more efficient upper limb work (elbows flexed rather than in hyperextension). PT also noted that endurance increased progressively during training, as did walking on un-even surfaces.

Subject 2 was able to step cleanly over an obstacle of 40 cm un-aided (whereas, clearing a 14 cm obstacle was impossible on day 1). Walking on uneven and sloping grass surfaces without the stick became possible and endurance and gait quality improved.

The patients own remarks. Subject 1 reported feeling generally more supple with general muscle tone more "relaxed". He reported his gait is smoother with steps less "jerky". He feels he uses less muscle work to achieve the same actions and with less tiredness. He noticed that knee bending during walking became possible whereas previously he reported always walking with lower limbs "stiff" (knees remained in extension or hyperextension). He finds general balance much improved especially regarding stability in standing which is possible for longer periods. He reported a better tactile awareness of the ground with more equal weight distribution throughout the soles of the feet where as he only perceived contact at the heels before. He thinks this is due to a transfer of learning from the concentration on lingual tactile sensation in a signal of the system of the present invention to adjust balance, to an application of a similar procedure for an increase in awareness of tactile sensation and adjustment of posture in foot sensitivity.

He also reported that transfers are performed more easily and smoothly. He felt that the systems and methods of the present invention aided postural stability during use and allowed muscular relaxation of non-involved groups. He found using the device simple after initial training and stimulation was comfortable. He also reported an improved length and quality of sleep.

Subject 2 reported feeling more supple in the whole vertebral region and in muscle groups controlling the knees. She finds all movement smoother. Shoulder girdle relaxation is much improved and she is able to stand still for longer periods without the onset of tremor. Loss of balance is markedly reduced. She finds her speech is more easily understood by others and postulates that this is due to better respiratory control and/or better articulation of words.

She reports that heel strike and push off phases in gait are better perceived. She is more able to maintain a "head-up, looking straight ahead" posture in walking (she had previously complained that she looked at feet while walking).

She found the physical exercises accompanying training to be well adapted and important. She found the systems and methods of the present invention were easy to use and she found it quite straightforward to learn to maintain balance with a device of the present invention and found it especially useful to rely on it towards the end of the 20 minute training sessions when balance became difficult through fatigue. She reported really trusting the systems and methods of the present invention during fatigue to maintain upright posture. She also reported that physical endurance improved and that the training period was a positive experience. No adverse sensations were reported.

Other external observers' spontaneous remarks (e.g., family, other health professionals etc.).

Friends of Subject 1 found Subject 1's speech more easy to understand. Walking with the support of two people was easier, they reported "carrying" less and noticed the improved quality of gait especially in stepping with knee flexion, reduced foot drag, narrower gait base and appropriate step length (reduction in exaggerated paces).

Subject 2's family noted improved speech, and general smoothness of movement. During a longer walk on grass with no assistance (2×500 m) accompanied by a family member, both observed a better quality of stepping, (suppleness and smoother leg movements), and an improved head position. The family found improved respiratory coordination in speech and longer sentence length.

Example 22

Pervasive Developmental Disorders

Pervasive Developmental Disorders

Autism is a complex developmental disability that typically manifests itself within the first three years of life. The result of a neurological disorder that affects the functioning of the brain, autism impacts normal development of the brain in areas of social interaction and communication skills. Children and adults with autism typically have difficulties with verbal and non-verbal communication, social interactions, and leisure or play activities.

Autism is one of five disorders covered under the umbrella term Pervasive Developmental Disorders (PDD), a category of neurological disorders characterized by severe and pervasive impairment in several areas of development, including social interaction and communication skills.

PDD can be classified as follows: Autistic Disorder, Asperger's Disorder, Childhood Disintegrative Disorder (CDD), Rett's Disorder, and PDD-Not Otherwise Specified (PDD-NOS). Each of these five disorders has specific diagnostic criteria as outlined by the American Psychiatric Association (APA) in its Diagnostic & Statistical Manual of Mental Disorders.

In spite of meaningful successes in diagnosis, classification and understanding of Autism Spectrum Disorders (ASDs), many uncertainties and challenges for research still remain. For example, the causes of the various autistic disorders remain, to a large extent, unidentified. There has not been a "cure" for autism, although some management strategies exist that seem to be effective for some individuals. Individuals with autism also suffer from a number of physiological problems the significance of which—in terms of cause and development of ASDs—is unclear and sometimes controversial.

Prevalence of Autism

Autism is the most common Pervasive Developmental Disorder, affecting an estimated 1 in 250 births (Centers for Disease Control and Prevention, 2003). This means that as many as 1.5 million Americans today are believed to have some form of autism. Based on statistics from the U.S. Department of Education and other governmental agencies, autism is growing at a rate of 10-17 percent per year. At these rates, the Autism Society of America estimates that autism could affect 4 million Americans in the next decade. The overall incidence of autism is consistent around the globe, though it appears to be four times more prevalent in boys than girls. Autism is a national health crisis that some estimate costs our economy $90 billion a year in programs and services, according to the Autism Society of America.

Sensory Integration

The phenomenon of sensory integration provides a theoretical means of explaining and understanding brain dysfunction in many PDD cases. Simultaneously, it has become a popular practical method of helping many individuals with autism. It is believed that children and adults with autism, as well as those with other developmental disabilities, often have a dysfunctional sensory system. Sometimes one or more senses are either over- or under-reactive to stimulation. Such sensory problems may be the underlying reason for such behaviors as rocking, spinning, and hand-flapping. Although receptors for the senses are located in the peripheral nervous system (which includes everything but the brain and spinal cord), it is believed that the problem stems from neurological dysfunction in the central nervous system—the brain. As observed in individuals with autism, sensory integration techniques, such as pressure-touch, can facilitate attention and awareness, and they can reduce overall arousal.

Sensory integration is an innate neurobiological process that refers to the integration and interpretation of sensory stimulation from the environment by the brain. In contrast, sensory integrative dysfunction is a disorder in which sensory input is not integrated or organized appropriately in the brain, which may produce varying degrees of problems in cognitive development, information processing, and behavior.

Sensory integration focuses primarily on three basic senses—tactile, vestibular, and proprioceptive. Their interconnections start forming before birth and continue to develop as a person matures and interacts with his/her environment. The three senses are not only interconnected, but they are also connected with other systems in the brain. Although these three sensory systems are less familiar to our awareness than our visual and auditory systems, they are critical to our basic survival. The inter-relationship among these three senses is complex. Basically, they allow us to experience, interpret, and respond to different stimuli in our environment.

According to Lorna Jean King, OTR, FAOTA (the Founder and Director of the Center for Neurodevelopmental Studies, Inc. in Phoenix, Ariz.) 85 to 90 percent of children with autism have sensory integration problems, some of which are much more obvious than others. A therapist's trained eye may recognize subtle signs that may prove quite significant, whereas a parent may not realize their significance. Often small changes in helping the child to be less sensitive to sensory input produced significant changes in behavior. For instance, sitting on a beach ball or a T-stool can help the child to improve his/her attention. It is believed that increased vestibular and proprioceptive input might help the nervous system to organize and process information better.

Tactile System

The tactile system includes nerves under the skin's surface that send information to the brain. This information encompasses light touch, pain, temperature, and pressure. These play an important role in perceiving the environment as well as in protective reactions for survival.

Dysfunction in the tactile system can be observed as withdrawing when being touched, refusing to eat certain 'textured' foods and/or to wear certain types of clothing, complaining about having one's hair or face washed, avoiding getting one's hands dirty (e.g., glue, sand, mud, fingerpaint), and using one's finger tips rather than whole hands to manipulate objects. A dysfunctional tactile system may lead to a misperception of touch and/or pain (hyper- or hyposensitive) and may lead to self-imposed isolation, general irritability, distractibility, and hyperactivity.

Tactile defensiveness is a condition in which an individual is extremely sensitive to a light touch. Theoretically, when the tactile system is immature and working improperly, abnormal neural signals are sent to the cortex in the brain, which can interfere with other brain processes. This, in turn, causes the brain to be overly stimulated resulting in excessive brain activity, which can neither be turned off nor organized. This type of over-stimulation in the brain can make it difficult for an individual to organize one's behavior and concentration, and may lead to a negative emotional response to touch sensations.

Vestibular System

The vestibular system refers to structures within the inner ear (the semi-circular canals) that detect movement and changes in the position of the head. For example, the vestibular system tells you when your head is upright or tilted (even with your eyes closed). Dysfunction within this system may manifest itself in two different ways. Some children with autism may be hypersensitive to vestibular stimulation and have fearful reactions to ordinary movement activities (e.g., swings, slides, ramps, inclines). They may also have trouble learning to climb or descend stairs or hills; and they may be apprehensive walking or crawling on uneven or unstable surfaces. As a result, they seem fearful in space. In general, these children appear clumsy. On the other extreme, some children may actively seek very intense sensory experiences such as excessive body whirling, jumping, and/or spinning. These children demonstrate signs of a hypo-reactive vestibular system; that is, they are trying continuously to stimulate their vestibular systems.

Proprioceptive System

The proprioceptive system refers to components of muscles, joints, and tendons that provide a person with a subconscious awareness of body position. When proprioception is functioning efficiently, an individual's body position is automatically adjusted to different situations; for example, the proprioceptive system is responsible for providing the body with the necessary signals to allow us to sit properly in a chair and to step off a curb smoothly. It also allows us to manipulate objects using fine motor movements, such as writing with a pencil, using a spoon to drink soup, and buttoning one's shirt.

Some common signs of proprioceptive dysfunction are clumsiness, a tendency to fall, a lack of awareness of body position in space, odd body posturing, minimal crawling when young, difficulty manipulating small objects (buttons, snaps), eating in a sloppy manner, and resistance to new motor movement activities.

Another dimension of proprioception is praxis or motor planning. This is the ability to plan and execute different motor tasks. In order for this system to work properly, it must rely on obtaining accurate information from the sensory systems and then to organize and interpret this information efficiently and effectively.

Implications

In general, dysfunction within these three systems manifests itself in many ways. Autistic children may be over- or under-responsive to sensory input; their activity level may be either unusually high or unusually low; they may be in constant motion or may get fatigued easily. In addition, some children with autism may fluctuate between these extremes. Gross and/or fine motor coordination problems are also common when these three systems are dysfunctional. Consequently, speech/language delays and academic under-achievement may occur. Behaviorally, the child may become impulsive, easily distractible, and show a general lack of planning Some children may also have difficulty adjusting to new situations and may react with frustration, aggression, or withdrawal. Usually, evaluation and treatment of basic sensory integrative processes is performed by occupational therapists and/or physical therapists. The therapist's general goals are: (1) to provide the child with sensory information, which helps to organize the central nervous system, (2) to assist the child in inhibiting and/or modulating sensory information, and (3) to assist the child in processing a more organized response to sensory stimuli.

Application of the Systems of the Present Invention for Autism and Related Conditions The systems of the present invention have been developed in order to enhance sensory integration and address sensory dysfunction. Experiments conducted during the development of the present invention have demonstrated that healthy as well as sick or diseased subjects (e.g., bipolar vestibular dysfunction patients) demonstrate improvement or correction of, among other things, their vestibular function (e.g., balance), proprioception, motor control, vision, posture, cognitive functions, tinnitus, emotional conditions and sleep as a direct consequence of training procedures with the systems of the present invention.

In some embodiments, the present invention provides systems and treatments for treating or improving misperception of touch and/or pain (hyper- or hyposensitive), self-imposed isolation, general irritability, distractibility, tactile defensiveness, vestibular dysfunction, and activity level (e.g., hyper- or hypo-activity) in a subject with a Pervasive Developmental Disorder (PDD), including, but not limited to an Autistic Disorder, Asperger's Disorder, Childhood Disintegrative Disorder (CDD), Rett's Disorder, and PDD-Not Otherwise Specified (PDD-NOS). In some embodiments the present invention provides systems and methods of treatment to intensify and extend vestibular performance, posture control, sensory-motor coordination and sensory integration; provide stress relief and relaxation; improve sleep patterns and cognitive function; and to extend the range of everyday physical and mental activity in subjects with autism.

It is contemplated that, in some embodiments of the present invention, the systems of the present invention are used in combination with other treatments (e.g., drugs currently used to treat PDDs in general or Autism in particular) for treating a subject with a PDD (e.g., autism). Thus, the present invention provides complimentary or supplementary treatments that can be used in combination with other known treatments. It is contemplated that systems and methods of the present invention (e.g., systems of the present invention with training) intensify the positive effects of current treatments for Autism, and decrease or prevent adverse side effects. In some embodiments, use of systems and methods of the present invention permits a decrease in the dosage of a drug prescribed to treat Autism or a related PDD.

General Balance.

In some embodiments, autistic subjects experience the return of their sense of balance, increased body control, steadiness, and a sense of being centered after treatment with the systems and methods of the present invention. In some embodiments, a constant sense of moving is eliminated. In some embodiments, subjects are able to walk unassisted, and experience an increase in the ability to walk in dark environments, to walk briskly, to walk in crowds, and to walk on patterned surfaces after treatment with the systems and methods of the present invention. In some embodiments, subjects gain the ability to stand with their eyes closed, with or without a soft base, to walk a straight line, to walk while looking side to side and to walk while looking up and down. In some embodiments, subjects gain the ability to carry items, walk on uneven surfaces, walk up and down embankments, and to ride a bike. In some embodiments, a subject with a Pervasive Developmental Disorder (PDD), (e.g., including, but not limited to an Autistic Disorder, Asperger's Disorder, Childhood Disintegrative Disorder (CDD), Rett's Disorder, and PDD-Not Otherwise Specified (PDD-NOS)) becomes more physically active after treatment with the systems and methods of the present invention.

Posture, Proprioception and Motor Control.

In some embodiments, a subject with a Pervasive Developmental Disorder (PDD), enjoys more fluid body movements, and movements that are more confident, light, relaxed and quick after treatment with the systems and methods of the present invention. In some embodiments, fine motor skills are refined and gait improves. In some embodiments, subjects enjoy improved posture, body segment alignment, stamina, and general energy levels.

Vision

In some embodiments, PDD patients display improved vision after receiving treatments according to the present invention. Improved vision includes, but is not limited to, vision becoming clearer, more stable, clearer, and brighter, reduction of oscillopsia, widening of peripheral vision, improvement of depth perception, reduction of or elimination of double vision, and reduction of or elimination of movement of stationary objects and visual fatigue.

In some embodiments, PDD subjects experience improvements of all components of sensory integration when exposed to BrainPort balance therapy.

Stress Relief and Relaxation

Since individuals with autism typically have communication problems, they are more likely to experience stress in their daily life than individuals with good communication skills. June Groden, PhD (Director of the Groden Center in Providence, R.I.), suggests that a relaxation program constituted of teaching subjects, including individuals with autism, how to discriminate between tense muscles and relaxed muscles can be highly effective.

Children and adults are taught the relaxation procedure, usually in a one-on-one teaching session lasting for as long as the participant can maintain attention. This usually ranges from a few minutes to twenty minutes. The person learns to tighten and relax the arms, hands, and legs, and to practice deep breathing in a sitting position.

The patient is then taught relaxing without tensing. Finally, the person is taught to tighten and relax all remaining muscle groups of the body.

Such relaxation program can be used to develop self-control by the individual learning to achieve a relaxation response in place of the typical maladaptive behavior he or she exhibits during stressful situations.

Accordingly, in some embodiments, PDD subjects experience an improvement in relaxation ability after treatment with the systems and methods of the present invention.

In some embodiments, use of systems of the present invention with training results in physical and emotional relaxation in PDD patients. In some embodiments, deep muscular and emotional relaxation is achieved. In further embodiments, the state of relaxation is reproducible or increases through subsequent sessions. Importantly, because the systems and methods of the present invention do not possess negative side effects, such systems and methods avoid the unwanted side effects of antidepressants, which often cause significant difficulties in individuals with autism.

Sleep Adjustment

Sleep abnormalities are common in individuals with autism.

Accordingly, in some embodiments, treatments (e.g., treatments with the systems of the present invention) provided by the present invention to a subject (e.g., a PDD subject) improves sleep. It is contemplated that sleep improvement occurs and is perceived as being fuller, longer, and more restful, often with no awakenings during the night. As an additional impact, in some embodiments, treatment with the systems of the present invention results in improved sleep patterns.

It is further contemplated that the systems and methods of the present invention provide both direct (e.g., balance, etc.) and indirect (e.g., sense of well being) benefits that provide a general therapeutic value. For at least some subjects, it is contemplated that use of the systems of the present invention provides temporary or permanent reduction or removal of symptoms associated with PDD. For example, through use of the systems and methods of the present invention, a subject may be trained or treated to perceive and/or filter out (e.g., ignore) sensory information so as to effect an improvement in function. The associated indirect effects further improve the subject's capabilities. In one exemplary embodiment, a subject that has difficulty filtering sound is provided with audio information (e.g., a parent's voice) via electrotactile stimulation of the tongue so as to provide second source of the information. Likewise, in other embodiments, sensory information that is perceived as unpleasant is masked by the addition of electrotactile stimulation of the tongue that provides an alternative or counteracting sensory response. In some embodiments, the general improvements to cognitive function and overall well-being provided by the systems of the present invention reduce or eliminate symptoms of the diseases and conditions. Thus, it is contemplated that such treatments, at least for some subjects, may be curative or substantially curative of the disease or condition.

Example 23

Parkinson's Disease

Parkinson's Disease

Parkinson's disease is a slowly progressive neurodegenerative disorder caused by damaged or dead dopamine-neurons in the substantia nigra, a region of the brain that controls balance and coordinates muscle movement. Dopamine is a neurotransmitter that carries information from neuron to neuron and eventually out to the muscles. When these dopamine neurons start to die, the lines of communication between the brain and the body become progressively weaker. Eventually, the brain is no longer able to direct or control muscle movement in a normal manner.

Parkinson's disease causes substantial morbidity and results in a shortened life span. Mortality rates in 1967 for patients with Parkinson's disease were three times those of control subjects; 30 years later, mortality rates were found to be largely unchanged. Thus, despite breakthroughs in medical treatment and the availability of exciting new surgical procedures, chronic progression to severe disability is still the rule. Nevertheless, current therapy can slow symptom progression and improve quality of life.

Parkinson's disease severely compromises quality of life. Patients with this illness can find it difficult to read, write and drive. With advanced disease, they often cannot manage basic activities of daily living. Thus, Parkinson's disease can result in loss of employment and, ultimately, loss of personal autonomy.

Prevalence and Cost

Parkinson's disease is the most common neurodegenerative disease after Alzheimer's disease, with an estimated incidence of 20 per 100,000 and a prevalence of 150 per 100,000. The disease has a roughly equal sex distribution, with a slight male predominance, and no ethnic group is spared.

The mean age at onset of Parkinson's disease is 55 to 60 years. An estimated 1% of the US population over 50 years of age, or about 1 million people, have the disease. However, some physicians have reportedly noticed more cases of "early-onset" Parkinson's disease in the past several years.

Pesticides and other toxins have been suspected, but none has been proved to be a definite causative factor. On the other hand, the search for genetic causes has yielded at least four independent gene loci in various forms of familial Parkinson's disease. The autosomal dominant adult-onset type is linked to a site on chromosome 4q6 and the gene for autosomal recessive juvenile parkinsonism maps to chromosome 6q. Because most patients do not have a clear history of either familial or environmental risk factors, the disorder may be due to a combination of genetic and environmental "influences" or "causes."

In 1990, more than half of all patients with a diagnosis of Parkinson's disease were being treated in the primary care setting. Although in its later stages the condition can be very difficult to treat, initial diagnosis and early management can usually be accomplished by primary care physicians. These physicians are also in an ideal position to help address the impact that the illness has on the patient's lifestyle and on his or her spouse and family.

According to the National Parkinson Foundation, each patient spends an average of $2,500 a year for medications. After factoring in office visits, Social Security payments, nursing home expenditures, and lost income, the total cost to the Nation is estimated to exceed $5.6 billion annually.

Primary Symptoms

People with Parkinson's disease may have trouble walking, talking, or completing simple tasks that depend on coordinated muscle movements. The four primary symptoms of Parkinson's disease often appear gradually but increase in severity with time. They are: Tremor or trembling in hands, arms, legs, jaw, and face; Rigidity or stiffness of the limbs and trunk; Bradykinesia, Slowness of motor movements; and Postural instability or impaired balance and coordination Tremor The tremor of Parkinson's disease is one of the most common presenting signs, being the initial complaint in 70% to 75% of cases. Typically, it is a 4- to 6-Hz resting tremor that may be intermittent in early stages. The tremor associated with Parkinson's disease has a characteristic appearance. Typically, the tremor takes the form of a rhythmic back-and-forth motion of the thumb and forefinger at three beats per second. This is sometimes called "pill rolling." Tremor usually begins in a hand, although sometimes a foot or the jaw is affected first. It is most obvious when the hand is at rest or when a person is under stress. In three out of four patients, the tremor may affect only one part or side of the body, especially during the early stages of the disease. Later it may become more general. Tremor is rarely disabling and it usually disappears during sleep or improves with intentional movement.

Stress or anxiety may precipitate the tremor. It usually begins unilaterally, affecting one or both limbs, but it can also involve the jaw, lips, and lower facial muscles. It is possible to distinguish the tremor of Parkinson's disease from essential tremor. One study of patients diagnosed with Parkinson's disease by a nonneurologist showed that about 25% actually had essential tremor only.

Essential tremor is typically postural and is not usually seen at rest. It may become more prominent at the termination of a movement. It is faster (6 to 9 Hz) than a parkinsonian tremor and is usually bilateral. A pill-rolling quality is usually not present, but a head tremor (titubation) often occurs. The voice of a patient with essential tremor may be tremulous. The patient often has a family history of tremor, which usually resolves temporarily with ingestion of small amounts of alcohol, whereas a parkinsonian tremor is not usually relieved by alcohol. A parkinsonian tremor generally responds to antiparkinsonian medication, whereas essential tremor generally does not.

Rigidity

Rigidity, or a resistance to movement, affects most parkinsonian patients. A major principle of body movement is that all muscles have an opposing muscle. Rigidity is an increase in muscle tone that is noted as an increase in resistance to passive maneuvers. Movement is possible not just because one muscle becomes more active, but because the opposing muscle relaxes. In Parkinson's disease, rigidity comes about when, in response to signals from the brain, the delicate balance of opposing muscles is disturbed. The muscles remain constantly tensed and contracted so that the person aches or feels stiff or weak. The rigidity becomes obvious when another person tries to move the patient's arm, which will move only in ratchet-like or short, jerky movements known as "cogwheel" rigidity. It can be elicited by having the patient perform similar movements in the opposite limb (activated rigidity). Parkinsonian rigidity is usually more prominent in the extremities than axially. A cogwheeling phenomenon may also be superimposed on the rigidity. As illness progresses, rigidity becomes more severe and the patient may acquire a characteristic stooped posture with the head tilted forward and the arms flexed at the elbows and wrists.

Akinesia (or Bradykinesia):

Patients with Parkinson's disease often have evidence of akinesia, which is a lack or poverty of movement. They are also likely to display bradykinesia, that is, a slowness and fatiguing of voluntary movement. Bradykinesia, or the slowing down and loss of spontaneous and automatic movement, is particularly frustrating because it is unpredictable. One moment the patient can move easily. The next moment he or she may need help. This may well be the most disabling and distressing symptom of the disease because the patient cannot rapidly perform routine movements. Activities once performed quickly and easily—such as washing or dressing—may take several hours. As noted, these abnormalities may be manifested as decreased facial expression, slowness of movement, or clumsiness in an extremity. A patient may also be slow in such activities as getting dressed or writing. The fatiguing of voluntary movement can be seen in the phenomenon of micrographia, in which a patient's handwriting decreases in fullness and legibility from the beginning of a sentence to the end. Fatiguing can also be elicited by having a patient repeatedly tap a finger or perform another repetitive motion. Amplitude and continuance of motion are gradually lost.

All of these symptoms can progress in severity. Later in the course of the illness, akinesia and bradykinesia contribute to disabling postural difficulties.

Deficits in Gait and Postural Instability

Initially, the only change in a patient's gait may be decreased arm swing or, possibly, easy fatigability. Later, the stride becomes shortened, and eventually it becomes a shuffle. A patient may drag the foot on the predominantly affected side. As the disease progresses, patients may have "freezing episodes," particularly when turning. They may also have difficulty initiating a gait.

In later stages of the disease, deficits in postural reflexes develop. Postural instability, or impaired balance and coordination, causes patients to develop a forward or backward lean and to fall easily. When bumped from the front or when starting to walk, patients with a backward lean have a tendency to step backwards, which is known as retropulsion. Postural instability can cause patients to have a stooped posture in which the head is bowed and the shoulders are drooped. As the disease progresses, walking may be affected. Patients may halt in mid-stride and "freeze" in place, possibly even toppling over. Or patients may walk with a series of quick, small steps as if hurrying forward to keep balance. This is known as festination. Ultimately, this leads to falls, which greatly increase morbidity and mortality rates.

When postural reflexes are inadequate, patients may fall if they are pushed even slightly forward or backward, or if they are standing in a moving vehicle such as a bus or train. Clinical scales rating the presence and severity of these signs are useful.

Additional Symptoms

Various other symptoms accompany Parkinson's disease; some are minor, others are more bothersome. Many can be treated with appropriate medication or physical therapy. No one can predict which symptoms will affect an individual patient, and the intensity of the symptoms also varies from person to person. None of these symptoms is fatal, although swallowing problems can cause choking.

Depression. Depression is a common problem and may appear early in the course of the disease, even before other symptoms are noticed. Depression may not be severe, but it may be intensified by the drugs used to treat other symptoms of Parkinson's disease.

Emotional changes. Some people with Parkinson's disease become fearful and insecure. Perhaps they fear they cannot cope with new situations. They may not want to travel, go to parties, or socialize with friends. Some lose their motivation and become dependent on family members. Others may become irritable or uncharacteristically pessimistic. Memory loss and slow thinking may occur, although the ability to reason remains intact. Whether people actually suffer intellectual loss (also known as dementia) from Parkinson's disease is a controversial area still being studied.

Difficulty in swallowing and chewing, Muscles used in swallowing may work less efficiently in later stages of the disease. In these cases, food and saliva may collect in the mouth and back of the throat, which can result in choking or drooling. Medications can often alleviate these problems.

Speech changes. About half of all parkinsonian patients have problems with speech. They may speak too softly or in a monotone, hesitate before speaking, slur or repeat their words, or speak too fast. A speech therapist may be able to help patients reduce some of these problems.

Urinary problems or constipation. In some patients bladder and bowel problems can occur due to the improper functioning of the autonomic nervous system, which is responsible for regulating smooth muscle activity. Some people may become incontinent while others have trouble urinating. In others, constipation may occur because the intestinal tract operates more slowly. Constipation can also be caused by inactivity, eating a poor diet, or drinking too little fluid. It can be a persistent problem and, in rare cases, can be serious enough to require hospitalization.

Skin problems. In Parkinson's disease, it is common for the skin on the face to become very oily, particularly on the forehead and at the sides of the nose. The scalp may become oily too, resulting in dandruff. In other cases, the skin can become very dry. These problems are also the result of an improperly functioning autonomic nervous system. Standard treatments for skin problems help. Excessive sweating, another common symptom, is usually controllable with medications used for Parkinson's disease.

Sleep problems. These include difficulty staying asleep at night, restless sleep, nightmares and emotional dreams, and drowsiness during the day. It is unclear if these symptoms are related to the disease or to the medications used to treat Parkinson's disease. Patients should never take over-the-counter sleep aids without consulting their physicians.

It is estimated that dementia occurs in 20% to 25% of patients with Parkinson's disease, making the illness difficult to distinguish from Alzheimer's disease. However, the dementia of Parkinson's disease is usually a late feature. Prominent early dementia may indicate coexisting Alzheimer's disease or another illness.

Current Treatments

Presently, there is no cure for Parkinson's disease. Since most of the symptoms are due to the lack of dopamine in the brain, effective medications aim at temporarily replenishing or mimicking dopamine's actions. These drugs—levodopa and the dopamine agonists ropinirole, pramipexole, and pergolide—reduce muscle rigidity, improve speed and coordination of movement, and relieve tremor.

Without doubt, the gold standard of present therapy is the drug levodopa (also called L-dopa). L-Dopa (from the full name L-3,4-dihydroxyphenylalanine) is a simple chemical found naturally in plants and animals. Levodopa is the generic name used for this chemical when it is formulated for drug use in patients. Nerve cells can use levodopa to make dopamine and replenish the brain's dwindling supply. Dopamine itself cannot be given because it doesn't cross the blood-brain barrier, the elaborate meshwork of fine blood vessels and cells that filters blood reaching the brain. Usually, patients are given levodopa combined with carbidopa. When added to levodopa, carbidopa delays the conversion of levodopa into dopamine until it reaches the brain, preventing or diminishing some of the side effects that often accompany levodopa therapy. Carbidopa also reduces the amount of levodopa needed.

Levodopa's success in treating the major symptoms of Parkinson's disease is a triumph of modern medicine. First introduced in the 1960s, it delays the onset of debilitating symptoms and allows the majority of parkinsonian patients—who would otherwise be very disabled—to extend the period of time in which they can lead relatively normal, productive lives.

Levodopa is not a cure. Although it can diminish the symptoms, it does not replace lost nerve cells and it does not stop the progression of the disease. Although levodopa helps at least three-quarters of parkinsonian cases, not all symptoms respond equally to the drug. Bradykinesia and rigidity respond best, while tremor may be only marginally reduced. Problems with balance and other symptoms may not be alleviated at all.

Side Effects of Levodopa

The most common side effects are nausea, vomiting, low blood pressure, involuntary movements, and restlessness. In rare cases patients may become confused. Dyskinesias, or involuntary movements such as twitching, nodding, and jerking, most commonly develop in people who are taking large doses of levodopa over an extended period. These movements may be either mild or severe and either very rapid or very slow. The only effective way to control these drug-induced movements is to lower the dose of levodopa or to use drugs that block dopamine, but these remedies usually cause the disease symptoms to reappear. Doctors and patients must work together closely to find a tolerable balance between the drug's benefits and side effects.

In addition, many doctors recommend physical therapy or muscle-strengthening exercises to help people handle their daily activities. Because movements are affected in Parkinson's disease, exercising may help people improve their mobility. Some doctors prescribe physical therapy or muscle-strengthening exercises to tone muscles and to put underused and rigid muscles through a full range of motion. Exercises will not stop disease progression, but they may improve body strength so that the person is less disabled. Exercises improve balance, helping people overcome gait problems, and they can also strengthen certain muscles so that people can speak and swallow better. Exercises can also improve the emotional well-being of parkinsonian patients by giving them a feeling of accomplishment. Although structured exercise programs help many patients, more general physical activities, such as walking, gardening, swimming, calisthenics, and using exercise machines, also appear to provide some benefit.

In some cases, surgery may be appropriate if the disease doesn't respond to drugs. A therapy called deep brain stimulation has been approved by the U.S. Food and Drug Administration, as well, as Globus pallidus internal-segment pallidotomy and Fetal nigral transplantation.

In deep brain stimulation, electrodes are implanted into the brain and connected to a small electrical device called a pulse generator that can be externally programmed. Deep brain stimulation can reduce the need for levodopa and related drugs, which in turn decreases the involuntary movements called dyskinesias. It also helps to alleviate fluctuations of symptoms and to reduce tremors, slowness of movements, and gait problems. Deep brain stimulation requires careful programming of the stimulator device in order to work correctly.

Prognosis

Although medications can relieve symptoms for a period of time, they do not slow or stop the natural progression of the disease. The course of the disease varies widely. Some people have mild symptoms for many years, while others have severe symptoms and a quicker progression. Despite new medical and surgical therapy, mortality rates for Parkinson's disease remain unchanged.

Although Levodopa is the most effective drug for Parkinson's disease, its long-term use is associated with significant motor complications. Dopamine agonists hold promise because of more sustained stimulation of dopamine receptors and possibly an antioxidant effect. Selegiline, amantadine, and anticholinergics are still used but must be employed with caution in the elderly. COMT inhibitors may be useful adjuncts to levodopa therapy but are plagued with serious adverse effects.

Parkinson's and the Systems of the Present Invention

Experiments conducted during the development of the present invention have demonstrated that healthy as well as sick or diseased subjects (e.g., bipolar vestibular dysfunction patients) demonstrate improvement or correction of, among other things, their vestibular function (e.g., balance), proprioception, motor control, vision, posture, cognitive functions, tinnitus, emotional conditions and sleep as a direct consequence of training procedures with the systems of the present invention.

Accordingly, in some embodiments, the present invention provides systems and methods for correcting or improving motor control (e.g., walking, talking, or completing simple tasks that depend on coordinated muscle movements) in a subject with Parkinson's disease.

In some embodiments, the present invention provides systems and methods for correcting or improving tremor or trembling in hands, arms, legs, jaw, and face; correcting or improving rigidity or stiffness of the limbs and trunk; correcting or improving bradykinesia, correcting or improving slowness of motor movements; and correcting or improving postural instability or impaired balance and coordination in a subject with Parkinson's disease.

In some embodiments, the present invention provides systems and treatments for correcting or improving depression, emotional changes, difficulty in swallowing and chewing, speech changes, urinary problems or constipation, and sleep problems in a subject with Parkinson's disease.

In some embodiments, the present invention provides systems and methods for low cost, highly sensitive diagnostic tremor tool. In some embodiments, the device provides spectral analysis of head stability can be especially useful for diagnosis of the Parkinson's tremor, no matter which body part is affected. Even though the head is the most sensitive part of the body, in some embodiments, the present invention uses an external accelerometer instead of an internal one (e.g. hand-based, instead of head-based).

In some embodiments, the systems of the present invention differentiates peaks within a frequency range of 2-10 Hz, which is important for separation of Parkinson's and essential tremors. In other embodiments, the device differentiates between peaks in a range of 5-10 Hz, 10-20 Hz, 15-25 Hz, 1-10 Hz, or 10-100 Hz. It is contemplated that diagnostic procedures with quantitatively measurable and scaleable data are used for early diagnosis of tremor and balance problems. The present invention provides a portable system designed to be comparable with desktop and laptop computers. It is contemplated that data recording and analytical routines will quantify postural stability, thereby enabling description of postural stability.

The systems of the present invention have been shown to improve and recover postural control and gait stability in both BVD patients and normal subjects. Thus, in some embodiments, the present invention provides systems and methods that provide and facilitate the muscular relaxation in all muscular groups in subjects who typically suffer from rigidity in neck and upper back muscles (e.g., Parkinson's subjects). Festination and Parkinson's jerk movement are similar to the sharp, spike- and step-like movement in BVD patients. These abnormal movements were completely eliminated after training Consequently, BVD patients achieved a "superstability" stage. Accordingly, the present invention provides systems and methods to eliminate or correct jerk like movements associated with Parkinson's disease.

In addition, it is contemplated that, in some embodiments of the present invention, the systems of the present invention are used in combination with other treatments (e.g., Levadopa or similar drugs) for treating a subject with Parkinson's disease. Thus, the present invention provides complimentary or supplementary treatments that can be used in combination with other known treatments. It is contemplated that systems and methods of the present invention intensify the positive effects of current treatments for Parkinson's (e.g., Levadopa), and decrease or prevent adverse side effects (e.g., prevent abnormal motor pattern associated with Levadopa). In some embodiments, use of systems and methods of the present invention will permit a decrease in the dosage of a drug prescribed to treat Parkinson's.

In some embodiments, the systems and methods of the present invention are used in combination with a training regiment based on advanced physical therapy. In some embodiments, such combination results in an overall improvement of motor control, posture and balance, among other things.

In some embodiments, the systems and methods of the present invention are used in place of, or in combination with, surgically invasive procedures (e.g., deep brain stimulation) for treating Parkinson's patients. Long term potentiation, the systems and methods of the present invention, and deep brain stimulation share a few common features, including: long therapy times (more than few minutes); electrical stimulation (rectangular impulses); similar pulse rates (100-200 Hz) of the neural (or sensory) tissue; and long lasting (from hours to days) effects. Accordingly, it is contemplated that, in some embodiments, subjects undergoing treatment with the systems of the present invention experience long term potentiation (e.g., long lasting changes lasting from hours to days to weeks or longer) in brain and body functions.

In some embodiments, the present invention provides systems and methods for reducing or correcting speech problems resulting from tongue mobility loss associated with Parkinson's disease or other diseases. For example, in some embodiments, the systems of the present invention are used to keep muscular tonus within normal range as a consequence of antidromic stimulation (e.g., stimulation from the tongue to the nerve center) of the hypoglossal nerve (major motor nerve of the tongue).

The present invention also provides systems and methods for improving or correcting cognitive decline observed in a Parkinson's subject.

In some embodiments, the present invention provides systems and methods for preventing or diminishing involuntary movements. For example, in some embodiments, it is contemplated that the systems and methods of the present invention are capable of changing the signal-to-noise ratio in vestibular and motor-control circuitries in the human brain, and of suppressing the "noise" and "error" signals in posture control groups of muscles.

In some embodiments, the present invention provides systems and methods for improving or correcting motor control (e.g., improvement of fine finger movement control); relieving stress; eliminating depression; and improving the emotional status of Parkinson's patients.

Example 24

Stroke

Stroke in General

More than 2,400 years ago the father of medicine, Hippocrates, recognized and described stroke, the sudden onset of paralysis. Until recently, modern medicine has had very little control over this disease, but the world of stroke medicine is changing and new and better therapies are being developed. Today, some people who suffer from stroke can recover from the attack with no or few disabilities if they are treated promptly. Doctors can finally offer stroke patients and their families the one thing that until now has been so hard to give—hope.

In ancient times, stroke was called apoplexy, a general term that physicians applied to any condition in which a patient was suddenly struck with paralysis. Because many conditions can cause sudden paralysis, the term apoplexy did not indicate a specific diagnosis or cause.

Scientists now know that there is a very short window of opportunity for treatment of the most common form of stroke. Nevertheless, systems and methods of the present invention, used alone or in combination with other advances in the field of cerebrovascular disease, provide stroke patients a chance for survival and recovery.

A stroke is a sudden interruption of the blood supply in the brain. Most strokes are caused by an abrupt blockage of arteries leading to the brain (ischemic stroke). Other strokes are caused by bleeding into brain tissue when a blood vessel bursts (hemorrhagic stroke). A stroke, also called a brain attack, happens when brain cells die because of inadequate blood flow. A stroke is considered to be a cardiovascular disease and a neurological disorder. When the symptoms of a stroke last only a short time (less than an hour), this is called a transient ischemic attack (TIA) or mini-stroke.

Stroke has many consequences. The effects of a stroke depend on which part of the brain is injured, and how severely it is injured. Stroke may cause sudden weakness, loss of sensation, or difficulty with speaking, seeing, or walking Since different parts of the brain control different areas and functions, it is usually the area immediately surrounding the stroke that is affected. Stroke can be accompanied by a headache, but it can also be completely painless. It is very important to recognize the warning signs of stroke and to get immediate medical attention if they occur.

There are several other types of injury that can affect the brain, including aneurysms, subdural hematomas (bleeding adjacent to the brain), trauma, infection, among others, that are also contemplated to be treatable via systems and methods of the present invention.

Stroke appears to run in some families who may either have a genetic mutation that predisposes them to stroke, or share a lifestyle that contributes to stroke risk factors. Other than genetic predisposition, additional risk factors for stroke are high blood pressure, heart disease, smoking, diabetes, and high cholesterol. Controlling these risk factors can decrease the likelihood of getting a stroke.

Health Statistics

Each year, more than 700,000 strokes occur in the United States, making stroke the third leading cause of death (behind heart disease and cancer) and the leading cause of long-term disability in the U.S. About 500,000 of these are first attacks, and 200,000 are recurrent attacks. Stroke killed 275,000 people in 2002 and accounted for about 1 in almost 15 deaths in the United States.

On average, someone in the United States suffers from a stroke every 45 seconds; every 3.1 minutes someone dies of a stroke. 22% of men and 25% of women who have an initial stroke die within a year. At all ages, 40,000 more women than men have a stroke. 28% of people who suffer a stroke in a given year are under age 65.

According to the National Stroke Association: 10% of stroke survivors recover almost completely; 25% recover with minor impairments; 40% experience moderate to severe impairments that require special care; 10% require care in a nursing home or other long-term facility; 15% die shortly after the stroke; and approximately 14% of stroke survivors experience a second stroke in the first year following the initial stroke.

About 4.7 million stroke survivors (2.3 million men, 2.4 million women) are alive today. In addition, there are millions of husbands, wives, children and friends who care for stroke survivors and whose own lives are personally affected. Approximately 10 percent of stroke survivors resume prior activity levels. Mild to moderate disability results in about 50 percent of strokes, while severe disability affects the remaining 40 percent of individuals who survive a stroke.

Cost of Stroke to the United States (Data from 1997)

The total cost of stroke to the United States: estimated at about $43 billion/year. The direct costs for medical care and therapy: estimated at about $28 billion/year while indirect costs from lost productivity and other factors: estimated at about $15 million/year. The average cost of care for a patient up to 90 days after a stroke: $15,000 (The Stroke/Brain Attack Reporter's Handbook, National Stroke Association, Englewood, Colo., 1997).

Symptoms

The most common sign of a stroke is sudden weakness of the face, arm or leg, most often on one side of the body. Other warning signs can include sudden changes, such as: numbness of the face, arm, or leg, especially on one side of the body; confusion, trouble speaking or understanding speech; vision disturbances, trouble seeing in one or both eyes; trouble walking, dizziness, loss of balance or coordination; severe headache with no known cause; slurred speech, inability to speak or understand speech; difficulty reading or writing; swallowing difficulties or drooling; loss of memory; vertigo (spinning sensation); personality changes; mood changes (depression, apathy); drowsiness, lethargy, or loss of consciousness; and uncontrollable eye movements or eyelid drooping The warning signs of a stroke depend on such factors as which side and what part of the brain are affected, and how severely the brain is injured. Therefore, each person may have different stroke warning signs. Stroke may be associated with a headache, or may be completely painless. If one or more of these symptoms are present for less than 24 hours, it may be a transient ischemic attack (TIA). A TIA is a temporary loss of brain function and a warning sign for a possible future stroke.

Stroke Effects

Stroke can affect people in different ways. It depends on the type of stroke, the area of the brain affected and the extent of the brain injury. Brain injury from a stroke can affect the senses, motor activity, speech and the ability to understand speech. It can also affect behavioral and thought patterns, memory and emotions.

Paralysis or weakness on one side of the body is common. Most of these problems can improve over time. In some patients they will disappear completely. Motor deficits can result from damage to the motor cortex in the frontal lobes of the brain or from damage to the lower parts of the brain, such as the cerebellum, which controls balance and coordination.

Loss of awareness: Stroke often causes people to lose mobility and/or feeling in an arm and/or leg. If this affects the left side of the body (caused by a stroke on the right side of the brain), stroke survivors may also forget or ignore their weaker side. This problem is called neglect. As a result, they may ignore items on their affected side and not think that their left arm or leg belongs to them. They also may dress only one side of their bodies and think they're fully dressed. Bumping into furniture or doorjambs is also common.

Perception: A stroke can also affect seeing, touching, moving and thinking, so a person's perception of everyday objects may be changed. Stroke survivors may not be able to recognize and understand familiar objects the way they did before.

When vision is affected, objects may look closer or farther away than they really are. This causes survivors to have spills at the table and collisions or falls when they walk.

Hearing and speech: Stroke usually doesn't cause hearing loss, but people may have problems understanding speech. They also may have trouble saying what they're thinking. This is called aphasia. Aphasia affects the ability to talk, listen, read and write. It's most common with a stroke affecting the left side of the brain, which may also weaken the body's right side.

A related problem is that a stroke can affect muscles used in talking (those in the tongue, palate and lips). Speech can be slowed, slurred or distorted, so stroke survivors can be hard to understand. This is called dysarthria. It may require the help of a speech expert.

Chewing and swallowing food: The problem with chewing and swallowing food is called dysphagia. It can occur when muscles on one side of the mouth are weak. One or both sides of the mouth can also lack feeling, increasing the risk of choking.

Ability to think clearly: Specific parts of the brain allow us to form long-term and short-term memories. (Short-term memories help us remember why we got up and walked into the next room, for example.) With injury to these areas, it may be hard to plan and carry out even simple activities. Stroke survivors may not know how to start a task, they confuse the sequence of logical steps in tasks, or forget how to do tasks they've done many times before.

Emotions: Some areas of the brain produce emotions, just as other parts produce movement or allow us to see, hear, smell or taste. If these areas are injured by a stroke, a survivor may cry easily or have sudden mood swings, often for no apparent reason. This is called emotional lability. Laughing uncontrollably may also occur, though it isn't as common as crying.

Depression is common as stroke survivors recover and as they come to terms with any permanent impairment. It is a clinical behavioral problem that can hamper recovery and rehabilitation and may even lead to suicide. Post-stroke depression is treated as any other depression, namely, with antidepressant medications and therapy.

Stroke patients may experience pain, uncomfortable numbness, or strange sensations after a stroke. These sensations may be due to many factors, including damage to the sensory regions of the brain, stiff joints, or a disabled limb. An uncommon type of pain resulting from stroke is called central stroke pain or central pain syndrome (CPS). CPS results from damage to an area in the mid-brain called the thalamus.

The pain is a mixture of sensations, including heat and cold, burning, tingling, numbness, sharp stabbing and underlying aching pain. The pain is often worse in the extremities—the hands and feet—and is increased by movement and temperature changes, cold temperatures in particular. Unfortunately, since most pain medications provide little relief from these sensations, very few treatments or therapies exist to combat CPS. It's important for stroke survivors to receive appropriate rehabilitation to help alleviate these deficits.

Stroke Treatment

Physicians have a range of therapies to choose from when determining a stroke patient's individual therapeutic plan. The type of stroke therapy a patient should receive depends upon the stage of disease. Generally, there are three treatment stages for stroke: prevention, therapy immediately after stroke, and post-stroke rehabilitation.

Prevention

Therapies to prevent a first or recurrent stroke are based on treating an individual's underlying risk factors for stroke, such as hypertension, atrial fibrillation, and diabetes, or preventing the widespread formation of blood clots that can cause ischemic stroke in everyone, whether or not risk factors are present.

Prevention is the best possible stroke treatment. Many stroke risk factors can be modified with lifestyle changes, so taking an active role in reducing risk factors can help prevent strokes. Practicing stroke prevention has other health benefits—many aspects of stroke prevention also reduce the risk of heart attack, hypertension, and diabetes. To prevent bleeding strokes, it is recommended to take steps to avoid falls and injuries.

Therapies for stroke include immediate (or acute) treatment: medications, surgery and long-term rehabilitation.

Acute Stroke Therapies

Acute stroke therapies try to stop a stroke while it is happening by quickly dissolving a blood clot causing the stroke or by stopping the bleeding of a hemorrhagic stroke.

Medication or drug therapy is the most common treatment for stroke. The most popular classes of drugs used to prevent or treat stroke are antithrombotics (antiplatelet agents and anticoagulants), thrombolytics, and neuroprotective agents. Other medications may be needed to control associated symptoms. Analgesics (pain killers) may be needed to control severe headache. Anti-hypertensive medication may be needed to control high blood pressure.

Surgery can be used to prevent stroke, to treat acute stroke, or to repair vascular damage or malformations in and around the brain. There are two prominent types of surgery for stroke prevention and treatment: carotid endarterectomy and extracranial/intracranial (EC/IC) bypass.

For hemorrhagic stroke, surgery is often required to remove pooled blood from the brain and to repair damaged blood vessels. Life support and coma treatment are performed as needed.

Long Term Stroke Treatment

The purpose of post-stroke rehabilitation is to overcome disabilities that result from stroke damage. The goal of long-term treatment is to recover as much function as possible and prevent future strokes. Depending on the symptoms, rehabilitation includes physical therapy, occupational therapy, speech therapy and psychological therapy. The recovery time differs from person to person.

Physical Therapy (PT): Helps stroke victims to relearn walking, sitting, lying down, switching from one type of movement to another. For most stroke patients, physical therapy (PT) is the cornerstone of the rehabilitation process. A physical therapist uses training, exercises, and physical manipulation of the stroke patient's body with the intent of restoring movement, balance, and coordination. The aim of PT is to have the stroke patient relearn simple motor activities such as walking, sitting, standing, lying down, and the process of switching from one type of movement to another.

Occupational Therapy (OT): Helps stroke patients to relearn eating, drinking, swallowing, dressing, bathing, cooking, reading, writing, toileting. The goal of OT is to help the patient become independent or semi-independent Speech Therapy: The focus of speech therapy is on relearning language and communication skills. Speech and language problems arise when brain damage occurs in the language centers of the brain. Due to the brain's great ability to learn and change (called brain plasticity), other areas can adapt to take over some of the lost functions (See, e.g., Ptito et al., Brain, 128(Pt 3):606-14 [2005]). Speech therapy helps stroke patients relearn language and speaking skills, or learn other forms of communication. Speech therapy is appropriate for patients who have no deficits in cognition or thinking, but have problems understanding speech or written words, or problems forming speech. A speech therapist helps and instructs stroke patients on how to improve their language skills, to develop alternative ways of communicating, and to expand coping skills enabling them to deal with the frustration of not being able to communicate fully. With time and patience, a stroke survivor should be able to regain some, and sometimes all, language and speaking abilities.

Psychological/Psychiatric Therapy: These methods alleviate some mental and emotional problems. Many stroke patients require psychological or psychiatric help after a stroke. Psychological problems, such as depression, anxiety, frustration, and anger, are common post-stroke disabilities. Talk therapy, along with appropriate medication, can help alleviate some of the mental and emotional problems that result from stroke. Sometimes it is beneficial for family members of the stroke patient to seek psychological help as well.

Stroke and the Systems of the Present Invention

Experiments conducted during the development of the present invention have demonstrated that healthy as well as sick or diseased (e.g., bipolar vestibular dysfunction patients) subjects demonstrated improvement or correction of, among other things, their vestibular function (e.g., balance), proprioception, motor control, vision, posture, cognitive functions, tinnitus, emotional conditions and sleep as a direct consequence of training procedures with the systems of the present invention. Thus, the systems of the present invention benefits stroke patients in numerous ways.

In some embodiments, the present invention provides systems and treatments for correcting or improving loss of awareness, pain or numbness, the senses (e.g., seeing, touching, and balancing), motor activity, speech, perception and thinking (e.g., the ability to understand/comprehend speech), behavioral and thought patterns, chewing and swallowing food, memory (e.g., long and short term memory), and emotions in a subject displaying stroke-like symptoms.

In some embodiments, systems and methods of the present invention are used in combination with other treatments (e.g., antithrombotics including antiplatelet agents and anticoagulants, thrombolytics, and neuroprotective agents) or therapies (e.g., physical therapy, occupational therapy, speech therapy and psychological therapy) for treating a stroke subject. Thus, the present invention provides complimentary or supplementary treatments that can be used in combination with other known treatments. It is contemplated that systems and methods of the present invention intensify the positive effects of current treatments for stroke, and decrease or prevent adverse side effects. In some embodiments, use of systems and methods of the present invention permits a decrease in the dosage of a drug prescribed to treat stroke or a subject exhibiting stroke-like symptoms.

It is contemplated that as a part of stroke prevention therapy, focusing on the prevention of falls and injuries, a training regimen based on advanced physical therapy reinforced with the systems of the present invention improves posture, balance, and motor control.

Additionally, it is contemplated that as a part of long term stroke treatment, the systems of the present invention combined with a training regimen are effective in post-stroke rehabilitation, enabling stroke victims to overcome disabilities (e.g., slurred speech and other disabilities mentioned herein) that result from stroke damage.

The systems of the present invention have been shown to improve and recover postural control and gait stability in both BVD patients and normal subjects. Data recording and analytical routines are capable of quantifying postural stability, enabling the quantitative description of postural stability and the ability to control the recovery process. As such, the systems of the present invention fully correspond to the general intent of recovery of stroke patients' movement, balance, and coordination. Accordingly, in some embodiments, the present invention provides systems and treatments for correcting or improving movement, balance, and coordination in a stroke patient. In further embodiments, walking, talking, and completing simple tasks that depend on coordinated muscle movements are improved or corrected in a stroke patient.

In some embodiments, training with the systems of the present invention overcomes patient paralysis and weakness and provides and facilitates muscular relaxation in all muscular groups, (e.g., as observed in BVD patients suffering from typical rigidity in neck and upper back muscles).

In some embodiments, recovery of perceptual and sensory deficits (including loss of awareness) is reinforced with systems of the present invention (e.g., BVD patients with such deficits improved not only their balance and coordination, but also their vision, hearing and proprioception).

In some embodiments, systems of the present invention assist the amelioration of mental and emotional problems associated with stroke. For example, in some embodiments, systems and methods of the present invention improve sleep, reduce stress and depression and improve emotional status in a stroke patient. In some embodiments, training improves cognitive functions (e.g., the ability to think clearly, to remember and to act in multitasking environments). These functions are typically affected in BVD patients.

In some embodiments, the present invention provides systems and methods for reducing or correcting speech problems resulting from tongue mobility loss associated with stroke. For example, in some embodiments, the systems of the present invention are used to keep muscular tonus within normal range as a consequence of antidromic stimulation (e.g., stimulation from the tongue to the nerve center) of the hypoglossal nerve (major motor nerve of the tongue).

In some embodiments, the systems of the present invention are used to regain brain function by activating, utilizing, and/or training a portion of the brain to learn a task that was previously facilitated by a region of the brain now damaged.

A subject with a central cerebellar lesion due to stroke was treated for one week with the systems and methods of the present invention. The subject's response to treatment is documented in Table 8 below.

TABLE 8

| Test | Pre-treatments Score | Post-treatment Score |
|---|---|---|
| Neurocom SOT composite | 48 | 61 |
| Total # of falls on SOT | 3 | 0 |
| # of falls on SOT 5 and 6 | 3 | 0 |
| Dynamic Gait Index | 18/24 | 18/24 (24 best) |
| Activities-Specific Balance Confidence Scale (ABC) | 46/100 | 55/100 (100 best) |
| Dizziness Handicap Inventory (DHI) | 52/100 | 38/100 (0 best) |

As described in Table 8 above, the subject demonstrated improvements with the quality of life indicators (ABC, DHI), and on the SOT. Additionally, walking in crowds became significantly easier for the subject.

Example 25

Meniere's Disease

A subject with Meniere's disease was treated with the systems and methods of the present invention. The subject responded well to treatment. For example, post-treatment, the subject enjoyed stable, smooth and rhythmic motion in his gait, with the ability to turn with his eyes closed. The subject further enjoyed the ability to look at walls and the ceiling while he walked (e.g., down a hallway). His visual acuity improved providing the subject with the ability to change his visual focus more smoothly and without impairment or disorientation (e.g., the subject was able to change his focus from the instrument panel of a car to outside traffic and surrounding environments in a smooth, focused manner). No adverse events were observed or reported by the subject Example 26

Migraine

A subject with migraines as well as bilateral vestibular loss was treated twice a day over a period of 4½ days with the systems and methods of the present invention. The subject displayed positive results from treatment.

Prior to treatment, the subject exhibited a wide base of support in normal gait and was unable to stand in a tandem Romberg position with eyes closed or open. She was further unable to stand on one leg without falling to one side. She suffered from functional defects including daily headaches, balance difficulty, inability to walk on uneven surfaces, difficulty walking up stairs without a railing and walking in the dark. She had difficulty sleeping and driving at night. The subject suffered from an impaired ability to carry out multitasking functions. Slightly more than a year prior to treatment, the subject had a NEUROCOM test with a composite score of 55, below normal for her age group.

Post treatment with the systems and methods of the present invention, the subject enjoyed a normal base of support in gait and was able to stand with eyes open and closed in a tandem Romberg position. The subject was also able to stand on one leg without falling. She noted functional improvement including experiencing no difficulty walking up stairs, no headaches, improved sleeping, decreased difficulty with driving, improved clarity of vision, and the ability to walk on a treadmill without dizziness thereafter. She noted that her overall confidence increased. Additionally, the subject gained the ability to perform physical/mental multitask routines (e.g., walking, tossing a ball, and counting). Her composite score on the NEUROCOM test was 65, with the NEUROCOM test taking place two days after her final treatment.

Example 27

Mal De Debarquement

Mal de debarquement (MDD), literally "sickness of disembarkment," refers generally to inappropriate sensations of movement after exposure to motion. For example, the syndrome (e.g., recurrence of symptoms associated with the syndrome) typically follows a sea voyage (e.g., a sea cruise), but similar sensations have been described following extended train travel, space flight (See, e.g., Stott, In: Crampton, ed. *Motion and Space Sickness*. Boca Raton, Fla.: CRC Press; 1990), and experience within a slowly rotating room (See, e.g., Graybiel, *Aerospace Med.* 1969; 40:351-367). Symptoms usually include vague unsteadiness (e.g., imbalance) and disequilibrium or sensations of rocking and swaying, and may also include tilting sensations, ear symptoms, nausea and headache. Mal de debarquement can be distinguished from motion sickness, airsickness, simulator sickness, or seasickness (e.g., mal de mer) because subjects are predominantly symptom free during the period of motion (e.g., as opposed to experiencing symptoms during the period of motion). Mal de debarquement can also be distinguished from "landsickness" or postmotion vertigo by the duration of the syndrome (e.g., the duration of the symptoms associated with the syndrome—e.g., unsteadiness or sensations of rocking and swaying). Landsickness typically lasts less than 48 hours (See, e.g., Cohen, *J Vestib Res.* 1996; 6:31-35; Gordon et al., *J Vestib Res.* 1995; 5:363-369). Most researchers reporting on MDD define it as a syndrome presenting symptoms that generally persists for at least 1 month (See, e.g., Brown et al., *Am J Otolaryngol.* 1987; 8:219-222; Murphy, *Otolaryngol Head Neck Surg.* 1993; 109:10-13; Mair, *J Audiol Med.* 1996; 5:21-25). Others refer to the common short-lived postmotion vertigo as MDD, and the longer duration form as "persistent MDD" (See, e.g., Gordon et al., *J Vestib Res.* 1995; 5:363-369).

Two patients with MDD were treated over the period of one week with the systems and methods of the present invention. Prior to treatment, both patients exhaustively sought and received treatment for their symptoms, but received no benefit (e.g., no reduction of symptoms) from such treatments. The results of treatment with the systems and methods of the present invention are shown in Tables 9 and 10 below. Both patients experienced significant improvement of their symptoms after treatment (e.g., training) with the systems and methods of the present invention.

TABLE 9

Patient 1 data.

| Test | Pre-treatments Score | Post-treatment Score |
| --- | --- | --- |
| Dynamic Gait Index | 22/24 | 24/24 |
| ABC Scale (higher = better) | 75/100 | 96/100 |
| Dizziness Handicap Inventory (lower = better) | 60/100 | 24/100 |
| Neurocom SOT Composite | 64 | 80 |
| Total # of falls on SOT | 0 | 0 |
| # of falls on SOT 5 & 6 | 0 | 0 |

TABLE 10

Patient 2 data.

| Test | Pre-treatments Score | Post-treatment Score |
| --- | --- | --- |
| Dynamic Gait Index | 24/24 | 24/24 |
| ABC Scale (higher = better) | 94/100 | 100/100 |
| Dizziness Handicap Inventory (lower = better) | 56/100 | 8/100 |
| Neurocom SOT Composite | 58 | 81 |
| Total # of falls on SOT | 0 | 0 |
| # of falls on SOT 5 & 6 | 0 | 0 |

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in the relevant fields, are intended to be within the scope of the following claims.

The section below provides a more detailed description of the command codes. The protocol supports writing commands to the TDU as well as reading the current status and memory contents of the TDU. The opcode for each command is one byte long and is made of a single letter (A\a through P\p). The case of the letter determines whether it is read (lower case) or write (upper case) command. The opcode byte is the ASCII representation of the letter. In all commands the opcode is followed by a byte [NOF] holding the number of bytes to follow. That is the total number of bytes in any command is equal to 2+NOF. The protocol commands are grouped into three operations categories: I-Electrode-level operations, single electrode, real time (Commands A,B,C,D): II-Electrode level operations, block udate on array (Commands E,F,G,H,T): and III-Array level operations and system commands (Commands I,J,K,L,M, M,O,P,Q,R,S). In the section below, angle brackets are used to indicate ASCII representation of the information enclosed. For example, [<A>] indicated a byte holding the ASCII representation of A. Data and Parameter ranges are indicated for each parameter. All the data are integers. If the data sent to the TDU is below the minimum value, the TDU treats that value as if zero was sent.

```
COMMAND : A\a      (Write\Read )    Amplitude (PA) for
                                    one electrode
Write Format :(5 bytes)             [A][NOF*][Address][Data][CKSUM]
                                    *[NOF] = Number of bytes to follow
TDU Response :(1bytes)              [Res*]
                                    *See TDU result codes below
Read Format :(3 bytes)              [a][NOF][Address]
TDU Response :(1 bytes)             [Data]
Comment              Address range 1-144
;
                     Data range 0-255        (Parameter range ; 0-40 Volts)
                     Data = 0 No Stimulation
                     CKSUM is one byte resulting from summing the
                     address and data bytes
COMMAND : B\b      (Write\Read )    Pulse width (PW) for
                                    one electrode
Write format :(5 bytes)             [B][NOF][Address][Data][CKSUM]
                                    *[NOF] = Number of bytes to follow
TDU Response :(1 bytes)             [Res*]
                                    *See TDU result codes below
Read Format :(3 bytes)              [b][NOF][Address]
TDU Response :(1 bytes)             [Data]
Comment              Address range 1-144
;
                     Data range 0-255        — (Parameter range ; 0-510 us)
                     CKSUM is one byte resulting from summing the
                     address and data bytes
                     Data = No Stimulation
COMMAND : C\c      (Write\Read )    Number of inner bursts
                                    in outer burst (OBN) for one electrode
Write Format :(5 bytes)             [C][NOF][Address][Data][CKSUM]
                                    *[NOF] = Number of bytes to follow
TDU Response :(1 bytes)             [Res*]
                                    *See TDU result codes below
```

-continued

```
Read Format ;(3 bytes)                         [b][NOF][Address]
TDU Response ;(1 bytes)                        [Data]
Comment            Address range 1-144
;
                   Data range 0-255            (Parameter range ; 0 - 255
                                               bursts)
                   Data = 0 No Stimulation
                   CKSUM is one byte resulting from summing the
                   address and data bytes
COMMAND : D\d      (Write\Read )   Number of pulses per
                   inner burst (IBN) for one electrode
Write Format :(5 bytes)                        [D][NOF][Address][Data][CHSUM
                                               ]
                                               *[NOF] = Number of bytes to
                                               follow
TDU Response :(1 bytes)                        [Res*]
                                               *See TDU result codes below
Read Format :(3 bytes)                         [d][NOF][Address]
TDU Response :(1 bytes)                        [Data]
Comment            Address range 1-144
;
                   Data range 0-255            (Parameter range ; 0-255
                                               pulses)
                   Data = 0 No Stimulation
                   CKSUM is one byte resulting from summing the
                   address and data bytes
COMMAND : E\e      (Write\Read )   Pulse Amplitude (PA)
                   for each electrode in a block
Write Format :(up t0 149 byt.)                 [E][NOF*][ul][rl][Data1][Data2][Da
                                               ta3]..........[Datan-
                                               1][Datan][CHSUM]
                                               *[NOF] = Number of bytes to
                                               follow
TDU Response :(1 bytes)                        [Res*]
                                               *See TDU result codes below
Read Format :(4 bytes)                         [e][NOF][ul][lr]
TDU Response :(up to 144 by.)                  [Data1][Data2][Data3]..........[Data
                                               n-1][Datan]
Comment            Block Update ; block of tactors defined by [ul = upper
;                  left tactor] and [lr=lower right tactor]
                              when ul = 1 and lr = 144 then the entire
                   array is selected [datan]=[data144]
                   Data range 0-255            (Parameter range ; 0-40Volts)
                   Data = 0 No Stimulation
                   CKSUM is one byte resulting from summing all the
                   bytes following the [NOF] byte
COMMAND : F\f      (Write\Read ) Pulse with (PW) for
                   each electrode in a block
Write Format :(up t0 149 byt.)                 [F][NOF*][ul][rl][Data1][Data2][Da
                                               ta3]..........[Datan-
                                               1][Datan][CHSUM]
                                               *[NOF] = Number of bytes to
                                               follow
TDU Response :(1 bytes)                        [Res*]
                                               *See TDU result codes below
Read Format :(4 bytes)                         [f][NOF][ul][lr]
TDU Response :(up to 144 by.)                  [Data1][Data2][Data3]..........[Data
                                               n-1][Datan]
Comment            Block Update ; block of tactors defined by [ul = upper
;                  left tactor] and [lr=lower right tactor]
                              when ul = 1 and lr = 144 then the entire
                   array is selected [datan]=[data144]
                   Data range 0-255            — (Parameter range ; 0-510 us)
                   CKSUM is one byte resulting from summing all the
                   bytes following the [NOF] byte
                   Data = No Stimulation
COMMAND : G\g      (Write\Read ) — Number of inner
                   bursts in outer burst (OBN) for each
                              electrode in a
                              block
Write Format :(up t0 149 byt.)                 [G][NOF][ul][rl][Data1][Data2][Da
                                               ta3]..........[Datan-
                                               1][Datan][CHSUM]
                                               *[NOF] = Number of bytes to
                                               follow
TDU Response :(1 bytes)                        [Res*]
                                               *See TDU result codes below
```

| | | |
|---|---|---|
| Read Format :(4 bytes) | | [g][NOF][ul ][lr] |
| TDU Response :(up to 144 by.) | | [Data1][Data2][Data3].........[Datan-1][Datan] |
| Comment ; | Block update ; block of tactors defined by [ul =upper left tactor] and [lr=lower right tactor] when ul = 1 and lr = 144 then the entire array is selected [datan]=[data144] Data range 0-255 — (Parameter range ; 0-255 bursts) Data = 0 No Stimulation CKSUM is one byte resulting from summing all the bytes following the [NOF] byte | |
| COMMAND : H\h | (Write\Read ) — Number of pulses per inner burst (IBN) for each electrode in a block | |
| Write Format :(up t0 149 byt.)v | | [H][NOF*][ul][rl][Data1][Data2][Data3]..........[Datan-1][Datan][CHSUM] *[NOF] = Number of bytes to follow |
| TDU Response :(1 bytes) | | [Res*] *See TDU result codes below |
| Read Format :(4 bytes) | | [h][NOF][ul][lr] |
| TDU response :(up to 144 by.) | | [Data1][Data2][Data3].........[Datan-1][Datan] |
| Comment ; | Block Update ; block of tactors defined by [ul = upper left tactor] and [lr=lower right tactor] when ul = 1 and lr = 144 then the entire array is selected [datan]=[data144] Data range 0-255 — (Parameter range ; 0-255 pulses) Data = 0 No Stimulation CKSUM is one byte resulting from summing all the bytes follwing the [NOF] byte | |
| COMMAND : T\t | (Write Only) — PA, PW, OBN, IBN for each electrode in the block | |
| Write Format :(up t0 10 byt.) | | [H][NOF][ul][rl][field*][Data]..........[Datan][CHSUM] * when field = 0 then [Data] = PA (n=1) when field = 1 then [Data] = PW (n=1) when field = 2 then [Data] = OBN (n=1) when field = 3 then [Data] = IBN (n=1) when field = 4 then [Data] = [PA][PW][OBN][IBN](n=4) |
| TDU Response :(1 bytes) | | [Res*] *See TDU result codes below |
| Comment ; | Block Update ; block of tactors definted by [ul =upper left tactor] and [lr=lower right tactor] when ul = 1 and lr = 144 then the entire array is selected [datan]=[data144] Data range ; as defined for each paramenter CKSUM is one byte resulting from summing all the bytes following the [NOF] byte | |
| COMMAND : I\i | (Write\Read ) — Pulse Period (PP) for entire Array | |
| Write Format :(4 bytes) | | [I][NOF][Data][CKSUM] |
| TDU Response :(1 bytes) | | [Res*] *See TDU result codes below |
| Read Format :(2 bytes) | | [i][NOF] |
| TDU Response :(1 bytes) | | [Data] |
| Comment ; | Common to all electrodes Data range 1-255 — (Parameter range ;2-510 us) CKSUM is a copy of the data byte in this command | |
| COMMAND : J\j | (Write\Read ) — Outer burst period (OBP) for entire Array | |
| Write Format :(4 bytes) | | [J][NOF][Data][CKSUM] |
| TDU Response :(1 bytes) | | [Res*] *See TDU result codes below |

```
-continued

Read Format :(2 bytes)                          [i][NOF]
TDU Response :(1 bytes)                         [Data]
Comment         Common to all electrodes
;
                Data range 0-255 — (Parameter range ;5-1275
                                    ms)
                CKSUM is a copy of the data byte in this command
COMMAND : K\k   (Write\Read ) — Inner burst period
                (IBP) for entire Array
Write Format :(4 bytes)                         [K][NOF][Data][CKSUM]
TDU Response :(1 bytes)                         [Res*]
                                                *See TDU result codes below
Read Format :(2 bytes)                          [k][NOF]
TDU Response :(1 bytes)                         [Data]
Comment         Common to all electrodes
;
                Data range 0-255 — (Parameter range ; 100-25500
                                    us)
                CKSUM is a copy of the data byte in this command
COMMAND : L\l   (Write\Read ) — Inter-channel period
                (ICP) for entire Array
Write Format :(4 bytes)                         [L][NOF][Data][CKSUM]
TDU Response :(1 bytes)                         [Res*]
                                                *See TDU result codes below
Read Format :(2 bytes)                          [l][NOF]
TDU Response :(1 bytes)                         [Data]
Comment         Common to all electrodes
;
                Data range 1-255  — (Parameter range 2-510 us)
                CKSUM is a copy of the data byte in this command
COMMAND:M\m     (Write\Read ) — Amplitude scaling
                (PAS) for entire Array
Write Format :(2 or 4 bytes)                    [M][NOF][Data][CKSUM]**
                                                ** if [data][CKSUM]are omitted
                                                then the TDU uses the local
                                                intensity
                                                   control for the PAS valus,
                                                otherwise the value in [Data] will
                                                be used
                                                   and the local control will be
                                                sampled but not used. The TDU
                                                will continue
                                                   to use the last written value
                                                until a new command tells it
                                                otherwise
TDU Response :(1 bytes)                         [Res*]
                                                *See TDU result codes below
Read Format :(2 bytes)                          [m][NOF]
TDU Response :(1 bytes)                         [Data]
Comment         Common to all electrodes
;
                Data range 0-255  — (Parameter range 0-100%)
                CKSUM is a copy of the data byte in this command
COMMAND : N\n   (Write\Read ) — (Update a pre-
                programmed pattern
Write For.:(150,21,6, or 4 byt.)                [N][NOF][Access][ID][field*][Data
                                                1]..........[Data144][CKSUM]
                                                * field = 0 ; Pulse Amplitude for
                                                each electrode in the array
                                                   field = 1 ; Pulse Width for each
                                                electrode in the array
                                                   field = 2 ; Number of inner
                                                bursts in outer burst for each
                                                electrode
                                                   field = 3 ; Number of pulses per
                                                inner burst for each electrode
                                                [N][NOF][Access][ID][field*][Data
                                                1]..........[Data16][CKSUM]
                                                *field = 9 ; Pattern ID (all bytes
                                                must be included)
                                                [N][NOF][Access][ID][field*][Data]
                                                [CKSUM]
                                                * field = 4 ; Pulse period for the
                                                entire array
                                                   field = 5 ; Outer burst period for
                                                the entire aray
                                                   field = 6 ; Inner burst period for
                                                the entire array
```

-continued

|  |  |
|---|---|
|  | field = 7 ; Inner channel period for the entire array |
|  | field = 8 ; Amplitude scaling for the entire array |
|  | [N][NOF][Access][ID][field*][CKSUM] |
|  | * field = 10 ; Load pattern from memory |
|  | field = 11 ; Store pattern in memory |
| TDU Response :(1 bytes) | [Res*] |
|  | *See TDU result codes below |
| Read Format :(5 bytes) | [n][NOF][Access][ID][field] |
| TDU Response :(1 or 144 bytes) | [Data] |
|  | [Data1]..........[Data144] |
| Comment | ID is the number of pattern being updated |
| ; |  |
|  | Access is a code used for security. (Access = 199) |
|  | Data ranges are the same as indicated in the previous commands |
|  | TDU must be in Pattern Update mode. Otherwise an invalid Opcode response will be sent |
|  | CKSUM is one byte resulting from summing the ID, Access, field, and data bytes |
| COMMAND : O | (Write ONLY) — Start stimulation of the currently loaded pattern |
| Write Format :(2 bytes) | [O][NOF] |
| TDU Response :(1 bytes) | [Res*] |
|  | *See TDU result codes below |
| Comment: |  |
| COMMAND : P | (Write ONLY) — Stop stimulation |
| Write Format :(2 bytes) | [P][NOF] |
| TDU Response :(1 bytes) | [Res*] |
|  | *See TDU result codes below |
| Comment: |  |
| COMMAND : Q | (Write ONLY) — Display a pre-programmed pattern |
| Write Format :(4 bytes) | [Q]NOF][Data][CKSUM] |
| TDU Response :(1 bytes) | [Res*] |
|  | *See TDU result codes below |
| Comment: | Data range 0-52        (53 pre-programmed patterns) |
|  | CKSUM is a copy of the data byte |
| COMMAND : R | (Write ONLY) — Deliver a sequence of outer burst |
| Write Format :(4 bytes) | [R][NOF][Data][CKSUM] |
| TDU Response :(1 bytes) | [Res*] |
|  | *See TDU result codes below |
| COMMENT | Data ramge 0-255       (Parameter range 0-255 bursts) |
| ; |  |
| COMMAND : s | (Read ONLY) — Current analog value for a channel |
| Read Format :(3 bytes) | [a][NOF][CH] |
| TDU Response :(1 or 7 bytes) | [Data ] |
|  | [Data1]..........[Data7] |
| Comment |  |
| ; |  |
|  | Data range 0-255     (Parameter range : CH0 : intensity 0-100%) |
|  | [CH] = 0 for Intensity |
|  | [CH] = 1 for Al1 |
|  | [CH] = 2 for Al2 |
|  | [CH] = 3 for Al3 |
|  | [CH] = 4 for Al4 |
|  | [CH] = 5 for Al5 |
|  | [CH] = 6 for Al6 |
|  | [CH] = 7 for Intensity, Al1, Al2, Al3, Al4, Al5, Al6 |

Response Byte For Write Commands:

|  |  |  |  |
|---|---|---|---|
| *[Res] = | [1] | Operation Successful |
|  | [2] | Parameter(s) not initialized |
|  | [3] | Pattern not initialized |
|  | [4] | Invalid opcode |
|  | [5] | Invalid address |
|  | [6] | Invalid field |
|  | [7] | Wrong check sum |
|  | [8] | Invalid data |

| | |
|---|---|
| [9] | Parameter combination Invalid |
| [10] | Stimulation is already ON |
| [11] | Stimulation is already OFF |
| [12] | Invalid access code |

The invention claimed is:

1. A method of treating a patient with impaired motor control or function due to a nervous system impairment comprising:
   A) having the patient participate in a rehabilitative therapy program comprising physical movement or exercise, wherein the patient's ability to perform the physical movement or exercise is inhibited by the patient's nervous system impairment;
   B) providing electrotactile stimulation to the patient's tongue while the patient concurrently engages in a physical movement or exercise of the rehabilitative therapy program, wherein the physical movement or exercise comprises a body stabilization exercise and wherein the electrotactile stimulation:
      1) is provided by an array of electrodes in contact with the top surface of the patient's tongue, wherein the array of electrodes is in communication with a processor configured to:
         a) receive information from a program or detector;
         b) process or translate the information into a pattern to be transmitted to the array; and
         c) transmit the patterned information to the array to be displayed as electrical stimulation;
      2) stimulates one or more cranial nerves of the subject; and
      3) assists the subject in activating, utilizing, and/or training a portion of the brain to learn a task related to the rehabilitative therapy previously facilitated by a region of the brain damaged by the nervous system impairment;
   C) ceasing the physical movement or exercise and electrotactile stimulation; and
   D) repeating steps (B) and (C) until such time that the patient displays a rehabilitative improvement of motor control or function that persists after ceasing the physical movement or exercise and electrotactile stimulation.

2. The method of claim 1, wherein the body stabilization exercise is selected from the group consisting of attempting to maintain an upright posture in a sitting position, attempting to maintain an upright posture in a standing position, attempting to maintain an upright posture in a sitting position on an exercise ball, attempting to maintain an upright posture in a standing position on a soft material, and attempting to maintain an upright posture in a standing position in a tandem Romberg stance.

3. The method of claim 1, wherein the rehabilitative improvement is selected from the group consisting of alleviation of dyskinesias, alleviation of dystonia, alleviation of tremor, alleviation of gait problems, and alleviation of slowness of movement.

4. The method of claim 1, wherein the rehabilitative improvement comprises improved motor control and function associated with the patient's gait.

5. The method of claim 1, wherein the rehabilitative improvement comprises improved motor control and function associated with the patient's balance.

6. The method of claim 1, wherein the patient is a traumatic brain injury patient and the rehabilitative improvement is selected from the group consisting of improved motor control, improved posture, improved balance and improved clarity of speech.

7. The method of claim 1, wherein the patient is selected from the group consisting of a patient with bilateral vestibular dysfunction, a patient with traumatic brain injury, a patient with stroke or cerebellar lesion, and a patient with Mal de Debarquement syndrome.

8. The method of claim 1, wherein the information received by the processor is selected from the group consisting of a preprogrammed pattern of electrical stimulation and information regarding angular and/or linear motion of the patient's head.

9. The method of claim 1, wherein the array of electrodes displays pre-programmed patterns of electrotactile stimulation.

10. The method of claim 1, wherein the physical movement or exercise comprises attempting to maintain a normal, upright posture in a sitting or standing position.

11. The method of claim 1, wherein the physical movement or exercise comprises attempting to maintain a normal, upright posture in a sitting position on an exercise ball.

12. The method of claim 1, wherein the physical movement or exercise comprises attempting to maintain a normal, upright posture in a standing position on a soft material.

13. The method of claim 1, wherein the physical movement or exercise comprises attempting to maintain a normal, upright posture in a standing position in a tandem Romberg stance.

14. The method of claim 1, wherein the patient is provided electrotactile stimulation while attempting to engage in a physical movement or exercise at a first, baseline level of activity, and subsequently while attempting to engage in the same or different physical movement or exercise at a more challenging level of activity.

15. The method of claim 14, further comprising providing the patient electrotactile stimulation while the patient attempts to engage in the physical movement or exercise at the first, baseline level of activity subsequent to providing the patient electrotactile stimulation while attempting to engage in the same or different physical movement or exercise at a more challenging level of activity.

16. The method of claim 1, wherein providing electrotactile stimulation to the patient's tongue while the patient concurrently engages in a physical movement or exercise, wherein the patient's ability to perform the physical movement or exercise is inhibited by the patient's nervous system impairment, occurs for at least 20 minutes a day for at least 5 consecutive days.

17. The method of claim 16, wherein the patient extends their limits of physical conditioning and balance control over the course of the at least 5 consecutive days.

18. A method of treating a patient with impaired motor control or function due to a nervous system impairment comprising:
   A) having the patient participate in a rehabilitative therapy program comprising physical movement or exercise, wherein the patient's ability to perform the physical movement or exercise is inhibited by the patient's nervous system impairment;

B) providing electrotactile stimulation to the patient's tongue while the patient concurrently engages in a physical movement or exercise of the rehabilitative therapy program, wherein the physical movement or exercise comprises a body stabilization exercise;

C) ceasing the physical movement or exercise and electrotactile stimulation; and D) repeating steps (B) and (C) until such time that the patient displays a rehabilitative improvement of motor control or function that persists after ceasing the physical movement or exercise and electrotactile stimulation.

19. The method of claim 18, wherein the rehabilitative improvement is selected from the group consisting of alleviation of dyskinesias, alleviation of dystonia, alleviation of tremor, alleviation of gait problems, and alleviation of slowness of movement.

* * * * *